(12) United States Patent
Goodwin

(10) Patent No.: US 11,369,609 B2
(45) Date of Patent: Jun. 28, 2022

(54) SMALL MOLECULE WNT INHIBITOR AS TREATMENT FOR DYSLIPIDEMIA

(71) Applicant: Yale University, New Haven, CT (US)

(72) Inventor: Julie Goodwin, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 112 days.

(21) Appl. No.: 16/864,521

(22) Filed: May 1, 2020

(65) Prior Publication Data

US 2020/0360375 A1 Nov. 19, 2020

Related U.S. Application Data

(60) Provisional application No. 62/842,003, filed on May 2, 2019.

(51) Int. Cl.
*A61K 31/506* (2006.01)

(52) U.S. Cl.
CPC .................. *A61K 31/506* (2013.01)

(58) Field of Classification Search
None
See application file for complete search history.

(56) References Cited

U.S. PATENT DOCUMENTS

2011/0237573 A1\* 9/2011 Cheng .................. A61K 31/497
514/227.8

FOREIGN PATENT DOCUMENTS

WO 2016007775 \* 1/2016

OTHER PUBLICATIONS

Bauersachs, et al.; Burden of Coronary Artery Disease and Peripheral Artery Disease: A Literature Review; Cardiovascular Therapeutics, vol. 2019, Article ID 8295054; https://doi.org/10.1155/2019/8295054; 9 pages.

Malakar, et al.; A review on coronary artery disease, its risk factors, and therapeutics; 2019 Wiley Periodicals, Inc., J Cell Physiol 2019, 234:16812-16823, https://doi.org/10.1002/jcp.28350; 12 pages.

\* cited by examiner

*Primary Examiner* — Kahsay Habte
(74) *Attorney, Agent, or Firm* — Troutman Pepper Hamilton Sanders LLP

(57) ABSTRACT

Compositions and methods for treating cardiovascular diseases and dyslipidemias are provided. The compositions can inhibit Wnt signaling and can reduce inflammation. The levels of cholesterol can be reduced when the compositions are administered to a subject, such as a human.

16 Claims, 77 Drawing Sheets
(63 of 77 Drawing Sheet(s) Filed in Color)

Specification includes a Sequence Listing.

Total=1000 and

Total=65

Total=29

Chr 19:Tcf7l2

Chr 17:Arid1b

Chr 18:Smad4

MLEC            A549

Total Genes:    708            1626
Pathway Hits    279            633

1. Wnt signaling
2. Inflammation by chemokine/cytokine
3. Cadherin signaling
4. Angiogenesis

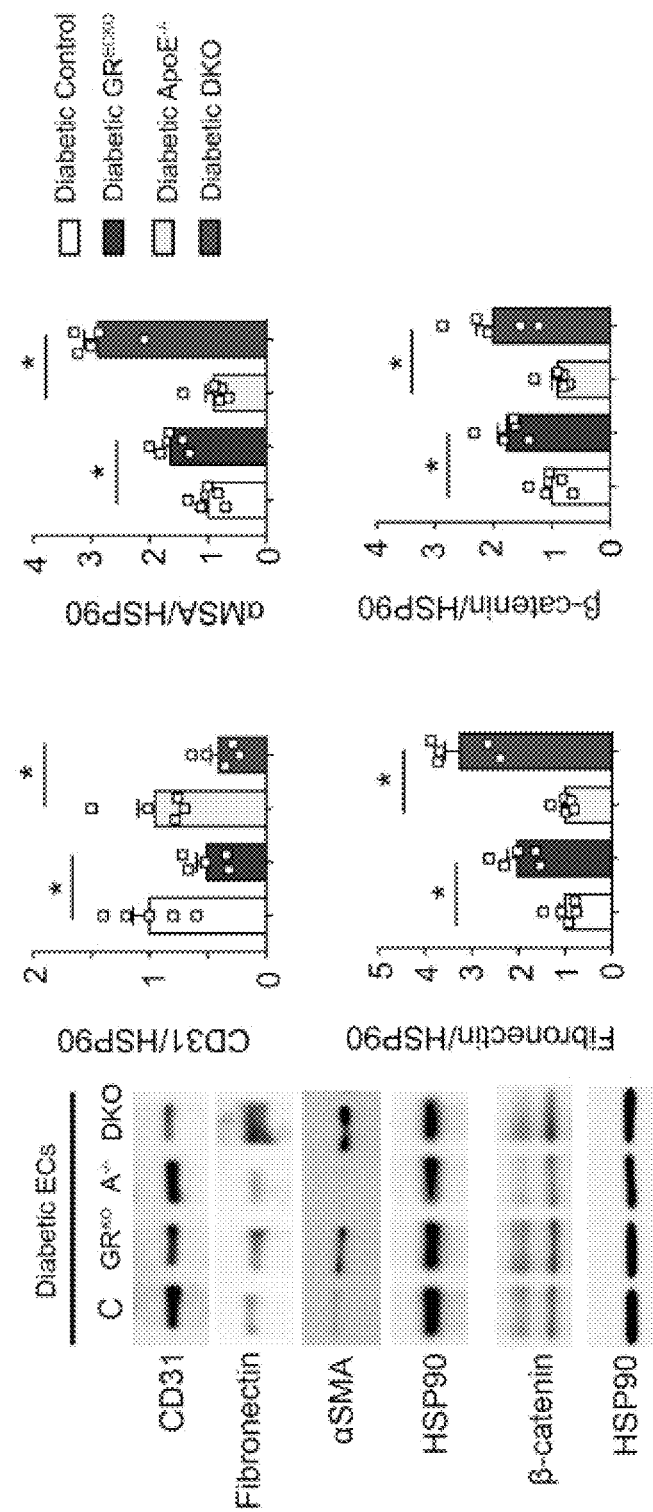

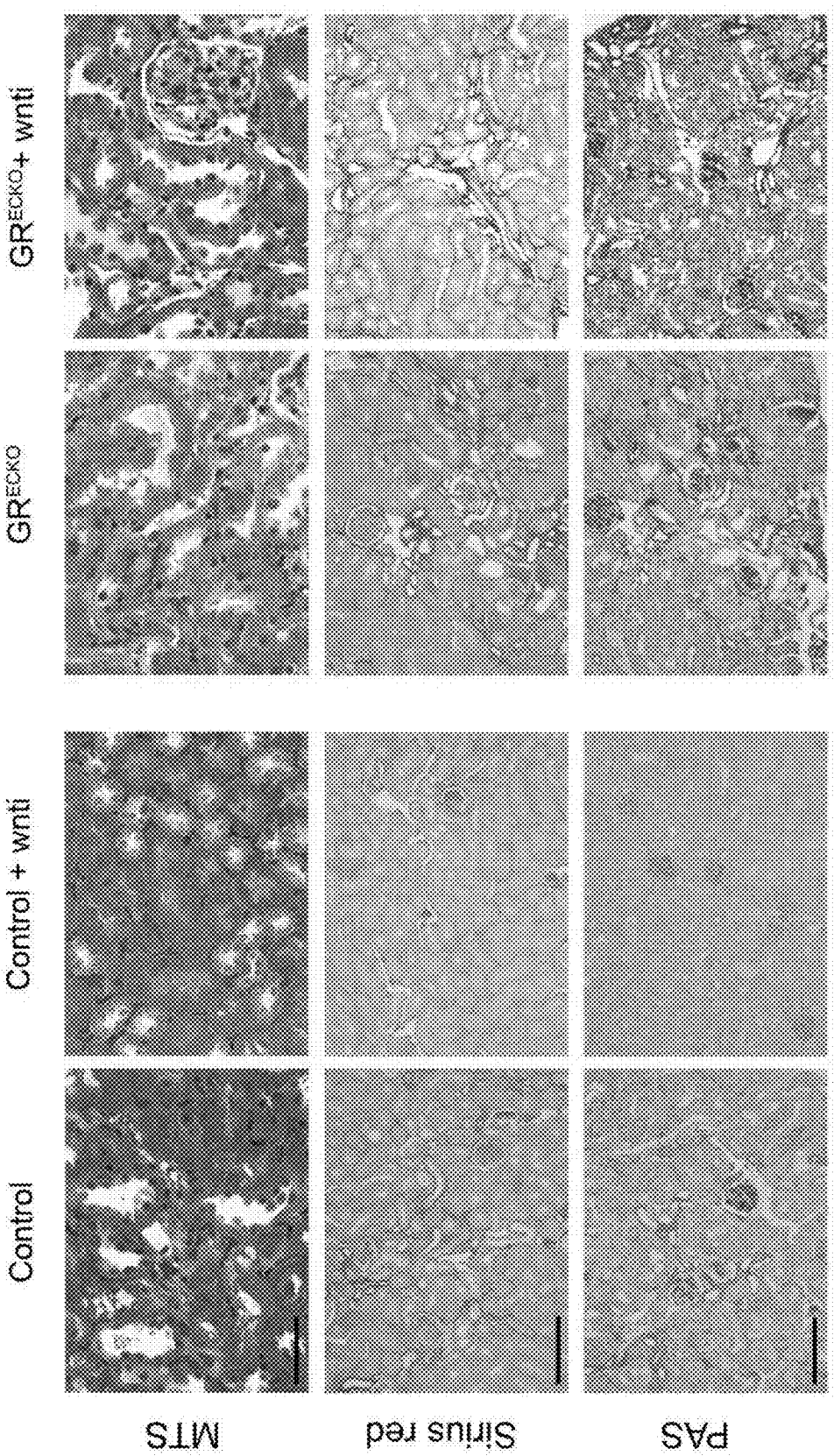

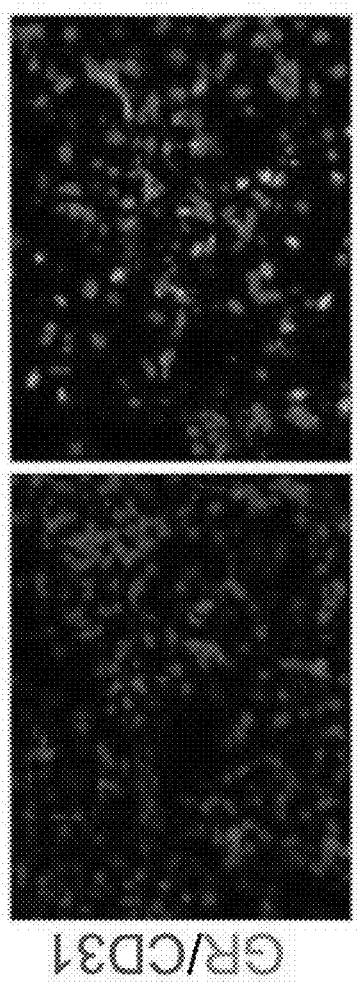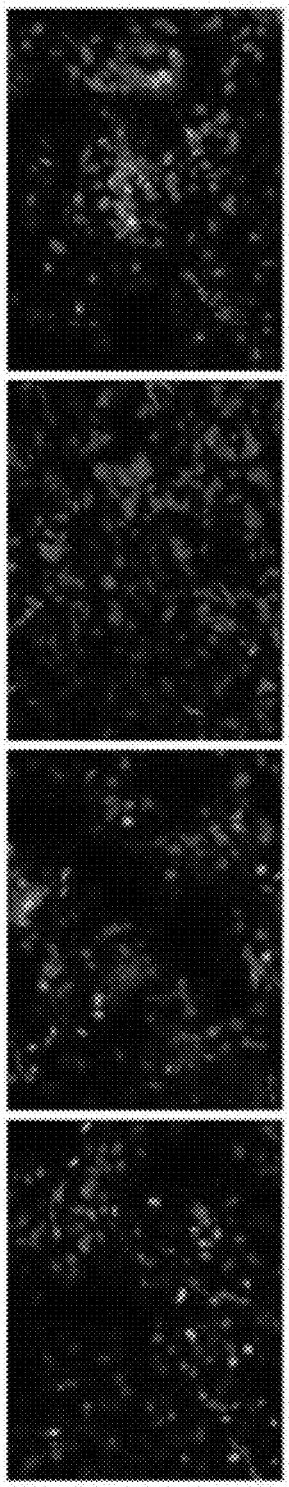

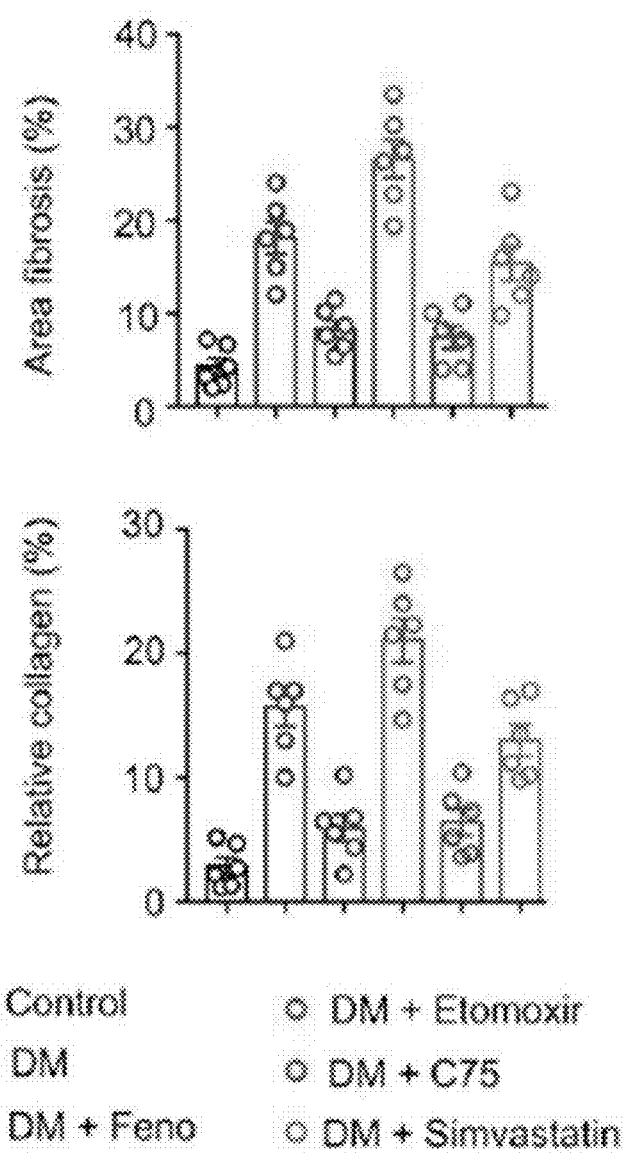

SMALL MOLECULE WNT INHIBITOR AS TREATMENT FOR DYSLIPIDEMIA

CROSS REFERENCE TO RELATED APPLICATIONS

This application claims priority to U.S. provisional patent application No. 62/842,003 entitled "Small Molecule Wnt Inhibitor as Treatment for Dyslipidemia" and filed May 2, 2019, the contents of which are incorporated herein by reference in their entirety as if set forth verbatim.

STATEMENT REGARDING FEDERALLY SPONSORED RESEARCH

This invention was made with government support under HL131952, HL128406, and HL135820 awarded by National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 9, 2020, is named 251609_000029_SL.txt and is 56,750 bytes in size.

FIELD OF THE INVENTION

The invention provides compositions and methods for treating cardiovascular diseases and dyslipidemias.

BACKGROUND

Vascular inflammation is present in many cardiovascular diseases and dyslipidemias. Exogenous glucocorticoids have traditionally been used as a therapy to suppress inflammation. However, recent data has shown that endogenous glucocorticoids, acting through the endothelial glucocorticoid receptor, act as negative regulators of inflammation. The glucocorticoid receptor (GR) is a nuclear hormone receptor that is expressed ubiquitously in most cell types and is important in many states of health and disease. Glucocorticoid receptors (GRs) mediate the action of steroid hormones in a variety of tissues, including the kidney. Tissue-specific loss of this receptor can produce profound phenotypes (6, 7, 65, 66). The role of glucocorticoids in cardiovascular and kidney disease is complex. Endothelial GR was identified as a negative regulator of vascular inflammation in models of sepsis (7) and atherosclerosis (6).

Administration of glucocorticoids on their own, in a systemic manner, can yield serious side effects that render them intolerable and ineffective on their own for vascular inflammatory disorders. There is a need for new compounds, compositions, and methods for treating cardiovascular diseases and dyslipiedemias.

Approximately one-third of diabetic patients will develop diabetic nephropathy (DN), a leading cause of end-stage renal disease (ESRD) that causes more than 950,000 deaths globally each year (46, 47). Diabetic nephropathy is characterized by excess deposition of extracellular matrix, loss of capillary networks and accumulation of fibrillary collagens, activated myofibroblasts and inflammatory cells (49). In renal fibrosis, myofibroblasts are believed to be an activated fibroblast phenotype that contributes to fibrosis (50). There are six well-reported sources of matrix-producing myofibroblasts: (1) activated residential fibroblasts, (2) differentiated pericytes, (3) recruited circulating fibrocytes, (4) those from macrophages via macrophage-to-mesenchymal transition (5) those from mesenchymal cells derived from tubular epithelial cells via epithelial-to-mesenchymal transition (EMT) and (6) those from mesenchymal cells transformed from endothelial cells (ECs) via endothelial-to-mesenchymal transition (EndMT) (51, 52).

Over the last two decades, no new drugs have been approved to specifically prevent diabetic nephropathy or to improve kidney function (48). This lack of advancement stems, in part, from poor understanding of the mechanism of progressive kidney dysfunction. Improved understanding of mechanisms of pathogenesis of diabetic kidney disease is urgently needed to catalyze the development of novel, effective and safe therapeutics which can be targeted to the early stages of diabetes, before kidney damage becomes irreversible.

SUMMARY OF THE INVENTION

As specified in the Background Section, above, there is a great need in the art to develop new therapeutic tools for treating dyslipidemias and cardiovascular diseases. The present invention addresses this and other needs by providing small molecule Wnt inhibitors for use in such treatment.

In one aspect is provided a method for treating a condition or a disease in a subject in need thereof, which method comprises administering to the subject a therapeutically effective amount of a compound having the structure according to formula (I):

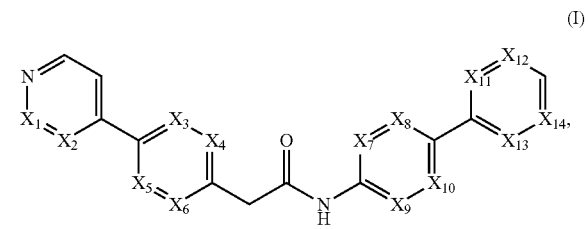

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In some embodiments, the condition is dyslipidemia, hypertension or nephropathy. In some embodiments, the dyslipidemia is hyperlipidemia or hypercholesterolemia. In a specific embodiment, the hypercholesterolemia is familial hypercholesterolemia. In some embodiments, the nephropathy is diabetic nephropathy.

In some embodiments, the disease is cardiovascular disease (e.g., atherosclerosis, coronary artery disease, coronary heart disease, a condition associated with coronary artery disease or coronary heart disease, transient ischemic attack, and stroke) or peripheral artery disease.

In some embodiments, the condition associated with coronary artery disease or coronary heart disease is angina or myocardial infarction.

In some embodiments, the method is effective to reduce the size of an atherosclerotic deposition in the artery of the subject.

In some embodiments, the method further comprises administering to the subject an additional agent effective to treat dyslipidemia, hypertension, hyperlipidemia, hypercholesterolemia, cardiovascular disease, peripheral artery disease, atherosclerosis, coronary artery disease, coronary heart disease, and/or stroke. In some embodiments, the method further comprises administering to the subject an additional agent effective to treat nephropathy.

In various embodiments, the subject is human.

In another aspect is provided a method for treating a condition or a disease in a subject in need thereof, which method comprises administering to the subject a therapeutically effective amount of a pharmaceutical composition comprising a compound having the structure according to formula (I):

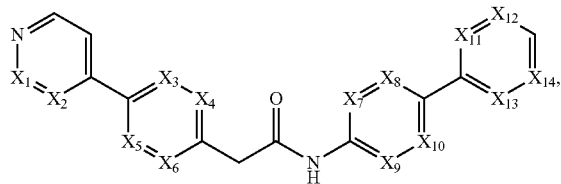

(I)

wherein $X_1$ and $X_2$ are selected from N and CR;

one of $X_3$, $X_4$, $X_5$ and $X_6$ is N and others are selected from N and CR;

one of $X_7$, $X_8$, $X_9$ and $X_{10}$ is N and others are selected from N and CR;

one of $X_{11}$, $X_{12}$, $X_{13}$ and $X_{14}$ is N and others are selected from N and CR, and R is independently at each occurrence selected from hydrogen, halo, cyano, methyl, difluoromethyl, and trifluoromethyl, or a pharmaceutically acceptable salt thereof.

In some embodiments, the condition is dyslipidemia or hypertension. In some embodiments, the dyslipidemia is hyperlipidemia or hypercholesterolemia. In a specific embodiment, the hypercholesterolemia is familial hypercholesterolemia.

In some embodiments, the disease is cardiovascular disease (e.g., atherosclerosis, coronary artery disease, coronary heart disease, a condition associated with coronary artery disease or coronary heart disease, transient ischemic attack, and stroke) or peripheral artery disease.

In some embodiments, the condition associated with coronary artery disease or coronary heart disease is angina or myocardial infarction.

In some embodiments, the method is effective to reduce the size of an atherosclerotic deposition in the artery of the subject.

In some embodiments, the method further comprises administering to the subject an additional agent effective to treat dyslipidemia, hypertension, hyperlipidemia, hypercholesterolemia, cardiovascular disease, peripheral artery disease, atherosclerosis, coronary artery disease, coronary heart disease, and/or stroke.

In various embodiments, the subject is human.

In various embodiments of any of the above aspects, one of $X_3$, $X_4$, $X_5$ and $X_6$ is N and the others are CR. In some embodiments, one of $X_7$, $X_8$, $X_9$ and $X_{10}$ is N and the others are CR. In some embodiments, two of $X_{11}$, $X_{12}$, $X_{13}$ and $X_{14}$ are N and the others are CR. In some embodiments, $X_1$ is CR and R is methyl, and/or $X_5$ is CR and R is methyl. In some embodiments, one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH.

In a certain embodiments, $X_1$ is CR, where R is methyl; $X_2$ is CH; $X_3$ is N; $X_5$ is CR, where R is methyl; $X_4$ and $X_6$ are each CH; $X_7$ is N; $X_8$, $X_9$ and $X_{10}$ are each CH; $X_{11}$ and $X_{14}$ are each N; $X_{12}$ and $X_{13}$ are each CH. In a specific embodiment, the compound has the structure

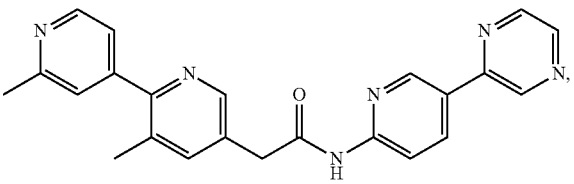 [SMILES: Cc1cc(-c2ncc(CC(=O)Nc3ccc(-c4cnccn4)cn3)cc2C)ccn1]

or a pharmaceutically acceptable salt thereof.

BRIEF DESCRIPTION OF DRAWINGS

This patent application file contains at least one drawing executed in color. Copies of this patent application with color drawing(s) will be provided by the Office upon request and payment of the necessary fee.

(FIG. 1A) 6 conditions were submitted for ChIP-seq analysis. Control siRNA cells treated with DEX (ConDEX) showed the largest peak, reflecting binding of GR by its ligand. A smaller peak was observed from the GR siRNA cells treated with DEX (GRDEX) as siRNA knockdown is not 100% complete. The other 4 conditions had overlapping peak profiles indicating non-specific background. Normalized coverage per 1,000,000 reads is plotted as a function of position within 1 kB of the peak. (FIG. 1B) Histogram of the top 10,000 peaks in comparison to the distance from the transcriptional start site (TSS) indicating enormous enrichment very close to the TSS. (FIG. 1C) Binding within ±1 kB of the transcriptional start site in each of the conditions tested. Only the control siRNA+DEX condition showed any appreciable binding, as expected. Two small clusters of genes (clusters 1, 3) had well defined binding areas with regard to the TSS. The vast majority (cluster 2) had no discernible pattern. (FIG. 1D) Pie chart of the top 10,000 peaks indicating the location of binding in the genome. (FIG. 1E) Characterization of the top 1000 ChIP-seq peak binding sites by location. (FIG. 1F) 65/1000 peaks were found to have both the classic GRE motif (top) and a de novo motif (bottom). (FIG. 1G) Binding site by location of the 65 peaks with both motifs.

(FIG. 2A) ChIP peak binding location by region. (FIG. 2B) The peak location of each of the 29 genes was examined individually in the ENCODE database. The number of genes with TF binding at the peak location based on the location of the peak binding site is shown. The 7 most abundant transcription factors are quantified and the corresponding motifs are shown. (FIG. 2C) The number of regulatory elements is quantified as a function of peak location for each of the 29 genes surveyed.

(FIG. 3A) Control siRNA- or GR siRNA-treated MLECs. Data represent 3 separate experiments. (FIG. 3B) DKO (n=6) or control (Apoe −/−) mice (n=3) fed with high-fat diet for 3 weeks. Whole aortas were dissected for RNA isolation and qPCR. *p<0.05. Alignment of the input DNA with the Con DEX condition from the ChIP-seq data demonstrates massively enriched GR binding at the peak locations for (FIG. 3C) Tcf7l2, (FIG. 3D) Arid1b and (FIG. 3E) Smad4.

(FIG. 4C) Control siRNA or GR siRNA MLECs were treated with Wnt3a 200 ng/ml for 4 hours in the presence of absence of DEX 100 nM for 1 hour and qPCR for Sox17 was performed. (FIG. 4D) MLECs were stably transfected with a TCF/LEF luciferase construct and subjected to either control siRNA or GR siRNA treatment, with and without Wnt3a 200 mg/ml for 4 hours. (FIG. 4E) MLECs were treated with either control siRNA or GR siRNA and lysates were subjected to Western blot for GR and ß-catenin expression. (FIG. 4F) Quantification of GR and ß-catenin expression by densitometry. Data represent 3 independent experiments. *p<0.05. **p<0.01.

(FIG. 5A) Heat map of fold-expression changes of 16 genes identified through advanced analysis of sequencing data. Trends are conserved for both GR replete and GR knock out conditions. (FIG. 5B) Novel motif detected from analysis of 16 genes in FIG. 5A. (FIG. 5C) Luciferase assay showing fold induction for cells treated with media alone, RU486 alone for 4 hours, DEX alone for 4 hours or RU486 4 hour pre-treatment followed by 4 hours with DEX. Data represent 3 separate experiments. *p<0.05.

(FIG. 6A) Representative aortas stained with Oil Red O from Apoe −/− and DKO mice; scale bar 1 cm. (FIG. 6B) Quantification of lesion size in each genotype (n=5/group). (FIG. 6C) Representative aortas stained with X-gal demonstrate significantly higher β-galactosidase staining in DKO mice. A LacZ(−) control is included for comparison; scale bar 1 cm. (FIG. 6D) Quantification of β-gal expression in each genotype (n=6-7 mice/group). (FIG. 6E) mRNA expression of axin 2, ctnnb and TCF/Lef is significantly higher in aortic endothelial cells from DKO mice than Apoe −/− mice after diet feeding (n=5/group). **p<0.05.

(FIG. 8A) In vitro angiogenesis (FIG. 8B) In vitro cadherin (FIG. 8C) In vitro inflammation by cytokine/chemokine. In vivo, DKO (n=6) or Apo E KO mice (n=3) were fed with high-fat diet for 3 weeks. Whole aortas were dissected for RNA isolation and qPCR. (FIG. 8D) In vivo angiogenesis, (FIG. 8E) in vivo cadherin, and (FIG. 8F) in vivo inflammation by cytokine/chemokine Data represent 3 separate experiments. *p<0.05.

(FIG. 11A) Apoe$^{-/-}$; GR$^{fl/fl}$, Tie2 Cre−; TCF/Lef-LacZ (Apoe$^{-/-}$) mice were bred with Apoe$^{-/-}$; GR$^{fl/fl}$, Tie2 Cre+; TCF/Lef-LacZ (DKO) mice. Apoe$^{-/-}$ and DKO mice were fed a high fat diet (HFD) for 12 weeks. The Wnt inhibitor (wnti) LGK974 at a dose of 5 mg/kg body weight, or vehicle, was administered 6 days/week by oral gavage from 4-12 weeks. (FIG. 11B) LacZ (blue) staining in the aortas of vehicle-treated control animals and wnti-treated animals. (n=6-7/group). A LacZ(−) aorta was included as a control. Aortic area stained is quantified in the corresponding graph. (FIG. 11C) Measurement of body weight in animals of both genotypes with and without Wnti treatment. (FIG. 11D) Triglycerides, total cholesterol and HDL cholesterol were measured after 12 weeks of diet feeding in animals of both genotypes in the presence of absence of Wnti. (FIG. 11E) Lipid deposition (red=lipid) in aortas of wnti- or vehicle-treated Apoe$^{-/-}$ and DKO treated mice was analyzed by Oil Red O staining. Atherogenic lesion area was calculated by using the Image J program. (FIG. 11F) Masson Trichrome and H&E staining in the brachiocephalic artery of Wnti- or sham-treated Apoe$^{-/-}$ and DKO treated mice. Lesion size was measured using Image J program. (FIG. 11G) H&E and (FIG. 11H) Oil Red O staining in the aortic root of heart sections.

(FIG. 12A) Immunofluorescence analysis was performed in the kidneys of control and diabetic CD-1 and C57Bl6 mice fluorescence microscopy using FITC-labeled GR, Rhodamine-labeled CD31 and DAPI (blue). Merged images are shown. Scale bar: 50 mm in each panel. Representative pictures are shown. N=6/group. Data in the graph are shown as mean±SEM. (FIG. 12B) Western blot and qPCR analysis of GR protein and mRNA levels in isolated endothelial cells from the kidneys of control and diabetic CD-1 mice. Densitometry analysis was normalized to β-actin. mRNA expression was normalized to 18S. N=6/group. Data in the graphs are shown as mean±SEM. Tukey test was used for analysis of statistical significance. *p<0.05

(FIG. 13A) Schematic diagram, showing induction of diabetes in the GR fl/fl; Tie1 Cre− (Control) GR fl/fl; Tie1 Cre+ (GR$^{ECKO}$), Apoe−/−; GR fl/fl; Tie1 Cre− (Apoe$^{-/-}$) and Apoe$^{-/-}$; GR fl/fl; Tie1 Cre+ (DKO) mice. Five doses of STZ (50 mg/kg/day i.p.) were injected to induce fibrosis. (FIGS. 13B-13I) Physiological parameters including body weight, blood glucose, kidney weight, heart weight, liver weight, albumin-to-creatinine ratio (ACR), plasma trigycerides and plasma cholesterol were measured. N=6/group. (FIG. 13J). Masson trichome and Sirius red staining in kidneys of non-diabetic and diabetic control, GR$^{ECKO}$, ApoE$^{-/-}$ and DKO were analyzed. Representative images are shown. Relative area fibrosis (%) and relative collagen (%) were measured using the ImageJ program. N=6 non-diabetic group, N=7 diabetic groups. Scale bar: 50 mm in each panel. Data are shown as mean±SEM. (FIG. 13K) Immunofluorescence analysis of collagen I was analyzed in the kidneys of diabetic control, diabetic GR$^{ECKO}$, diabetic ApoE$^{-/-}$, and diabetic DKO with FITC-labeled Collagen 1 and DAPI (blue). Representative images are shown. (FIG. 13L) Rhodamine-labeled fibronectin and DAPI (blue). Representative images are shown. Scale bar: 50 mm in each panel. N=6/group. Tukey test was used for the analysis of statistical significance. * p<0.05.

(FIG. 14A) Cytokines and chemokines were measured in the plasma by using a cytokine array analysis (Luminex). The plasma of control and diabetic mice was analyzed. N=5/group. (FIG. 14B) The plasma of non-diabetic and diabetic GR$^{ECKO}$ and DKO mice were analyzed. N=5/group. Data are shown as mean±SEM. (FIG. 14C) Relative gene expression analysis of the indicated molecules in the diabetic kidneys. N=6/group. 18S was used to normalize the expression level. Tukey test was used for the analysis of statistical significance. *p<0.05.

FIGS. 15A-15C. Up regulation of Wnt signaling and fibrogenic markers with loss of endothelial GR. (FIG. 15A) Relative mRNA levels determined by qRT-PCR of Axin2, Tcf, αSMA, CD31 and fibronectin were analyzed in isolated EC from the kidneys of diabetic control, GR$^{ECKO}$, Apoe$^{-/-}$ and DKO mice. N=6/group. (FIG. 15B) Western blot analysis of CD31, αSMA, fibronectin, and β-catenin in isolated endothelial cells from the kidneys of diabetic control, GR$^{ECKO}$, Apoe$^{-/-}$ and DKO mice. N=5/group. Representative blots are shown. Densitometry normalization was performed to HSP90. (FIG. 15C) Immuno-fluorescence analysis of αSMA/CD31 and TGFβR1/CD31 was performed in the kidneys of diabetic control, GR$^{ECKO}$, Apoe$^{-/-}$ and DKO mice. FITC-labeled αSMA and TGFβR1 and rhodamine-labeled CD31 and DAPI (nuclei, blue) were used. Merged images are shown. Scale bar: 50 mm in each panel. Representative pictures are shown. N=5/group. Data are shown as mean±SEM. Tukey test was used for the analysis of statistical significance. * p<0.05.

(FIG. 16A) Schematic diagram, showing the treatment protocol of wnti in the diabetic GR$^{ECKO}$ and DKO mice. (FIG. 16B) Physiological parameters including body weight, blood glucose and kidney weight were analyzed in the wnti-treated diabetic GR$^{ECKO}$ and DKO mice. N=6/group. (FIG. 16C) Masson trichrome, Sirius red and PAS staining in the kidneys was analyzed. Representative images are shown. Relative area fibrosis (%) and relative collagen deposition (%) were measured using the ImageJ program. N=6/group Scale bar: 50 mm in each panel. Data are shown as mean±SEM. (FIG. 16D) Immunofluorescence analysis of fibronectin in the kidneys of wnti-treated diabetic GR$^{ECKO}$ and DKO mice using rhodamine-labeled fibronectin and DAPI (nuclei, blue). Representative images are shown. Scale bar: 50 mm in each panel. N=6/group. (FIG. 16E) Immuno-histochemical analysis of β-catenin level in the wnti-treated diabetic GR$^{ECKO}$ and DKO mice. (FIG. 16F-16G) Immunofluorescence analysis of αSMA/CD31 and αSMA/E-cadherin were performed in the kidneys of Wnti treated diabetic control, and GR$^{ECKO}$. In the first panel FITC-labeled αSMA, rhodamine-labeled CD31 and DAPI (nuclei, blue) were sued. In the second panel FITC-labeled E-cadherin, rhodamine-labeled αSMA and DAPI were used. Merged images are shown. Scale bar: 50 mm in each panel. N=6/group. Tukey test was used for the analysis of statistical significance. * p<0.05.

(FIG. 17A) Radiolabeled [1H$^3$]triolein uptake analysis in kidneys in three sets of experiments 1) control and diabetic mice of CD-1 and C57BL/6 strains 2) diabetic and wnti-treated diabetic mice 3) control, GR$^{ECKO}$, Apoe$^{-/-}$ and DKO mice. CPM of each samples were counted. N=5/group. (FIG. 17B) Radiolabeled [$^{14}$C]palmitate oxidation and [$^{14}$CO$_2$] release were measured. CPM of each sample was counted. N=5-6/group (FIG. 17C) Body weight, blood glucose, and kidney weight was measured at the end of these experiments. Ex vivo radiolabeled [$^{14}$C] palmitate oxidation and [$^{14}$CO$_2$] released were measured. CPM of each sample was counted. N=5-6/group. (FIG. 17D) Masson trichrome, Sirius red and PAS staining were analyzed in the kidneys of control, diabetic, fenofibrate-, etomoxir-, C75-, simvastatin-treated diabetic mice. Representative images are shown. Relative area fibrosis (%) and relative collagen deposition (%) were measured using the ImageJ program. N=6/group. Scale bar: 50 mm in each panel. Data are shown as mean±SEM. (FIG. 17E) Immunohistochemical analysis of CPT1a and β-catenin. Representative images are shown. Scale bar: 50 mm in each panel. N=6/group. Tukey test was used for the analysis of statistical significance. *p<0.05. C—control, DM—diabetic, G$^{KO}$—GR$^{ECKO}$, A$^{-/-}$—Apoe$^{-/-}$.

(FIG. 18A) Conditioned media experiment design. HUVECs were transfected with scrambled or GR siRNA; after 6 h, the medium was changed and cells were incubated for 72 h. The subsequently harvested media was transferred to HK-2 cells. (FIG. 18B) Representative western blotting analysis of E-cadherin, αSMA, TGFβR1 and β-catenin expression. Five independent experiments were performed. Densitometric analysis of the levels relative to β-actin is shown. (FIG. 18C) Immunofluorescence microscopy analysis of E-cadherin and α-SMA expression in conditioned medium treated TECs. For each slide, images of six different fields of view at Å~400 magnification were evaluated. Scale bar 30 μm. (FIG. 18D) [$^{14}$C]palmitate oxidation measured by [$^{14}$CO$_2$] release. CPM were counted and normalized to the protein in the well. Three independent set of experiments were performed. (FIG. 18E) Oxygen consumption rate (OCR) in conditioned medium treated-TECs; each data-point represents the mean of eight independent samples. OCR were measured in a Seahorse XF96 analyzer. (FIG. 18F) Cellular ATP measurement. N=6 were analyzed. (FIG. 18G) Relative mRNA levels determined by qRT-PCR of regulators of FAO in conditioned media-treated TECs. (FIG. 18H) Experimental design for conditioned media. EC from the kidneys of diabetic GR$^{ECKO}$ and diabetic control were cultured for 96 h. The subsequently harvested media was transferred to TECs from diabetic control mice. (FIG. 18I) Representative western blotting analysis of αSMA, E-cadherin, TGFβR1 and β-catenin expression. Five independent experiments were performed. Densitometric analysis of the levels relative to β-actin is shown. Data are mean±SEM. Tukey test was used for the analysis of statistical significance. *p<0.05.

(FIG. 19A) Western blot analysis of GR protein level and (FIG. 19B) qPCR analysis of GR expression level were analyzed in EC from the kidneys of control and GR$^{ECKO}$ mice. N=5/genotype. Data in the graph are shown as mean±SEM. Student t-test was used for the analysis of statistical significance. *p<0.05.

(FIG. 20A)

Schematic presentation of mouse model of UUO. Left kidneys were ligated in control littermates and $GR^{ECKO}$ mice. Kidneys were excised at day 5 or 10. (FIG. 20B) Masson trichome and Sirius red staining in the contralateral and UUO-operated kidneys in control and $GR^{ECKO}$ mice was analyzed. Representative images are shown. Area fibrosis (%) and relative collagen deposition (RCD %) were measured using the ImageJ program. N=8/group. Data are shown as mean±SEM. Scale bar: 50 mm in each panel. (FIG. 20C) Immunofluorescence analysis of collagen I, aquaporin/αSMA and aquaporin/fibronectin were performed in the contralateral and UUO-operated kidneys of control and $GR^{ECKO}$ mice. FITC labeled collagen I, αSMA and fibronectin, and rhodamine-labeled aquaporin and DAPI (blue) were used. Representative images are shown. Scale bar: 50 mm. N=7/group. Data are shown as mean±SEM. Tukey test was used for the analysis of statistical significance. * p<0.05.

FIGS. 21A-21H. Inhibition of canonical Wnt signaling abolishes the fibrogenic phenotype in mice. (FIG. 21A) Schematic diagram, representing the treatment protocol of wnt inhibitor (LGK974, at a dose of 5 mg/kg body weight) in diabetic CD-1 mice and (FIG. 21B) in UUO mice. (FIG. 21C) Masson trichrome, Sirius red and PAS staining in kidneys of diabetic and wnt inhibitor-treated diabetic CD-1 mice. Representative images are shown. Relative area fibrosis (%), relative collagen deposition (%) and glomerular surface area (μm²) were measured using the ImageJ program. N=7/group. Scale bar: 50 mm in each panel. Left bars (blue) represent diabetic control and the left bars (yellow) represent wnt-treated. (FIG. 21D) Masson trichrome, Sirius red and PAS staining in kidneys of UUO and wnt inhibitor-treated UUO mice. Representative images are shown. Relative area fibrosis (%) and relative collagen deposition (%) were measured using the ImageJ program. N=6/group. Scale bar: 50 mm in each panel. (FIG. 21E-21F) GR protein levels in CD31-positive cells were analyzed by immunofluorescence analysis of kidneys of wnti-treated diabetic mice and wnti-treated UUO mice. FITC-labeled GR, rhodamine-labeled CD31 and DAPI blue. Merged images and representative pictures are shown. N=6/group. Scale bar: 50 mm in each panel. (FIG. 21G-21H) Immunohistochemical analysis of β-catenin protein expression in wnti-treated diabetic mice and wnti-treated UUO mice. N=5/group. Data are shown as mean±SEM. Tukey test was used for the analysis of statistical significance. *p<0.05.

(FIG. 23A) Masson trichrome, Sirius red and PAS staining were analyzed in the kidneys of control, diabetic, and fenofibrate-, etomoxir-, C75-, and simvastatin-treated diabetic mice. Representative images are shown. Relative area fibrosis (%) and relative collagen deposition (%) were measured using the ImageJ program. N=6/group. Scale bar: 50 mm in each panel. (FIG. 23B) Co-immunolabeling of GR/CD31 was analyzed by fluorescence microscopy. FITC green-GR, rhodamine red-CD31 and DAPI (blue-nuclei) were used. Representative images are shown. Scale bar: 50 mm in each panel. N=6/group. (FIG. 23C) qPCR gene analysis of fibronectin and α-SMA in the kidneys. 18S was used as the internal control. N=6/group. (FIG. 23D) Blood glucose was measured by glucometer. N=6/group. (FIG. 23E) Radiolabeled [$^{14}$C]palmitate oxidation and [$^{14}CO_2$] release were measured. CPM of each sample was counted. (FIG. 23F) Immunohistochemical analysis of CPT1a and β-catenin in the kidneys of control, diabetic, and fenofibrate-, C75-, etomoxir-, and simvastatin-treated diabetic mice. N=5/group. Data are shown as mean±SEM. Tukey test was used for the analysis of statistical significance. *p<0.05. Con—control, DM—diabetic, feno—fenofibrate.

DETAILED DESCRIPTION

Figure 1A:
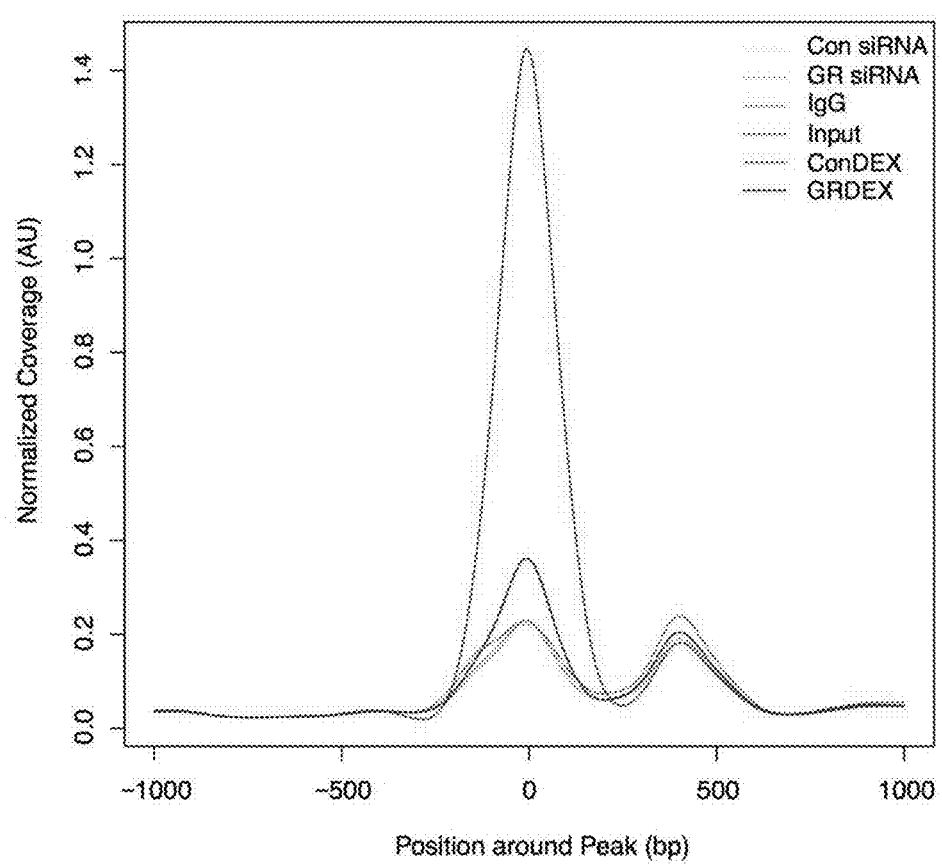
FIGS. 1A-1G. ChIP-seq results.

Animals lacking the endothelial glucocorticoid receptor (GR) have heightened vascular inflammation and worsened atherosclerosis. The loss of endothelial GR may result in upregulation of the canonical Wnt signaling pathway. Notably, this pathway is known to be up regulated in renal fibrosis (67). However, whether endothelial GR contributes to the regulation of fibrogenic processes during kidney fibrosis is not known. Described herein are studies assessing the role endothelial GR in regulating renal fibrosis using endothelial specific GR-knock out mice in both diabetic and non-diabetic conditions.

Described herein is next generation sequencing of GR in endothelial cells that revealed that GR is a potent repressor of the Wnt pathway. A mouse model is provided with a reporter gene for Wnt activation that was bred into an atherogenic model. Also described herein is the in vivo use of the Wnt inhibitor LGK974 that resulted in a surprising improvement in atherosclerosis prognosis, along with a decrease cholesterol levels by about 50%.

Described herein is a novel method of treating atherosclerosis and other diseases and conditions relating to cholesterol levels, lipidemia, etc. The Wnt pathway has not previously been implicated in cholesterol metabolism. Additionally the magnitude the cholesterol-lowering effect with the Wnt inhibitor LGK974 is enormous, potentially rivaling that of statins.

The inventors of the present disclosure discovered an endothelial GR-Wnt interaction that may provide a mechanism to explain the striking phenotypes of heightened atherosclerosis in DKO mice (7), or impaired survival after low-dose lipopolysaccharide (LPS) in endothelial cell-specific GR KO mice (6), two phenotypes largely dependent on endothelial GR. Inhibition of the Wnt signaling pathway in endothelial cells may provide a valuable therapeutic opportunity for inflammatory disorders.

Unless defined otherwise, technical and scientific terms used herein have the same meaning as commonly understood by one of ordinary skill in the art to which this invention belongs.

As used herein, the singular forms "a", "an" and "the" include plural references unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The terms "patient", "individual", "subject", "mammal", and "animal" are used interchangeably herein and refer to mammals, including, without limitation, human, veterinary animals (e.g., cats, dogs, cows, horses, sheep, pigs, etc.) and experimental animal models (e.g., mouse, rabbit, rat). Animals include all vertebrates, e.g., mammals and non-mammals, such as mice, sheep, dogs, cows, avian species, ducks, geese, pigs, chickens, amphibians, and reptiles. In a preferred embodiment, the subject is a human. In some embodiments, a subject is in need of prevention or treatment for dyslipidemia or a related disorder or condition.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "therapeutically effective amount" and "effective amount" are used interchangeably herein to refer to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like.

The term "pharmaceutically acceptable", as used herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" or "a pharmaceutically acceptable carrier" as used herein, refers to any clinically useful solvents, diluents, adjuvants, excipients, recipients, vehicles and the like for use in preparing admixtures of a pharmaceutical composition.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wley and Sons, Inc. 1994; among others.

Without wishing to be bound by theory, endothelial cells are involved in the regulation of disease and other developmental processes. Defective regulation of endothelial cell homeostasis may cause mesenchymal activation of other endothelial cells by autocrine effects or of neighboring cell types by paracrine effects, and in both cases contribute to organ fibrosis.

Among diverse origins of matrix-producing fibroblasts, mesenchymal cells transformed from EC via EndMT (51, 52), are an important source of myofibroblasts in several organs, including the kidney (53). EndMT is characterized by the loss of endothelial markers, including cluster of differentiation 31 (CD31), and acquisition of the expression of mesenchymal proteins including α-smooth muscle actin (αSMA), vimentin, and fibronectin proteins (51, 52).

EC may contribute to the formation of new blood vessels in health and life-threatening diseases (54). Disruption in the central metabolism of EC contributes to disease phenotypes (55, 56). Carnitine palmitoyltransferase 1a (CPT1a)-mediated fatty acid oxidation (FAO) regulates the proliferation of EC in the stalk of sprouting vessels (57-59). EC can use metabolites or precursors for epigenetic regulation of their sub-type differentiation and maintain crosstalk through metabolites release with other cell types (54, 59). Notably, EndMT may cause alteration of endothelial cell metabolism, and is an area of active investigation (60, 61). For example, mesenchymal cells derived from EndMT reprogram their metabolism and show defective fatty acid metabolism (61).

Not wishing to be bound by theory, the contribution of EndMT to renal fibrosis has been analyzed in several mouse models of chronic kidney disease (44, 50, 51, 62). Zeisberg et al., performed experiments and reported that approximately 30-50% of fibroblasts co-expressed the EC marker CD31 along with markers of fibroblasts and myofibroblasts such as fibroblast specific protein-1 (FSP-1) and αSMA in the kidneys of mice subjected to unilateral ureteral obstruction nephropathy (UUO) (44). The complete conversion from EC into mesenchymal cell types is not needed as intermediate cell types are sufficient to cause activation of profibrogenic pathways. EndMT can induce profibrogenic signaling by its autocrine and/or by paracrine manner to neighboring cells thereby contributing to global fibrosis in kidneys (50, 63).

However, regulatory control of endothelial cell homeostasis, has not been well studied. Described in this application are the results of experiments in which diabetes induced renal fibrosis in endothelial GR knock out mice ($GR^{fl/fl}$; Tie 1 Cre; $GR^{ECKO}$) but not in control mice ($GR^{fl/fl}$). Also described are results of experiments in which hypercholesterolemia further enhanced severe renal fibrosis in diabetic $GR^{ECKO}$; $Apoe^{-/-}$ (DKO) but not in diabetic littermates ($GR^{fl/fl}$; $Apoe^{-/-}$). The fibrogenic phenotype in the kidneys of diabetic $GR^{ECKO}$ and diabetic DKO may be associated with aberrant cytokine and chemokine reprogramming. Canonical Wnt signaling may be a new target for the action of endothelial GR. Wnt inhibition may improve kidney fibrosis by mitigating endothelial-to-mesenchymal transition (EndMT) and epithelial-to-mesenchymal transitions (EMT). Similarly, activation of fatty acid oxidation may also suppress kidney fibrosis. Conditioned media from endothelial cells from diabetic $GR^{ECKO}$ stimulated Wnt signaling-dependent epithelial-to-mesenchymal transition in tubular epithelial cells from diabetic controls. The data described in connection with these results demonstrate that endothelial GR is an essential antifibrotic core molecule in diabetes.

Compositions of the Invention

In one aspect the invention provides a compound having the structure according to formula (I):

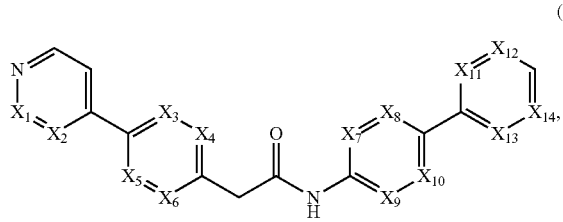

(I)

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In some embodiments of the compound described above, one of $X_3$, $X_4$, $X_5$ and $X_6$ is N and the others are CR. In some embodiments, one of $X_7$, $X_8$, $X_9$ and $X_{10}$ is N and the others are CR. In some embodiments, two of $X_{12}$, $X_{13}$ and $X_{14}$ are N and the others are CR. In some embodiments, $X_1$ is CR and R is methyl, and/or wherein $X_5$ is CR and R is methyl. In some embodiments, one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH.

In a specific embodiment, the compound is a compound having the structure according to formula (I), wherein
$X_1$ is CR, wherein R is methyl; $X_2$ is CH;
$X_3$ is N; $X_5$ is CR, wherein R is methyl; $X_4$ and $X_6$ are each CH;
$X_7$ is N; $X_8$, $X_9$ and $X_{10}$ are each CH;
$X_{11}$ and $X_{14}$ are each N; $X_{12}$ and $X_{13}$ are each CH.

In a specific embodiment, the compound has the structure

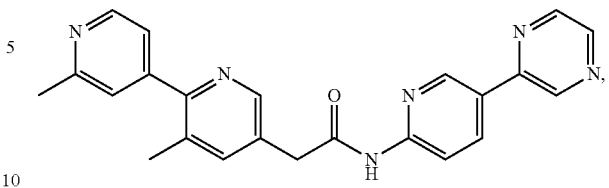

or a pharmaceutically acceptable salt thereof.

In another aspect the invention provides a pharmaceutical composition comprising a compound having the structure according to formula (I):

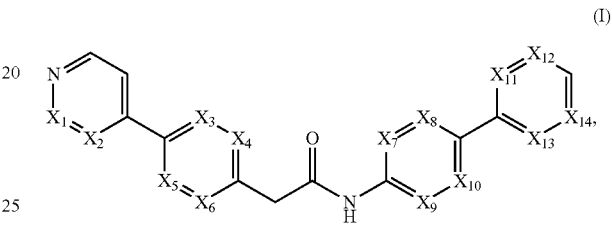

(I)

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In some embodiments of the pharmaceutical composition described above, one of X3, X4, X5 and X6 is N and the others are CR. In some embodiments, one of X7, X8, X9 and X10 is N and the others are CR. In some embodiments, two of X11, X12, X13 and X14 are N and the others are CR. In some embodiments, X1 is CR and R is methyl, and/or wherein X5 is CR and R is methyl. In some embodiments, one or more of X2 is CH, X4 is CH, X6 is CH, X8 is CH, X9 is CH, X10 is CH, X12 is CH, and X13 is CH.

In a specific embodiment, the pharmaceutical composition comprises a compound having the structure according to formula (I), wherein
$X_1$ is CR, wherein R is methyl; $X_2$ is CH;
$X_3$ is N; $X_5$ is CR, wherein R is methyl; $X_4$ and $X_6$ are each CH;
$X_7$ is N; $X_8$, $X_9$ and $X_{10}$ are each CH;
$X_{11}$ and $X_{14}$ are each N; $X_{12}$ and $X_{13}$ are each CH.

In a specific embodiment, the pharmaceutical composition comprises a compound LGK974 having the structure

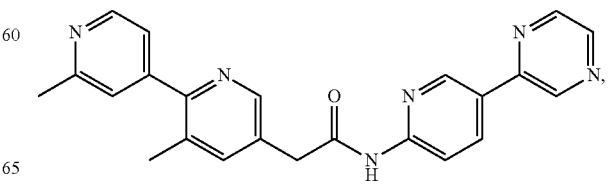

or a pharmaceutically acceptable salt thereof.

LGK974 can inhibit PORCN, which without wishing to be bound by theory is understood to be required for the palmitoylation of Wnt ligands. LGK974 may inhibit one or more of the following Wnt ligands: Wnt1, Wnt2, Wnt2B, Wnt3, Wnt3a, Wnt4, Wnt5a, Wnt5B, Wnt6, Wnt7a, Wnt7b, Wnt8a, Wnt8b, Wnt9a, Wnt9b, Wnt10a, Wnt10b, Wnt11, Wnt16. LGK974 may also inhibit phosphorylation of LRP5 and LPR6.

Other suitable Wnt inhibitors that can be used in the compositions and/or methods of the present invention include but are not limited to those described in U.S. Pat. No. 9,045,416, which is hereby incorporated by reference in its entirety.

Chemical structures herein are drawn according to the conventional standards known in the art. Thus, where an atom, such as a carbon atom, as drawn appears to have an unsatisfied valency, then that valency is assumed to be satisfied by a hydrogen atom even though that a hydrogen atom is not necessarily explicitly drawn. Hydrogen atoms should be inferred to be part of the compound.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Compounds described herein include, but are not limited to, their optical isomers, racemates, and other mixtures thereof. In those situations, the single enantiomers or diastereomer, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Thus, in accordance with some embodiments of the invention, a compound as described herein, including in the contexts of pharmaceutical compositions and methods of treatment is provided as the salt form. A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include: (1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic acid, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like; (2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

The pharmaceutical compositions of the invention may comprise the compounds described herein and a pharmaceutically acceptable carrier or excipient. Pharmaceutically acceptable carriers can include a physiologically acceptable compound that acts to, e.g., stabilize, or increase or decrease the absorption or clearance rate of a pharmaceutical composition. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of glycopeptides, or excipients or other stabilizers and/or buffers. Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. Detergents can also be used to stabilize or to increase or decrease the absorption of the pharmaceutical composition, including liposomal carriers. Pharmaceutically acceptable carriers and formulations are known to the skilled artisan and are described in detail in the scientific and patent literature, see e.g., the latest edition of Remington's Pharmaceutical Science, Mack Publishing Company, Easton, Pa. ("Remington's"). One skilled in the art would appreciate that the choice of a pharmaceutically acceptable carrier including a physiologically acceptable compound depends, for example, on the route of administration of the composition, and on its particular physio-chemical characteristics.

Compositions may be administered by any suitable means, for example, orally, such as in the form of pills, tablets, capsules, granules or powders; sublingually; buccally; parenterally, such as by subcutaneous, intravenous, intramuscular, intraperitoneal or intrastemal injection or using infusion techniques (e.g., as sterile injectable aqueous or non-aqueous solutions or suspensions); nasally, such as by inhalation spray, aerosol, mist, or nebulizer; topically, such as in the form of a cream, ointment, salve, powder, or gel; transdermally, such as in the form of a patch; transmucosally; or rectally, such as in the form of suppositories. The present compositions may also be administered in a form suitable for immediate release or extended release. Immediate release or extended release may be achieved by the use of suitable pharmaceutical compositions, or, particularly in the case of extended release, by the use of devices such as subcutaneous implants or osmotic pumps.

In various embodiments, the pharmaceutical composition is formulated for oral administration. Suitable forms for oral administration include, but are not limited to, tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known in the art for the manufacture of pharmaceutical compositions, and such compositions may contain one or more agents such as, for example, sweetening agents, flavoring agents, coloring agents and preserving agents in order to provide pharmaceutically acceptable preparations. Tablets, capsules and the like generally contain the active ingredient in admixture with non-toxic pharmaceutically acceptable carriers or excipients which are suitable for the manufacture of tablets. These carriers or excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

Tablets, capsules and the like suitable for oral administration may be uncoated or coated using known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinyl acetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, using hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil. Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadeca ethyleneoxy cetanol), or condensation products of ethylene oxide with partial esters derived from fatty acids and a hexitol (e.g., polyoxy ethylene sorbitol monooleate), or condensation products of ethylene oxide with partial esters derived from fatty acids and hexitol anhydrides (e.g., polyethylene sorbitanmonooleate). The aqueous suspensions may also contain one or more preservatives.

Other suitable formulations for oral use include oily suspensions. Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known in the art.

Pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soybean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions of the invention can be produced in useful dosage units for administration by various routes including, among others, topical, oral, subcutaneous, intravenous, and intranasal administration.

The pharmaceutical compositions of the invention can also include other biologically active substances in combination with the compounds of the invention. Such additional biologically active substances can be also formulated as separate compositions and can be administered simultaneously or sequentially with the compounds of the invention.

Non-limiting examples of useful biologically active substances include statins, niacin, bile-acid resins, fibric acid derivatives, cholesterol absorption inhibitors, and other lipid-lowering drugs.

Administration

The optimal therapeutically effective amount of a compound or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

Following methodologies which are well-established in the art, effective doses and toxicity of the compounds and compositions of the present invention, which performed well in in vitro tests, can be determined in studies using small animal models (e.g., mice, rats) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compounds or compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

The compounds the invention can be formulated for parenteral, oral, topical, transdermal, transmucosal, intranasal, buccal administration, or by any other standard route of administration. Parenteral administration includes, among others, intravenous (i.v.), subcutaneous (s.c.), intraperitoneal (i.p.), intramuscular (i.m.), subdermal (s.d.), intradermal (i.d.), intra-articular, intra-synovial, intra-arteriole, intraventricular, intrathecal, intrasternal, intrahepatic, intralesional, or intracranial administration, by direct injection, via, for example, bolus injection, continuous infusion, or gene gun. A preferred route of administration according to the present invention will depend primarily on the indication being treated and includes, among others, topical, oral, subcutaneous, intravenous, and intranasal administration.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use. Suitable formulations for parenteral administration may contain substances which increase viscosity, for example, sodium carboxymethyl cellulose, sorbitol, and/or dextran. Optionally, the formulation may also contain stabilizers. Additionally, the compounds of the present invention may also be administered encapsulated in liposomes. The compounds, depending upon their solubilities, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

In specific embodiments, the compounds and/or compositions of the present invention are formulated for oral administration. For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Therapeutic Methods of the Invention

In conjunction with the compounds and/or compositions of the present invention, provided herein are methods of treatment using such compounds and/or compositions. Specifically, the invention provides a method for treating a disease in a subject in need thereof, which method comprises administering to the subject a therapeutically effective amount of one or more compounds of the invention or a composition comprising such one or more compound(s). Non-limiting examples of the diseases treatable by the method of the invention include dyslipidemias (such as, e.g., hyperlipidemia [elevated lipid levels], hypercholesterolemia [elevated cholesterol levels], Familial hypercholesterolemia, low HDL/LDL ratio) and cardiovascular diseases (such as, e.g., atherosclerosis, coronary heart disease, peripheral artery disease, stroke, hypertension), and nephropathy (e.g., diabetic nephropathy). In a preferred embodiment, the subject is human.

In one aspect is provided a method for increasing plasma high-density lipoprotein cholesterol (HDL-C) level and/or reducing plasma low-density lipoprotein cholesterol (LDL-C) level in a subject in need thereof. The method comprises administering to the subject a therapeutically effective amount of a pharmaceutical composition described herein.

The level of LCL-cholesterol may be reduced. The level of triglycerides may be reduced.

In another aspect is provided a method for increasing plasma high-density lipoprotein cholesterol (HDL-C) level and/or reducing plasma low-density lipoprotein cholesterol (LDL-C) level in a subject in need thereof. The method comprises administering to the subject a therapeutically effective amount of a pharmaceutical composition described herein. In various embodiments, the level of triglycerides is also reduced.

In yet another aspect is provided a method for increasing plasma high-density lipoprotein cholesterol (HDL-C) level and/or reducing plasma low-density lipoprotein cholesterol (LDL-C) level in a subject in need thereof. The method comprises administering to the subject a therapeutically effective amount of a compound having the structure according to formula (I):

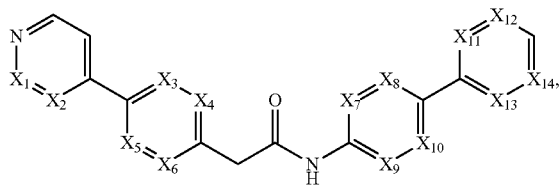

where $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In various embodiments, the level of LCL-cholesterol is reduced. In various embodiments, the level of triglycerides is also reduced.

In yet another aspect is provided a method for increasing plasma high-density lipoprotein cholesterol (HDL-C) level and/or reducing plasma low-density lipoprotein cholesterol (LDL-C) level in a subject in need thereof. The method comprises administering to the subject a therapeutically effective amount of a compound having the structure according to formula (I):

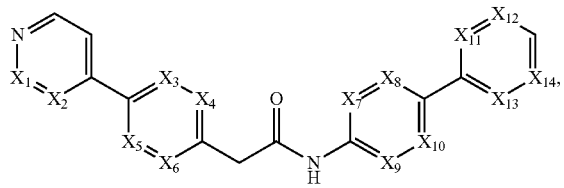

where $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

The level of LCL-cholesterol may be reduced. The level of triglycerides may be reduced.

In some embodiments, one of $X_3$, $X_4$, $X_5$ and $X_6$ is N and the others are CR. In some embodiments, one of $X_7$, $X_8$, $X_9$ and $X_{10}$ is N and the others are CR. In some embodiments, two of $X_{11}$, $X_{12}$, $X_{13}$ and $X_{14}$ are N and the others are CR. In some embodiments, $X_1$ is CR and R is methyl, and/or wherein $X_5$ is CR and R is methyl. In some embodiments, one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH. In some embodiments, $X_1$ is CR, wherein R is methyl; $X_2$ is CH; $X_3$ is N; $X_5$ is CR, wherein R is methyl; $X_4$ and $X_6$ are each CH; $X_7$ is N; $X_8$, $X_9$ and $X_{10}$ are each CH; $X_{11}$ and $X_{14}$ are each N; $X_{12}$ and $X_{13}$ are each CH. In some embodiments, the compound has the structure

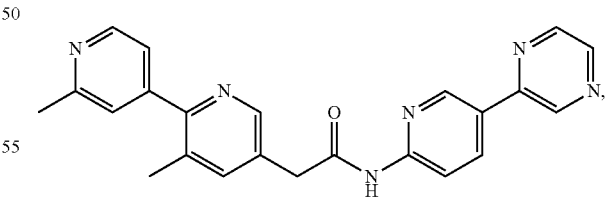

or a pharmaceutically acceptable salt thereof.

In various embodiments of the above aspects, the subject has a dyslipidemia or a cardiovascular disease.

In another aspect is provided a method for treating a disease in a subject in need thereof. The method comprises administering to the subject a therapeutically effective amount of a pharmaceutical composition described herein. The level of LCL-cholesterol may be reduced. The level of triglycerides may be reduced.

In another aspect is provided a method for treating a disease in a subject in need thereof, which method comprises administering to the subject a therapeutically effective amount of a compound having the structure according to formula (I):

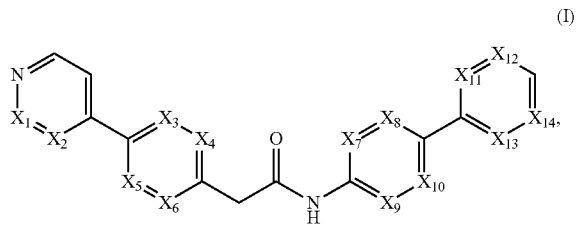

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In some embodiments, one of $X_3$, $X_4$, $X_5$ and $X_6$ is N and the others are CR. In some embodiments, one of $X_7$, $X_8$, $X_9$ and $X_{10}$ is N and the others are CR. In some embodiments, two of $X_{11}$, $X_{12}$, $X_{13}$ and $X_{14}$ are N and the others are CR. In some embodiments, $X_1$ is CR and R is methyl, and/or wherein $X_5$ is CR and R is methyl. In some embodiments, one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH. In some embodiments, $X_1$ is CR, wherein R is methyl; $X_2$ is CH; $X_3$ is N; $X_5$ is CR, wherein R is methyl; $X_4$ and $X_6$ are each CH; $X_7$ is N; $X_8$, $X_9$ and $X_{10}$ are each CH; $X_{11}$ and $X_{14}$ are each N; $X_{12}$ and $X_{13}$ are each CH. In some embodiments, the compound has the structure

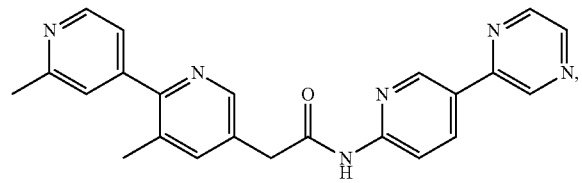 [SMILES: Cc1cc(-c2ncc(CC(=O)Nc3ccc(-c4cnccn4)cn3)cc2C)ccn1]

or a pharmaceutically acceptable salt thereof.

In some embodiments, the disease is a dyslipidemia or a cardiovascular disease. Exemplary cardiovascular diseases include, but are not limited to, atherosclerosis, coronary artery disease, coronary heart disease, a condition associated with coronary artery disease or coronary heart disease, transient ischemic attack, and stroke. The condition associated with coronary artery disease or coronary heart disease may be angina or myocardial infarction. In specific embodiments, the dyslipidemia is selected from the group consisting of hyperlipidemia, hypercholesterolemia, and low HDL/LDL ratio.

The above methods may be effective to inhibit low density lipoprotein (LDL) biogenesis in the subject. The above methods may be effective to reduce the size of an atherosclerotic deposition in the artery of the subject.

In one aspect is provided a method for treating nephropathy (e.g., diabetic nephropathy) in a subject in need thereof. The method comprises administering to the subject a therapeutically effective amount of a compound having the structure according to formula (I):

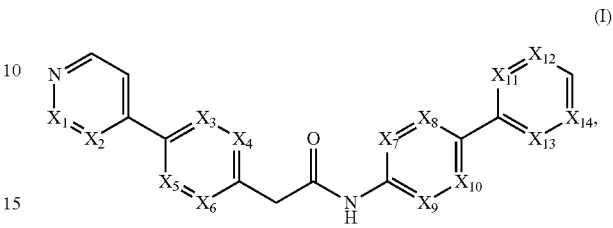

where $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

In various embodiments, one of $X_3$, $X_4$, $X_5$ and $X_6$ is N and the others are CR. In some embodiments, one of $X_7$, $X_8$, $X_9$ and $X_{10}$ is N and the others are CR. In some embodiments, two of $X_{12}$, $X_{13}$ and $X_{14}$ are N and the others are CR. In some embodiments, $X_1$ is CR and R is methyl, and/or $X_5$ is CR and R is methyl. In some embodiments, one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH.
In various embodiments, $X_1$ is CR, where R is methyl; $X_2$ is CH; $X_3$ is N; $X_5$ is CR, where R is methyl; $X_4$ and $X_6$ are each CH; $X_7$ is N; $X_8$, $X_9$ and $X_{10}$ are each CH; $X_{11}$ and $X_{14}$ are each N; $X_{12}$ and $X_{13}$ are each CH. In a specific embodiment, the compound has the structure

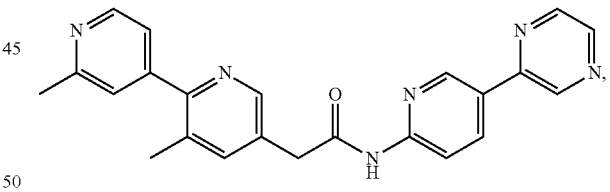

or a pharmaceutically acceptable salt thereof.

In some embodiments, the method is effective to prevent or treat a nephropathy. In some embodiments, the method is effective to reduce fibrosis in the kidney of the subject. In some embodiments, the method is effective to reduce collagen deposition in the kidney of the subject. In some embodiments, the method is effective to reduce accumulation of collagen in the kidney of the subject. In some embodiments, the method is effective to reduce glomberulosclerosis in the subject.

In various embodiments of the above methods, the subject is human.

In some embodiments of methods provided herein, there is further provided the use of the Wnt inhibitor compounds and compositions described herein in combination with one or more additional agents. Such agents may comprise, without limitation, cholesterol-lowering drugs (e.g., statins, fibrates, inhibitors of proprotein convertase subtilisin/kexin type 9), blood pressure-lowering therapies (e.g., angiotensin-converting enzyme (ACE) inhibitors and angiotensin II receptor blockers (ARBs)), antiinflammatory agents, antithrombotic agents, anti-coagulant agents, inhibitors of the renin-angiotensin aldosterone system (RAAS inhibitors), beta-adrenergic blockers, calcium channel blockers, blood sugar reducing medications (e.g., metformin, insulin, glucose-dependent insulinotropic polypeptide (GIP), and glucagon-like peptide 1 (GLP-1), sodium/glucose co-transporter 2 (SGLT2) inhibitors), and/or other treatment modalities of a non-pharmacological nature. When combination therapy is used, the Wnt inhibitor(s) and one additional agent(s) may be in the form of a single composition or multiple compositions, and the treatment modalities can be administered concurrently, sequentially, or through some other regimen. A combination therapy can have an additive or synergistic effect.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "hypercholesterolemia" as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced herein). "Familial hypercholesterolemia" refers hypercholesterolemia caused by a mutation in a gene located on chromosome 19.

The term "nephropathy" as used herein refers to a disease, dysfunction or a non-function of one or both kidneys. The term "diabetic nephropathy" as used herein includes both incipient and overt stages of diabetic nephropathy, whether diagnosed or not, though diabetic nephropathy is most typically as diagnosed by a clinician or physician.

As used herein, the term "atherosclerosis" refers to a disease of the arteries characterized by the narrowing of arteries due to plaque buildup in the arteries. The term "atherosclerosis-related disorder" refers to atherosclerotic cardiovascular disease (ASCVD) and other such cholesterol deposition-driven chronic inflammatory diseases. Atherosclerosis-related disorders include, without limitation: ASCVD, coronary heart disease, such as myocardial infarction, angina, and coronary artery stenosis; cerebrovascular disease, such as transient ischemic attack, ischemic stroke, and carotid artery stenosis; peripheral artery disease, such as claudication; aortic atherosclerotic disease, such as abdominal aortic aneurysm and descending thoracic aneurysm; hypertension; peripheral vascular disease; coronary artery disease; aortic aneurysm; carotid artery disease; coronary atherosclerosis; heart attack; acute coronary syndromes, and stroke.

As used herein, the term "coronary heart disease" refers to a narrowing of the small blood vessels that supply blood and oxygen to the heart, which is often a result of atherosclerosis.

Without wishing to be bound by theory, inflammation is a complex cascade of adaptive cellular responses to injurious stimuli which occurs in many cardiovascular diseases (1). Vascular inflammation may be manifested in several ways, including enhanced expression of endothelial cell adhesion molecules, inflammatory cell recruitment, cytokine release and impaired nitric oxide (NO) bioactivity (2, 3). Physiologically, endogenous glucocorticoids (GC; corticosterone in rodents and cortisol in humans) may exert a permissive role in suppressing local and systemic inflammation. The methods described herein may be performed along with other modes of suppressing inflammation, for example but not limited to, administration of exogenous GC, such as hydrocortisone and dexamethasone (DEX).

Administration of exogenous GCs as anti-inflammatory agents with the compounds and compositions of the present invention may provide a systemic ligand to all cells expressing the glucocorticoid receptor (GR). The compounds and compositions of the present invention can overcome the following disadvantages of administering GCs alone. For example, the particular role of a tissue-specific GR in resolving inflammation might not be able to be examined. The role of the endogenous ligand, cortisol, also might not be examined. Additionally, side effects from systemic GC are common and can be severe, to the point of rendering them intolerable and therefore ineffective for vascular inflammatory disorders (5). In such cases, the compounds and compositions of the present invention can be administered instead of systemic GC.

Without wishing to be bound by theory, endothelial GR may be a negative regulator of vascular inflammation in models of sepsis and atherosclerosis. Mice lacking endothelial GR bred onto an Apo E knockout background may develop more severe atherosclerotic lesions when fed a high-fat diet as compared to controls that cannot be explained by changes in circulating lipids. It is possible that circulating cortisol bound to endothelial GR is vasculoprotective. Described herein are experiments to show how endothelial GR regulates vascular inflammation. For instance, GR-specific chromatin-immunoprecipitation was performed followed by next-generation sequencing from primary endothelial cells, which allowed for elucidation of a unique GR-DNA landscape. A novel role of the Wnt signaling pathway is described in this setting, indicating that loss of the endothelial glucocorticoid receptor can result in upregulation of Wnt signaling both in vitro and in vivo using a validated mouse model described in Example 7. Endothelial GR can repress several genes involved in the Wnt signaling pathway. This pathway is independent from that of NF-κB, a classic target for GR, (8, 9) and therefore highlights the permissive effects of cortisol in physiologically relevant states. These results described herein suggest a novel role for endothelial Wnt signaling modulation in states of vascular inflammation.

Loss of endothelial GR may result in up-regulation of canonical Wnt signaling (Zhou et al, JCI Insight, In press). GR can perform an anti-inflammatory action by targeting the NF-kB signaling pathway (82). However, GR can also target canonical Wnt signaling in endothelial cells (EC), which is independent of its classic target, NFkB (Zhou et al., JCI Insight, In press; 82). Inhibition of Wnt signaling in EC may prove to be a valuable therapeutic opportunity for combating diabetic kidney disease. The Wnt pathway can contribute to renal fibrosis, and activated canonical Wnt signaling can contribute to the disruption of cytokine and chemokine homeostasis (67, 83-85). The data provided in Examples 10-17 herein demonstrate that higher levels of GR-deficient-associated canonical Wnt signaling are associated with the induction of mesenchymal and fibrogenic markers.

Without wishing to be bound by theory, metabolic reprogramming in endothelial cells may play a role in the development of myo-fibroblast formation, proliferation and fibrosis in diabetic kidneys (56, 61, 76, 78, 79). Also, inflammation may be a factor during the fibroblast activation process in the kidneys of diabetic mice (71, 72), with disruption of cytokine and chemokine homeostasis contributing to the development of diabetic kidney disease (73-75).

Without wishing to be bound by theory, disruption of endothelial FA metabolism may contributes to activation of EndMT in diabetic kidneys (39, 40, 52). FAO activation may cause remarkable suppression of fibrosis by restoring the endothelial GR level in diabetic mice. In contrast, FAO inhibition may cause acceleration in fibrosis by diminishing the level of endothelial GR in diabetic control mice, suggesting that endothelial GR plays a role in the action of FAO modulators.

In another aspect, there are provided kits for preventing or treating atherosclerosis, the kits comprising one or more Wnt inhibitor compounds or compositions as described herein. Instructions for use or for carrying out the methods described herein may also be included. A kit may further include additional reagents, solvents, buffers, etc., required for carrying out the methods described herein. Kits for diagnosing atherosclerosis or related disorders comprising reagents for detecting Wnt expression are also provided.

In another aspect, there are provided kits for preventing or treating nephropathy, e.g., diabetic nephropathy, the kits comprising one or more Wnt inhibitor compounds or compositions as described herein. Instructions for use or for carrying out the methods described herein may also be included. A kit may further include additional reagents, solvents, buffers, etc., required for carrying out the methods described herein. Kits for diagnosing nephropathy, e.g., diabetic nephropathy, or related disorders comprising reagents for detecting Wnt expression are also provided.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods for Examples 1-9

Below are the materials and methods used in Examples 1-9 presented above.
Reagents and Antibodies
Dexamethasone phosphate was purchased from MP Biomedicals. Recombinant mouse Wnt3a protein was purchased from Abcam. AllStars negative control siRNA and Stealth RNAi for NR3C1 were from Qiagen.
ChIP-Seq
ChIP-seq was performed using the EZ-ChIP kit (Millipore) according to the manufacturer's instructions. Five micrograms of ChIP-grade GR antibody (Abcam3578) was used for each experimental condition. GR-enriched ChIP DNA was confirmed by qPCR using primers for Per1. Data analysis was provided by the Yale Center for Genomic Analysis as follows: The fastq files obtained from the sequencer were trimmed for quality using fastx_trimmer. The reads were aligned to the mm10 (UCSC) version of the mouse genome using bwa mem. Peaks were called using macs peak-caller (34), and the reads from input DNA sample were used as control. Visualization of the peaks was done using R (cummeRbund) and Integrated Genome Browser using .bw files was used to generate visual images of the experimental conditions with the reference sequence.
Custom qPCR
A custom PCR array was designed with the Qiagen on-line tool. MLECs were treated with control or GR siRNA for 48 hours. Total RNA was isolated using the RNeasy kit (Qiagen) and cDNA was generated using the iScript cDNA synthesis kit (Bio-Rad) using 1 µg RNA. The PCR array was run using SYBR green reagents according to the manufacturer's instructions.
Primer-Specific qPCR
ChIP DNA or total RNA was used for qPCR. Total RNA was isolated using standard Trizol protocol. RNA was reverse transcribed using the iScript cDNA Synthesis kit (Bio-Rad) and qPCR was performed on a Bio-Rad C1000 Touch thermal cycler using the resultant cDNA, qPCR master mix and gene specific primers. The following primers were used:

```
Per1:
                                           (SEQ ID NO: 3)
Forward        5' AAGGCTGTGTGCATGTCCT 3'
and (SEQ ID NO: 4)
Reverse        5' AGAGGGAGGTGACGTCAAAG 3'

Sox17:
                                           (SEQ ID NO: 5)
Forward        5' TCAGATGTCTGGAGGTGCTG 3'
and (SEQ ID NO: 6)
Reverse        5' TGGAACCTCCAGTAAGCCAG 3'

Axin2:
                                           (SEQ ID NO: 7)
Forward        5' AACCTATGCCCGTTTCCTCTA 3'
and (SEQ ID NO: 8)
Reverse        5' GAGTGTAAAGACTTGGTCCACC 3'

Wnt3a:
                                           (SEQ ID NO: 9)
Forward        5' TTCTTACTTGAGGGCGGAGA 3'
and (SEQ ID NO: 10)
Reverse        5' CTGTCGGGTCAAGAGAGGAG 3'

Ctnnb1:
                                           (SEQ ID NO: 11)
Forward        5' TGACACCTCCCAAGTCCTTT 3'
and (SEQ ID NO: 12)
Reverse        5' TTGCATACTGCCCGTCAAT 3'

TCF:
                                           (SEQ ID NO: 13)
Forward        5' GGTGGCCGAATGCACATTGAAAGA 3'
and (SEQ ID NO: 14)
Reverse        5' TTTGCCTGTTCTTCCCTGGACA 3'

Frzb primer 1:
                                           (SEQ ID NO: 15)
Forward        5' TCTCAATGTATCACTCTGTG 3'
and
```

```
                                      (SEQ ID NO: 16)
Reverse      5' TTTCCAAGAGTTGTTTGTG 3'

Frzb primer 2:
                                      (SEQ ID NO: 17)
Forward      5' TCTGTCCCCAAAGAGACATAT 3'
and (SEQ ID NO: 18)
Reverse      5' TGGCCTACTATTAAGAGAAA 3'

CTCF:
                                      (SEQ ID NO: 19)
Forward      5' CATCATTCAACGTTTAGTTT 3'
and (SEQ ID NO: 20)
Reverse      5' GCCAGGGCTATACAGAGAAAC 3'
```

Gene expression was normalized to the housekeeping gene 18s and is presented as fold change.

Stable Cell Line

The Cignal Lenti TCF/LEF Reporter (Qiagen) was transduced into mouse lung endothelial cells using SureENTRY Transduction Reagent (Qiagen) according to the manufacturer's instructions.

Animal Studies

Apoe –/– and endothelial GR KO/Apo E KO double knockout (DKO) mice were fed a high fat diet containing 1.25% cholesterol (Research Diets) for the time indicated. In some experiments, animals of both genotype were bred to the BAT-GAL (ß-catenin/TCF/LEF) reporter transgenic mouse. Mice were sacrificed and the aortas removed. Aortas were stained with X-galactosidase (Sigma-Aldrich) according to the manufacturer's instructions. In other aortas, total RNA was extracted and cDNA was made as described above. The custom PCR array was used to evaluate pathways of interest as described. All studies were performed according to a protocol approved by the Institutional Care and use Committee at Yale University School of Medicine and were consistent with the National Institutes of Health Guidelines for the Care of Laboratory Animals.

RNA-Seq

MLECs were cultured in EBM-2 and 10% serum. Cells were treated with control or GR siRNA for 48 hours with and without dexamethasone 100 nM for 18 hours. Total RNA was isolated using the RNeasy kit (Qiagen) and sequenced on an Illumina platform by the Yale Center for Genomic Analysis. Data analysis was provided by the Yale Center for Genomic Analysis as follows. The fastq files obtained from the sequencer were trimmed for quality using fastx_trimmer. The reads were then aligned to the mm10 (UCSC) version of the mouse genome using TopHat (35). The transcript abundance estimation and differential gene expression was carried out using cuffdiff (cufflinks) (36). The results were visualized using R (cummeRbund).

Motif Detection

MEME was used for de-novo motif detection, and MAST (37) was used to scan the sequences for known motifs.

Wnt Treatment of Cells

MLECS were cultured and starved for 4 hours in 0.5% FBS. Cells were treated for 4 hours with Wnt3a (200 ng/ml). At the conclusion of the 4-hour time period, cells were additionally treated with 100 nM DEX for 1 hour. In other experiments, cells were treated with 10% Wnt3a conditioned media for 6 hours, followed by DEX 100 nM for 1 hour.

Plasmid Constructs and Luciferase Assay

The synthetically synthesized gBlocks Gene Fragments (ITD Integrated Technologies, Coralville, Iowa) containing four GR motifs (underlined) and homologues region to the destination vector (italics):

```
                                                   (SEQ ID NO: 21)
GAACATTTCTCTATCGATAAGGTACCctctgCCTCCCAAGTGCTGGGATT aaaggcgtgactctgCCTCCCAAGTGCTGGGATTaaaggcgtgactctg CCTCCCAAGTGCTGGGATTaaaggcgtgactctgCCTCCCAAGTGCTGGG ATTaaaggcgtgaCTCGAGATCTGCGATCTGCATCTCAA
``` were cloned between KpnI and XhoI into pGL3-Promoter Vector (Promega) using DNA assembly strategy (NEBuilder HiFi DNA Assembly Kit, NEB). The GR motif is followed by an SV40 promoter and then by the luciferase gene; the quantified luciferase expression is a direct measure of transcriptional activity. The empty pGL3 promoter vector was used as a negative control. 293T cells were transformed with Lipofectamine.

Plasma Measurements

Mice were fasted for 12-15 hours and blood was collected by retro-orbital venous puncture. Whole blood was spun down and plasma stored at –80° C. Total cholesterol and triglyceride levels were measured enzymatically by kits from Wako and Sigma, respectively, according to the manufacturer's instructions.

Atherosclerotic Lesion Analysis

At the completion of high-fat diet feeding mice were anesthetized and euthanized. Mouse hearts were perfused with PBS and then 4% paraformaldehyde (PFA) and the aortas and were dissected out using a dissecting microscope and maintained in PFA overnight. Whole aortas were stained with Oil Red O (Sigma) to quantify lesion area. Oil Red O stock solution (35 ml, 0.2% weight/volume in methanol) was mixed with 10 ml 1 M NaOH and filtered. Aortas were briefly rinsed in 78% methanol, incubated in Oil Red O for 45 minutes and then destained in 78% methanol for 5 minutes and mounted on microscopic slides. Lipid staining and lesion size were quantified by averaging six sections from the same mouse using the IMAGE J program.

Western Blot

Tissues were snap frozen in liquid nitrogen, pulverized, and resuspended in lysis buffer (50 mM Tris.HCl pH 7.4, 0.1 mM EDTA, 0.1 mM EGTA, 1% Nonidet P-40, 0.1% sodium deoxycholate, 0.1% SDS, 100 mM NaCl, 10 mM NaF, 1 mM sodium pyrophosphate, 1 mM sodium orthovanadate, 1 mM Pefabloc SC, and 2 mg/mL protease inhibitor mixture; Roche Diagnostics). Cells were lysed on ice with lysis buffer. Protein concentrations were determined with the DC Protein assay kit (Bio-Rad Laboratories). Lysates were analyzed by SDS/PAGE and immunoblotted. Primary antibodies used include the following: GR (Thermo Scientific), β-catenin (BD Biosciences), and Hsp90 (Affinity Bioreagents). Secondary antibodies were fluorescence-labeled antibodies (LI-COR Biosciences). Bands were visualized with the Odyssey Infrared LI-COR system.

Statistical Analyses

Binary comparisons were analyzed using Student's t-test. Multiple comparisons were analyzed using one-way ANOVA with Tukey's post-test. Data are expressed as mean±SEM. Statistical significance was accepted for $p<0.05$ and, where indicated, also $q<0.05$.

Example 1: Genome-Wide GR DNA Binding in Endothelial Cells

To begin to understand the mechanisms by which GR regulates endothelial cell functions, ChIP-seq for GR was performed in primary mouse lung endothelial cells (MLECs) using a commercially available, ChIP-quality GR antibody. Six conditions were submitted for GR ChIP-seq analysis as follows: 1. control siRNA treated cells, 2. GR siRNA treated cells, 3. control siRNA treated with dexamethasone (DEX) 100 nM for 1 hour, 4. GR siRNA treated with DEX 100 nM for 1 hour, 5. IgG control, and 6. whole cell input. The duration of DEX treatment was replicated from a previous ChIP study (10), and knockdown of GR using this siRNA is greater than 80% (6). The control siRNA DEX-treated sample was treated as the 'control' sample, reflecting agonist activation of GR. Control siRNA samples were 2.63% enriched in GR elements, which is within the expected range of 1-7% for ChIP experiments (11); after treatment with GR siRNA, enrichment was reduced to 0.02% confirming excellent knockdown via siRNA and high specificity of the GR ChIP antibody.

Normalization of peaks to each 1,000,000 base pair reads resulted in the distribution shown in FIG. 1A. There were approximately 35,000 GR-enriched peaks overall. As expected, the 'control' sample in which GR was activated by DEX shows the greatest number of GR-enriched peaks, approximately 7-fold higher than the other conditions. The residual smaller peak present in the GR siRNA DEX-treated cells is approximately 5-fold less than the DEX GR replete conditions but ~2-fold higher than the other conditions. This was anticipated since this GR siRNA knockdown is not 100% (6). The other 4 conditions tested are completely overlapping and represent background.

Figure 1B:
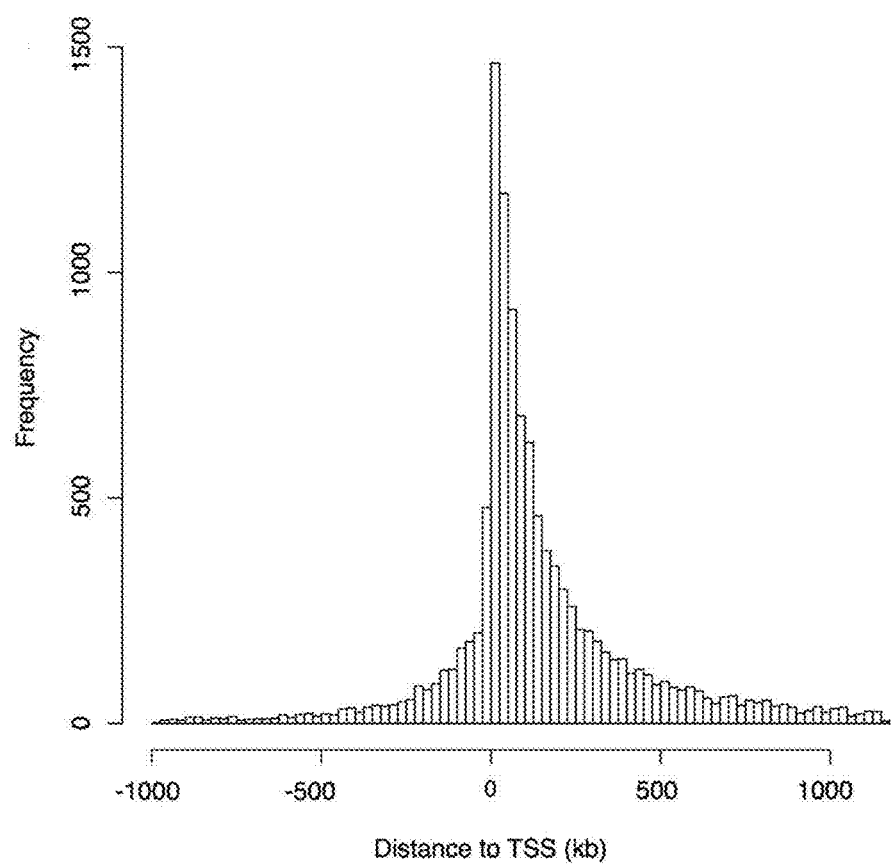
Figure 1C:
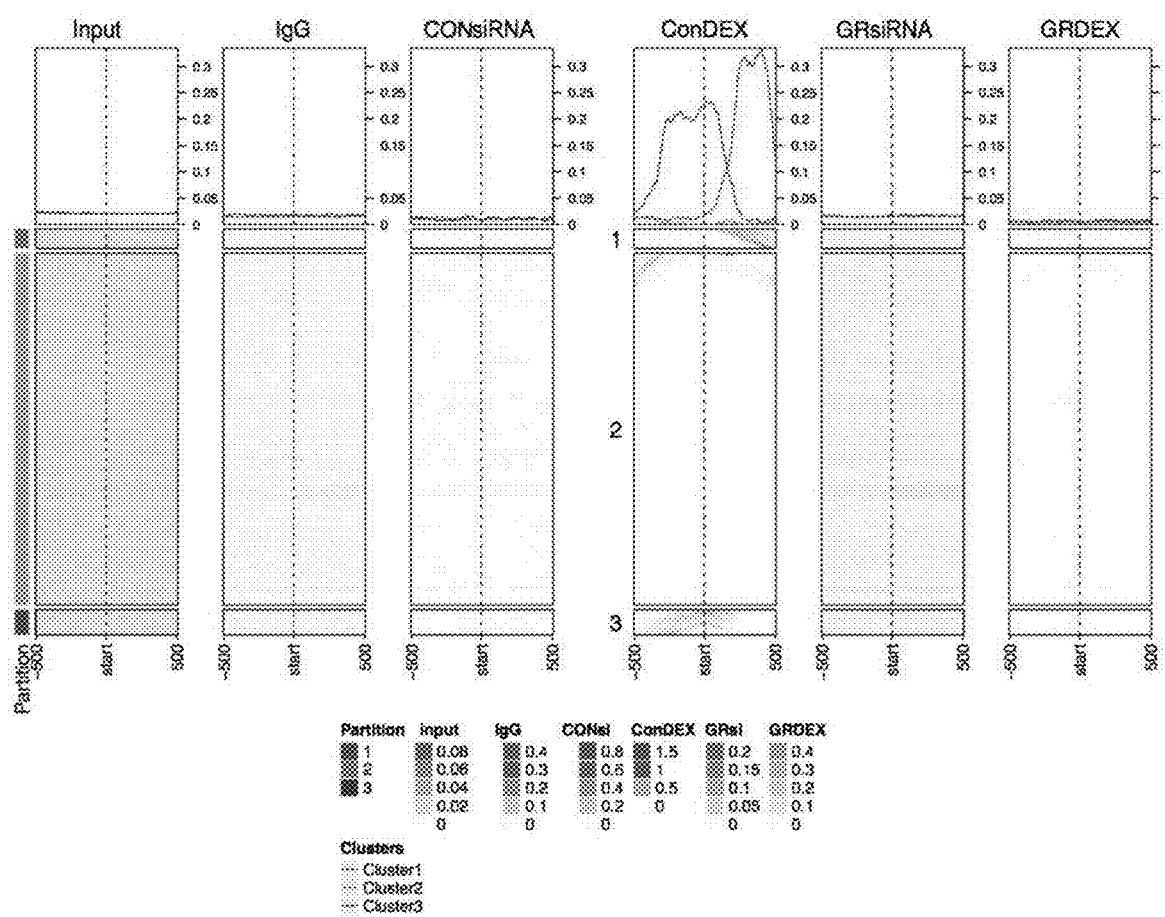

Analysis of the top 10,000 DEX-stimulated, GR-enriched peaks shows very tight localization around the nearest transcriptional start site (TSS, FIG. 1B). Further refinement of the subset of peaks within 1000 base pairs of transcriptional start sites resulted in the identification of three clusters of genes: cluster 2, which was the largest group, had no discernible pattern of binding over the interval examined, cluster 1 showed enriched binding slightly upstream of the TSS and cluster 3 showed enriched binding at TSS (FIG. 10).

Figure 1D:
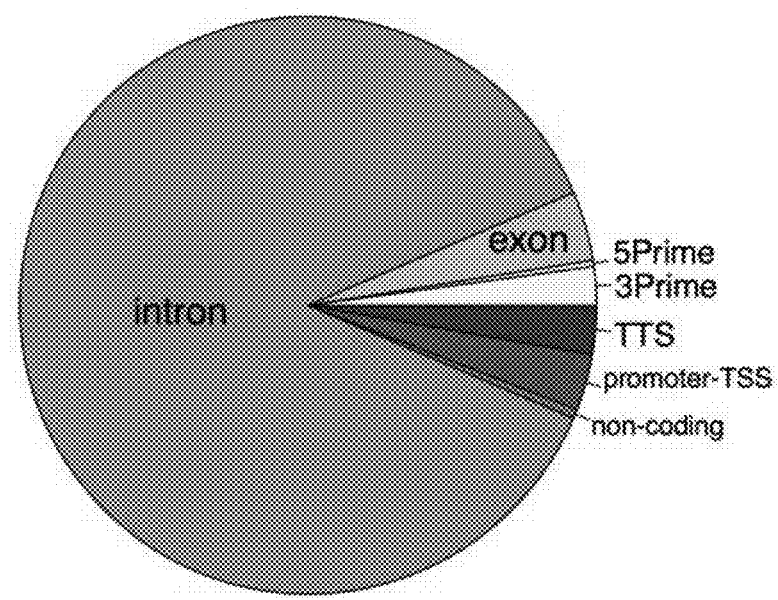

Peaks were also analyzed to determine the breakdown of the GR binding location based on genomic region. As shown in FIG. 1D, the vast majority (87%) of GR-enriched peaks are in introns, with about 7% binding to promoter-TSS or TSS regions. Further analysis revealed that 97% of intronic GR-enriched peaks are found in protein-coding genes while 84% of TSS GR sites map to protein coding genes. If intronic GR peaks are restricted to those within 5 kb of the TSS there are 59 genes with GR binding upstream of the TSS and 361 genes with GR binding downstream of the TSS.

Figure 1E:
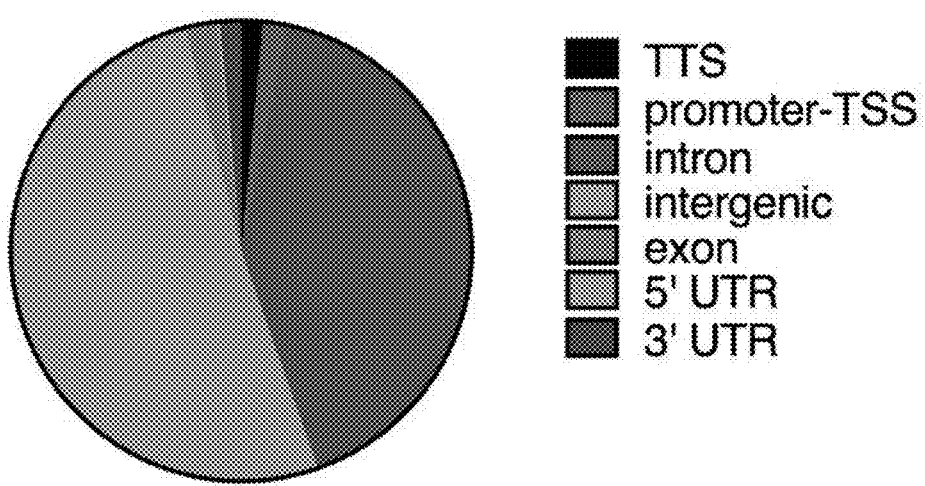
Figure 1F:
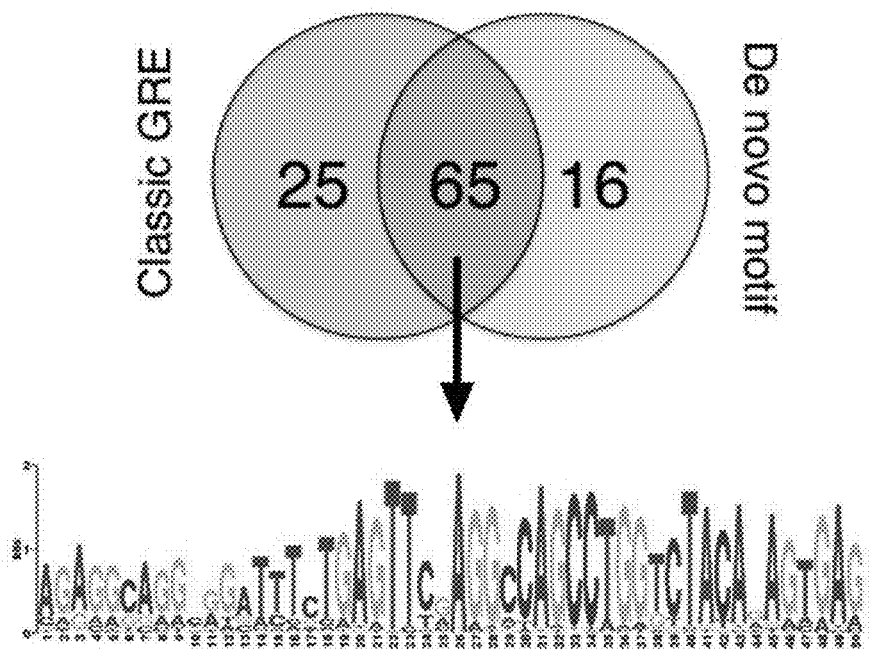
Figure 1F:
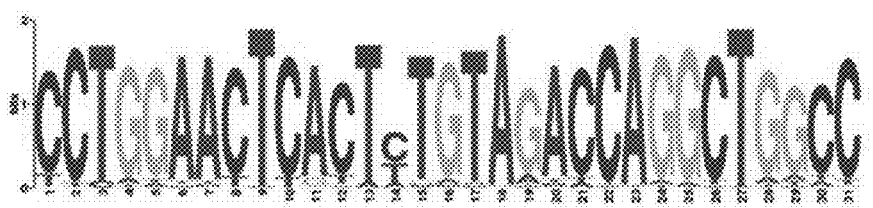
Figure 1G:
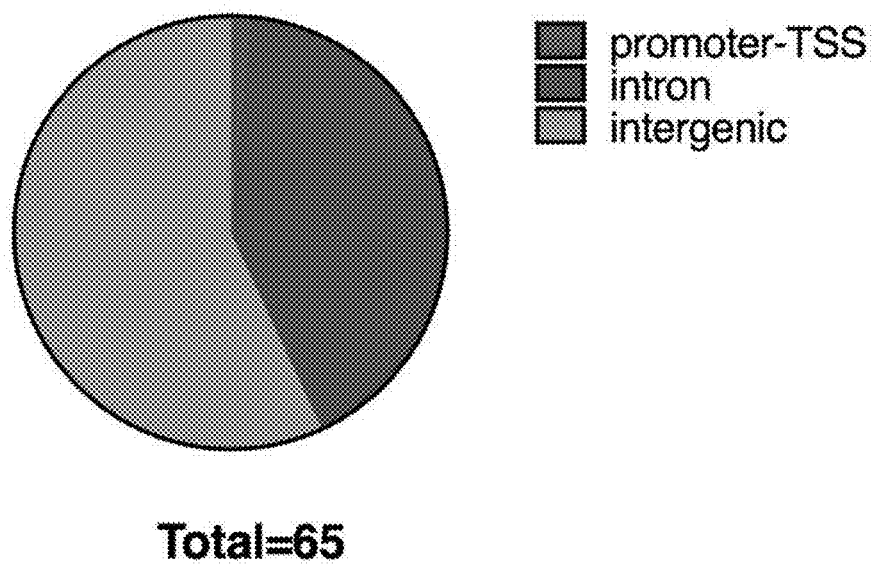

The analysis was further refined to examine the top 1000 peaks in more detail. First, peak binding sites were characterized by location as shown in FIG. 1E. Using motif detection algorithms, these 1000 peaks were queried for any plausible motifs by inputting the classic 6-bp palindromic GRE (5'AGAACAnnnTGTTCT3', where n can be any base; SEQ ID NO: 1) (12) as a seed sequence, as well as searched for de novo motifs. Ninety genes (Table 1) resulted when searching by the classic GRE and 81 genes resulted containing a de novo motif (Table 2). Cross-referencing both lists resulted in 65 genes (Table 3), which possessed both motifs (FIG. 1F). It was suspected that peaks having both motifs may be enriched in certain regulatory elements or have other common features. When the peak binding location for these 65 genes was mapped, the vast majority were either intergenic or intronic (FIG. 1G). Using the ENCODE ChIP-seq Significance Tool and the mm10 reference genome, the top 10 enriched ENCODE transcription factors within ±500 base pairs of the TSS/5' end were identified for this list of 65 genes (Table 4). Interestingly, these genes were noted to have ChIP peak binding sites ranging from −272 kb to +400 kb from the TSS.

TABLE 1

Genes from the top 1000 peaks with a classic GRE

| NEGR1-IT1 | MYEOV | DDR2 | GRM5 | CHEK2P2 |
|---|---|---|---|---|
| EMBP1 | PARP11 | CSF3R | CNTN5 | CHEK2P2 |
| RASAL2 | CTDSP2 | ANK3 | PCF11 | KIAA1024 |
| SLC25A33 | LINC00374 | LOC100499489 | USP47 | SNORD115-31 |
| LOC100499489 | RPL23AP87 | ACTR3BP5 | LOC105369423 | FLJ26245 |
| LOC646813 | ZNF507 | LINC00839 | EMSY | ANKRD26P1 |
| WNT11 | NKPD1 | SLC16A9 | TRIM48 | LOC102723692 |
| OR10W1 | KLF9 | NEUROG3 | LOC646813 | KCNJ2 |
| CHRNA10 | LINC01474 | SGMS1 | LOC105369443 | POLG2 |
| OR4C46 | LHX8 | TMEM72 | HOXC13 | SNORA111 |
| MPEG1 | ANKRD20A12P | MIR4490 | SLC2A3 | C19orf33 |
| OR5AN1 | EMBP1 | TYR | LMO3 | TNFSF14 |
| KDM4E | ROR1-AS1 | DNHD1 | MIR3169 | KCNJ3 |
| MARK2 | MEF2D | LOC100996455 | LOC101927780 | PTPN4 |
| LOC102724784 | FAM69A | DEPDC7 | GPHN | MYLK-AS2 |
| PPIC | KIFC1 | LZTS1-AS1 | NUTM2G | SPANXN2 |
| ARHGAP26-IT1 | MEI4 | RALYL | MIR651 | BRDTP1 |
| RFPL4B | AGK | CDCA2 | ARX | DANT2 |

TABLE 2

Genes from the top 1000 peaks with a de novo motif

| MIR4459 | LHX8 | TMEM72 | HOXC13 | SNORA111 |
|---|---|---|---|---|
| OR4C46 | ANKRD20A12P | MIR4490 | SLC2A3 | C19orf33 |
| FAM66C | EMBP1 | TYR | LMO3 | TNFSF14 |
| GLI1 | ROR1-AS1 | DNHD1 | MIR3169 | KCNJ3 |
| MON2 | MEF2D | LOC100996455 | LOC101927780 | PTPN4 |
| MTHFS | FAM69A | DEPDC7 | GPHN | MYLK-AS2 |
| CYFIP1 | DDR2 | GRM5 | CHEK2P2 | PPIC |

TABLE 2-continued

Genes from the top 1000 peaks with a de novo motif

| | | | | |
|---|---|---|---|---|
| B4GALT4 | CSF3R | CNTN5 | CHEK2P2 | ARHGAP26-IT1 |
| PAPSS1 | ANK3 | PCF11 | KIAA1024 | RFPL4B |
| ZNF608 | LOC100499489 | USP47 | SNORD115-31 | KIFC1 |
| TBX18 | ACTR3BP5 | LOC105369423 | FLJ26245 | MEI4 |
| LOC105373156 | LINC00839 | EMSY | ANKRD26P1 | AGK |
| PLXDC2 | SLC16A9 | TRIM48 | LOC102723692 | LZTS1-AS1 |
| OR51L1 | NEUROG3 | LOC646813 | KCNJ2 | RALYL |
| OR4A16 | SGMS1 | LOC105369443 | POLG2 | CDCA2 |
| NUTM2G | MIR651 | ARX | SPANXN2 | BRDTP1 |
| DANT2 | | | | |

TABLE 3

Genes possessing both a GRE and a de novo motif

| | | | | |
|---|---|---|---|---|
| LHX8 | TMEM72 | HOXC13 | C19orf33 | MIR651 |
| ANKRD20A12P | MIR4490 | SLC2A3 | TNFSF14 | ARX |
| EMBP1 | TYR | LMO3 | KCNJ3 | SPANXN2 |
| ROR1-AS1 | DNHD1 | MIR3169 | PTPN4 | BRDTP1 |
| MEF2D | LOC100996455 | LOC101927780 | MYLK-AS2 | DANT2 |
| FAM69A | DEPDC7 | GPHN | PPIC | |
| DDR2 | GRM5 | CHEK2P2 | ARHGAP26-IT1 | |
| CSF3R | CNTN5 | KIAA1024 | RFPL4B | |
| ANK3 | PCF11 | SNORD115-31 | KIFC1 | |
| LOC100499489 | USP47 | FLJ26245 | MEI4 | |
| ACTR3BP5 | LOC105369423 | ANKRD26P1 | AGK | |
| LINC00839 | EMSY | LOC102723692 | LZTS1-AS1 | |
| SLC16A9 | TRIM48 | KCNJ2 | RALYL | |
| NEUROG3 | LOC646813 | POLG2 | CDCA2 | |
| SGMS1 | LOC105369443 | SNORA111 | NUTM2G | |

TABLE 4

Top 10 most enriched transcription factors within ±500 base pairs of the TSS/5' end for 65 genes possessing both motifs

| Transcription Factor | # genes with factor | # genes observed | Q value |
|---|---|---|---|
| CTCF | 9919 | 49 | 1.79e-17 |
| p300 | 6918 | 36 | 1.17e-11 |
| Pol2 | 19191 | 54 | 2.844e-9 |
| TBP | 10622 | 38 | 1.056e-7 |
| HCFC1 | 11217 | 39 | 1.067e-7 |
| Mxi1 | 9375 | 35 | 1.88e-7 |
| NELFe | 10103 | 35 | 1.274e-6 |
| UBF | 5258 | 24 | 1.764e-6 |
| GCN5 | 7291 | 28 | 4.654e-6 |
| SIN3A | 9393 | 32 | 7.317e-6 |

Figure 2A:
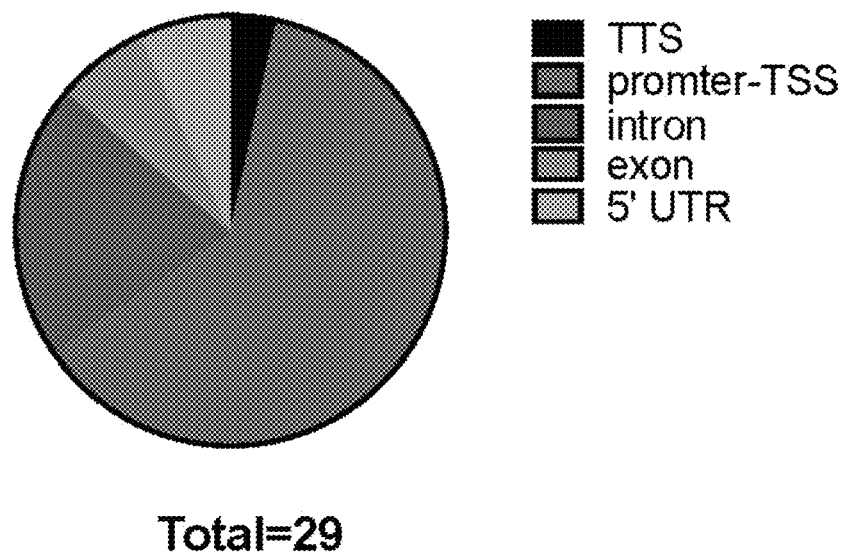
FIGS. 2A-2C. Characterization of 29 genes identified from the top 1000 peaks that exhibited ChIP peak binding within ±1 kb of the TSS.
Figure 2B:
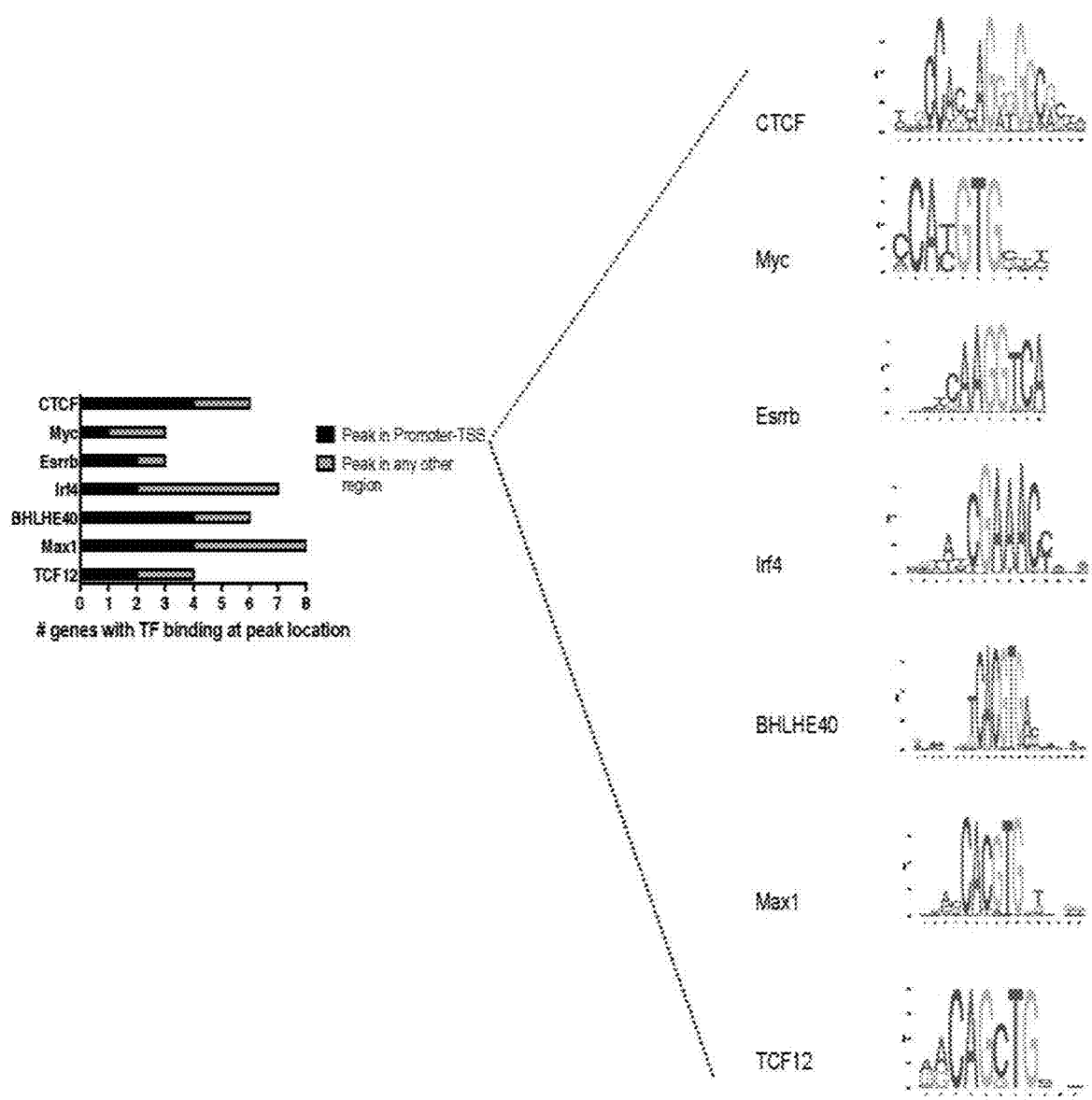
Figure 2C:
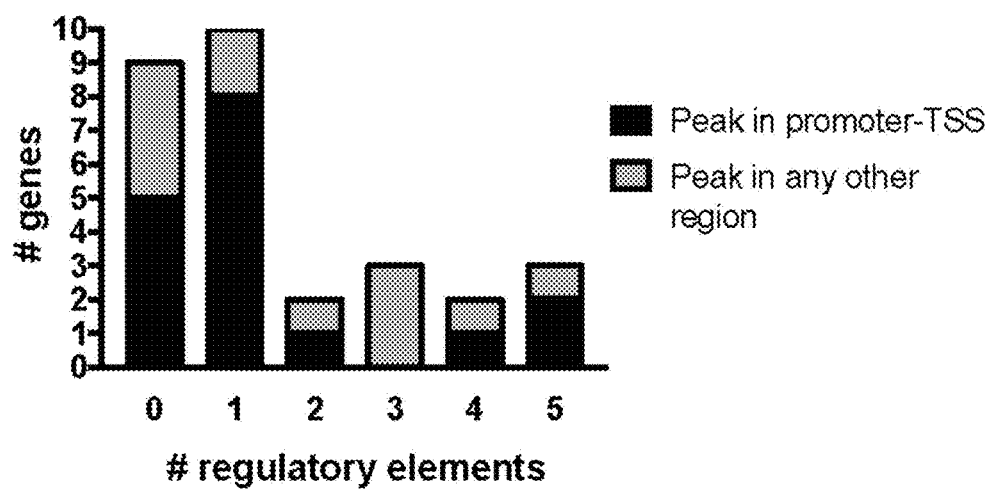

To assess if genes with ChIP peak binding sites closer to TSSs had a similar TF profile, the top 1000 peaks for those binding within ±1 kb from the TSS were also interrogated. This resulted in 29 genes (Table 5) with the peak binding locations shown in FIG. 2A. Each of these peaks and the surrounding ±5 kb region were examined in detail in the ENCODE database. As shown in FIG. 2B, transcription factor (TF) binding sites were abundant in these genes regardless of whether the ChIP-seq binding occurred in the promoter-TSS or in another region. Notably, the seven most abundant TFs detected have all been shown to interact with nuclear receptors (13-18), except for max1, though it is a binding partner of myc (19). Interestingly, when these genes were categorized according to how many regulatory elements (TF binding sites, enhancers, open chromatin) they had within ±5 kb of the ChIP-seq binding site, the majority had either none or only one (FIG. 2C). This list of 29 genes was again queried by using the ENCODE ChIP-seq Significance Tool and the mm10 reference genome for TF within ±500 base pairs of the TSS/5' end. The results, shown in Table 6, are very similar to those of the 65 genes with widely dispersed ChIP-seq binding peaks suggesting that endothelial cell-GR binding is likely influenced by spatially distant regulatory elements.

TABLE 5

Genes identified from the top 1000 peaks with binding sites within ±1 kb from the TSS

| | | | | |
|---|---|---|---|---|
| Hnrnpu | Mir132 | Sfpq | Srsf2 | Ifi27l2a |
| Ralgps2 | Ccm2 | Olfr1434 | Umps | Fzd5 |
| Awat2 | AA465934 | Ywhae | Taar5 | Pik3r6 |
| Fbxl20 | Mab21l2 | Rasl10a | Afmid | Fbxo5 |
| Smyd3 | Ifi47 | Myog | Eef1b2 | Gm11981 |
| Mir6950 | Shroom1 | Elk4 | Ahr | |

TABLE 6

Topmost enriched transcription factors within ±500 base pairs of the TSS/5' end with ChIP peak binding with ±1 kb from the TSS

| Transcription Factor | # genes with Factor | # genes observed | Q value |
|---|---|---|---|
| CTCF | 6944 | 22 | 4.457e-12 |
| p300 | 5053 | 16 | 7.817e-8 |
| Pol2 | 16854 | 25 | 1.758e-7 |
| NELFe | 10103 | 20 | 5.777e-7 |
| E2F4 | 2303 | 10 | 2.068e-6 |
| ZNF | 6652 | 16 | 2.068e-6 |
| COREST | 3857 | 11 | 3.509e-5 |
| HCFC1 | 10255 | 17 | 1.108e-4 |
| c-Myc | 5228 | 17 | 1.108e-4 |
| BHLHE40 | 6205 | 13 | 1.199e-4 |

Example 2: Characterization of Gene Expression Changes by RNA-Seq

To further understand if, and how, the GR binding patterns discovered by ChIP-seq influenced gene expression, RNA-seq was performed using the same experimental groups as for the ChIP-seq analysis in MLECs except cells were treated with DEX for 18 hours to allow adequate time for transcriptional responses. As a result of the fact that 4 groups were being compared (control siRNA, control siRNA+DEX, GR siRNA and GR siRNA+DEX), there were over 143,000 independent fold-change calculations. These data were further restricted to those comparisons that had both a significant p value and a significant q value resulting in a more manageable list of 902 comparisons. From this group, 231 genes were DEX-responsive and 203 genes were differentially regulated by GR. Of the genes regulated by GR, 111 genes were down regulated in the absence of GR (i.e. induced by GR at baseline) (Table 7), and 92 genes were up regulated in the absence of GR (i.e. repressed by GR at baseline) (Table 8).

TABLE 7

Genes down-regulated in the absence of GR

| | | | | | | |
|---|---|---|---|---|---|---|
| Chuk | Fkbp5 | Lyve1 | Per1 | Tcn2 | Bean1 | Ankrd1 |
| Mgat4a | Fry | Map3k6 | Pi15 | Tgoln1 | Cdc42ep4 | Galnt3 |
| Rcan1 | Glipr2 | Masp1 | Plat | Thrsp | Cntn1 | Hhipl1 |
| Ap1s1 | Gm12505 | Mctp2 | Pomp | Tmem252 | Man2a1 | Igfbp3 |
| Arl4a | Gpihbp1 | MPP3 | Prkacb | Tmem260 | Pcdh20 | Klk8 |
| Atoh8 | Gpr182 | Mum1l1 | Pttg1ip | Trp53i11 | Rhou | Pdlim1 |
| Cebpb | H19 | Mxd1 | Rab15 | Trp53inp1 | Shroom2 | Rn45s |
| Clca1 | Hif3a | Mxd4 | Rcan2 | Tsc22d3 | Atp6v0c | Asph |
| Cnot6 | Ifit1 | N4bp2l1 | Rgcc | Ttyh1 | Clec14a | Jazf1 |
| Crispld1 | Igfbp5 | Ndufc2 | Rpn2 | Ucp2 | Gpx3 | |
| Ctla2b | Inhbb | Nr3c1 | Rsad2 | Wdr92 | Hspe1 | |
| Ctnnbip1 | Itgb3 | Olfr1033 | Sema3a | Wipf1 | Tmem30a | |
| Ednrb | Kat2b | Ormdl3 | Sema7a | Wnt9b | Tmx3 | |
| Fabp5 | Kbtbd11 | Osbp2 | Sepp1 | Zbtb16 | Ndufs5 | |
| Fam63b | Kit | Ostm1 | Serinc3 | Zhx1 | Ctla2a | |
| Fgfr3 | Lcn2 | Pak3 | Slc40a1 | Ace | Kctd12b | |
| Fkbp14 | Lrg1 | Pde4c | Spsb1 | Alg10b | Amigo2 | |

TABLE 8

Genes upregulated in the absence of GR

| | | | | | | |
|---|---|---|---|---|---|---|
| Col5a3 | Ddc | Lpl | Tfcp2l1 | Atxn1 | Elovl4 | |
| Fbn1 | Deptor | Ltbp1 | Tgfb2 | Fbxl5 | Fam20a | |
| Fgd3 | Dram1 | Ndrg4 | Tgfb3 | Jarid2 | Htra3 | |
| Nppc | Ehd3 | Nov | Thbs2 | Mmp2 | Msi2 | |
| Abca1 | Emilin2 | Nrp1 | Tmem132a | Piezo2 | Nuak1 | |
| Afap1l2 | Ephx1 | Pde1b | Tmem37 | Prodh | Ptp4a3 | |
| Angptl4 | Fam189a2 | S100a4 | Tpbg | Arl4c | Pvrl1 | |
| Anxa6 | Fam213a | Scd1 | Txnrd3 | Megf6 | | |
| Aplnr | Flrt3 | Sema3d | Vegfc | Ank2 | | |
| Btg1 | Gad2 | Serpinb9b | Cst6 | Cyp1b1 | | |
| Ccdc80 | Gap43 | Sertad4 | Dnm3 | Htra1 | | |
| Ckb | Gfra1 | Slc12a8 | Eln | Pcolce2 | | |
| Col5a1 | Gja4 | Slc6a6 | Eltd1 | Sdc1 | | |
| Col8a1 | Itga4 | Smpdl3b | Gpr176 | Slc14a1 | | |
| Cxcl12 | Itga7 | Sprr2b | Kcnn4 | Tmem40 | | |
| Cyp51 | Itih5 | St14 | Tbxa2r | Armcx4 | | |
| Dcn | L1cam | Sybu | Atp6v0c-ps2 | Cd24a | | |

Figure 7:
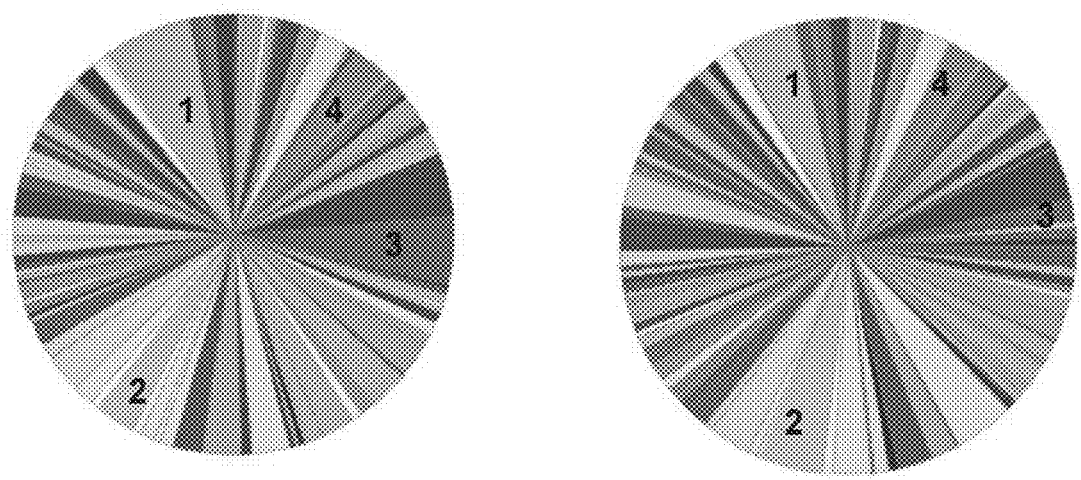
FIG. 7. Pie charts from the current ChIP-seq experiment and data from ENCODE in A549 cells subjected to GR ChIP-seq demonstrating similar enrichment in several key pathways of interest.

Example 3: Comparison of GR ChIP-Seq in Endothelial Cells to GR ChIP-Seq in A549 Cancer Cells To investigate which pathways were most enriched in the dataset Gene Ontology was used to analyze the top 1,000 peaks from the data and those available in ENCODE from a GR ChIP-seq experiment performed in A549 cells (10). FIG. 7 represents the pie charts from both data sets showing proportionally similar enrichment in 4 main pathways of interest: 1. Wnt signaling, 2. Inflammation by chemokine/cytokine, 3. Cadherin signaling, and 4. Angiogenesis, suggesting a similar pattern of GR responsive genes in these two cell types.

Figure 3A:
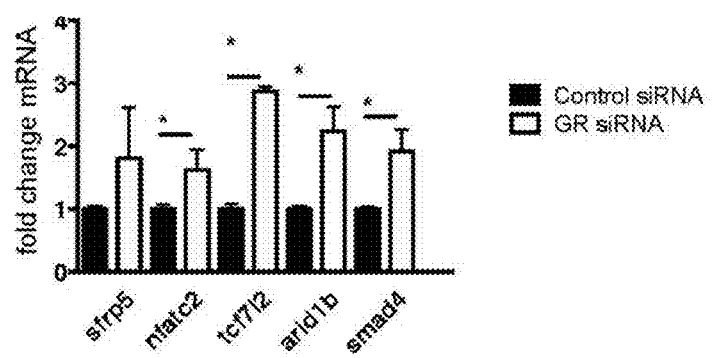
FIGS. 3A-3E. Primer-specific qPCR for genes in the Wnt signaling pathway, which were identified in the top 1,000 peaks of the GR ChIP-seq dataset, was performed both in vitro and in vivo.
Figure 3B:
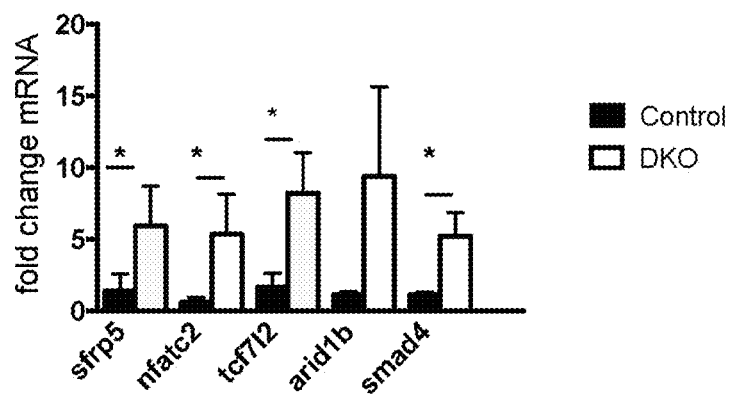
Figure 3C:
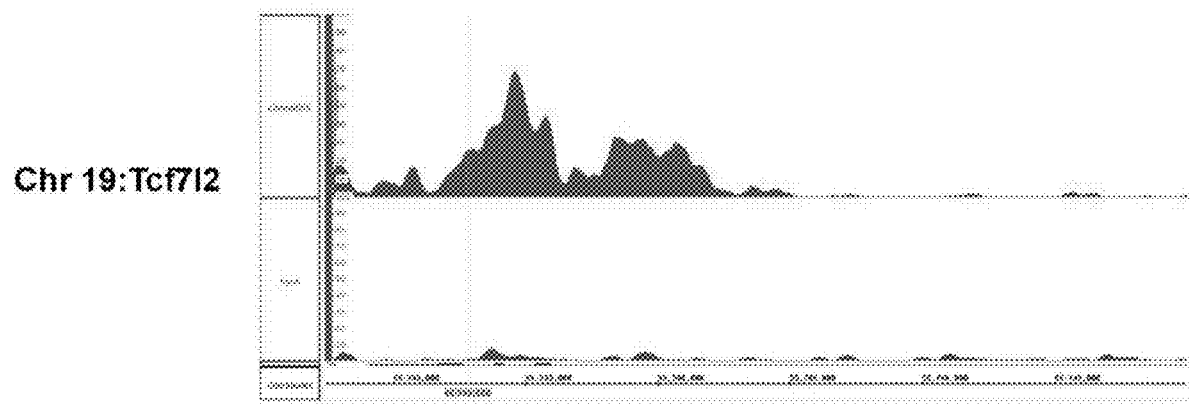
Figure 3D:
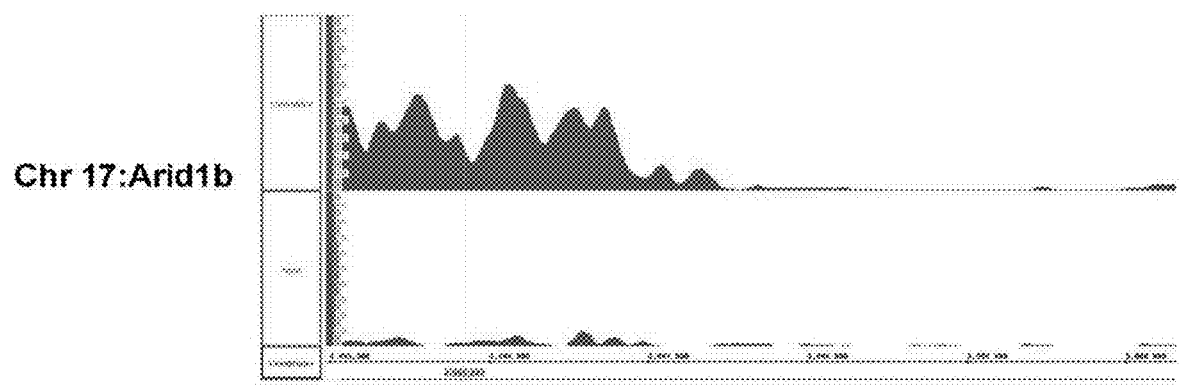
Figure 3E:
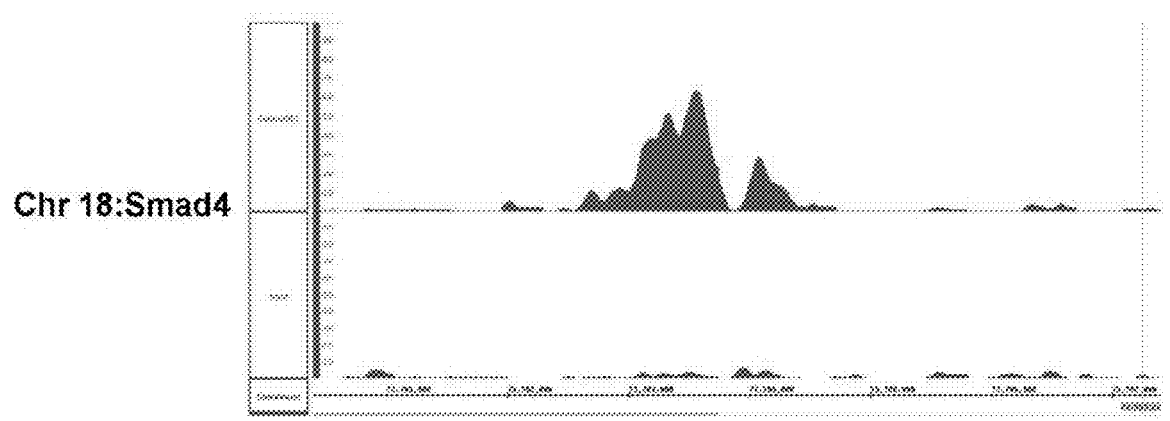
Figure 8A:
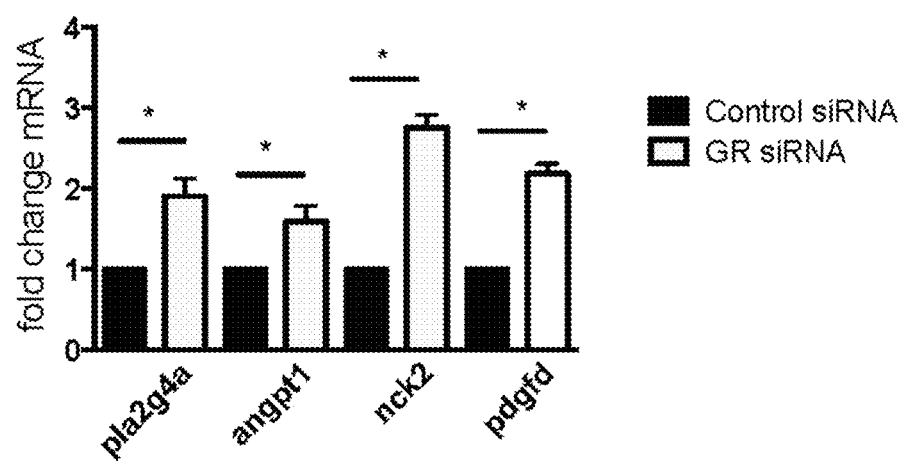
FIGS. 8A-8F. Primer-specific qPCR for genes in the angiogenesis, cadherin and inflammation by cytokine/chemokine pathways identified in the top 1,000 peaks of the GR ChIP-seq dataset was performed both in vitro and in vivo. In vitro, RNA from control siRNA- or GR siRNA-treated MLECs was isolated.
Figure 8B:
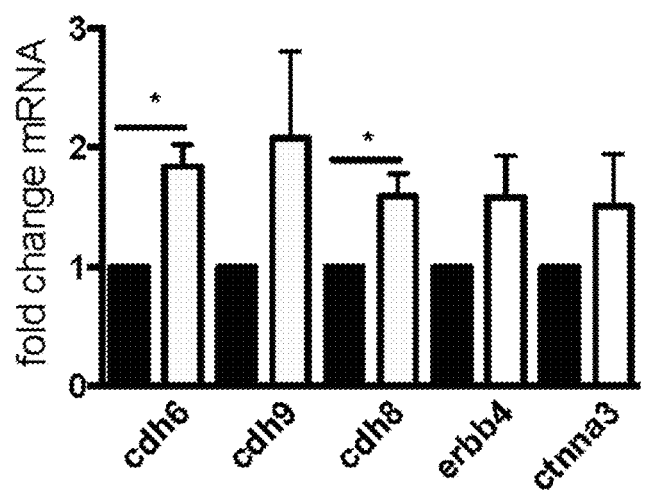
Figure 8C:
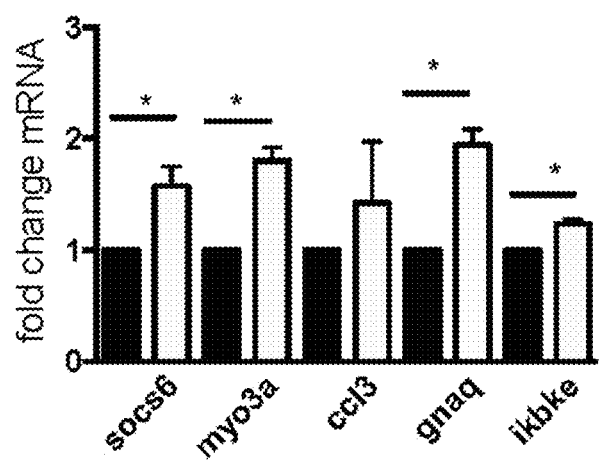
Figure 8D:
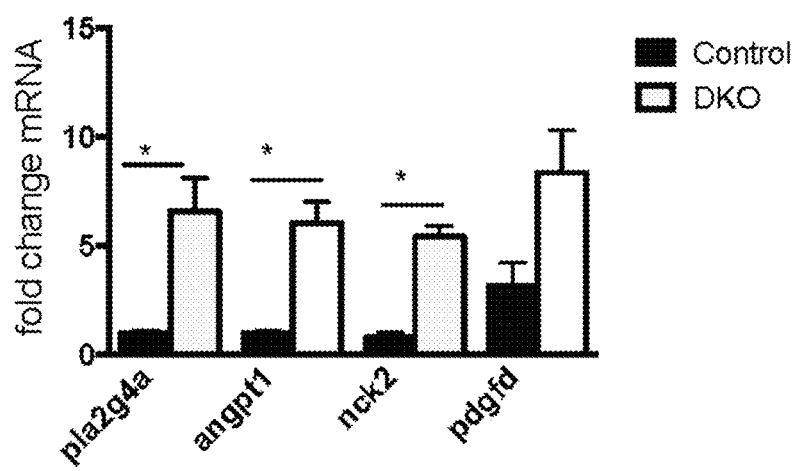
Figure 8E:
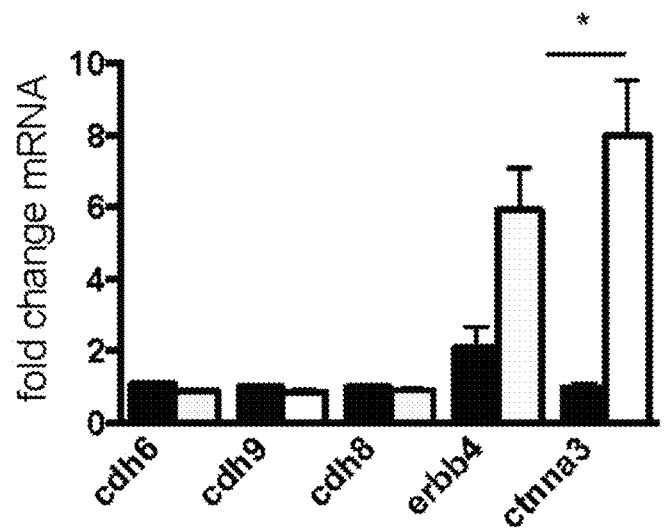
Figure 8F:
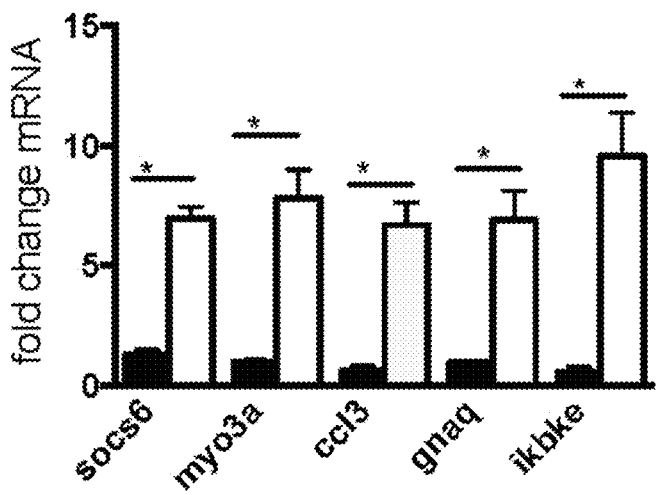

Example 4: Independent In Vitro and In Vivo Validation of Selected Genes Identified by GR ChIP-Seq Given that the false discovery rate (q value) may be >0.05 when dealing with such a large dataset, primer-specific validation of gene targets were pursued. Using several genes from each of the 4 pathways of interest, a custom qPCR plate was generated to independently assess expression of these genes in MLEC. Cells were treated with either control or GR siRNA and levels of gene expression assessed by qPCR. As shown in FIG. 3A, 4 of the 5 genes selected from the Wnt signaling pathway were highly up regulated in the absence of GR. Several genes in the 3 other pathways were also induced by the absence of GR (FIGS. 8A-8C). In a previous study, it was demonstrated that Apo E/endothelial GR double knockout mice (DKO) developed more severe atherosclerosis and increased inflammation when fed a high fat diet compared to Apoe −/− mice (7). To determine if these similar pathways were up regulated in vivo, Apoe −/− and DKO mice were fed a high fat diet for 3-4 weeks and RNA isolated from the whole aorta for qPCR analysis. As shown in FIG. 3B, DKO mice showed increased expression of the selected Wnt genes consistent with what was observed in vitro. Genes in the inflammation and cadherin pathway also mimicked in vitro results (FIGS. 8D-8F). These results were further verified by using the Integrated Genome Browser program to align the peaks generated by the input DNA and the control siRNA+DEX condition with the reference genome at the chromosomal location indicated by the sequencing data. Alignment data for three of these five genes are presented in FIGS. 3C-3E demonstrating massively enhanced binding when GR is activated by its ligand DEX with very little binding in the input condition.

Example 5: GR-Mediated Modulation of the Wnt Signaling Pathway In Vitro

Given the robust effects observed in the Wnt signaling pathway as well as the understudied role of Wnt in vascular disease, subsequent efforts were focused on the Wnt pathway. Table 9 shows the identity of the genes in the Wnt signaling pathway with GR binding sites with close proximity to the TSS based on intronic peaks.

TABLE 9

Genes in the Wnt signaling pathway with GR binding sites within 5 kB of TSS (upper panel) and GR binding sites between 5-10 kb from TSS (lower panel)

| Gene symbol | Gene name |
| --- | --- |
| Tbl1xr1 | F-box-like/WD repeat-containing protein TLB1XR1 |
| Lrp5 | Low-density lipoprotein receptor-related protein 5 |
| Ppp2r5a | Serine/threonine-protein phosphatase 2A |
| Arid1a | AT-rich interactive domain containing protein 1A |
| Mycl | Protein L-myc |
| Tcf7l2 | Transcription factor 7-like 2 |
| Smad5 | Mothers against decapentaplegic homolog 5 |
| Dact1 | Dapper homolog 1 |
| Csnk1e | Casein kinase 1 isoform epsilon |
| Plcg2 | Phospholipase C, gamma 2 |
| Gng2 | Guanine nucleotide protein subunit gamma 2 |
| Nkd2 | Protein naked cuticle homolog 2 |
| Adssl1 | Adenylosuccinate synthetase isozyme 1 |
| Ugdh | UDP-glucose 6-dehydrogenase |
| Hdac3 | Histone deacetylase 3 |
| Wnt5b | Protein Wnt 5b |

Figure 4A:
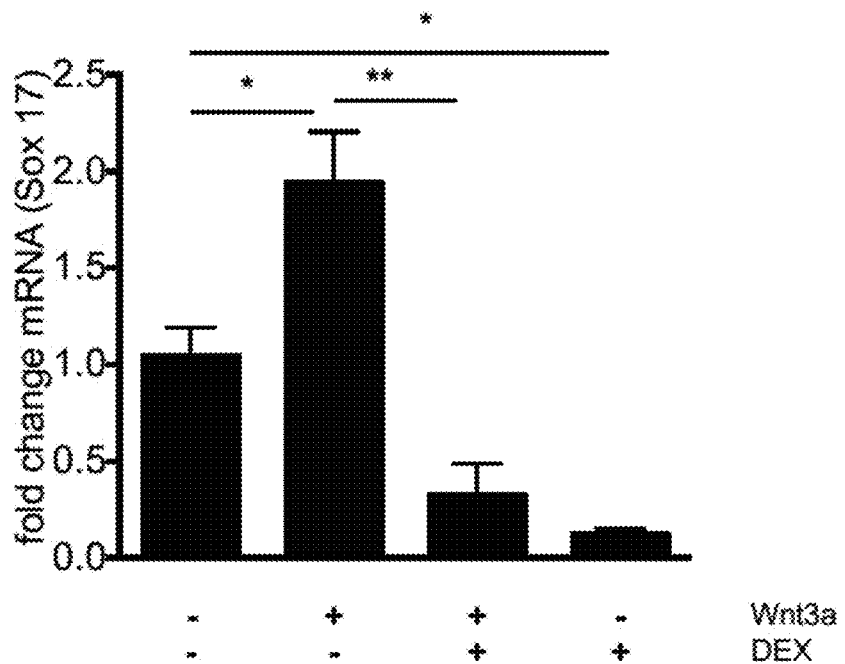
FIGS. 4A-4F. In vitro regulation of canonical Wnt signaling by GR. MLECs were serum starved in 0.5% FBS for 4 hours and then treated with 10% Wnt3a conditioned media for 6 hours. DEX 100 nM was added for 1 hour at the completion of the media incubation period. qPCR for (FIG. 4A) Sox17 and (FIG. 4B) Axin2 was performed.
Figure 4B:
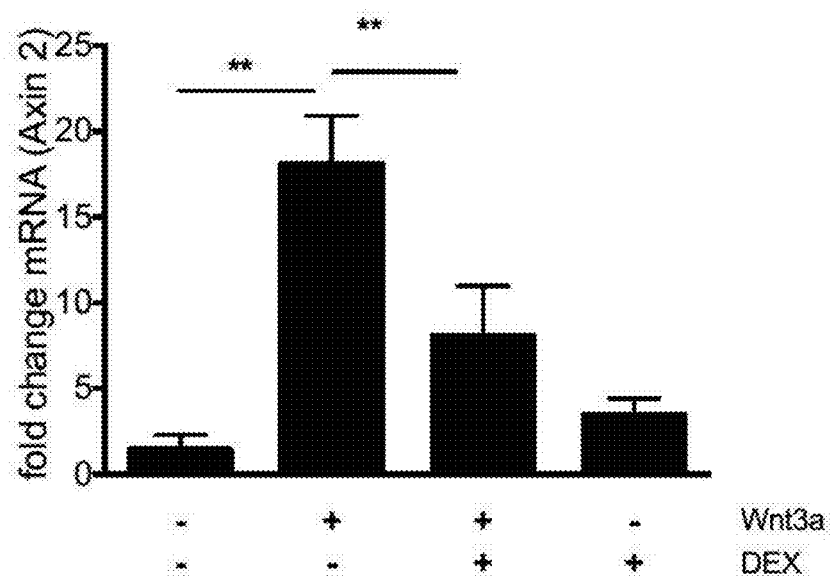
Figure 4C:
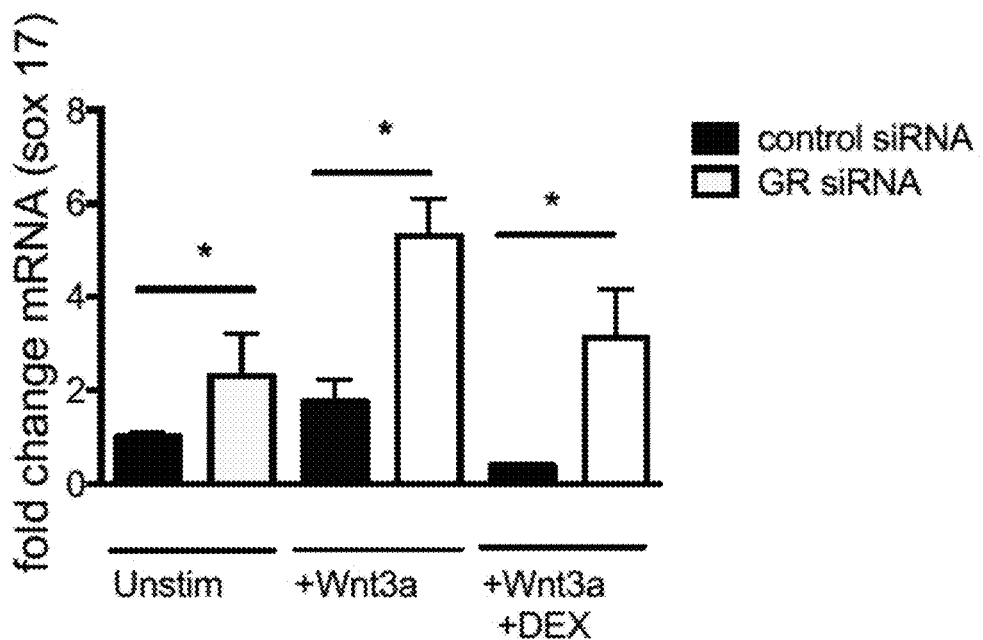
Figure 4D:
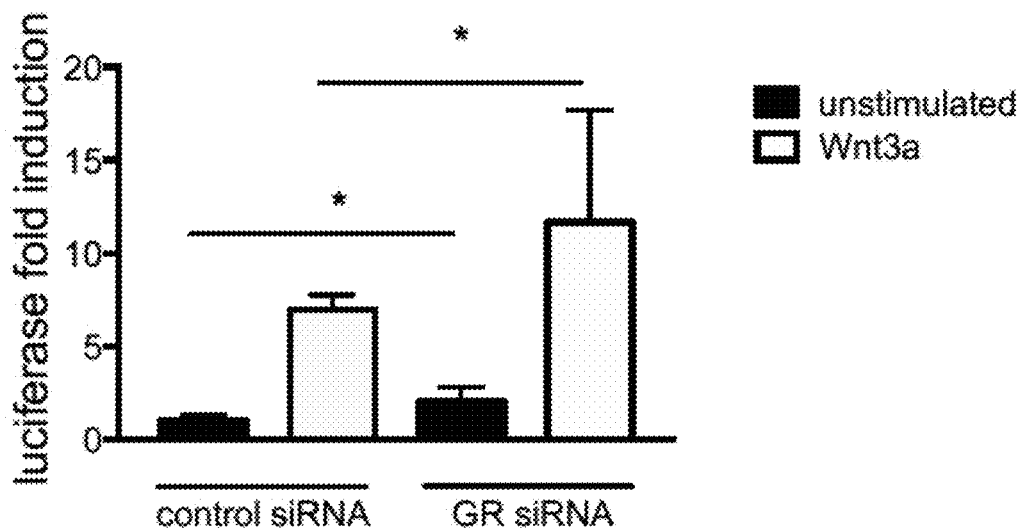
Figure 4E:
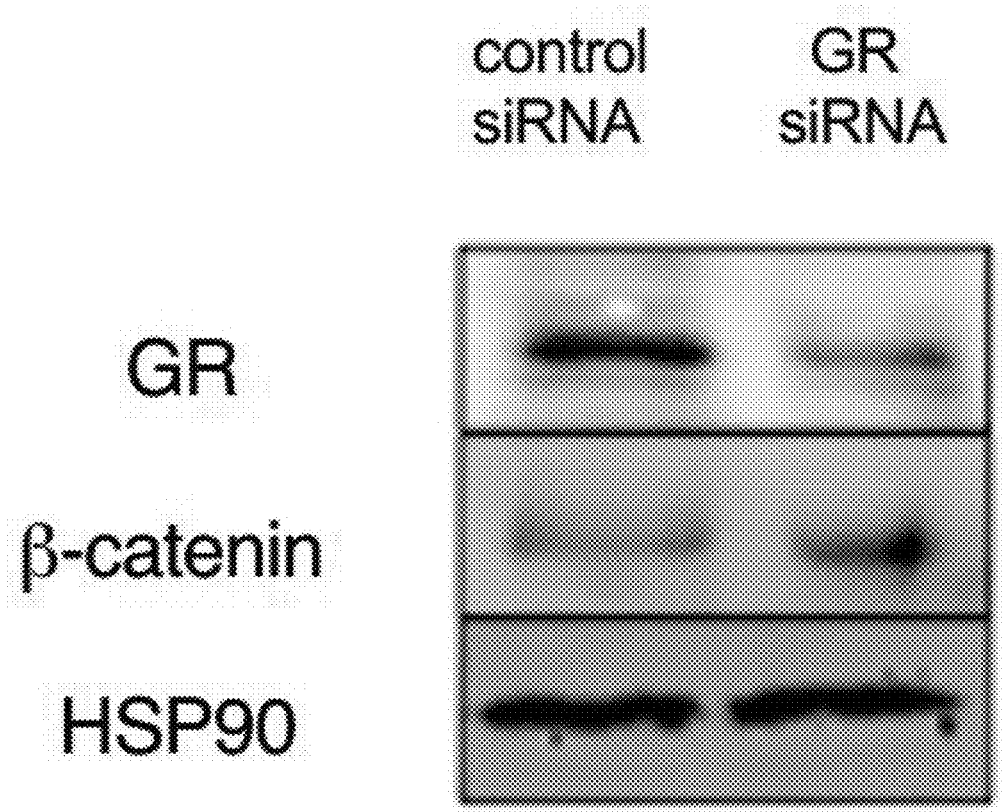
Figure 4F:
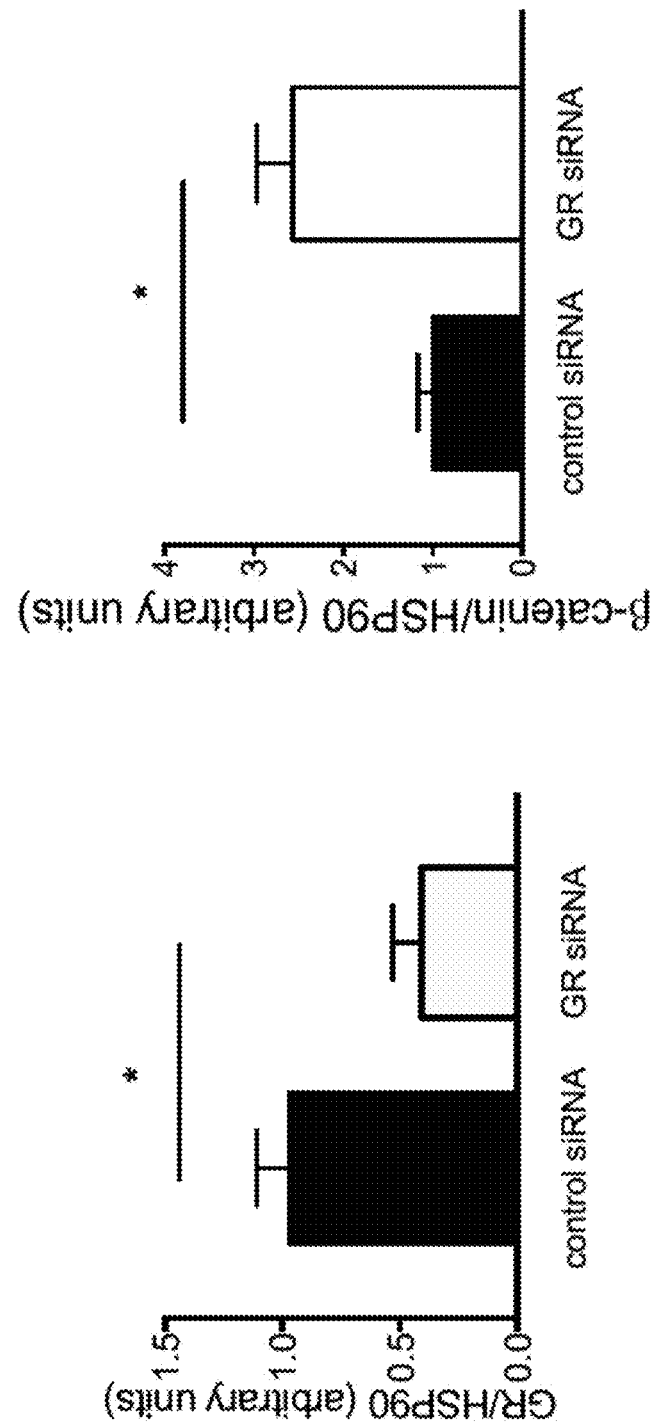

To directly test how the presence of absence of GR could affect downstream targets of the canonical Wnt signaling pathway, MLECs were treated with Wnt3a-conditioned media, in the absence or presence of DEX, and the expression of sox17, and axin2, both canonical Wnt-dependent genes, was assessed. As shown in FIG. 4A, sox17 expression was induced by Wnt3a and administration of DEX suppressed expression after 6 hours; a similar pattern was observed for axin2 (FIG. 4B). To further examine the specificity of GR in this interaction, a similar experiment in GR siRNA-treated cells was performed. As shown in FIG. 4C, GR knockdown caused increased basal sox17 expression in the unstimulated cells, and this enhanced expression was augmented by treatment with Wnt3a. Moreover, DEX treatment suppressed sox17 expression to a much greater extent in control-siRNA treated cells than in GR siRNA-treated cells demonstrating that GR represses the actions of Wnt3a on sox17 levels. These results were further verified by developing an endothelial cell line with stable expression of a TCF/LEF reporter construct, allowing assessment of canonical activation of the Wnt signaling pathway by quantification of luciferase activity. As shown in FIG. 4D, GR knockdown increased luciferase activity, both in the absence and in the presence of the canonical ligand, Wnt3a. Protein expression of β-catenin was significantly increased in vitro with GR knockdown in MLECs (FIG. 4E and quantified in 4F).

Example 6: Detection of a Novel GRE

Figure 5A:
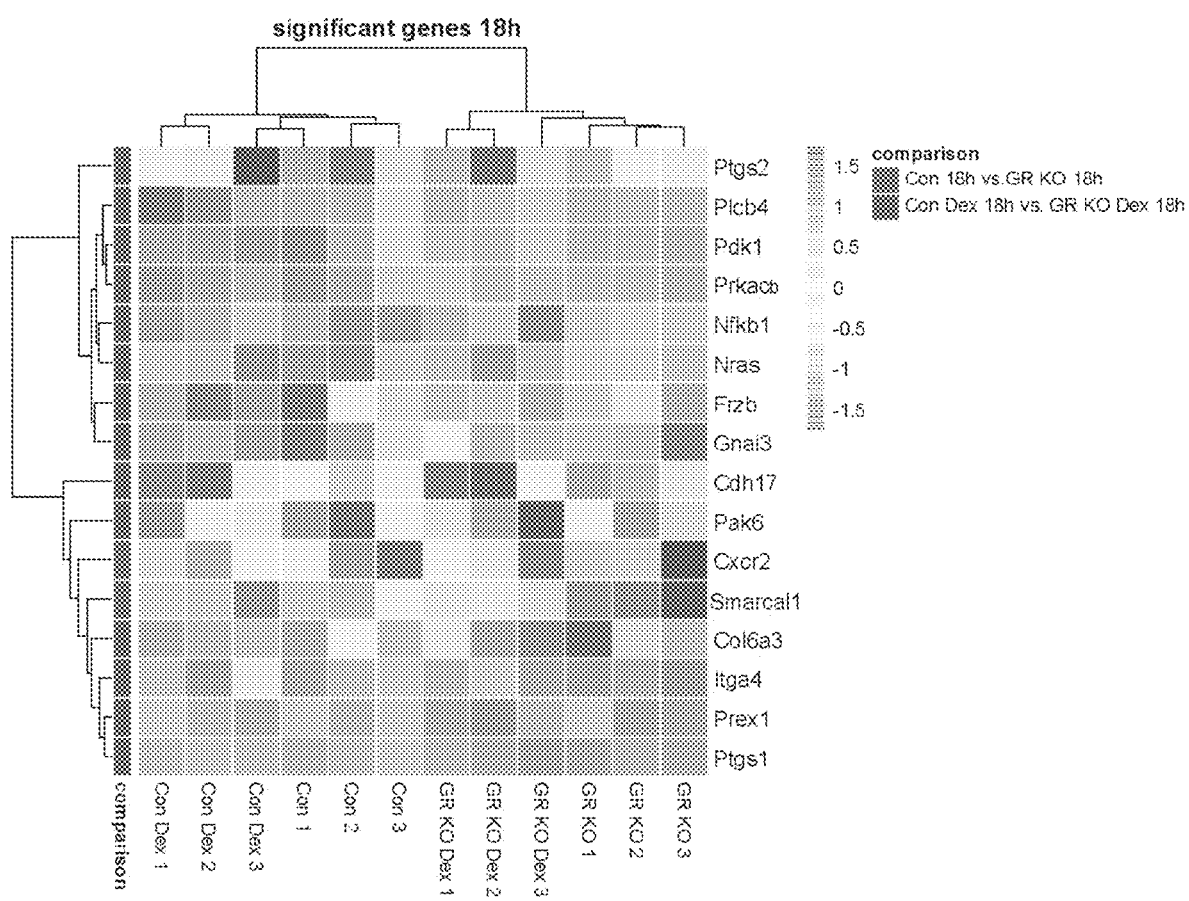
FIGS. 5A-5C. Detection of a novel motif.
Figure 5B:
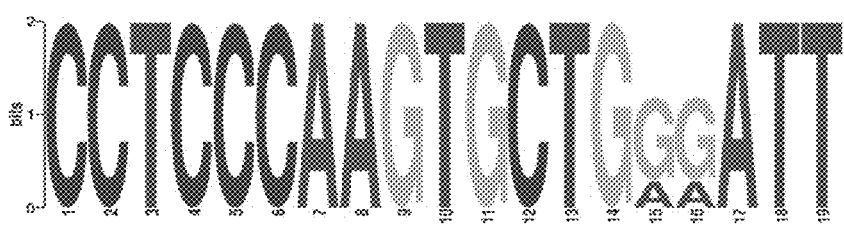

A subset of genes in each of the 4 pathways identified in FIG. 4 that: 1. had peaks in the ChIP-seq data set, 2. were present in clusters 1-3 (as shown in FIG. 10), and 3. had statistically significant fold changes in the RNA levels as determined by both p and q values was interrogated. This resulted in the 16 genes shown in FIG. 5A which are presented as a heat map analysis of biological replicates from the RNA-seq data. Using motif detection software, this group of genes was queried for conserved motifs and a new motif was detected as shown in FIG. 5B. Previous queries of larger gene subsets had failed to reveal any plausible motif. The genomic sequence of each of these 16 genes was reviewed individually to determine whether the detected motif was present. A perfect match for the motif with guanine residues at positions 15 and 16 was found in intron 5 of the frzb gene at position 80,415,049-80,415,068 on chromosome 2 (entire genomic DNA shown below; exons are bolded and the motif is underlined in intron 5). Frzb, a secreted Wnt antagonist, was found to be significantly down regulated in the absence of GR, again supporting the notion that absence of endothelial GR results in heightened Wnt signaling.

FRZB Genomic DNA with Exons Bolded and the Detected Motif Underlined (SEQ ID NO: 2)

aaaaggagcagatagactgtcttcttctgaaagttgtataagccatttaggaaagcagaagaacaaaaaatataaaagataat taacatactggcagatgccgaagaatattgtgcacacatgacagatgtttatgagaaacaatagagagaaggcacaggagcaga cagacaggtgcacacatcctcttctgggaggaatgcgaatccatctctggttttagtaaaaactaatttggattaaaggaaagt tgcaagtcccagttgtgatggtgcccacattagatcctagcactagggaggcagaagcaggcagatctctgtgagtttcaggct acctgggtctatatactgagttccaggacagccagggctatatagtgagatgctatttcaaaaacaaaaagaaaaacaaaacta agcaaaacaacagagaggggaagttgggaggttggtggaaggggagagcttgtgagaggatttggtggtaagtgggtatctat ctctgaagcaaagttcattcatacctgtggcaatgcgaccatcaaacactctactcctttcttcctaaaaaatgtgagatgaac acaaaatatgtttaacaacctcttgagttcatcgttccacttcgaattttttacagatccctatttcttttacctaataaagct tctaaatattcttttagtgactgtttataaatctcccttcagtatttgtgtttgtgtgtttgtgtgcatgtgtgtgtgtgtgc tttgccattttcattgaattaatttatataatgtttggctttcttttcttatatgacaccaaataattgtacatcagccagag tttatttattaattaaatggctccctagccaccatctgttgttgatttcctatgaagtagacacacttccttccgaaaacattg aagtcacaaaccgctggtaatgatcattttagagataaaaattccataaactcaagtcagccactgacattccctaagtgccat tgagccagcgcaggggattaaagccgtatcctactgtgtgctctgggaagtagagacagactttatctgcctagtattgacagc agggggtgggcggtgcggaaggctgggtaaatcagggctgctctagtgacgtccggctttgttgtaggttttgcctctgtgct cccgctgtcttctgacactgcaatccctctgctcaatggttttcctctgaagggggctcagtggttgggcctcggcaggacttcc -continued cacgtacaatgctcttaaagccagggggcagccggggtggaaacaggagacttctgggaggcgtagcctgggagggatctgttt tctattttctcctctgtattgaactcatctggatgggaaccgttctcctgtttactattatcattacctgtgtgggtattttg cttgcacgtttatttcccctgttagaagaaaccgcccgtgggaagagttagataataaatgcaattttcagtaagaacactctg ggggtgggggcggaatccaagtgcttaaagtgggctccacgcttcggttttaaaaagaaaaactcaaaagttcgaattcta cagggcaaagaaaaacccggaaggaagcagggagggagggaggaagggaaggaaagaaaaaaaagaaggagggaagggaggaa tcacaccatttccacgtttctgtgggtctatttgttctcttgcgatttcttcccctttgtgagggtcaatttctccacgttat tccaatcacagaccccccgaagtcattagtcctgccattgctcttaggaggctgctatctctgcgacatgacatttaaagtgac tttgctcgcgccttcctgtctgactttctgcaggcggaggtgcgctcgggtttgctgtgaggaaagagctgcgggcaacgaggg acggtgtgggctcgcggggcgggatacaggggtgcgcatctctgtggtgcgttgagaccgtttctcccgtggggaccaagggtt cgtctatggatccagagccgggggtggagtggggaaaggtgtgcggctcctgtcgggagctgcctggggctacagcatcacaga tagacagggtctcacactccagtcccctgaaaactcaaagccttctcggaaggaggagccggagggcaggggaccgcggggcgg agctcttgtcggccgaggtgggaaggcgcagctgcgagccaaggcgctgacctcctctgagctcctctggccgctcgcaggatc ttcccgaccctgcaggacttggcaaactcccacctccgctcccattagtcctcccaccccaccaaatcctccctcggaggt ccctatccatctcactttgcagaatttatcgcttcttccaacacctttttgcaacaccccagaactccgagtcccttaactga atttgacttttgttttatttctctctggcttcctcttctgcccctcatctgattgatgtgctaaggctgatgtctctgccag agcgagaggaataaatagatgctgcctcgcctagaggcttagacgcttgggaagagcagccggcgcagcgaggcaccgggctcc gccaagctagtggaccggacctgggagcacttggatccaagagaactgtgattgtcccaggggtgggggcagctccccaggtcg ttgggatcacccctcggaaccgcaggggagacttcggaacgaaagtgtctcccgcgtccgtcgctcggctgcgccctgcccca tcctgctgggacc**atggtctgctgcggcccgggacggatgctgctaggatgggccgggttgctagtcctggctgctctctgcct
gctccaggtgcccggagctcaggctgcagcctgtgagcctgtccgcatcccgctgtgcaagtccttccctggaacatgaccaa
gatgcccaaccacctgcaccacagcacccaggctaacgccatcctggccatggaacagttcgaagggctgctgggcacccactg
cagcccggatcttctcttcttcctctgtgcaatgtacgcacccatttgcaccatcgacttccagcacgagcccatcaagccctg
caagtctgtgtgtgagcgcgcccgacagggctgcgagcccattctcatcaagtaccgccactcgtggccggaaagcttggcctg
cgacgagctgccggtgtacgaccgcgcgtgtgcatctctcctgaggccatcgtcaccgcggacggagcggg**tgagtcctgaac tttgcccgacctctgagaagttagttatttgtctttatcggctagcttgctttctgcgctgagcccttaccttttcccttaagc acactcctctactgaatcctattcttttacttaaaagcaaaacaaaacaaaacaaaattcacttttatcattctcccagacaaa cgcagtctcttccaacaagtgatctgagcgatccatccgttccctacacttcacacccaacctccaaagcgccccttcccttcc cactcttttgcgtgtggggcttagctgctttactcttaacgacattggagtttcttctgtttcttggtgcattcttttgcaatct cgatcgttagtgttttcacggcttacaattgtatggagacatcagaaaaacaaaaaaccctattttcttctaatcatgaaaagt gctaatttagtctaaataaactgctaatacagaaatctcttagtgacatgtgcctgctcagagctcaatttcgtcggttgccat cgcctttcaacagatttcccttctcttgacaaaatagatggtgattccaatccagaatgaaacagctatgggacattattgct atgccctgctaattaacttcggttgctcacttcagtcagatagctggggaaccgaaaatagcaggccttttcacatgcccacg tgccttcaagtaattttgtatatagcatatgggtgagtggagttatatttgggccatgtcatcttcatagccttatataacttt gctttcaatcttgccggttattccacccatactgtgtgtatacatgacccacacgttcaccccctttccactaccgaactg tattttagctctacgtttaatgggtttaatcacagctgttttctcaccgatgtttggtctaattgtgacattcataacttcaag accaccccttacccccctgaccccaactcaatccagttcaaagtggaatattttcagtaaactcatcatttccctactaggtaac ccaagacttggattttatccttcatgttctttaaagagaacgcttgaacaaacaaaccatccatcatctttcagtctctcccag gatcaactgctgttaagtgtgcttcacttggttggtccatctctgttcatttcgttctgtttctcagttggctcaaactaggct catgtcctcagtccatagttaattaatcaacagggccgattcagaaaaattatgctcattaactaagagagggtaaaaggaaag gcaggaatagttgaaaaccaagactgaacagaaagatctcacatctttctcatggtcaatttccttagcaaatcaccacgaata -continued

```
taggtactgtcttcttaatatcaatgatgaatcaaaagctagttttataagacaatctgaaataaatacattcttttcactatt
gggtcaaagggaactctgagatcttgtactaactaacatcccaggccctgcagacattgctgttacagctcaatgcagttgcta
gcctggcttgacagacgctgttaaagtcagccaaatgctagcacgcctctctggccaagcactaggagtaattcatttcacact
gaaacgcatacttcccttagaagacaaactgctcctaagcctaagcgtaagcctagaggaggaccgggaaagagtgaggtttga
caaggctcagggctctcaaaggccacagtcactgtggatgggaagcagtttcattaagagtccctgagttacctatccccatgg
gccgaacatggcacaactgtctcaccgaagcactgaaagagacatgcatgccgacagacagttaggcactccctgattgctgag
tggctcaggagtcccagaggatttgttttactgaagcaaagcacctgccggcaggagatagtcagtatgctgacactcctcggt
tttggtttctttcgtaggaaacagaaaccatgagctaaagatgggggttggctcacagccttttgaaaaattacacattgcccct
gttcagtgaaactgccagacacctggaattacttaatgtggtgacatggggctggagagatggttcactcttaaccactcttct
agaggaccttggtttgattcctggtacagacatgggagattaataacctctgtaacgctcattctgggagctttgcctccctct
tctggcctccatgagtactgcacacctctggtgcacagacttagagtgcaaaaccagatggtgaatctctacgcatactccatg
ggcactgcatacatgtggtgtacagacatacaagcaggcaaaacacccatatacataccacatatcaccatttttagttaattta
ttgtttgatttattgggctgtaatagtttacaaaacagagtttatttgtctgtttgtttctccttcagatataagcagaattct
ggtgttttggtactgcattctatttagccagatatgaaaatgaaatctctccttaaagagtggtacaactgttcacattcctgt
agcaagaggattttagttaattcatcccattcacggttatctgtttgcacctaatatattgtgactcggcccataagcttagca
catttaacagagccgtctcaatgaaacacaccgatgtgccagacgattttttaactcctgaaacactgagaatgaacatattttt
atgaagaacatgtgacgccttgacaatcactagtaatttcatattaagtttattgtgtattttgtgtttactgtaaagtgtggc
tttgagcactactatttgggaacagctcaatttggccattttgccagttagttgagactcttgggcaaattcgtagtactgaac
caggtgctaaatttctacatgagcccatgcctactccagctatagggaatggtacaacctcttcaaccccttacctgggaataa
aggcaaaagtgtttgtatcctaatggcatggtgaagactagatggtatgtgaactggctgagtcaaacctggcgcagagcaatc
acagaacaaatcactgatattattttcctatttttttcttttgctaaaggttttttaaaattattatagtatgtaagtacagtg
ttgctgtcttcagacacaccagaagagggtgtcagatctcattatggattgctgttgagccaccatgtggttgctgggatttga
actcaggaccttccgaagaacagttggtgctcttaaccactgagccatcttgccgcagaccctctgggtccctgtgtctacgtg
gaatgagtctctcgacgtgggtgggcaaagcgtggatgaaagacaaacagacacacacaggagaggttgtgtggaatctgagtg
taattttcgaatcgagcatcagactttttatgcagaggacaataagccctattttcctatttttaatgttgctttatcaactta
actaacttttccttttttattttgttttgtctgtttgctccttttttaacttgctaaatacagcagatatagcctcattctcttat
tacttcatccctggagagcaagatttaacacttggatttaactggtgaagcaagggtcatttctctcagatacagaaaattagt
attttatttcatacaaatcaagctagaactcaggtttaggagtttactcctacgggaataatagaaagaaaagagtgagtttga
tgtctgttaactagaaatagtttattaggggaagagactcacaagcctccacctcttcctgaggacttccaagcagttaatggg
ggacaagggtaggggtgaggggtggaggtggatctgggggttccacctgcccttattattgcaggttgtggttgcaggcaagg
gagatagatacatgttcttcactagtggggccactgctaagcggccctgtcttctctcactggttcatcaaaaaggaaattaaa
aaaaaaagggaatcagtattttttttttaatttaaaaaatattgaccgtggaagacagatgataggtgtttcacagctgttt
ctgagactcctgcagcttgcagtaaggctctataatcaccctgttattgctggcttccagttcgtactaatatcccccgcacc
taccaggctcttgcacaacatattcttcaggctctggcctggcagagtcctgctacctttcacatgcagaaatggctatttaat
catctctccactctccaaggaacaggcagccttttctttagtgttagccctggtctacaaatatttgaaggggccaaataccaa
ggaggaaaggtctgaacatgaacatgcgatggaaagaagtgaaaatttgaagttaagactcgagagaaaccaggattctaagg
ctctctcagcatgtccataccaaaaagcagcctgcctgtcttgggcagagaatctgtgttattaattttatttagaagataacc
tagtcgtcagtgcttgtgaaatcttagactgcccctaagttattattttaatcagtcaccttttgtcttcttttttactgaacat
tgaaataattatttgaagagcaaatttgaccacactatctctggtctttgtctttctgctaggtgtttaaaggaacacagccac
tgggtagtcacgcaattttgagcagtggaacattaacttcagcatataaacttaaggccagtcacagcttcagagctgcaagcc
cttagttggttttgtcattcactttgtattttttagccacttgacattggcactggccagtattggtgtatgccaagggcagtga
``` atgattggtagttggtaaagcacatgcccgacagctcaaccgcaaccacaccagggagagaagacctgcagccttagggccagg gtccttagtgttgatagaataaaagctgacaacatatactgtgctctaggtattgccctgtgaggtgtacatgtgagttctcat cacagctacatggtacgtgttgttactcccatttacagcaaagaatggaaacgcacacagagaagtgactcgtcaaattaactc agtgtgtgagaagacaagggtttagactagagtctggtctacactacccaccttcctttgctaagaaaagggattttttgatcta tttggagaatctgtgcctttggttcatttggttaaagttaaaggagcaatgcattttcattatgttgacccccttggcttaaaag aataaaagagcacccaggacaatgggctccaagagataaggaatggctgtttggttgcactgctgagataggagagaatgcctc ttccagatccatccaacgaagggccctcaggctcagcatgccctagagctgcctgctcttctctagcatgcttttagtggttgc aaggctttgataccgcagttatccaggcttaggagcctgccttgattctttctcttttctcatccctggtgcacctgaaagctc tagaacaaaagaagcaaatacacccaagaggagtagactgcaggaaataatcaaactcagggctgaaatcaaccaaacagaga caaaagaactatacaaagaatcaacaaggggctagagagatggcacagaacttaagagcactgactgctctttcagaggacct gagttcaattcccagcaaccacatggtggctcacaaccatcgtaatgaaatctgatgccctcttctggggtatctgaagacagc tacagtgtactcatataaataaaaataaatctttaaaaaaaaaatcaacaaaaccaggagctggttcttggagaacatca acaagatagataaacccttagccagactaaccagagggcacagagacagtatccaaattaataaaatcagaaatgagaagggag acataacaacgaaacatatcttaaagtacttattctgtctgttgaatattaacagttgaaaatgttaaaatcatgttctcatcc ctggtggttagtaggtattaagtgctagtactcttttctgtgattctctttgggctctctgcaccccacaaggattatgacaga gcatgattgtctggctctttgtcctcagtattcctcttccctcttctggcgagatggttgtttggaaacagtgtatctattgct tacatccttcagacccactctcctccccgctctctgtaagttcactctttgcttgtcccatctctgttctagccaagcaggag gacatgcagggccctttgcagagcagttgtcacacaggctcttcctgaaatctccttgatgtcactacaaacacttgagatata gaatctagccatcacacactaccactatctaccacttccatccagaacaattttgatggtagaatttcagattttaactatgta aaaaaatgattggaaacctttgggttcttcttacacaattttaacaattgaatactcagtgtttaaaaagaaacatctctgcta gtaagcatacggaataaggaaaacttcctcagtggctacactgtttcaaaggcgttcttttttttccccaagagactttattt atttattttttatttcatataaaccttaactgcttggtgttttaaacgtggactaatataatttattaatcttgagggagatta tttaatataaaccatgtacattttaatctcatcattcttcaggaatggaaacattgtattttgctttaaaatttggagacgttt atcatgaataaagtctgaataggataaaagtcatcgaagttaatggtttatgtttaagttgagtcaagtgcttgtaaactcaac tagtatttgttattttcatctatttagagacctctaatatatatatatatatatatatatatatatatatatatatttatagt gttagctgacagccacatatgtagctcagtggtagaggcaatgtttagcatgcacgaagccctgggttcaatacacaacacctg gaatccttcctcatttatgttttatatgaagtataacgacaaagaaagaatgctggtttgttaggttaagtagaggcattgagc tcatttagcgttaagtgttaatacaagtgtactactcttggatgaaagtgtgagttgagtaccagcaagaatccatggttagtt actttgtctctcagcaggggtacacagcgcaattcattagaggctgctctcctaattagaacacagaaggccattatcattacc attttctgggattacagcatcgtgagaaggacccatgctgaatcccaattattgccacatctctgaattgtactggctagagag atctacaggcgctaggcttcctttgtgctgaactatttagtctgcattcaacagagggcctggagttctttctggatttcccat agatactgtgccaggagagtatgacacagccattcattgacaaggtgtgtttggttctatctgtcacaaagtcacacacattgg gccagtgcctaatatttgtatggcctttgctgggatacaacattcatttacagcatttatgaaactcaagaacacgttatttat taagtgctaaaatttttactcacacatgatgctgattcatgagcagcaactgtcaatcatatctgagaaaggacctcctccttat tcaatccccaatggtggggcagcctcacagccctaataagggaccatttcctggagacaactgattcttccaagtctagctg taatggaattacactttatagatgacgtcctgaggtagtcactctgtcatcattctttcttcattctgttgccttccagatttt cctatggattcaagtactggacactgcagaggggcaagcagcggtgagtgcacagctattcctgcctttcgtttgtggtgcaga taattttttgatatggtcttcatacttaagttttatttgcagatacttgtgtcctgttttaaaaacaaacataaaaaaatgaatt ctgcatttatgctgattttattttttgtgttattatattaaagtcaacctcttgggttaaagtttggtttacaaaaaatgctaa tgaatacatagattcatgtaaccacagccttcaggatacagaataattctgtcatctcttcccatactcctccatgtataatc -continued ttttataatcagaagtttcacctgcttttaagcactagctgttctctggcactgtaatgtcctgtaggaattgtcacatagatg gaatctagggatgtagcttcagtggtagagtatataatcttcctatctgccaatctatttccatacagcctgcaacctggaagt gggcactatagatctggctccaagagtacagaatctccagctgctcctgtctcttgcaacccatccctctagctatcccaaagc aatgctaatagtaatagctatgccaagtagcctaaaaccccacaaaggagacccttctctctgattagggaacctgtggtgct aagagaccaggcagatcctgttggttggttcataaccacccacttcttggcccagatgcagtagccatcaccataaatgaatt gcagaatggaagaaataatgtcctagctttctatcaagtggggtgctctaaggaattaaatagtactggggatcgagagagaga gagacagacagacagacagacagacagacagagacacacagagagaagcttgggaagtgatcttgcatgcatgattgcaaactg ctagactcacccctggctgtgtgttgatttgactaaacaatgtcccacagactgaataattaactatggattatgcatcacctt aagggcctgggttgaatctgaacactgttgagagtacagaaaagcccacaatcgttgtgtgttggtaatacaaacccaaaaagt cacatatgtgttttttgttttgccttgagacaaggtttcctttcctaatcttgctgttgtttatgcttgagcattcccaagtaac tgcttcatgccttctgctcaggctacgttcagtgagagagaaagaatgggtctaattattccatctaccacacagtaaacctt taataaagtgcaaaaagaacaaaaccaaatgagctggtgcaattttctttttttaagtacagccttgtaaagaccacacagc aggatatttgatgttagcgtgttctagattctgtgagtcactgccacttttacatttctttacaacgtggcttctagtcagggc tctaacaattgcagattagttttgcctgttcttgaattttgcatgaataaatccgcagcttttcctctttgtgcacaagagctt tctttgctcttcttatacacgatacagttttaggtttcattgataacactgtccatcactaaacataccaggcacagttcttc ctgctattactagatattaggattgcttcctatttctgttactgtgtctaaatgcggctcagtttctacctagttgttttcact gattttggtcagtatgctacagtttgtccagtacctcataagtgaaaggggaagcgtatttgtcaatttatgaataagttaggaa taaagattttcacagaactggccacatccattgagtattatcattaggttgacaagtatctgaccttaggtactgcccatcaaa agcagccctaaaaaccacttaccttatttatgtaaaaggaactgatttaaaaattattaagaattttgaagatgaaaccttca ttttagtatctaaattcaaattatacagaatgcagagcgtgggatgggagagtataagtggcgtcggcagccattgccctgatt agcattgtacactcatttcaatggccatagctgagcccaaggtgccaccaccgcatcgtgattcccagtgcctcacaccatctt gcaacccctcaccctgcttctgagacaggaaaaggtactcaagagtaccccacccaccccacagcagactccatgacaaagcc ggtttccatcctgctaaggcagctggcctgcagatgcccataaggacccatggccacccacatcttgctttctagagtatgct cattcctgatgcttatttagagtatcttaagttctggtgattcaatgagaaacatcttcggtcacacagagtagacattcttgg tgtctgtgctactctgaggaccactccttctgttgtatctgtgtacaacaaactaaaaaagctcacgaattgttcactaataca gttggtcagtcagaatttcttgtcatgtgtgtgtgtgaattgtcaattttttctgaaagttatggttacagtttcagtgtg tcagtaagcaaaggcatcaataacaaacaatatacagaaatgggtccatttggagcagggcacggtggtgcacacctttaattt caggtgtctagagacagagacagcgctctagagccagagccaaatgaaatctctgagttcaagaccagcctggtctgcagagtg ggttccaggaaactcggggctaaacagagaaaccttgtctcaaaaacaacaacaacaacaacaaaaaacccaaacatacaaaca cccacaaacaacaacaccccaaaactagctccacttggaaaacctcggagtgtgtggagtgttcctggaatcagagtttcc tgttcccttccctaaaaatgtttttctgttggctggtataatgggggcaaggagaacaagagagaaatgagagtcgattctgtt tatgggggggaaacacgttgacacagtcacatgtttcagaagtaggagtagtttgctcacagtcgggattttatccttagagaa aggtcgcagctgaaaaggctcacgataaaacaggaaatgaggaaggcccaaaccatcatacccgacatcctgaccccttcca aaatgtcaagctgtttgtgtctggaatttggggaagacattctttctctccaattagtttctttgttgccttaacacttaactt ttttttttcttcttctgtttcagagataatgactctgaacagcgtccaatttgtgagtgtattttactgtcgtaaatctaccat cataaaataaatagatgtcctgtattacaccacatggggtgtaaatcacatcaaaccaacatagaaaattaggagggatgttta actccttcagggaaagcgtatggattttgttcatttgtgttttagtttaattttgtttgtttttttgaggtagggtctgtgcaa cctaggctggcctcgaactcctgacgcttgtgaagatgagcacaggcttctgatcctgctgcctccacttcccaagctctggca tgatagctgacgccaccacacttggtttaagcactgctggagaggaagtcaggcctccatgcatgctaccaagcaccctaacaa ccaagctacagtcccaggccaatgtgttggtctttggaaataaatcaaaaataattctagttttgcgtgtgtgatgacaaccaa tttatgagcatttacatttaaaaaaaaacacacatctcctcacccccaccccccaggaggcaacagctgacaaattctgatatac -continued

```
tgtgtgtacatgaccaaatgacttcacgggtcattcccaatatgaatatcagcttgtgttagcctctactctcctttcttttat ctctctttctaaaaattggatatcttatttatttacattttcaaatgttatccccgttcctaatttccccccagaaacccctat cctctcccctcccctgttcctctaagtctcctttctacaaacacttgctgacttcagagactaagttaaccagtcacaactag gggaaattagtacttttgtgactgtactgcagtttacaatcataggtctttccccaacctacctgtcacacatgggagctgcc acttcaaaccaattttctttctttcccattcttttccttgaactgtcagcaagattgtcttagtgcttctgtgtcccaggcact ccaaaggatctcatgcctggcctcttctctctcttcacgagggtttcttcctcttagaattcatctgcctacagaggttcttac tcatatctctgactggccttctgttcactctctcaggaagaatggcatatttctatttcctatccacctatcctatttatattt caaacataattgattcaacaacaataatagtaacctttttgtttgtttgggggttttttttttgtttgtttgttttttttgttt tttgttttcaagacagggtttctctgtatagctctggctgtcctggaactcactttgtagaccaggctggcctcgaactcagaa atccgcctgcctctgcctcccaagtgcttggattaaaggtgtgcactactatgcccggcgaacagtaacctttaataaaaaaa caaaaaacaaaaaaccttccaccttgaaggatgtggcgtcatctccttcccaggctcctgcaggagagtgtcagcgttggtt tagtccattcattctcccattcctcaaaaaaaagtaatggaaacttgtttctcccagacccaccacatatcagggcatgagata atgtggtcactggacggcctttcctcattcctgtccttcttgtatggacttggtactgagcagacatgaccctgtcatggcggt gaggtctgtttcatcctttcattctttaactttaaggacattataaaacagttgaagggaaaacaaagttgaattgactcatat ttttgagaatttgaatgactcttagagccaaaatccttgtgaagaaccatttattaaatatttccgaaaatctaatcttgaag aaataaatggaatttcctcttcttagtgacgcaacgttagtccttgcaatcttaagcaatttcctcttacagagcacaaatcat tatgaactgagtcctttattaacaattccaggtttgttttcatagctgagtttgaccctatgctacttttgtttttcaaaattt tttgttacctaggctcagcagtcaatttcataatgttttcctctaactcaaaataaagatatatatatatatatatcacttc attttgtggaaaaatgagatgttctgtgaatttctaattaatggtatttctaaggtctagtttacttagagtaaaatgaacca atgtctagtgtgtgctgccctgagttttgacattgtctgcacgcatgcagccattactgagtctgggattaagaacattgttgt cttagagatttcccattctagactagcagggttctaattttcactactatagattagaaccattacatcttcagctctctgcac acagatcaacagttcagatgtatcttatgcccttggcagttttttgcttcctataatgcttgagagatttacctactcagttgtg tttcattgtttccaatgtatagcgcaccttcaaatggtatgataccagtaaaattagaaaatactagccatttaactattgcgc ccagcttgatggagttactggtttctgattctgtagaaactgttatcataacaccctctcaaactctctcctcccacttcctgt tttattactgagatcagacaactaggattcggatggattttgttttaatgtcctagaaacaagaagactctagagattttttcc atcaagtattcttttgatgactagtaacattagggtgaggggtgtgcttggccaccagggtagactctctgatgtcttccagt ctccttgtttctagaaggctagtggaagtgcaaattatttctaggccactctcggtcagaaagctgccctaacaagtctgacat ccgtcctgatccgtcctgttctgtttggatggtttgtgactgagttgaagagcctgcatcttctacccactcccctagagccac gttccacggtggccattctctttcacaggcaggctttgctctgccatggttctgattttgtaatcttaatctcaagcattccac tcttcagtaacttaccccccttcttcctgatgattcgttctgaagctgtagctgctggttttttcttactcctttgtcactgtctg tccatcagttgtacttactatctgtccagcctctgacttcttatttaagtgagattttactgtttctgagaatggtttccttg aaattttcttcaattctttatttccccatctctcttttttggtctcaaattcttttttcttcttcttcttttttcttttc ttttcttttttttcttttcttttcttttttttttttggcttttagacagggtttctctgtgtagccttggctgtcctgg aactcactttgtagaccagactggcctccaactcagaaatctgcctgcctctgcatcctgagtactggaattaaaggcgtgcac caccacgcccgattggtctcaaattcttaacagattcaacggagtgaatcactcaaattggtgacacacgtcaggaaagaaac tttattgaagaagcaatttgagtgcaggttttatctactacacagattgtccttaatttaaaacatcagtttcatgttttctcc ttgttccccacaagctgtgtccctcatcttcatgctgcacagctgacaacatcattccatctttcaaggagagagtaaaagctg ttgaagggacggctctcacaccccacccccaaccccattcatctttcggtctctgccaataccccctgcccttacctcttgt gtggtgaacaagtgtctggctttcaaagccctgttctcctttttttttttttttttttcttttccagggccctgttatctcct tgccaattaaattcaatggaccctttttatttgttaactaacttcagctgtgagtgtcaaagagattgccctcttccccttg
```

-continued

```
actcctgttttccagcttttgggactccatcccctcctgtgtttgctccacgtctcttgatgatgcttctcctcagtttctc
tttcttttttctttctctctcttttttcttttctctttcttccttccttccttcccttctttctccttcctccttccttcccc
caccccacctctctttctttcaaattagtgagaagtatttcatgacttgcttattgtaactcacctttctagatttaggtttt
gcattgcacacacataatgtgattcttttcatatcacacacagagttgcagattgtcttcgtgttgttgttttgtaccttctg
ccctggcagtgttgcccatcaggtgtcctgtagtcaagggacagagcctagaatgtgacatgccaagtaaatattagcacagca
aattagtggacataccagtggctgaaagacttcagtagatgttccatttccttgttccacttcatatctagggaggtgtggctg
acccaggggtatgaagtagagaacactgtcttttctacagcaggaaggcacagtcatggtgtggtagatattttagatgtcta
aaactacttaaggaaagagtcacaaacactattttgaggcagttgaagatataggaaggccagaattgagggtacaggtcctca
cattgtaggaatttattttgtgagtctttaaaagtttgttgtggtttcctcctaagtgttttagagtagaagggaggagacaag
tagattttttttcccacatcctttgaccacaagtccaaagtatagactggagataccttcttagtaaagttagataaatatcta
ctcaaaggtagactcttccaaagccataattggtttatggggtgttgacatccagtgaggttaattatagtcttacagctgtgc
atgagatcaaaatgagttcaaacaaaggtcaggacgagttagaaagttgtatcacacttaagcttggtcccagacaatgttgta
ctaaacagcaataacccagccagtaacaaattttataattgtatcagtcctttggaattgtttagatcttttaaacccatataa
aaataatattctgtgtgtttctaataagtgaggctgctgtcatgatcaaagtggcttttgctcgccagaagtctcactgtagcc
atagtaggcagtgcattggttcaaacactgctgagtaacttggggcatctcagtgctggggatggaatccagggccttgcttat
gctagctccgcctctgcgctcgcatctctgattctgaggggtgttggacatgtttggctttctcgtttgtataagagtgataca
ctcctgctcataatagcataatcgacaatattcctagcagctgggctggaagagatggatgaacaactgagagaatataaagag
tagcctgaggcagagacctagccaaggccactcacggatgagtgctactctctgtctcacagttcagggtattgtgtttaatgc
tggacagtgaagggaacaaacttctaacatcaaaacttttgaagattgtcttaatttgggttttattgctgtgaagggacacca
tgaccaggacaacttttataaaagcacactttaattgaggctggcctacagggtcagaggtttagtccattatcatcatggcgg
gaaacatggcaacatgcaggcagacatggtgccggaggatactgggggattctgattccacatttcatggagcttgagcatagg
aaatctcaaacccatgtctccacactgacacacttcctccaacaaggccacacctaccccaaaaaggccacgtcttctaatagt
gccacttcttatgaccaagcattcaaacacatgaatctatgagggccagacctattcaaaccactacaaagactttcttatcac
ttcagttagaaaaagtaaaattagcacctttaatgaaaaggttccttccacaaaataaaccaccaaggcagcctaagttttata
tgtatatatatatatatacatatatatatatacacatacacacacatatatatattatatatatatatataatata
tatatatgaatttttattcatatatctatgaatacactctaactgtcttcagacacaccagaagagggcatcagatcttattac
agatgtttgtgagctaccatgtagttgctgggaattgaactcaggacttctggaagagcagtcagtgctcttaacctctgagcc
atctctccagcccctataattctttttataagatttcactcttgatatgtaatgttttattcaaagtccagtattatatttca
ttttgtcatcaaagaacccaagactttaagttctggtctcacccggaagctggaaggggaagaacactaacagttacatcagta
ggaatggtaatcctactggctcaataaaaagtccaagaataaagaaatcaaactgctgatagaaaaaaatatatggtcacagc
tttatttatggtggtggacacaaaaaatttgcaaaagatgatgcatgcaggttctctttccatggcttttcccccctaggctt
tgtggacgtaagtgtgagtatgcacatgtgtgtgcatgagtgtgtgtgtgagtatgcgtttgtgtgatttaggacagagataat
actttgggtctattaatgtaaggtatgaatacatttggattaaatgattttaagtaagtggaaggaaatgatacacttgtactt
ggtggaggtaaaattctacttacactgttgataatatattgaactattagtcaaattagaaaggtatttgcttataccagaagc
taagaattagggcagaaagggtcatattttttatgcagtgtgataaaattccttttgtgaccagtaagagtaatgagtatgttgc
agaggaacaacttcagtccccaaggacatatttgcctagctcattagattttaggcaatctctgcagaggcaactgtacatatc
actacgtaaatgtcctcctgagatattcctaagtcattttacaatgcaattaagaataatctctgccttgtaagtttgatgtaa
tgcatttgtttacgcttcaggcaaaattacaaacactatcaaattagattcaattcagtgacacttggtagatagttttttaact
gaattttttaataattagagcataagcagtttctgaagattagaaatgtataactaacttatgaacatgtattattttaacgtta
tttttgcaatgctggggaccaaatccaagacactttcccagcttgttaaacagtcaagtgctcaggtaaaatcttagtccttgc
aggcatcttggtgacactcatgtacttctaagtagagaaataacaaatgtattttatgaggataatttgtaaattcaaactac
```

-continued

```
agcattttaaaaatgattttattttattttatgtatgtgagtacactgtagctgtacagatggttgtgagccttgatgtggttgt
tgggaattgaattttaggacctctgcttcctccagtcaaccccactcgctccagttggccccacttactctggtcaaccctgc
tcgctcaatccctgtttgctccagcccaaagatttatttattattatacataagtacactttagctgtcttgtgacataccaga
agagggtgtcagatctcattatgggtggttgtgagcatttgaactcaggaccttcagaagagcagtcttacctactgagccatc
tcgccagcccatagcattttttttcttcagaaatattctcacatttaggacacctttataaaatgtacaatattacaacatatt
agaaaaaatcaaacagctaacaaggcaagacctagataacttaattttctttaaaaggtaatacaaacattttaataataggg
tattaattttgaagtagttgtctttataaaatccaattgttctgtgtgtgttttctttctctttctctctctctctctctctctct
ctctctctctctctctgtttctctccccctctctccctccttctctctgtctctatctgtctgtctgtctgtctctctctctct
ctctctctctctgtgtgtgtgtgtgtgtgtgtgtgtgatatgtgatgtgatatgtgtgagggagggcaaccttggggattgt
ttttttttttttttttctttttcctccaccttttttgtcagttccaggcattgaactcagccactttgcttgctgagtcatct
tgtcaactgtggagtagtcctcttcaaagtgtccacagacactgataatatccattgtttactggactgagctcctacagaaat
ctgctgaaagttacttgcagagcaaagaaagggcaatgccatgtgcagtgttgagactttcccatcaccaccatgacaggaaca
atgacaacagtgactgataggagagatgcttacatctatgaaagctggcaggtagggtccatctagcctgtgaactgctgatgc
tcatgtgcaagttcaattaaagtgaaattaattttgattagaaaatataagggctggcaagatggtgtatcaggcaaagactcc
agctgccaggtcttatgacttgagtttgatcccaggccctacctagtagaaagagactcctgcaagttttcctttgacctacat
tcacaaactgtggcatgtgtgcactcctacaatacacatatgcacacataaatgcacttagaacaaatacatatgtaattaaga
atgtaaaatgtgggactggagagatggctccacactaagagatgttttccggaggacccaggattgatttttttctgcatct
acacagcagctcccaacccatttgtaatttcggctccagagaatccagtgcctccaaaagcattgtgcagatgtggtgcacagac
agacagatatgcaggcaaaatacccatgcatataaattaatataatagcaaacggtcaacacagaagtttgctttagttggtcc
ccatactaacgtaagacaattttaaacagaacaacaacaagaaattagcttgctttctctaattcctatgctccatgtcacca
tatggaaaacactcattacttttaggggagccttctcaggggactaacgaagaaacctttactaatcaaatatcatctaagg
aaattgtgttctttcttttatatagactttgctggcagttcacaatgcttaccatgtgtgtgtgtgtgtgtgtgtgtgtgtgt
gtgtgtgtgtgtatgtgtcttatttcagaagtttagtccactattgtcatccaggaggcatggcagcatacagggaggcta
tggtgctggaaaaagaattgagagttctacatcatgatctgaaggcacccaggatgaaactgtgagccactctgggcatagctt
gaacatacaagacttcaaagcccctcctctacagtggcacattcctccaataaggccacacctactccaataaggtcacactttc
taatggtgctgctccctatggccaagcattcaaacacctgagtcttagggggccacttatattcaaactgccagatgagcagat
atattataactgaggtacatctccaactccagtttctcagctaagtaattttggaagtatagtgtttccatagaagttttaaaa
aatacactcttgaagatgtcaacttgtctacaaatgaaagattttgagataatcagagattttatgacatacacctctactagg
taaagtgtgttcagggcaccactcacaaataccttttaccatttattttcactattaaaaaattttttaaaattagcatcacttt
cccttctcttttctccctccaacccctctcatatacttatataatatacttatatacttcctttattctttctcaaattcatg
gcctcttttctttaattgttgtcatatatatatgtatatatatgtatatatgtgtatatatatgtatatatatatgtatat
gtatatataaaacatataacatcacacatacatatattcctagatacagaactacagtctatataatgtctcttatatgcatat
tatttcagtgctaacaatttgcagatatttttatatatgggatttatgtttacaaaagacaaagtttgtctccaacaagcacag
atataccattttgtgtgatggcagctgttttaccagtggaaggggctccttggcttaaagcacttctagtttatctcctggagt
ggctttctgatccaggaactaataagtggagaaatgccgtgtaatttataaatgtatatatacagcaagtggtcttccacaggg
ccgcactagagcttaagtgcctctcagtgagctgacatttttacttctgaaaacactaagtgcccctcgttccagagtctgggg
tcctgagcagctcaagcaggacgatgagcagtgttgccgaaggttttgggtgggagagattgggaacgctcttcagagcctacg
gatgcagaggaacaggctgtgaagatggaagcaacagcaagatagttccaggagaaaagatcagacacagaaacccagagatc
tctcaccactaagttcatatagagtcttccttaaagcacatgggggaatgaaagactgctaatagagaaagtcactcaccatt
tcatctctttcagaacgttgcaaatgtaagcctgtcagagctacacagaagacctatttccggaacaattacaactatggtaag
```

-continued

```
gataccattaccgtctgcttatagattgctgtgttttgggaaaccttgcatgagcattttaaaagtaagccaggcagtgatggc acatgcctttaatcccagcacttgggaggcagaggcagatggatttctgagttcgaggccagcctggtctacagagtgagttcc aggacagccagggctacacagagaaactctgtcttggaaaaaaaaaaaagtaaggcttagaaacaaaggtcacttacaagtgt tgtttccagtttcatgtatcatagtgacaaagttcttctcaaatgtgtgattgtgagagcatcggttttattaattcattaatt aaaactatagcattgagtaccttaagatcagtttccaagtagaagttcttgtctctgggttagtacctggatcccggctgtgct ccacaagaaacacccaaaggacactgggaagcaacatttaatagttgtcgctattcatctgagggaatcctttgctatttaact tgaccaaatataacattttaataagttaagtgctaactgcagagcctcctgtacaagcagagctgactgacataatgggaggat gctatctcctggggacaacttcaggcgctttctgtggactatctcatttcaattctcatgagcacccttctcctcctggctt tatgagtgatgatgactgagcaaaagctacccttctttatcgtgtataatgtacgtttgggtactttatgcttcagtgaat gtcagtcactgttatgtgacacaggcaatcagtccctggtgttcctctgtcggaaggttgggctgctcagtgttactggtttcc acagattttttttttggggggggggggtgggtttcgagacagggtttctctgtgtagccctggctgtcctggagctcactttgt agaccaggctggcctcgaactcagaaatctgcctgcctctgcctcccgagtgctgggattaaaggcgtgcgccaccacacccgg cagatttttttttttaaactataatttcttttcaagtagatgctgagtattccttatccaaatgtttgggaccagaagtattta ggattataggctatcatttttgtattttggaatatttgtgaatgtgtgggaatactcttaggagcgggattcaggttcaagcat gacatttgtgtttccctgacagttcctgaaggtgcatcactaattggactgtgacctgtcacatgaagtcaggtgtggaattt ccatgtgtaacattgtgttggatttggtaggaggaatgcacagccagtcagtgaagctgacacgctcatgccgctctctgatcc cgagttaatgactaaacatggattagaaaattctaaagttaactatgctatgaaaatgagaagtttgtctttatgtgctttaat tttagaagacgaagggtgtatagagatttggctcaaattctagagcaggagttctcaacctgtgggtcaccaacccctcggggg tcaaatgagcctttcacaggggtttgcttaagaccacgggaaaaaggagctatagggaactgcaaccctataggtggaacaaca atatgaactaaccagtacccgggagctcttgtctttagctgcatatgtatcaaaagatggcctagtcggccatcactgcaaaga gaggcccattggacttgcaaactttatatgccccagtacaggggaacgccagggccaaaagggggagtgggtgggtagggggat tggggggtgggtatggggacctttgggatagcattgaaaatgtaaatgaggaaaatacctaatttaaaaaaaaagaaataa acttgaatccaagtcaaaaaaaaaaaaaaaaaaaaagaccacgggaaaatacagatatttacgttacagttcatagcaaaat tagttataaagcagcaatgaaaataatttatattaggggtcactacaacataaagtactgtattcaaggatcccaacactaga aaggttgagaaccactgttctagaatttgggattaggagagaagtggacatgaccaagacagtaatgtttggaagtgcaact tacgaaagagcataaaagaagctcttgggggtagatgagtctgaatgcaatttctttcccaaattttcttcagtaaaattata tctttatttttattatgatttatttgtttttagacagggagtctgcacttcaaaggctagtctagaacttgctctgtagccca ggttgcccctgaacttgtaacctcagcctctccagcactacagttataggcatgagctaccagttggcagagtgcttatcttaa gaggatcttagccactcttggttagagaggaacagacagacatcccaggggaggacagatgtccctgggtgaagggcttagttc atctaagaatcaaaagctggttacttatctacttctccttatgcaaactgccctgactgcagggatagggggggccttccgtttc agaaggccagcttttaagacttataaagtccatgtgaacttttaaatatagctatcataaaaagcaaaaccataatttcatac catgggtcaggtagtggtggtagaggccttgcttggcattcacggaactctggattagatcttcagcatcacataaaatcggtt gtgttgttcaatattattctttgatacatagcaagttggaggccagcctgggatacatgagaacctgtctccaagcaaaccagc agaaacacacacacacacacacacacacacacacacacacacacacagatgcacgaatgaagacagacactgaaaacagt aacaataaaaattatttcaaagatatgagttatttttatttatctttacttacaacttttaactttgcccagcttccttgttaa cacaatagctggtggtactcttaccattaaaagttaaaatactaatctttacaaatcattttggagaaggtagctgagtattat aacaattgataaaaaggaggagctttgtatggtaccctatctgtagtccctccaagcacttaggaataaggtcaagattgctgc ggtaaatctccaacccaaacccaaatatgcctggcaatgaaaacacaactcagttaatatgaatacatgctgtgcgcctagact gggcagagctactgctacactaccatcttcacatcttatgagacctcttcgaactttctccaggccatgtgcttctgctccac ttttcttcttcctcctcctcctctgtgtcctctccctcttccattttctccttcttctccctctccaccttctgctccacc ttcccttagtctgcccaatcatcaactcttcttttatttttacaaattaaggtgggaagcaggtttaccggaaatcacctgagtg
```

-continued ctgactctttccttgcgaagctactcacaggataacggaattaacatcaaatataattagccccagggctatccataacacaag aggatcaagagttcaagtccagttgagactgcattgcaagttcaaggtcagcctaggtttccccagtcgctattgagaaaaag aaagaaagagaagagaagagaagagaagagaagagaagagaagagaagagaagagaaggaaagaaggaaggaaggaaggaag gaaggaagacagacagacagacagaaagaaagaaagaaagagagagagagagaaaggaagaaagaaagagagagaaagaaagaa agaaaggaaggaagaaagaaagaggggagggggagaaaatattctctttgtcatagctagacactatagccaccaatgatttaaa gattgattttgggtgggactaacagattcttaggagaaaatagcccctccaacgcttggctagaaggcaaactaatggaaga aaatattttgttttaaaatatattgattttcactattgtatgcatttgcatgtttctgttgagacaggaacaactgctaattc atatgaaatctctgcctcattcctgaccgagtcagtaaaaaattgtgagctttagcaaaattacttgaataatgaagtaggtgt tgtagagaggtattattttttggaggcagtacatgtgctaaaaattcctaatgaaaatagtggatgcaccgagaaaataaatcac tggcctgacaaccttcgcccagctccctaatcgctcatggctcatggatactgggaagcacattcatttaagccaggactcaca caaacatgtctgctagctggtcttgggaacttaccgtctggagggaaaaccttatctcttgtcaaaatacagggcagagagaac gggcaaagacagggcctccagttgccattcaagccaggcagagccagctgggcagttagactttgtctgcaacaaactctcaca cttgtgttgcaacaaagtctctgaagattgaaatactcatgaataaagcttacagattttggtaactgagtctctgtccagtag attgtcatacctgtagaccattgagtcaccatataaaagttaggtcgatagtggaatgcattatcaggtggttttatgttttg gtggagggattttttttttttttttttttactcaatcctgtataatcctgaacacctaaaatacctgggagaatctgccagtg gcagtttgtacactcctacctacagagctcctccaaggtggattctcttgcatatattgtatttcctttgtggacattgtatta atatgacagagcttcctgagcaattgctgttggcttttttattaaataacaagtttgactctttcttttttaataaatataaaact ttcctgtacaaatgcatacttaccagaagcagatccctacacaatgtggctcttcaaaaaaaaaaaaaaaaaaagagacacgga gggaatagaagaaacatagcttctaggttctgagtcacctcatttgactttgcagatggaagacagtttgtctttgtgttgaaa agtgaagctgacacctgtagggagtgctggggtcactacttgcattgggggaagagaactgatgcaatcagcatgctagaacat tgtccccgacatagcagggtcacggggtagcagcgtggctgagtggaaggcagatggaggagacaaggtctaatggacaacttt tgctcacgaagaaagttcatcgtccctaaaggagatacaaaccataacgctgggggctggagagatggctcagtgattaagagc actgattgctcttccagaggtcctgagttcaattcccagcaaccacatggtggctcacaaccatctataatgagataccctctt ctggtgtgtctgactacagtgacattgtattcatataaataaataaataaattagaaaaaaaaaaaaacctaaaaccacataa cattggtgtgaaggaaggaaagtgccaatgtcagaatggcgagatgtggtgagggaggtgaatgtccaaggagttggtttggga acaccaataaacaagactgagttgtagctgggaagagagcctgccttgagaaaactgatcaactgaatagttctgatgaagaaa caaagcatcgagttgagtctaggccttaacatgggggtaaaattagtttaagttaatacctttcagcagccattggtaccacaca cacacatagccacacatccaaagtgaggctgtgtagggaaattataatagattactcaatcaactatgattacctaagtgggtt cgtgaaaatcaaacgtctatacacacatgcgtatataatcaccaatgtctgcatacacagatacatacacaaattggcagggaa tcagggctgagcaagaaggccagtatggcatttagtttctctaaagaaaaatgtctgcctgacatttcctttctaaccattgat catgaaattgagaggaattggctagaaagaggcctactggctttttttttttttgaagggtgtaccttactgtgtgtcatcat ataaatcaaatttactgtcttttattcagcatccgggctaaagttaaagaggtaaagatgaaatgtcatgatgtgaccgccgt tgtggaagtgaaggaaattctaaaggcatcactggtaaacattccaagggacaccgtcaatctttataccacctctggctgcct ctgtcctccacttactgtcaatgaggaatatgtcatcatgggctatgaagacgaggaacgttccaggtaaccttcccctaagg atgcaggggaattggttttccttccacatcttgctggcttttcttgtcttaggctctttctactttcttgagaactatggtta tatattttaattttacatattggatagaaagggatgtgagcatagcttatgggtatagattttctggaaagcaagatcatag ttcattttatttctaaaagggatccacgattcctaaatggttaagactcttctcagctctctggcatcagattctaggatgaaca tacttagttttttcttgccaccaattctttgaattttcaattatatactttggttttcaaaataatttgattttaaaatgca ggttactcttggtagaaggctctatagctgagaagtggaaggatcggcttggtaagaaagtcaaggtaagcttggattttatgt tcaaagtagtactggggctgggacttagctctgtggtagaatgcttacctagcaagtatgctccaggttcagtccccagcacca -continued gaagaaaaattctgtctgataatataatccatagaaaaccatctttcacataagctaaatagttgtcctcaactacatgagaat attaagacctgatacacacacacacacacacacacacacacacacacacacacacacacacatacacacacacacatgacta ttctgagaactgaaattattgttaatgtctattcatttatgaaattaatttcctctacgtgtatcaaagctctaagtacagttg ccctaacttcttgggaaatcgcctatagctagccaatcatgacagactggctttatgctagcattcagagcccagcctctgac agccatggtcgggtaccgcttccatcttcttgttcagtaggaatcacacagtgctgttctgccaccaacatcatacatcattcc aggcagaaagatgcaaggaggtcaacataggttttcaagaactcttccagacactttatcatgaaacttttgatccgaacatg ggccatgtctatctccacttgggaaagcagggagtaggggttttttattgcttctaaacaaattgcttttctctgagaagagggg gaaaaattagtgctgaatagaaaaataccactgtgtccaacggacagatatggactcctatgagtgagatgctgccacagtcat aagtgtagaagagatgtcaccaaactgggtacttaaaacaatgatgtggctttaatattttatattaagaccctagaccatata tatgcatgtatgtatgtatgtatgtatgtatgtatgtatcaagtagtacattactcaatagaaatggttttgtgtttc ttattactacactagcacatctttctcaaaaagaagaacgagtgggaggggggaatgcataggaggcagaggactcttctaggg tgtgtgctgggaagggggttgggagtggaaactgtaccaaacatacatcctcttctgagagctggagggcgtgggtagcatttc cagggaaagttaaaccctgaggcagtttatgacatatggcacccagcgtgggtggcagacacacctgagtcgaagagacctac agaaatgtcgagggcatggtttcattgatagaaactaccgctactaagttccttttgtctctagagttttgtcagaagtgagg agcatttcagatgcggactgtgagtgtttttgttcccatctctcaccaatgaacctggtgtttaattattagtggagaagtgg ctcttcttcagagtactgggatgtcctttcagcttttcaagtctgttttccgcttccaagtgcagaacaggaatttgtcctaaa ttcccgtaccagttgggagaacttcagcacctctgctgctgtgtgtaacaagcctcgccagttatgttcccactgggaggcacg gcttgtcctgttttgtagcatggtgaatatattcccttcagggaaatcatagttttatgggatcactgatgttctcagattga atttaaacacactaatgggaaacaatgaaccagtgacttgaataactaattaatctttgttgttttgagactgtcttgctatgc agctctggctggagtgatacttttgattcagcacaggctggactggtacctacaatgtagcacaggctggactggtacctacaa tgtagcacaggctggactggtacctacaatatagcacaggctggactggtacctacaatgtagcacaggctggactggtaccta caatgtagcacaggctggactggtacctacgatatagcacaggctgaactggtacctatgatgtagcacaggctggactggtac ctacaatgtagcacaggctggcccagtacctatgatgtagcacgggctggactggtacttgcaatgtagcataggctggcctca aactctgtcgtcctcctatactgctgctgtttttattatagtaatgtatcactgctcccaattctcttctgaggttcttctttt gaaaaagattcttaaattttttatttatatgtatgagtattgtctgtgtttatgtctatgcataagttcctcgtgcccaagaa ggccaggagagggtgtgggatccctaggaactggagttacaaatgtttgtgagctatcccctgggtgctgggaacctctggttc tctgctagatcagcaagtgtttttgttttttggttgcttggttggttggttggttttaaacagttctgtgtagccttggctgtcc tagaacttgctctgtagaccaagctgccctcaaactcagagatctgcctgtctttgcttcccaagttctgggactaaaggtgca ccaccactgccaccgtttccagcaagtgttcataaccgctaagctatctctccaggcccagtgggccattttttaattcacgttt atgctctgagtcagaagtttggggagaaaatcagttctggttggaattattagcatacctactgtagcttttcagttaactcag gaatgtttaaaagactcttatggaggatattattttttaaattcaatataagttgctctttagagctgatctttctctctctctt tttgttttgttttgttttgtttttcaagacagggtttctctgtatagccacggctgtcctggaactcactttgtataccagg ctggcctcgaactcagaaatccgcctgcctctgcctcccaagtgctgggattaaaggcgtgaatcaccacatctggcgctgaac tttctcttaatagtaggccagttaaaaagatcatttaccattttcctatgtaaatgattatttgtctctgtttcgagacagcca attgttcaagatatttgaattatcttggagagagttaagaatcagattatttttttaaatatgaaagcaatattactatgcaata aagtcagccaagatgaagatgtattttaatagaaaaacaagtaataactaatgtattaatgctgtgcactttgcaatttttttca atcttcagaataatgctattattagttattaatcccaatatagaaacaataaaaatgtcgattagttcagaagctttgtacggt taagtagtgagttagaatcaggatttgggccatctgccattagcttcttgctacttaaaatgaggtcattgaaccagcagccca cagatcatctgggagctcctggcctgtggaaatcatggactgcattcagagctgataaagaggagtctgttctcagtacgggcc tctggtttctatgtttgctgaagtttgtggagtacagatgttcttatcatttcatacactttcaccatgtaacttccattcaat ttcttatatcacaaataagcagtattgacatcattcatatgaaatacaagtcaatgtgacttttcttatttaaaaagatgtatg -continued

```
caacaacaattaacacctccctcccccatgcattgtaaagcctgtggcagggaaggatcttgtgggtttgctgtaattggtg gaaaatactagaaaaatattttagaggcaccattttcccttatatcttcactatttagatcagcttattttgtgtatatgtgt atgtacatgttcatacatatgcactttgtgcttactggtgaatgtgcatatgatggctggaagtcactgctaggggtcttcct caattgctctctgccctacttttccagacaaggtcttccctgaaactgattctcactcataagctagactcactgactatgga actctaggacctgcctgtctttgcccctggcttgctgctctcagcactgaggctgtagatacacacccagatgctcagtac caaacatcaggttcttgcacgtgtgccatctccctaaccactcaaccagtttttaaaaagtttcgttactttagtcttaagaaa atgatgagaaaaaaaagcccttctttcaaactgccaacataaatcttccacttaaatataaattctgaaagtatagatactgt tgacttttgtatcatttacagacatggaattttagttctatgttttggtacgatggcatccttgaatatcttacagatgagatg gcttctgctgtggttttttggaatcagagcattgtgtttatacagtgtcattgttatccttggatagagattttgtacttttgga aaagtagcaaaacactttagagatctgaccctggactctccctcggttgatagcatcatagaaataacaccccacgtgatgtgt cctcgtgactgttctctcttttacattttcacaggctgggatatgaaactccgacaccttggactgggtaaaactgatgctagc gattccactcagaatcagaagtctggcaggaactctaatccccggccagcacgcagctaaatcctgaaatgtaaaaggccacac ccacggactccctttctaagactggcgctgctggactaacaaaggaaaaccgcacagttgtgctcgtgaccgattgtttaccgca gacaccgcgtggctaccgaagttcattccggtcccctttctcctgcttcttaatggcctggggttagatcctttaatatgttat atattctgtttcatcaatcacgtggggactgttcttttgcaaccagaatagtaaattaaatatgttgatgctaaggtttctgta ctggactccctgggtttaatttggtgttctgtaccctgattgagaatgcaatgtttcatgtaaagagagaatcctggtcatatc tcaagaactagatattgctgtaagacagcctctgctgctgcgcttatagtcttgtgtttgtatgcctttggccatttccctcat gctgtgaaagttatacatgtttataaaggtagaacggcattttgaaatcagacactgcacaagcagagtagcccaacaccagga agcatttatgaggaaacgccacacagcatgacttattttcaagattggcaggcagcaaaataaatagtgttgggagccaagaaa agaatattttgcctggttaaggggcacactggaatcagtagcccttgagccattaacagcagtgttcttctggcaacgtttttg atttgttcataaatgtattcacgagcattagagatgaacttataactagacatctgttgttatcactatagctctgcttccttc taaatcaaacccattgttggatgctccctctccattcataaataaatttggcttgctgtattggccaggaaaagaaagtattaa agtatgcatgcatgtgcaccagggtgttatttaacagaggtatgtaactctataaaagactataatttacaggacacggaaatg tgcacatttgtttacttttttcttccttttgctttgggcttgtgattttggttttggtgtgtttatgtctgtatttgggg gtgggtaggtttaagccattgcacattcaagttgaactagattagagtagactaggctcattggcctagacattatgatttgaa tttgtgttgtttaatgctccatcaagatgtctaataaaaggaatatggttgtcaacagagacgacaacaacaacaaaaatgttt ttcttatgtgtgctgcactgagaccccaacaacccatgggtgggggggaacccacgatgccttttcttccttccctgcagcagg gatgtgcccatcacctgaaagtctcattccctgaaatttacacatgtggtagtagtaggtccagattcctaagttacagtgtgc tgaaaaataaaacaggtatgaagcaaatggtgctgtgtttccttctgtgagaacaaccacgcaaggatgaagatcattcccaag cggacgttttctatcttggcaacttttctaaattctttcttttagaagaaaaaaaaccatcctcactttccaatgagccctaaac accaaaaattcccccaattctagaaccatactcccatctttgcccctaggaggacagcacaggcttcaatctactatgtagtta ctttctggtaccttgtactgtgtgttctgatgctgggagagggttatcttttcctaggtgttgctattatcctttcaaggtgaa ttttgtgtccctgggtattgaggagtactgctctggggatgctgaggtaggggttgggggagggaagtgcagtactaaggatg ctggtctccaatctctcccagggtatctgtctcggctttgggctcccaggatgaacacatacatcctattcatagcaaccctgc agaaagggcaggacttggtgacaggagccttaagggatctggcatctggagtccctaacatgccatcagtgtttctagggtgta cttgaagctatttaagtgatgaaaattttacggtatatttatttccttttttatggtcctgaagatagaatctggccctatga atgctagatagctgttctatctacattgccatctgtatctgcctacatcaagctactcagccagtgatgaaatatctttacata aacaagaacctatatgtaggtgctttgtttaggtggatagatgggaaaacatatttgttttcagtgtaggaatttctcacatag tagatgtaactcctacacagttacactcatagataacggggcagtctctgagataaagcagaatttctactctcttccatttc tgggccaacacctgtgaactaaatgcatggctgtttctcagtttggtagctgcgacatcttcactaataaactgtgcagatatc
```

-continued

```
ttggagggaggcatgatttcatcatgacatgcaggttttttgtgcacactgcaaaaccatttccactccactattgtcatataag tctcaccagtgcctctctgcaggtcctttatgctcccttgaaagccactaaaagctgagttggtggtacattcatttcatctc atcactggggaggcagaggcaggcagatctctgagcgtgaggctagccctacagattgagttccaagatagtcagggcaacaca gagaaacctcttgttgaaaaacaaacaaacaaataaataaataaacaaaaccaaaacaaaaggccactacaaatttaacatgca tgcctgcttgttagtaaaccttgaggcctttgaaatcaattgaattttcttaagacaattttgctcaccttcaggattttaat tttctcacccagcacagcagcaaaacagtcgtgtgcacggtgaatgaaccatcgaaaacacgagcagcaagcatgtatcctctt tttcatggatccatgagtatgtgactgtgttgtatgtagtaatctgacccggtgccacatggtccactgagcattgggggtggg gtgggacaatcccgtgtctttctccatctggaacctattaccaagtcaaatacaagagttacaatcactgtgagtaaatagctc tgcttactgccttctgcaagaaattatttgctattacatttcaacagtaaaatgactccttaaaaagcatttcaaggctggtaa ttgttcagccctatggattttaacgtttaatacagaataaagaaagcagtaaggaagaagttaaaatccaagcccagactttt agtagtgtgtcactgaaatgcaagcatatggctcccagctgcatccaagttaccgaataacgaaaataacgtacgcatagcttt gatggggatctcctctgcatcctgtctagcagtggctaaaagttatacaaaccacttacacatgtcctgttggtgccttaaaac tttatggt
```

Examination of this region using Ensembl demonstrates that there are several CCCTC-binding factor (CTCF) sites in close proximity to the binding peak. Indirect frzb-GR binding was confirmed by designing 2 different sets of primers for frzb and performing DNA qPCR using the ChIP DNA; frzb was not detected using either primer set. Interestingly, using ChIP input DNA, the loss of GR reduced CTCF expression >80% suggesting that CTCF may regulate frzb in a spatiotemporal manner via GR as has previously been demonstrated (20, 21).

Figure 9A:
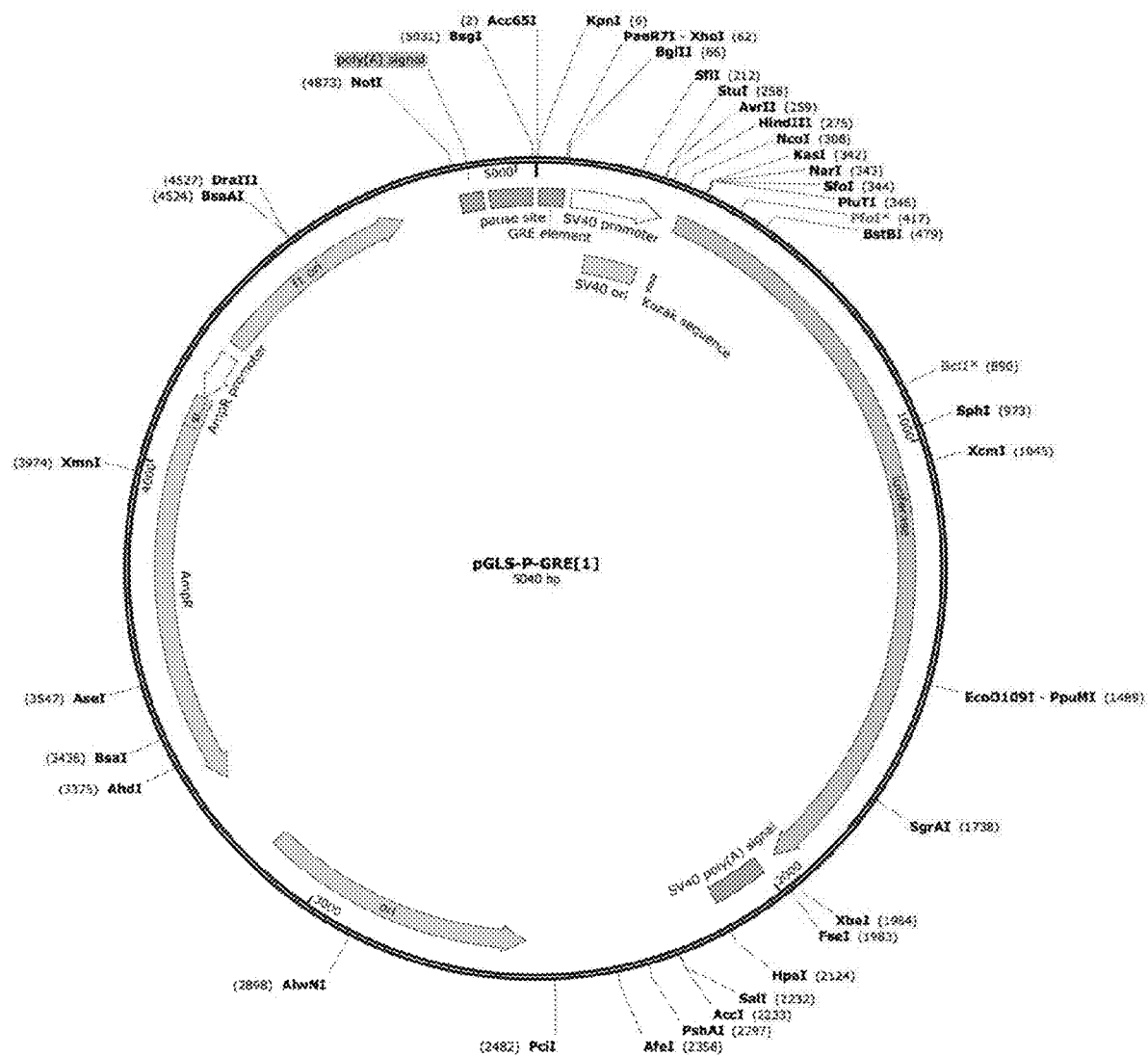
FIGS. 9A-9B. Luciferase constructs for (FIG. 9A) known GRE and (FIG. 9B) experimental motif.
Figure 9B:
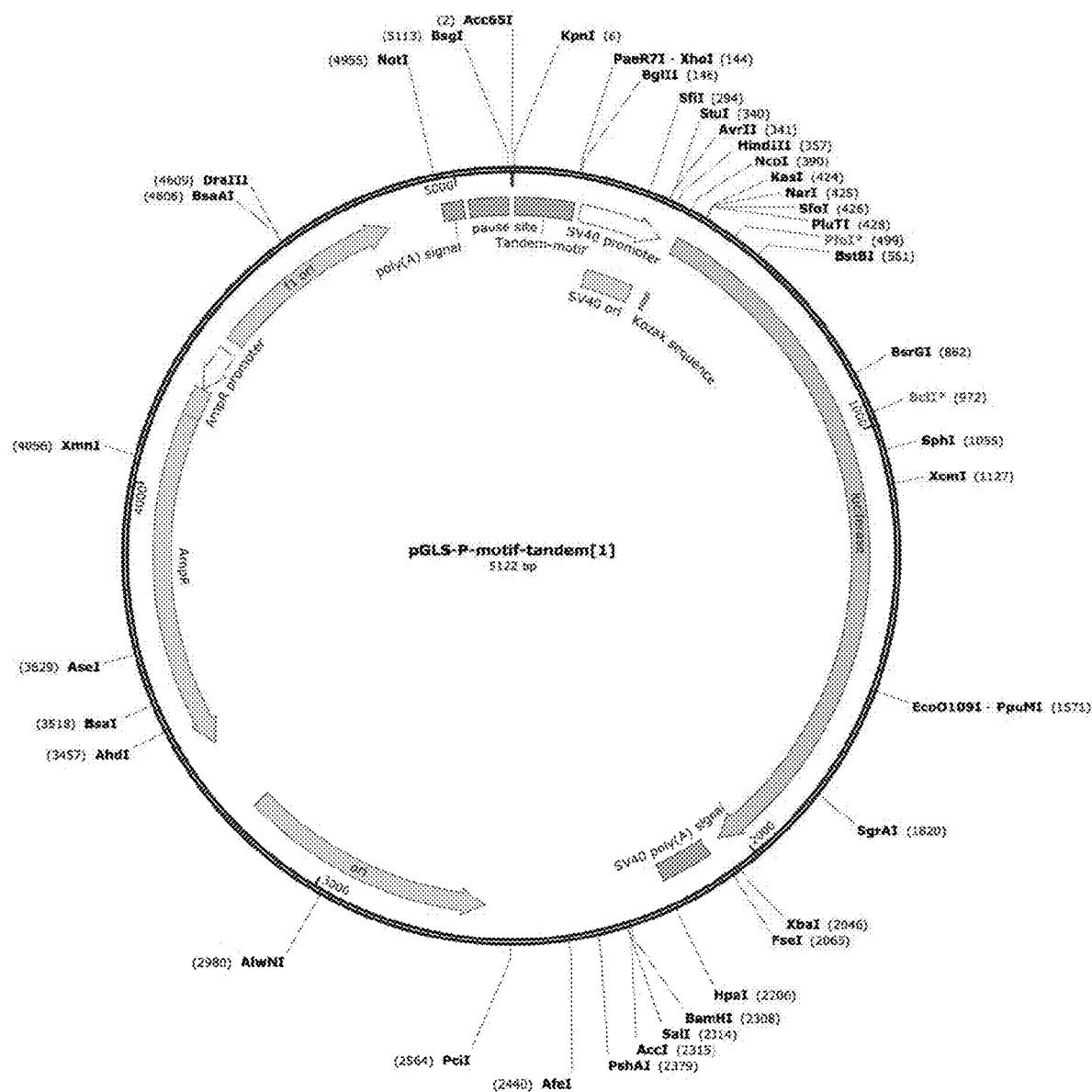

To test whether this motif demonstrated functional regulation by GR in vitro, several luciferase constructs were generated and expressed into 293T cells. The pGL3 basic vector was used as a negative control and a previously described GRE (22) (FIG. 9A) was used as a positive control. The experimental motif was cloned as four tandem repeats (FIG. 9B), while the positive control contained two classic consensus GRE sequences derived from the tyrosine aminotransferase (TAT) gene promoter.

Figure 5C:
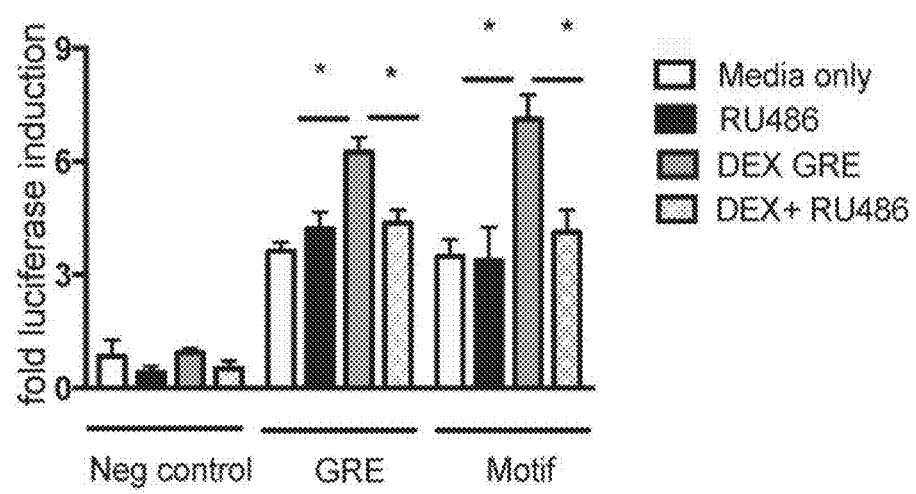

As shown in FIG. 5C, after 4 hours of treatment with DEX 100 nM, the new experimental motif resulted in luciferase activation that was very similar to that observed in the positive control. As expected, the negative control exhibited very low signal. The activity of both responsive constructs could be significantly down regulated, though not extinguished, by 4 hours of treatment with 1 µM RU486, a GR antagonist and this effect was unable to be reversed with subsequent DEX treatment validating the receptor-specific response. The high baseline activation observed in the media-only condition, for both the known GRE and the motif, but not the negative control, is a result of small amounts of endogenous steroid in the culture media and further confirms the validity of the assay.

Example 7: In Vivo Activation of Wnt Signaling in DKO Mice

Figure 6A:
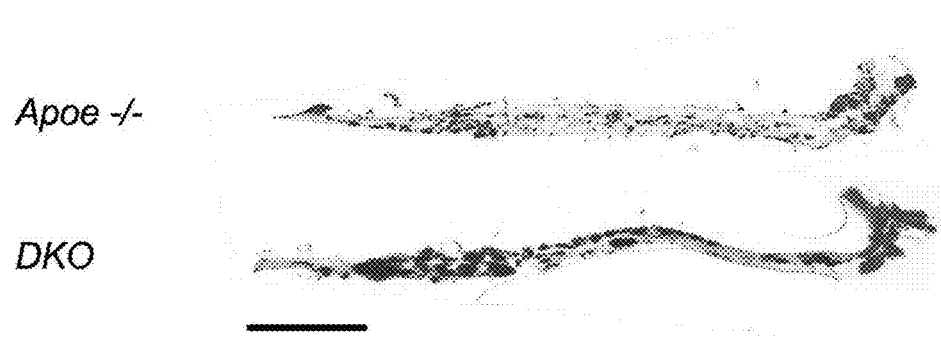
FIGS. 6A-6E. In vivo regulation of canonical Wnt signaling.
Figure 6B:
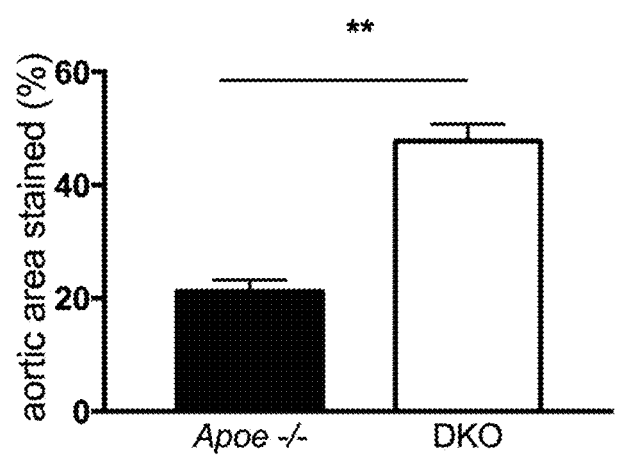
Figure 6C:
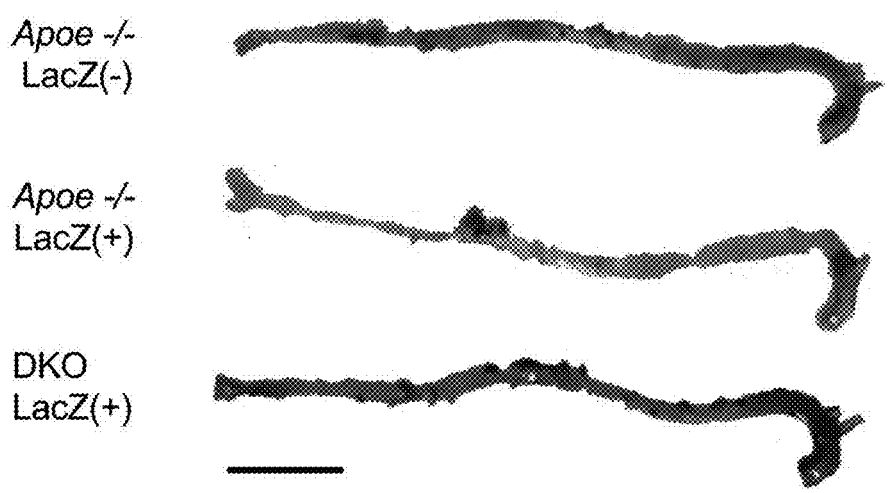
Figure 6D:
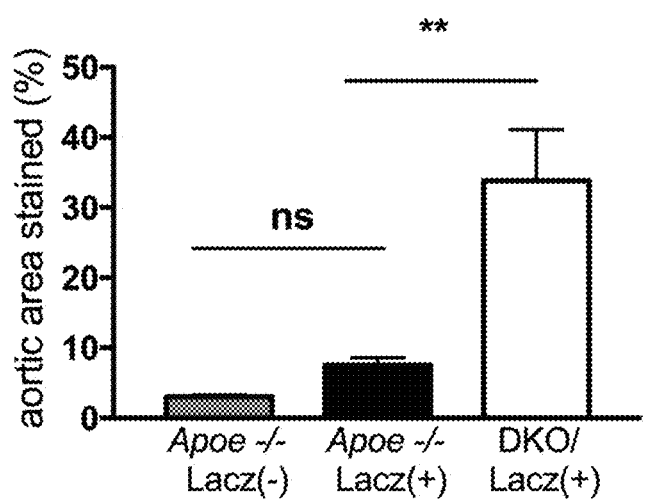
Figure 6E:
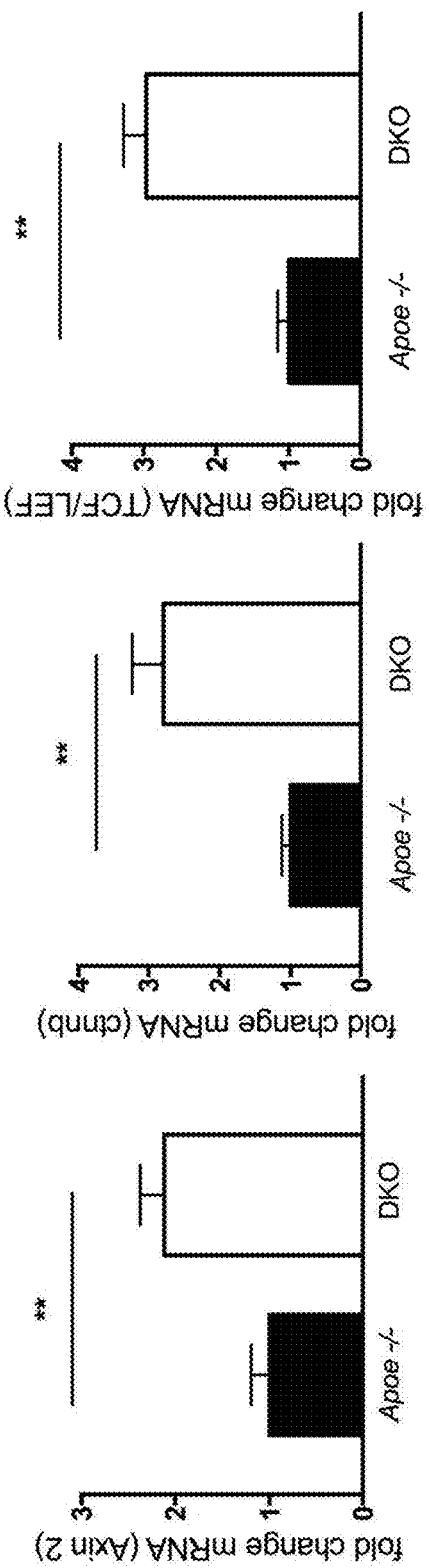
Figure 10A:
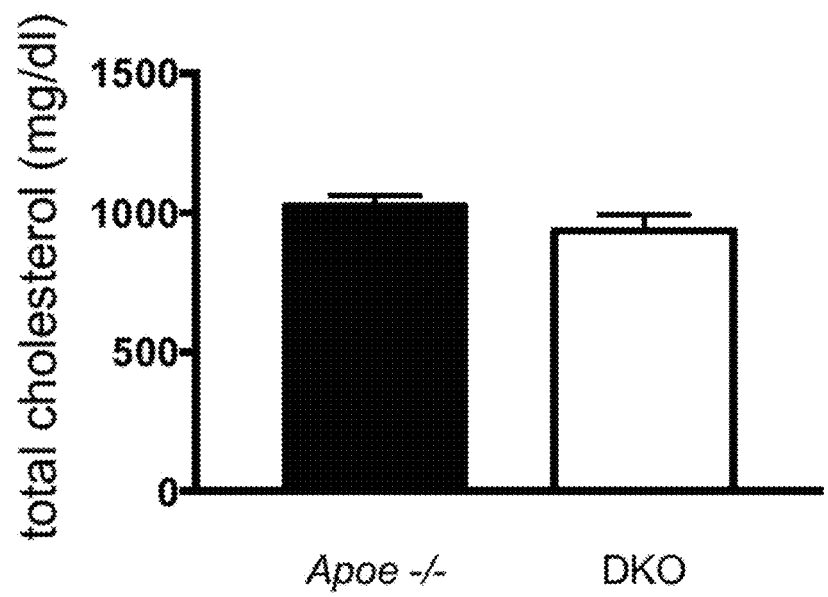
FIGS. 10A-10B. Plasma (FIG. 10A) cholesterol and (FIG. 10B) triglyceride measurements in Apoe −/− and DKO mice fed a high-fat diet for 12-weeks. N=6/group.
Figure 10B:
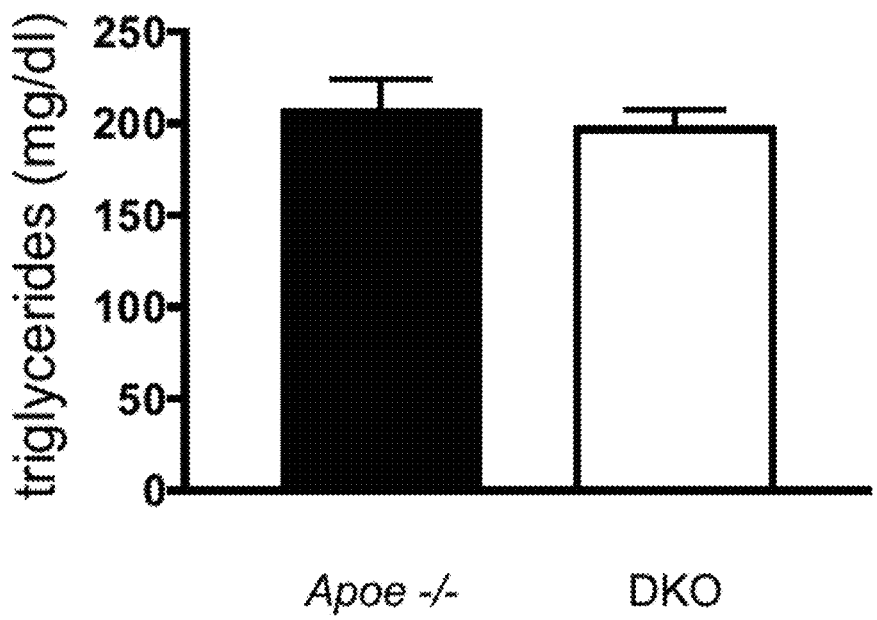

To enable direct visualization of the activation canonical Wnt signaling in vivo Apoe −/− and DKO mice were bred to the TCF/Lef-LacZ reporter mouse and subjected to 12 weeks of high fat diet feeding. At the conclusion of the feeding period, aortas were isolated and stained with Oil Red O and X-galactosidase. As shown in representative aortas in FIG. 6A and quantified in FIG. 6B, DKO animals had significantly more severe atherosclerotic lesions, consistent with previous results (7). LacZ staining in both genotypes, shown in FIG. 6C and quantified in FIG. 6D, revealed significantly more staining DKO animals consistent with up regulated canonical Wnt signaling. Aortic endothelial cells isolated from animals of both genotypes at the end of the feeding period showed significantly increased mRNA expression of the Wnt-dependent genes axin2, ctnnb1 and TCF/Lef (FIG. 6E). There were no differences in total cholesterol or triglyceride levels either before or after high-fat diet feeding, consistent with previous results (FIGS. 10A-10B).

This Example and the previous Examples show that endothelial GR is an important modulator of the Wnt signaling pathway, which influences inflammation, both in vitro and in vivo. Notably, the repressive effect of GR on the Wnt pathway is independent of the NF-κB pathway, a classic target for GR, and highlights the permissive role of this receptor in physiologically relevant states.

The Wnt signaling pathway is gaining prominence as an under-appreciated player during inflammatory disorders such as atherosclerosis. In vitro, Wnt ligands have been shown to induce endothelial cell proliferation and modulate inflammation (23-25). Non-canonical Wnt5a/$Ca^{2+}$-dependent signaling induces endothelial inflammation and release of inflammatory cytokines (26). In vivo, Wnt5a staining is up regulated in both murine and human atherosclerotic plaques (27).

In these examples it is shown conclusively, using both next-generation sequencing techniques and a novel mouse model, that endothelial GR is an important regulator of the canonical Wnt signaling pathway. These results are in good agreement with ChIP-seq experiments done in A549 cells which also show proportionately increased binding of Wnt-related genes based on publicly available data in the ENCODE database. Independent validation of selected targets in vitro and in vivo using a DKO mouse model further validated these results.

Figure 11A:
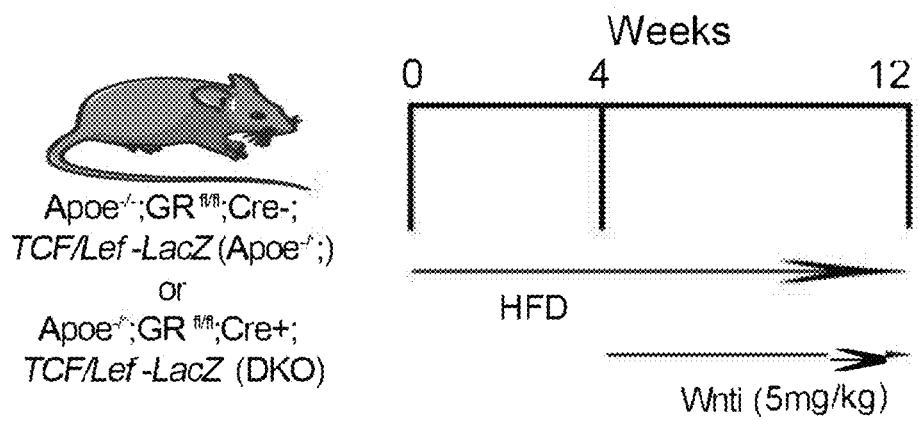
FIGS. 11A-11H. Inhibition of canonical Wnt signaling significantly improves the atherogenic phenotype in mice.
Figure 11B:
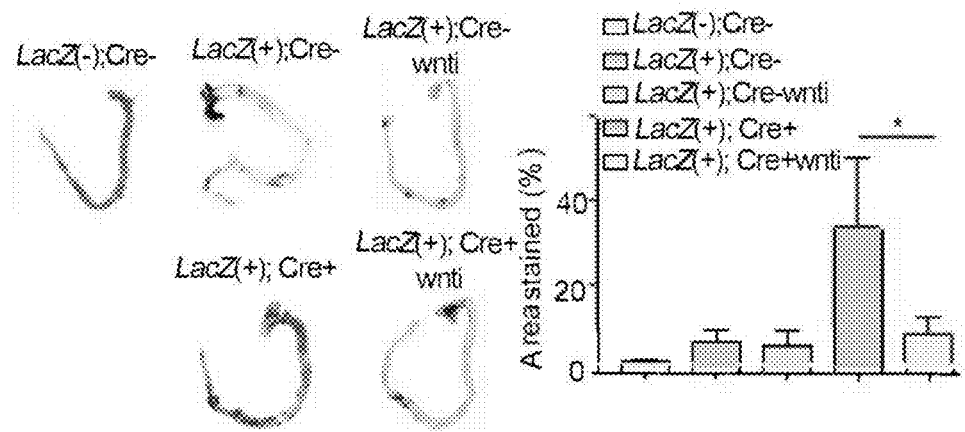
Figure 11C:
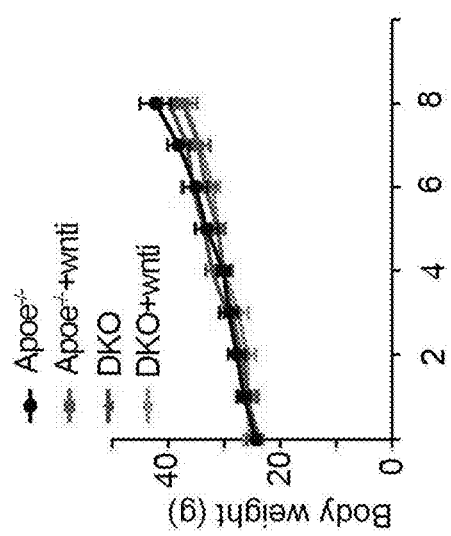
Figure 11D:
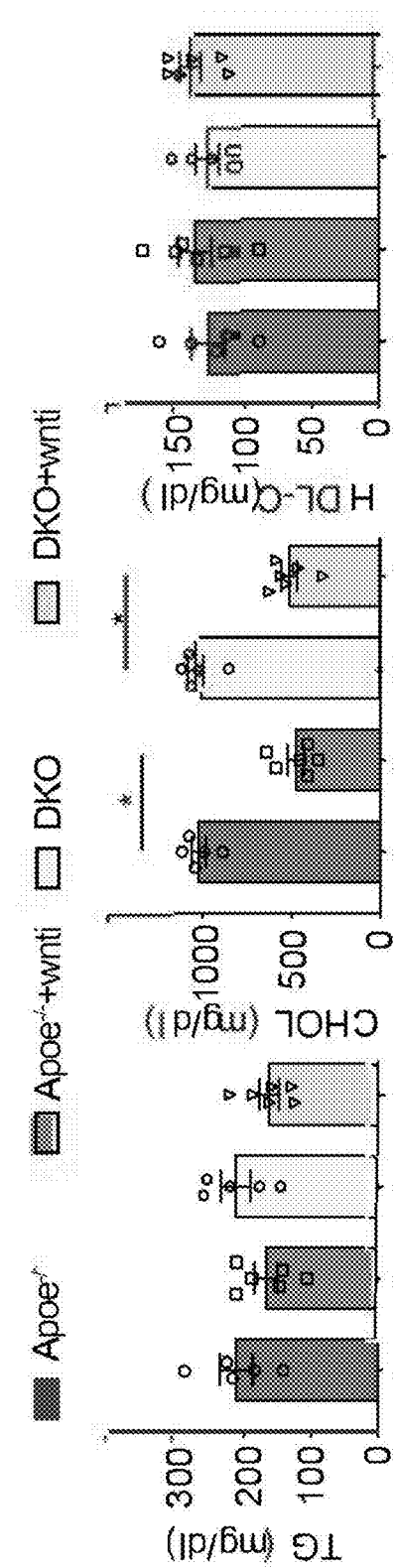
Figure 11E:
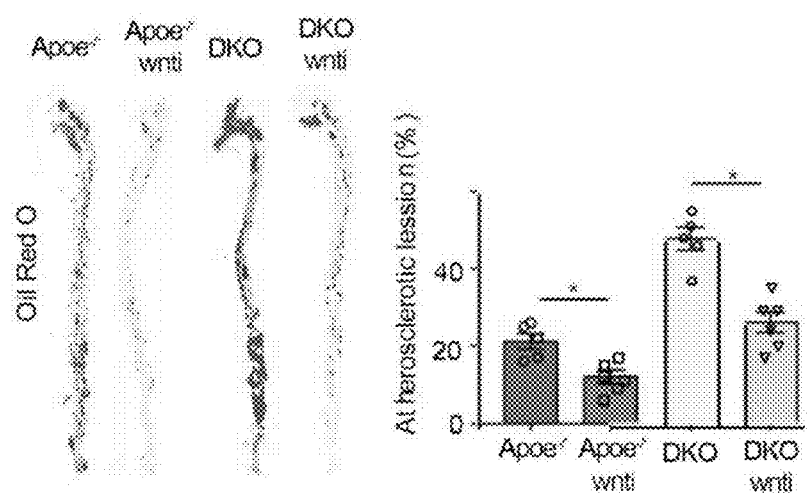
Figure 11F:
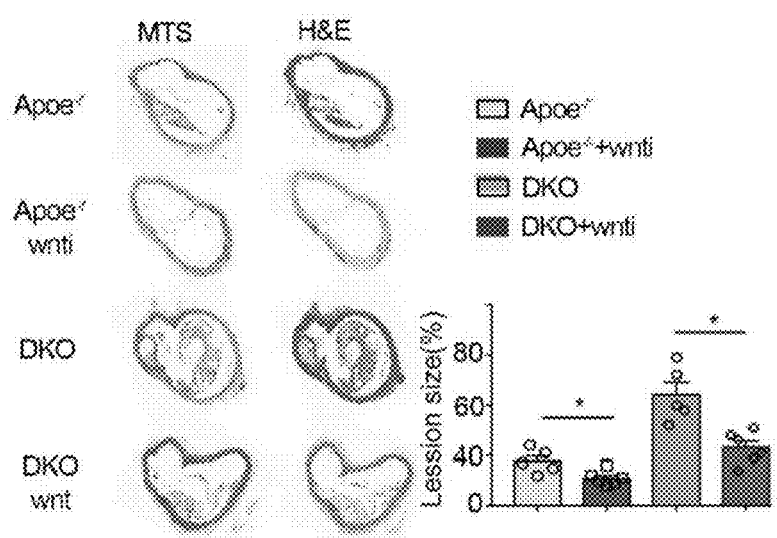
Figure 11G:
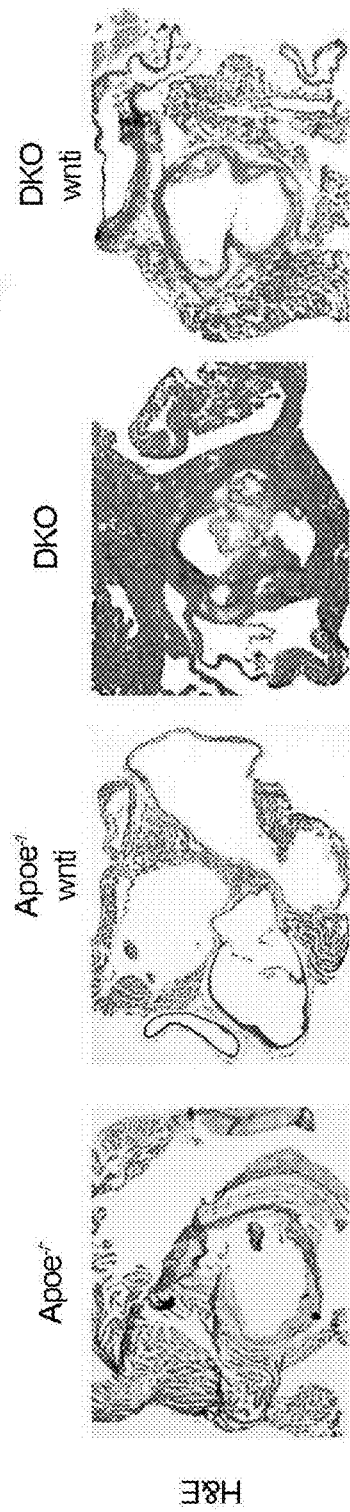
Figure 11H:
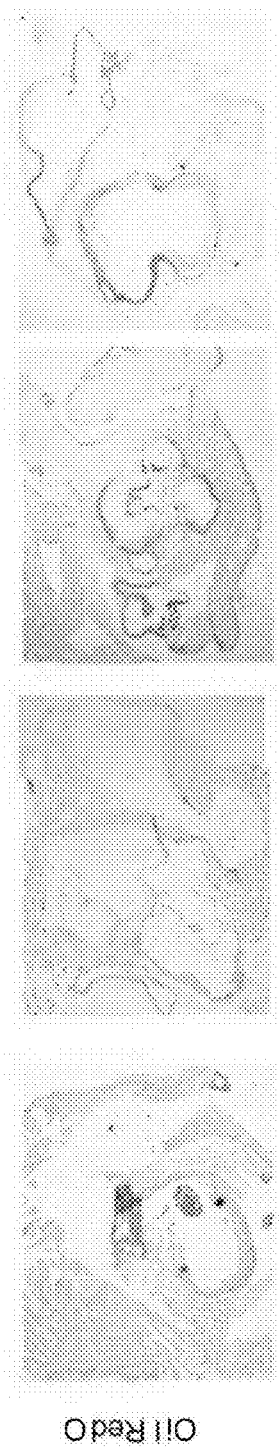

Example 8: Inhibition of Canonical Wnt Signaling Significantly Improves the Atherogenic Phenotype in Mice In order to visualize the activation of canonical Wnt signaling, $Apoe^{-/-}$, $GR^{fl/fl}$, Tie2 Cre−; TCF/Lef-LacZ (Apoe$^{-/-}$) mice were bred with Apoe$^{-/-}$, GR$^{fl/fl}$, Tie2 Cre+; TCF/Lef-LacZ (DKO) mice. Apoe$^{-/-}$ and DKO mice were fed a high fat diet (HFD) for 12 weeks. The Wnt inhibitor (wnti) LGK974 at a dose of 5 mg/kg body weight, or vehicle, was administered 6 days/week by oral gavage from 4-12 weeks. A schematic of the study design is shown in FIG. 11A. The aortas of vehicle-treated control animals and wnti-treated animals (n=6-7/group) were stained for LacZ (FIG. 11B). A LacZ(-) aorta was included as a control. Both genotypes showed activation of canonical Wnt signaling after HFD diet feeding (DKO>Apoe$^{-/-}$) which is clearly attenuated in the presence of Wnti. Aortic area stained is quantified in the corresponding graph (FIG. 11B). Body weight of the animals of both genotypes with and without Wnti treatment was measured. There was no weight loss noted with Wnti treatment (FIG. 11O). Triglycerides, total cholesterol and HDL cholesterol were measured after 12 weeks of diet feeding in animals of both genotypes in the presence of absence of Wnti. The inhibitor produced a dramatic reduction in cholesterol in both genotypes (FIG. 11D). Lipid deposition in aortas of wnti- or vehicle-treated Apoe$^{-/-}$ and DKO treated mice was analyzed by Oil Red O staining. Atherogenic lesion area was calculated by using the Image J program. Wnti treatment produced a dramatic reduction in lipid deposition in both genotypes (FIG. 11E). Masson Trichrome and H&E staining was performed in the brachiocephalic artery of Wnti- or sham-treated Apoe$^{-/-}$ and DKO treated mice (FIG. 11F). Lesion size was measured using Image J program. Wnti also dramatically reduced lesion size in brachiocephalic arteries. H&E (FIG. 11G) and Oil Red O (FIG. 11H) staining in the aortic root of heart sections also showed histological improvement after administration of the Wnti.

Example 9: Investigate the Regulation of Wnt Signaling by Endothelial GR

The goal of this Example is to dissect the role of the endothelial glucocorticoid receptor (GR) in states of vascular inflammation, such as atherosclerosis. Preliminary data generated through genomic sequencing experiments shows that endothelial GR interacts with a number of genes present in the Wnt signaling pathway.

The first set of experiments utilize data created in the course of GR-ChIP-seq experiments performed in mouse lung endothelial cells which show a relative enrichment of GR binding in genes relevant to the Wnt signaling pathway as well as a novel motif containing a putative glucocorticoid response element (GRE) which has not previously been described. To further characterize these findings RNA-seq of GR in endothelial cells is performed to gain direct information about gene expression patterns. Cloning techniques are used followed by luciferase assays to definitively identify GREs in endothelial cells.

Another set of experiments are carried out to evaluate the in vitro phenotypes of endothelial cells exposed to Wnt ligands that induce both the canonical and non-canonical Wnt signaling pathways. Assays to be employed include cell permeability assays, expression of pro-inflammatory cytokines and adhesion molecules and measurement of reactive oxygen species. By testing cells in the presence and absence of dexamethasone, a synthetic steroid acting through GR, the regulation of Wnt by the endothelial GR in the context of inflammation can be examined in depth.

In a separate set of experiments, an established mouse model of atherosclerosis is utilized in which mice lacking endothelial GR have been bred onto an Apo E knock out background. Levels of several Wnt related proteins are directly measured in atherosclerotic lesions and in serum. In addition a novel mouse model is generated that allows direct visualization of canonical Wnt signaling after Xgal staining by crossing the mice with the Bat gal reporter strain.

Materials and Methods for Examples 10-17

Below are the materials and methods used in Examples 10-17 presented above.

Reagents and Antibodies

Rabbit polyclonal anti-GR (Cat:SAB4501309) and mouse monoclonal anti-αSMA (Cat:A5228) antibodies were from Sigma (St Louis, Mo.). Anti-TGFβR1 (Cat:ab31013) antibody was purchased from Abcam (Cambridge, UK). Mouse anti-β-catenin antibody (Cat:610154) was purchased from BD Biosciences. Anti-fibroblast specific protein (FSP1, displayed as S100A4; Cat: 370003) was purchased from Biolegend, CA. Fluorescence-, Alexa Fluor 647-, and rhodamine-conjugated secondary antibodies were obtained from Jackson ImmunoResearch (West Grove, Pa.). TGFβ2, IL-1β and recombinant TNFα and TGFβ neutralizing antibody were purchased from PeproTech (Rocky Hill, N.J.).

Animal Experimentation

All experiments were performed in accordance with the National Institute of Health (NIH) Guidelines for the Care of Laboratory Animals. Mice lacking the endothelial glucocorticoid receptor (GR) (known as GR$^{ECKO}$) and those lacking this receptor on the Apo E null background (DKO) were generated as previously described (6). The induction of diabetes in CD-1 mice and C57B/L6 mice was performed according to previously established experimental protocols (38-42). Briefly, diabetes was induced in 10-week-old GR$^{ECKO}$ mice with five consecutive intraperitoneal (IP) doses of streptozotocin (STZ) 50 mg/kg in 10 mmol/L citrate buffer (pH 4.5). Wnt inhibitor (LGK974) was provided to GR$^{ECKO}$ and control littermate at 5 mg/kg at a frequency of six doses per week for 8 weeks (43). Etomoxir (20 mg/kg) and c75 (15 mg/kg) were dosed (ip) three times per week for 3 weeks in the GR$^{ECKO}$ and control littermate. A single IP dose of 200 mg/kg STZ was used to induce diabetes in CD-1 mice. Fenofibrate (100 mg/kg), simvastatin (40 mg/kg), were dosed orally for 4 weeks in diabetic CD-1 mice. All mice were sacrificed after 4 weeks of treatment and tissues and blood were harvested. Urine albumin levels were assayed using a Mouse Albumin ELISA Kit (Exocell, Philadelphia, Pa.).

Mouse Model of Unilateral Ureteral Obstruction (UUO)

UUO surgery procedure was performed as previously described (44). Briefly, mice were anesthetized with isoflurane (3%-5% for induction and 1%-3% for maintenance). Mice were shaved on the left side of the abdomen, a vertical incision was made through the skin with a scalpel, and the skin was retracted. A second incision was made through the peritoneum to expose the kidney. The left ureter was ligated twice 15 mm below the renal pelvis with surgical silk, and the ureter was then severed between the 2 ligatures. Then, the ligated kidney was placed gently back into its correct anatomical position, and sterile saline was added to replenish loss of fluid. The incisions were sutured and mice were individually caged. Buprenorphine was used as an analgesic. The first dose was administered 30 minutes before surgery and then every 12 h for 72 h, at a dose of 0.05 mg/kg subcutaneously. Mice were sacrificed and kidney and blood samples were harvested after perfusion with PBS at 10 days after UUO. Contralateral kidneys were used as a nonfibrotic control for all experiments using this model.

Lipid Analysis

Mice were fasted for 12-15 hours and blood was collected by retro-orbital venous puncture. Whole blood was spun down and plasma stored at −80° C. Total cholesterol and triglyceride levels were measured enzymatically by kits from Wako and Sigma, respectively, according to the manufacturer's instructions.

Morphological Evaluation

A point-counting method was utilized to evaluate the relative area of the mesangial matrix. PAS-stained glomeruli from each mouse were analyzed using a digital microscope screen grid containing 540 (27×20) points. Masson's trichrome-stained images were evaluated by ImageJ software, and the fibrotic areas were estimated.

Sirius Red Staining

Deparaffinized sections were incubated with picrosirius red solution for 1 hour at room temperature. The slides were washed twice with acetic acid solution for 30 seconds per wash. The slides were then dehydrated in absolute alcohol three times, cleared in xylene, and mounted with a synthetic resin. Sirius red staining was analyzed using ImageJ software, and fibrotic areas were quantified.

Immunohistochemistry

Paraffin-embedded kidney sections (5 µm thick) were deparaffinized and rehydrated (2 min in xylene, four times; 1 min in 100% ethanol, twice; 1 min in 95% ethanol; 45 s in 70% ethanol; and 1 min in distilled water), and the antigen was retrieved in a 10 mM citrate buffer pH 6 at 98° C. for 60 min. To block the endogenous peroxidase, all sections were incubated in 0.3% hydrogen peroxide for 10 min. The immunohistochemistry was performed using a Vectastain ABC Kit (Vector Laboratories, Burlingame, Calif.). Mouse anti-8-catenin antibody (1:100) and CPT1a (Abnova; H00001374-DO1P; 1:100) antibody was used. In the negative controls, the primary antibody was omitted and replaced with the blocking solution.

Immunofluorescence

Frozen kidney sections (5 µm) were used for immunofluorescence; double positive labeling with CD31/αSMA, CD31/TGFβR1 and E-cadherin/αSMA was measured. Briefly, frozen sections were dried and placed in acetone for 10 min at −30° C. Once the sections were dried, they were washed twice in phosphate-buffered saline (PBS) for 5 min and then blocked in 2% bovine serum albumin/PBS for 30 min at room temperature. Thereafter, the sections were incubated in primary antibody (1:100) for 1 hour and washed in PBS (5 min) three times. Next, the sections were incubated with the secondary antibodies for 30 min, washed with PBS three times (5 min each), and mounted with mounting medium with DAPI (Vector Laboratories, Burlingame, Calif.). The immune-labeled sections were analyzed by fluorescence microscopy. For each mouse, original magnification of ×400 pictures were obtained from six different areas, and quantification was performed.

EndMT and EMT Detection

Frozen sections (5 µm) were used for the detection of EndMT and EMT. Cells undergoing EndMT were detected by double-positive labeling for CD31 and αSMA and/or TGFβR1. Cells undergoing EMT were detected by double-positive labeling for E-cadherin and αSMA. Sections were analyzed and quantified by fluorescence microscopy.

Isolation of Endothelial Cells

Endothelial cells from the kidneys of non-diabetic and diabetic mice were isolated using a standardized kit (Miltenyl Biotech, USA) by following the manufacturer's instructions. Briefly, kidneys were isolated and minced into small pieces. Using a series of enzymatic reactions by treating the tissue with trypsin and Collagenase type I solution, a single cell suspension was created. The pellet was dissolved with CD31 magnetic beads and the CD31-labelled cells were separated on a magnetic separator. The cells were further purified on a column. Cell number was counted by hemocytometer and cells were plated on 0.1% gelatin coated Petri dishes.

Isolation of Kidney TECs

After sacrifice kidneys from diabetic $GR^{ECKO}$ and control littermate were excised and perfused with (10 mL) followed by collagenase type II digestion (2 mg/mL). After digestion, the cortical region of kidneys was used for further processing. the cortical region of kidneys was minced and further digested in collagenase buffer for an additional 5 minutes at 37° C. with rotation to release cells. Digested tissue and cell suspension were passed through a 70-µm cell strainer, centrifuged at 50 g for 5 min, and washed in PBS for 2 rounds to collect TECs. Isolated TECs were seeded onto collagen-coated Petri dishes and cultured in renal epithelial cell medium (C-26130, PromoCell) supplemented with growth factors for TEC growth.

Cellular Bioenergetic Analysis

FAO-associated oxygen consumption rate (OCR) was studied using extracellular flux analysis (Seahorse XFe96, Agilent Technologies). On the assay day, substrate-limited medium was replaced with Krebs-Henseleit buffer assay medium supplemented with 0.2% carnitine for 1 h at 37° C. without $CO_2$. Finally, just before starting the assay, BSA or 200 mM palmitate-BSA FAO substrate was added. After the assay, protein was extracted from wells with 0.1% NP-40-PBS solution and quantified with a bicinchoninic acid protein assay (Thermo Fisher Scientific) for data normalization. OCR was determined as described previously (45).

ATP Measurement

ATP content was determined using the ATP Colorimetric Assay kit (Biovision), following the manufacturer's instructions.

RNA Isolation and qPCR

Total RNA was isolated using standard Trizol protocol. RNA was reverse transcribed using the iScript cDNA Synthesis kit (Bio-Rad) and qPCR was performed on a Bio-Rad C1000 Touch thermal cycler using the resultant cDNA, as well as qPCR Master mix and gene specific primers. The list of mouse primers used is given in Table S1.

Results were quantified using the delta-delta-cycle threshold (Ct) method (ΔΔCt). All experiments were performed in triplicate and 18S was utilized as an internal control.

Western Blot

Protein lysates were boiled in sodium dodecyl sulfate (SDS) sample buffer at 94° C. for 5 min. After centrifugation at 17,000×g for 10 min at 4° C., the supernatant was separated on 6%-12% SDS polyacrylamide gels, and blotted onto PVDF membranes (Immobilon, Bedford, Mass.) via the semidry method. After blocking with TBS (Tris buffered saline containing 0.05% Tween 20) containing 5% bovine serum albumin (BSA), membranes were incubated with each primary antibody (GR: 1:1000; Anti-TGFβR1: 1:500; anti-αSMA: 1:500; anti-β-catenin:1:500 and anti-FSP-1: 1:100), in TBS containing 5% BSA at 4° C. overnight. Protein bands were visualized using the Odyssey Infrared Imaging System (LI-COR Biotechnology), and densitometry was performed using ImageJ software (NIH).

In Vitro Experiments and siRNA Transfection

HUVECs were used at passage 4-8 and cultured in Endothelial Basal Medium-2 media with growth factors and 10% serum. Human GR-specific siRNA (Invitrogen) was used at a concentration of 100 nM for 48 h to effectively knock down GR. Cells were treated with or without TGFβ2 (10 ng/ml) for 48 h and harvested for western blot analysis. Some transfected cells were treated with fenofibrate (1 µM) and etomoxir (40 µM) for 48 h. In a second set of experiments Human HK-2 cells were cultured in DMEM and Keratinocyte-SFM (1×) medium (Life Technologies Green Island N.Y.). When the cells reached 70% confluence, conditioned media from control siRNA and GR siRNA-transfected HUVECs was added to the HK-2 cell culture.

Fatty Acid Uptake

Cultured isolated kidney endothelial cells were incubated with medium containing 2 µCi [$^{14}$C]palmitate. [$^{14}$C]-palmitate uptake was measured by liquid scintillation counting.

Fatty Acid Oxidation

Cultured isolated kidney endothelial cells were incubated with medium containing 0.75 mmol/L palmitate (conjugated to 2% free fatty acid-free BSA/[$^{14}$C] palmitate at 2 µCi/mL) for 2 h. One mL of the culture medium was transferred to a sealable tube, the cap of which housed a Whatman filter paper disc. $^{14}CO_2$ trapped in the media was then released by acidification of media using 60% perchloric acid. Radioactivity that had become adsorbed onto the filter discs was then quantified by liquid scintillation counting.

Statistical Analysis

All values are expressed as means±SEM and analyzed using the statistical package for the GraphPad Prism 7 (GraphPad Software, Inc., La Jolla, Calif.). One-way Anova, followed by Tukey's test was employed to analyze the significance when comparing multiple independent groups. The post hoc tests were run only if F achieved $P<0.05$ and there was no significant variance in homogeneity. In each experiment, N represents the number of separate experiments (in vitro) and the number of mice (in vivo). Technical replicates were used to ensure the reliability of single values. Data analysis were blinded. The data were considered statistically significant at $P<0.05$.

Example 10 Endothelial GR Deficiency Results in a Fibrogenic Phenotype in the Kidneys of Diabetic Mice The streptozotocin (STZ)-induced diabetic CD-1 mouse is the established mouse model to study diabetic kidney disease (38, 29, 68), as the kidney fibrosis phenotype is dependent upon mouse strain specificity (68). Though STZ-induced diabetic CD-1 mice and diabetic C57B/L6 mice demonstrate similar blood glucose levels, the kidneys of diabetic CD-1 mice have been shown to have higher rates of EndMT and more severe fibrosis when compared to the kidneys of diabetic C57B/L6 mice (38, 69). Therefore, diabetic CD-1 mice are considered pro-fibrotic strain while diabetic C57B/L6 mice are considered to be a less-fibrotic strain (69, 70).

Figure 12A:
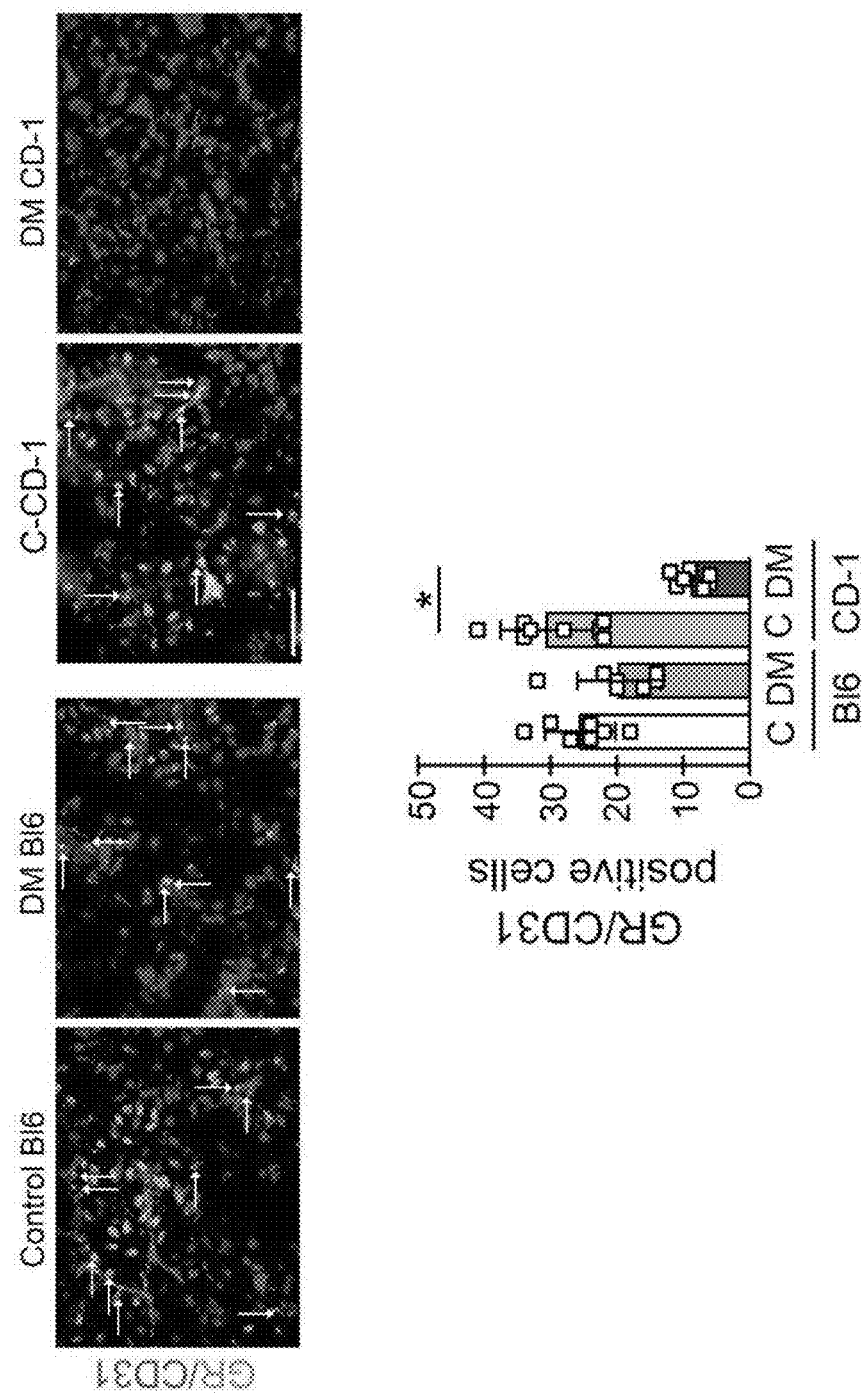
FIGS. 12A-12B. Loss of endothelial GR results in a fibrogenic phenotype in the kidneys of diabetic mice.
Figure 12B:
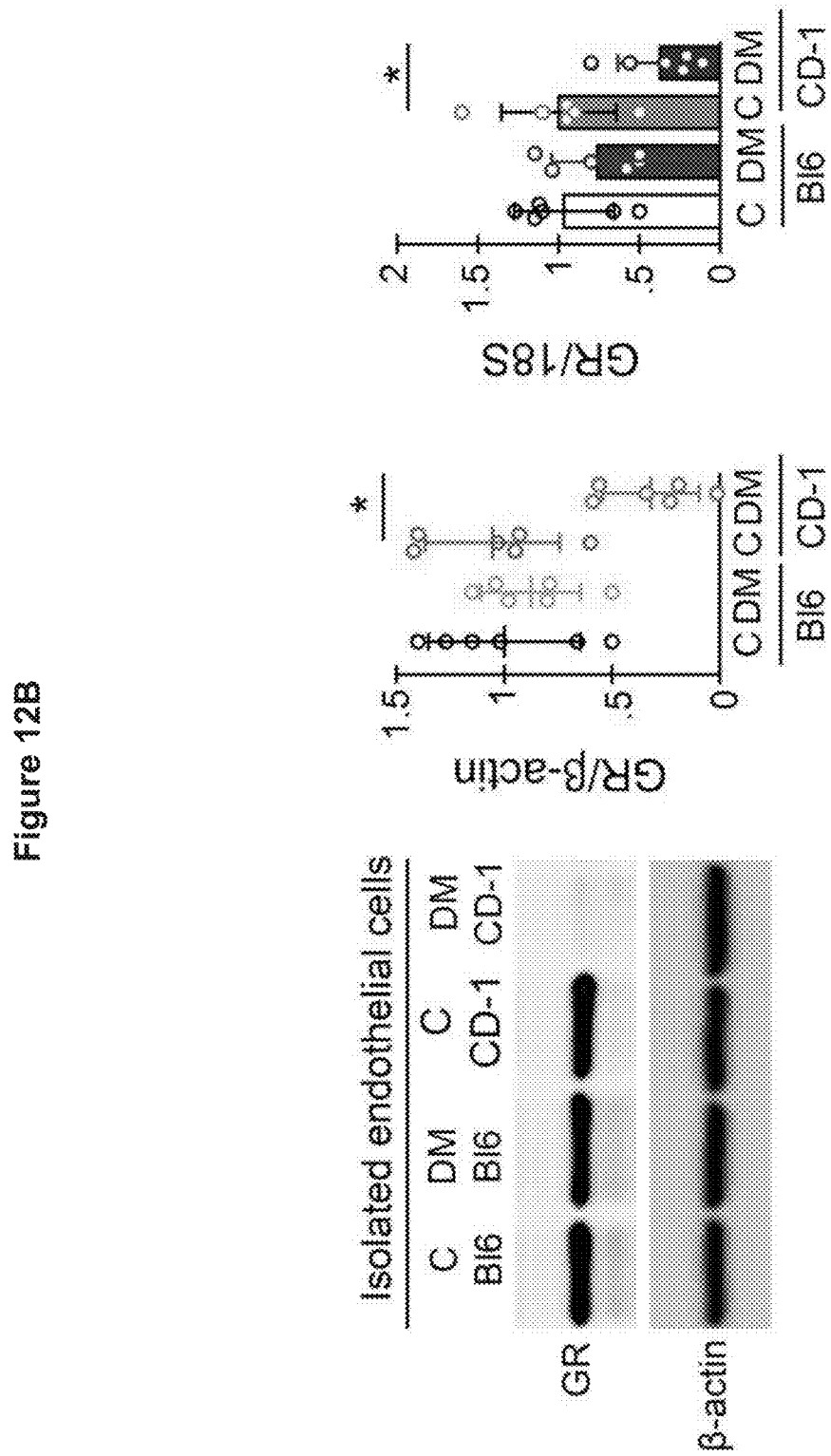

CD31-positive cells from diabetic CD-1 mouse kidneys displayed significant suppression of GR compared to those from diabetic C57B/L6 mice as assessed by immunofluorescent staining (FIG. 12B). Moreover, EC isolated from the kidneys of diabetic CD-1 mice showed dramatic suppression in both the GR protein level and GR mRNA level when compared to the diabetic C57B/L6 mice and the non-diabetic controls of both genotypes (FIG. 12B).

Example 11 Loss of EC GR Worsens Kidney Fibrosis

Figure 13A:
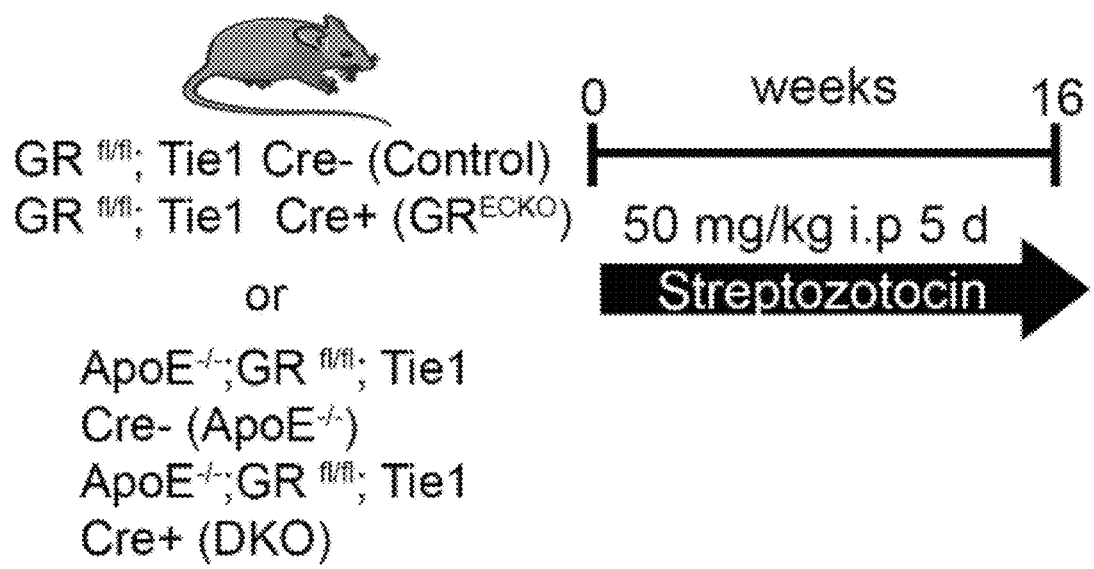
FIGS. 13A-13L. Loss of endothelial GR worsens fibrosis in kidneys of diabetic mice.
Figure 13B:
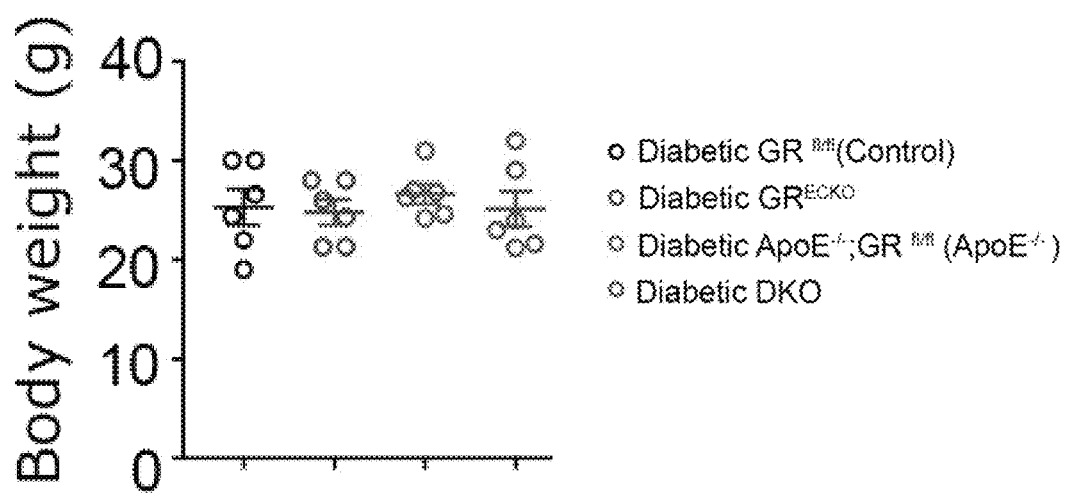
Figure 13C:
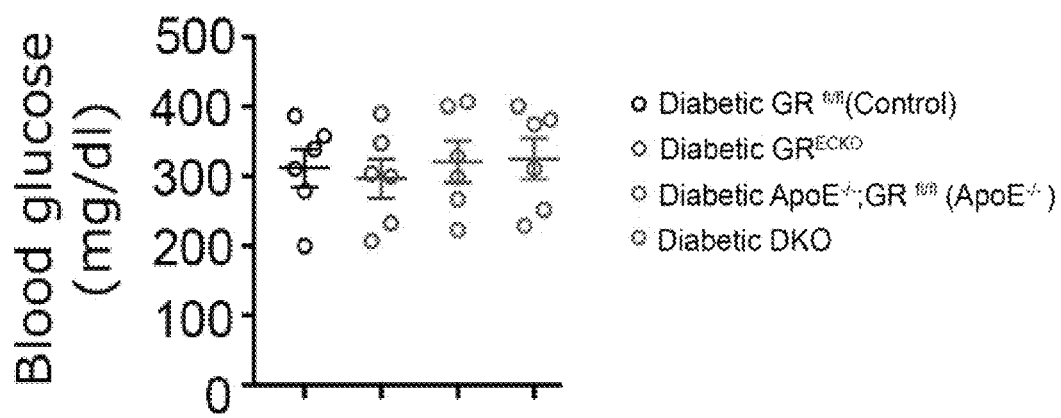
Figure 13D:
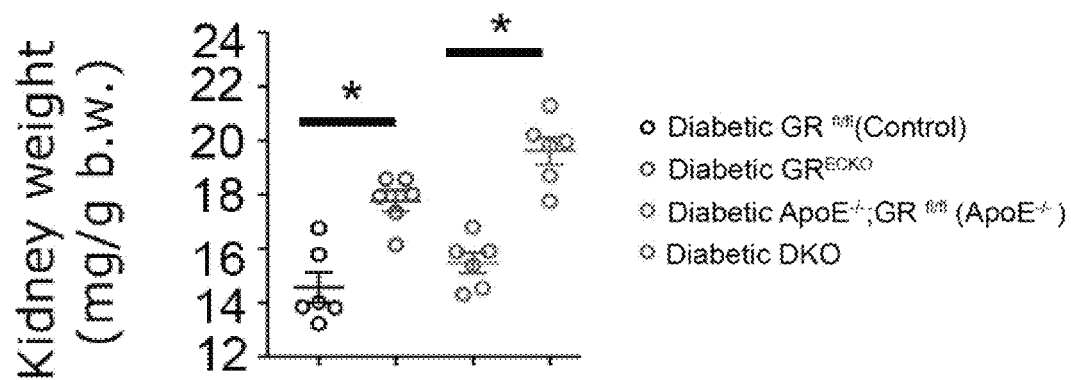
Figure 13E:
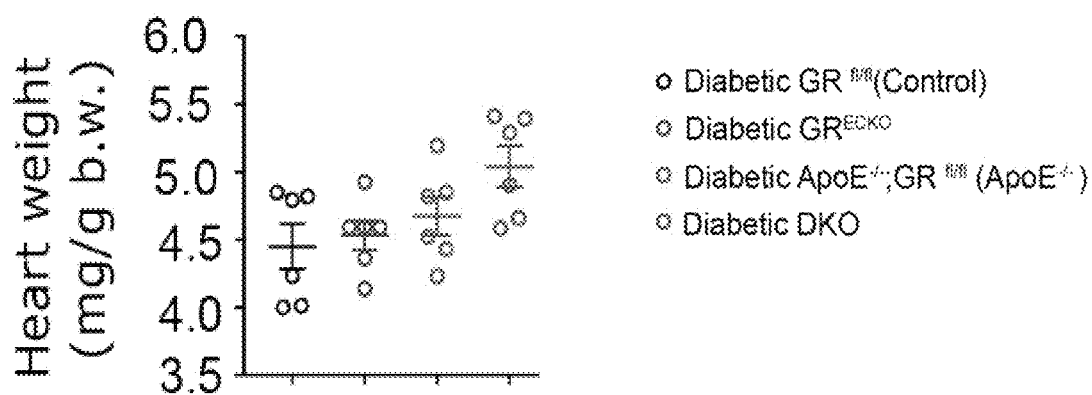
Figure 13F:
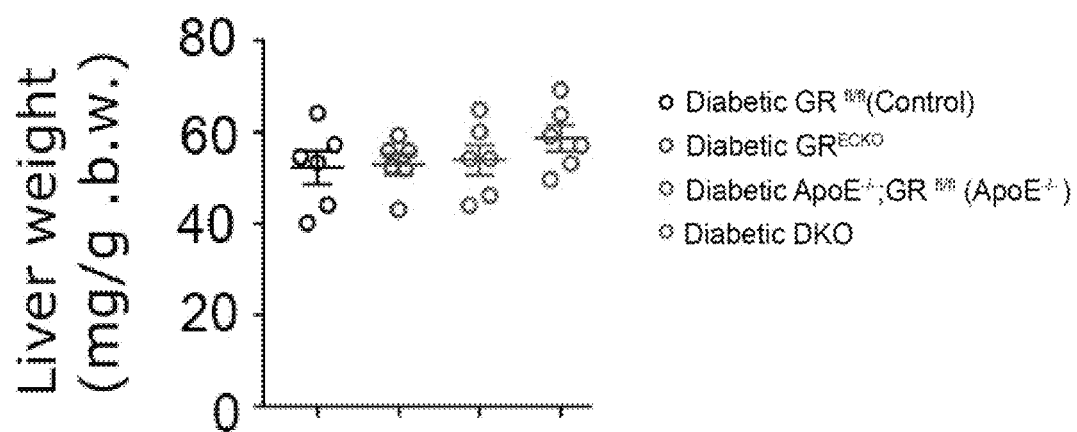
Figure 13G:
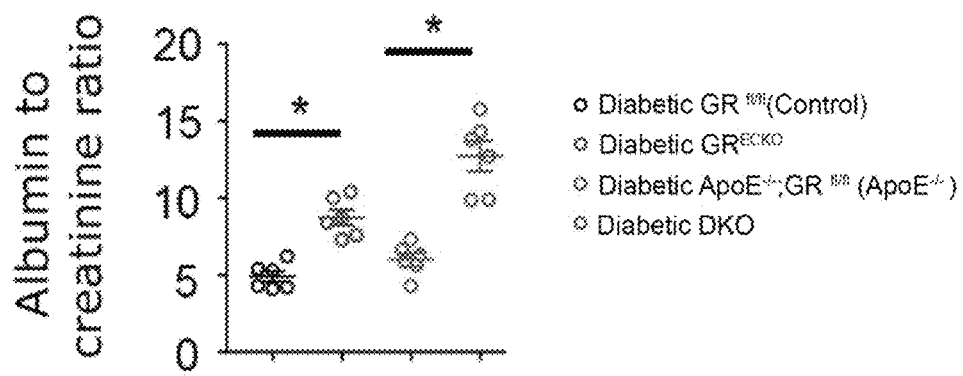
Figure 13H:
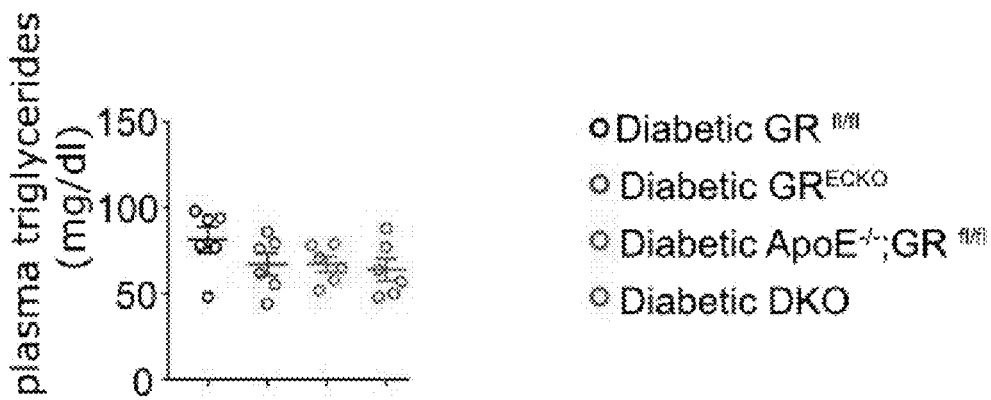
Figure 13I:
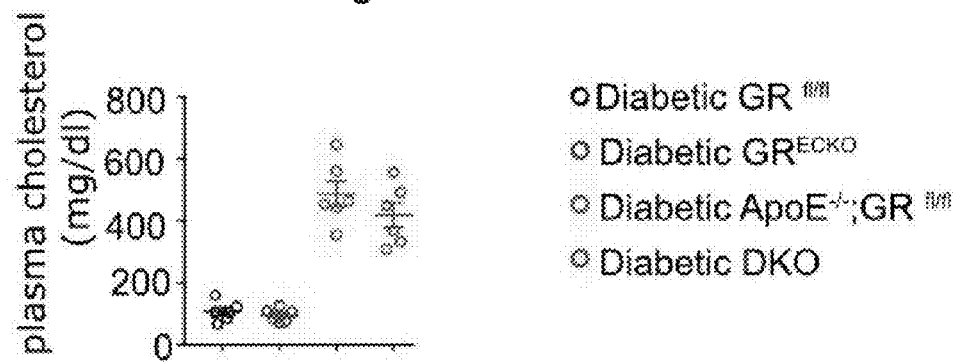
Figure 13J:
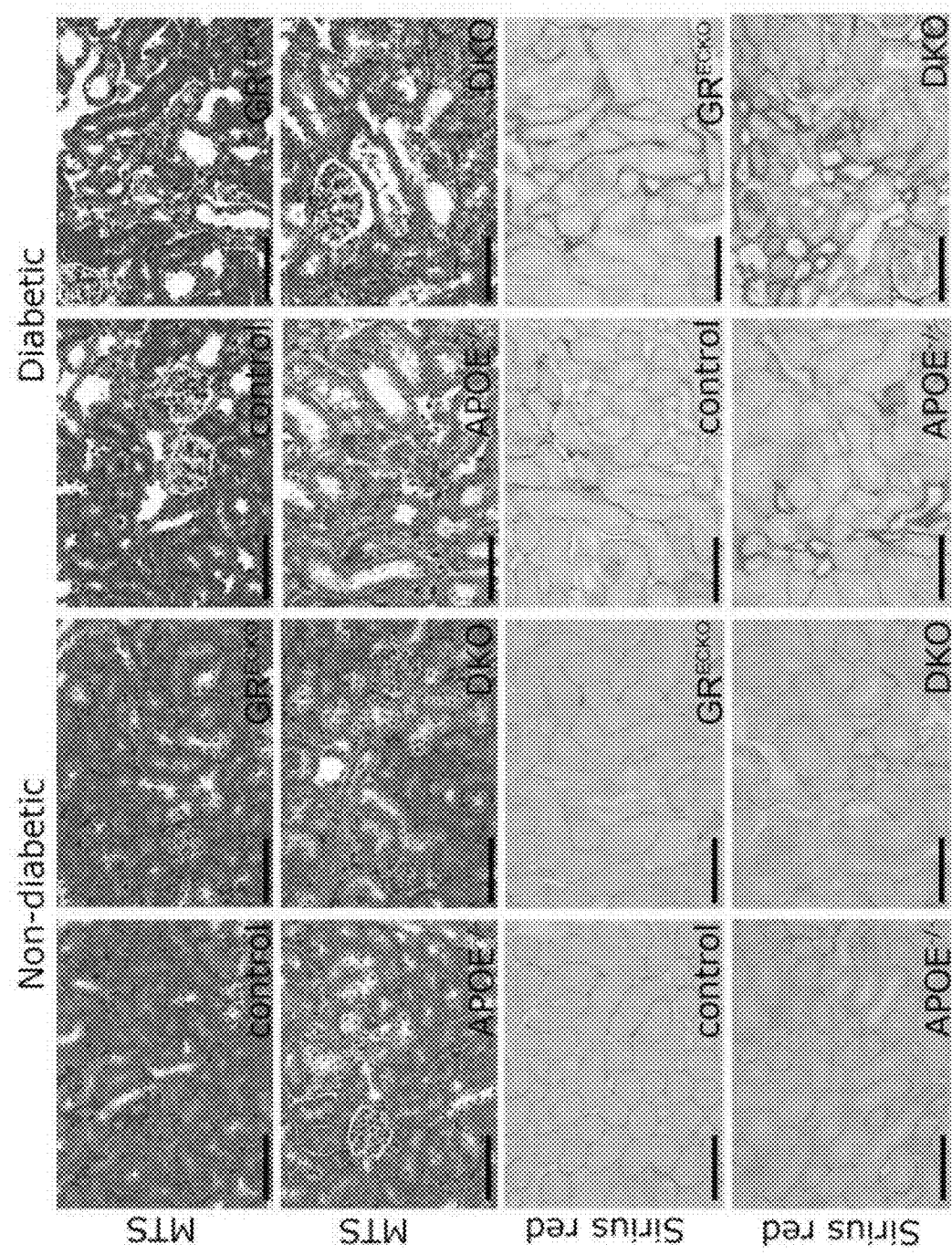
Figure 13J:
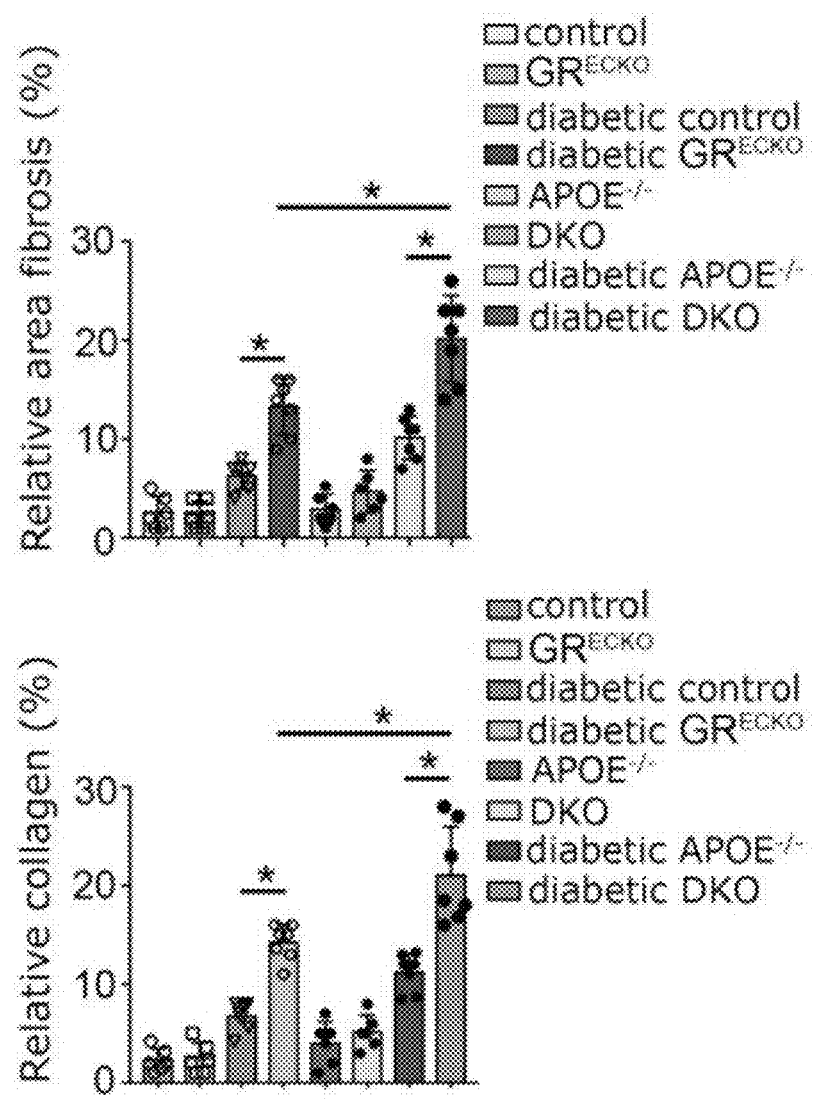
Figure 13K:
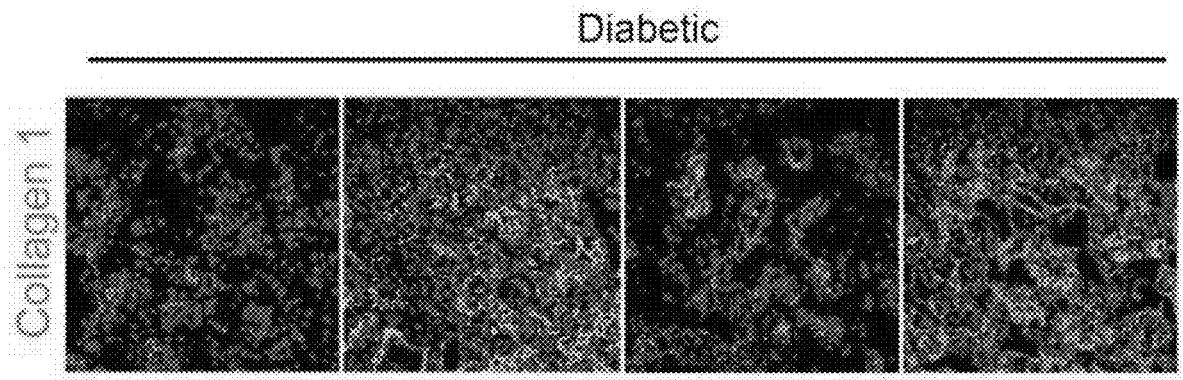
Figure 13L:
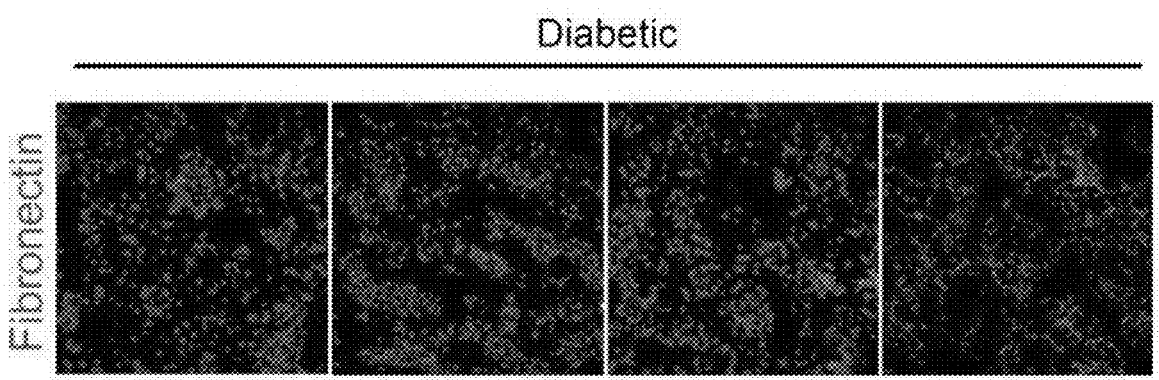
Figure 19A:
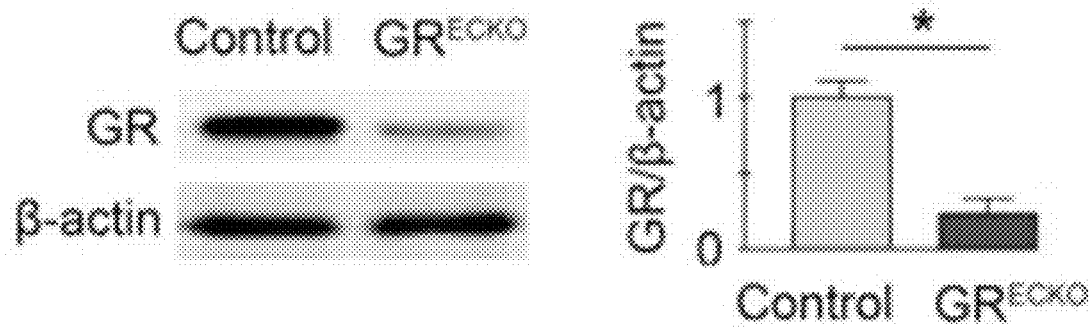
FIGS. 19A-19B. Analysis of GR protein and mRNA level in isolated EC.
Figure 19B:
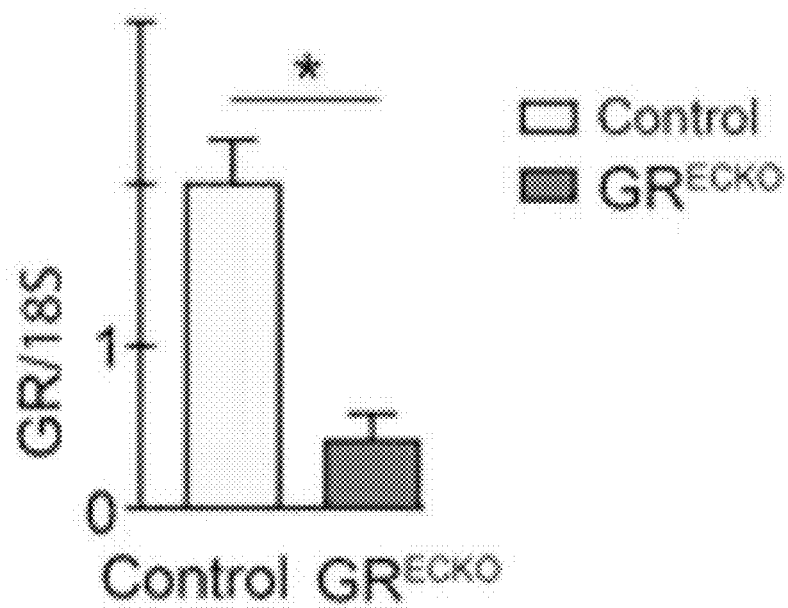

To verify efficient GR excision from endothelial cells in the kidneys of $GR^{ECKO}$ mice, Western blot and qPCR were performed for GR. As shown in FIGS. 19A-19B, mRNA and protein levels were significantly diminished, as expected. Diabetes was induced by injecting 5 consecutive low doses of STZ (50 mg/kg/day IP) in 8-week old $GR^{fl/fl}$; Tie1 Cre+ ($GR^{ECKO}$) and Cre– littermate controls ($GR^{fl/fl}$) and $GR^{fl/fl}$; Tie1 Cre+/Apoe$^{-/-}$ (DKO) mice and Cre– littermates ($GR^{fl/fl}$; Apoe$^{-/-}$) (FIG. 13A). Animals were monitored for 4 months post-STZ treatment before sacrifice. At the time of sacrifice, diabetic $GR^{ECKO}$ and diabetic DKO mice and their diabetic littermate controls had no significant change in body weight, blood glucose, heart weight, liver weight, triglycerides or cholesterol. However, diabetic $GR^{ECKO}$ and diabetic DKO had relatively higher kidney weight, spleen weight and albumin-to-creatinine ratios when compared to their respective diabetic controls. (FIGS. 13B-13I). Diabetic DKO had significantly higher kidney weight and albumin-to-creatinine ratios when compared to diabetic $GR^{ECKO}$. Renal fibrosis was assessed by histologic analysis of kidney sections from all genotypes. Diabetic $GR^{ECKO}$ mice exhibited a higher relative area of fibrosis, higher relative collagen deposition and more severe glomerulosclerosis at the 4-month timepoint when compared to diabetic littermate controls. Diabetic DKO exhibited greatly increased relative area of fibrosis and relative collagen deposition when compared to diabetic ApoE$^{-/-}$ controls and diabetic $GR^{ECKO}$ (FIG. 13J). Immunofluorescence data showed higher collagen I and fibronectin deposition in the kidneys of diabetic animals with $GR^{ECKO}$ with the highest deposition observed in DKO mice (FIG. 13K-L).

Figure 20A:
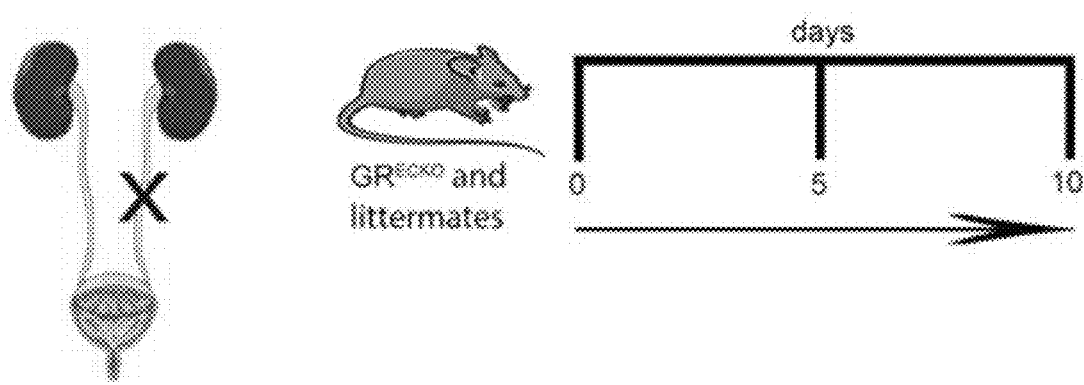
FIGS. 20A-20C. Loss of EC GR worsens fibrosis in a mouse model of urinary obstruction (UUO).
Figure 20B:
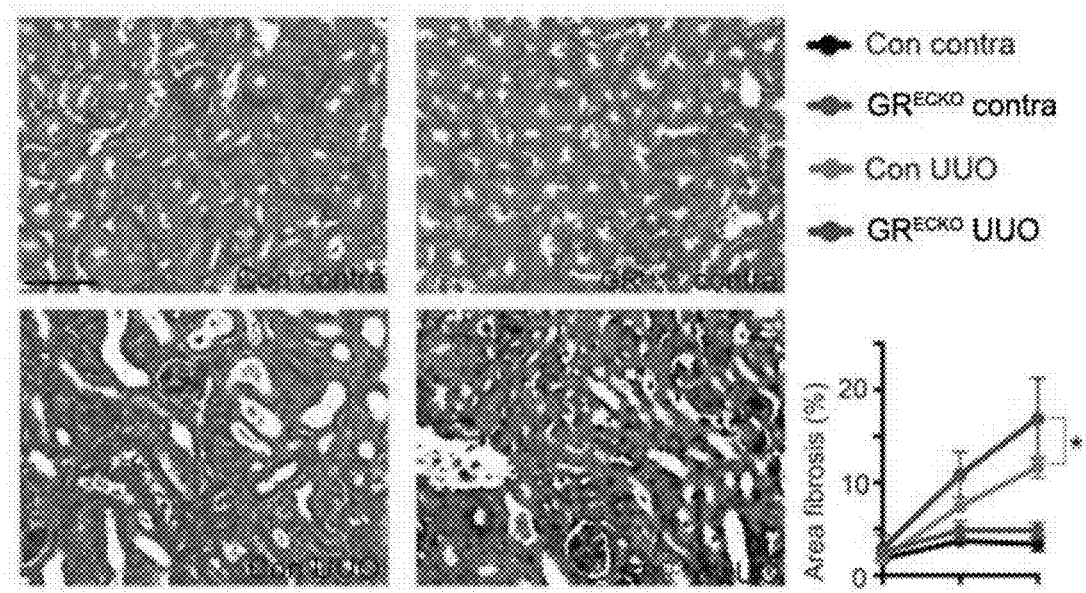
Figure 20B:
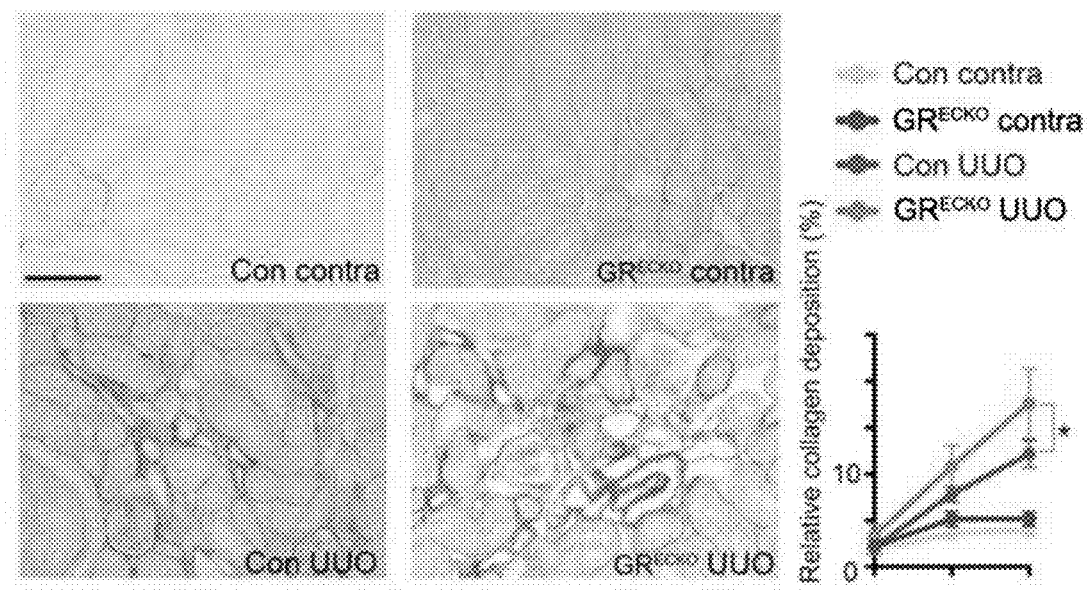
Figure 20C:
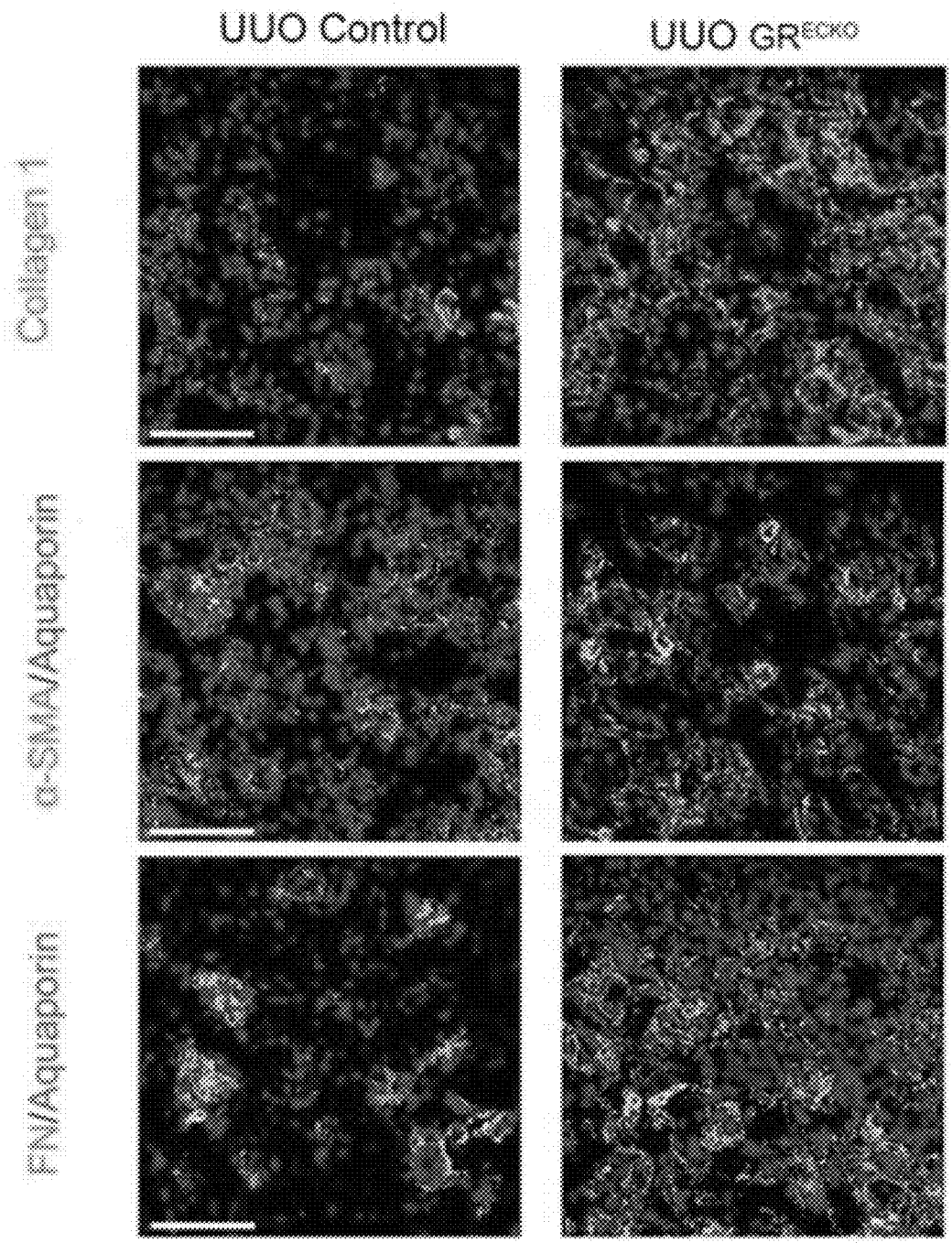

In order to test the role of endothelial GR in non-diabetic fibrosis, unilateral ureteral obstruction (UUO) was performed in 8-week-old $GR^{ECKO}$ and control littermates (FIG. 20A). There was no significant difference in renal fibrosis between contralateral kidneys of controls and $GR^{ECKO}$ mice. However, UUO kidneys from $GR^{ECKO}$ mice showed a greater relative area fibrosis and greater collagen deposition when compared to UUO kidneys of littermate controls (FIG. 20B). Immunofluorescence staining revealed higher collagen I, αSMA, and fibronectin deposition in the UUO kidneys of $GR^{ECKO}$ when compared to UUO kidneys of control littermates (FIG. 20C).

Example 12 Endothelial GR Loss Reprograms Cytokine and Chemokine Homeostasis

Figure 14A:
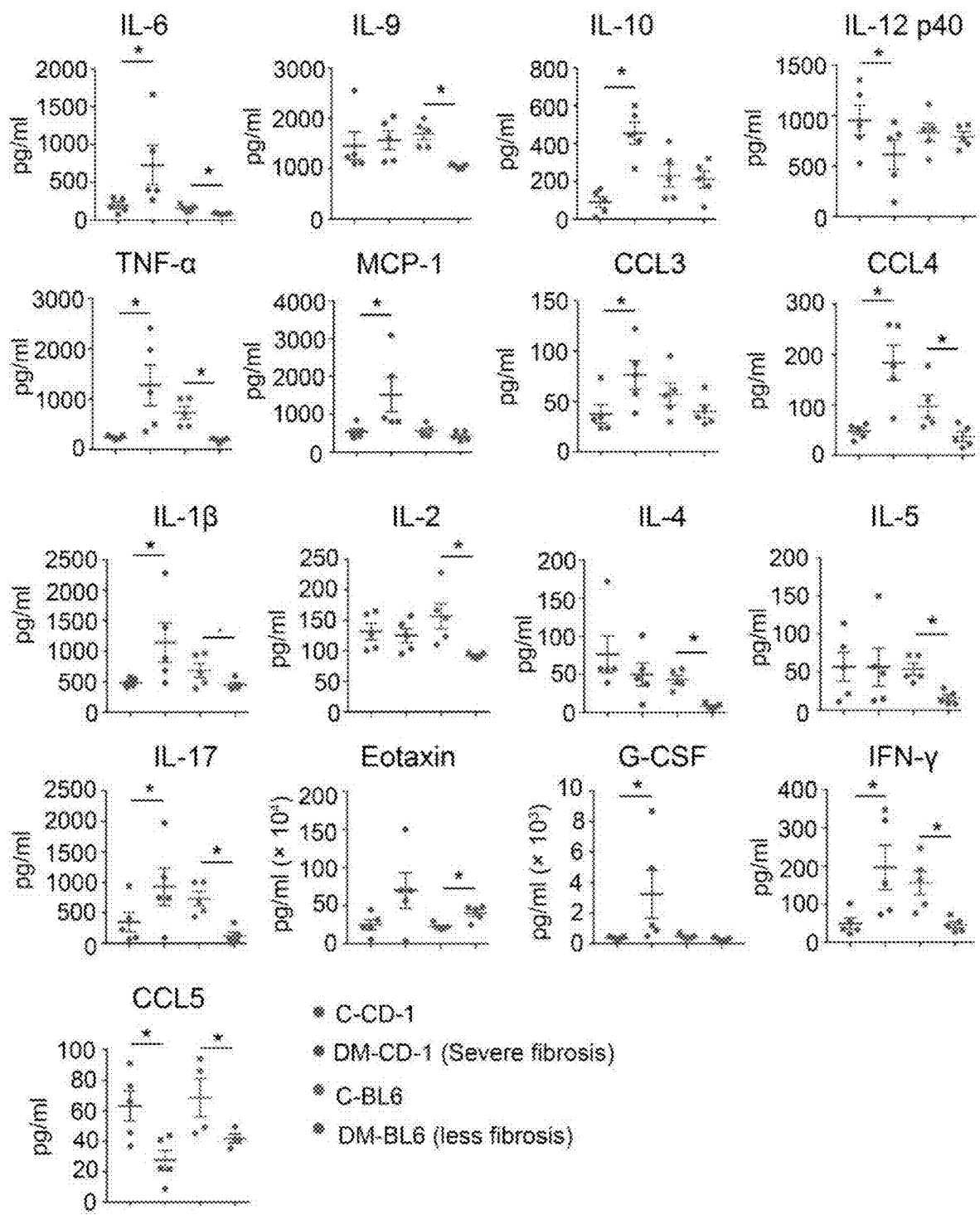
FIGS. 14A-14C. Diabetic kidney disease is associated with cytokine and chemokine reprogramming.
Figure 14B:
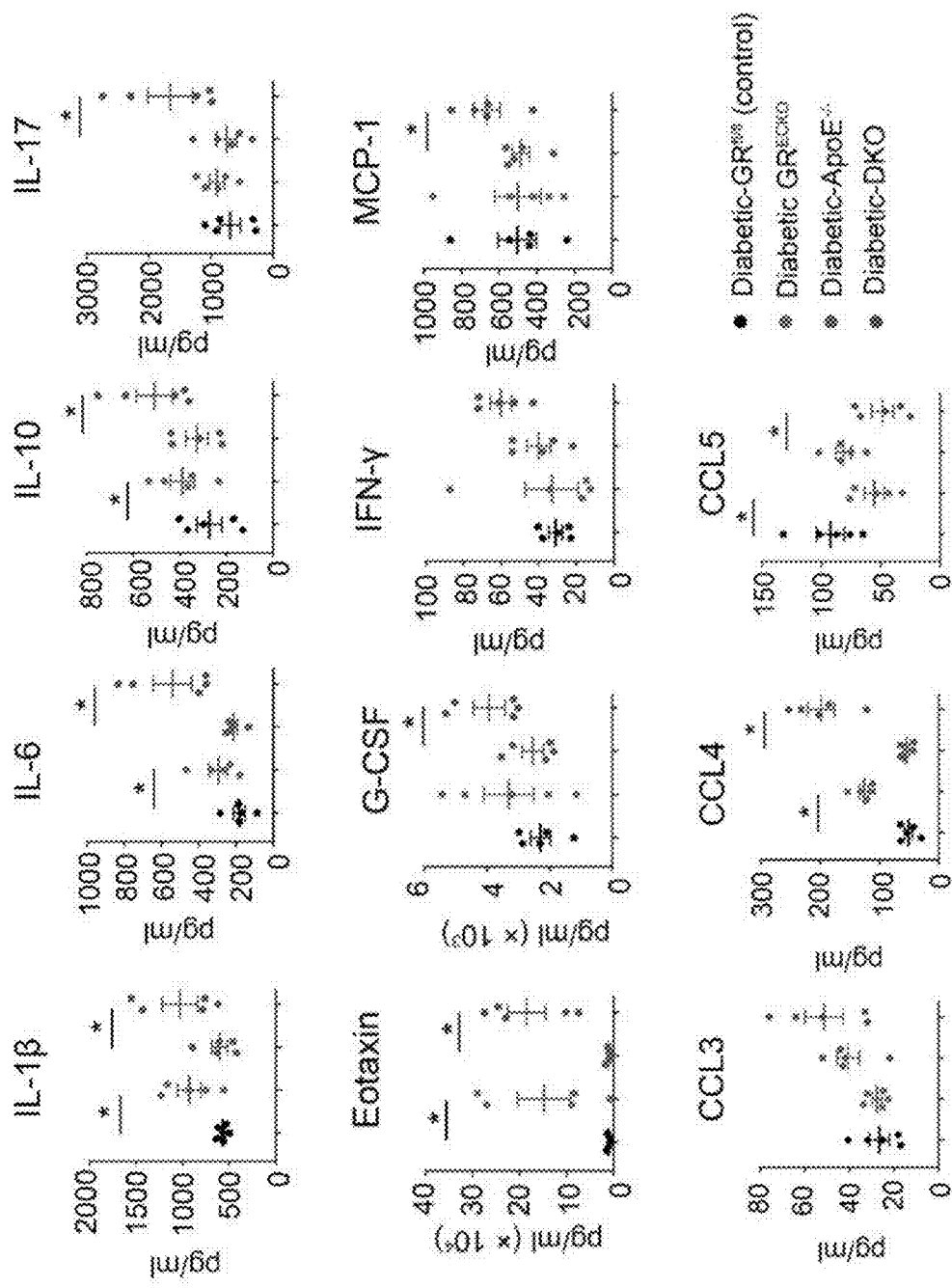
Figure 14C:
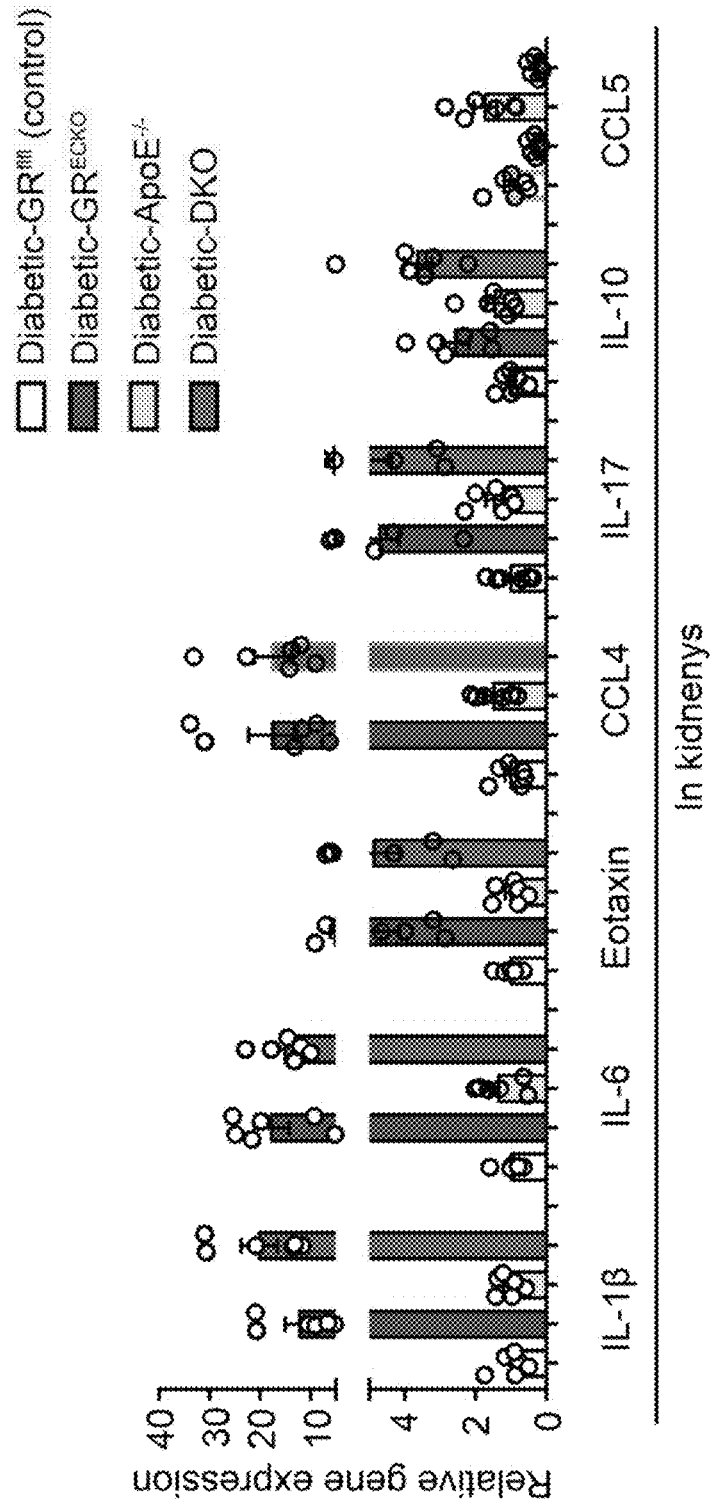

Inflammation is a key factor during the fibroblast activation process in the kidneys of diabetic mice (71, 72) and disruption of cytokine and chemokine homeostasis can contribute to the development of diabetic kidney disease (73-75). To investigate whether there where derangements in homeostasis in a mouse model, cytokine analysis was performed in the plasma of diabetic mice with severe fibrosis (diabetic CD-1) and the plasma of diabetic mice with less severe fibrosis (diabetic C57B/L6). Diabetic CD-1 mice demonstrated higher levels of plasma IL-1β, IL-6, IL-10, IL-17, G-CSF, IFN-γ, TNF-α, MCP-1, CCL3 and CCL4 levels, however the level of CCL5 were remarkably suppressed when compared to that of diabetic C57B/L6 mice (FIG. 14A). The same cytokines were also analyzed in the plasma from diabetic $GR^{ECKO}$ mice and littermate controls and diabetic DKO and diabetic Apoe$^{-/-}$ controls. A similar pattern was observed in both genotypes in that IL-1β, IL-6, IL-10, Eotaxin, G-CSF and CCL4 were significantly higher, while CCL5 was significantly lower, in the plasma of $GR^{ECKO}$ and DKO mice when compared to the plasma of their respective diabetic control littermates (FIG. 14B). Similarly, during mRNA gene expression analysis, the level of IL-1β, IL-6, IL-10, IL-17, Eotaxin, and CCL4 were significantly upregulated whereas, CCL5 was significantly downregulated, in the kidneys of diabetic $GR^{ECKO}$ and diabetic DKO mice when compared to the diabetic kidneys of their respective control littermates (FIG. 14C), indicating more EC inflammation in mice lacking endothelial GR.

Without wishing to be bound by theory, the data suggests GR deficiency is a critical step for the metabolic reprogramming in kidney EC. The altered cytokine levels of in the plasma of $GR^{ECKO}$ mice include elevated levels of pro-inflammatory cytokines (IL-1β, IL-6, and IL-17) and the anti-inflammatory cytokine IL-10. The role of IL-10 has not been fully investigated in renal fibrosis in diabetic kidney disease so far. There are a few reports showing that altered cytokine levels can affect renal lipid metabolism in diabetic kidney disease (80, 81).

Figure 15A:
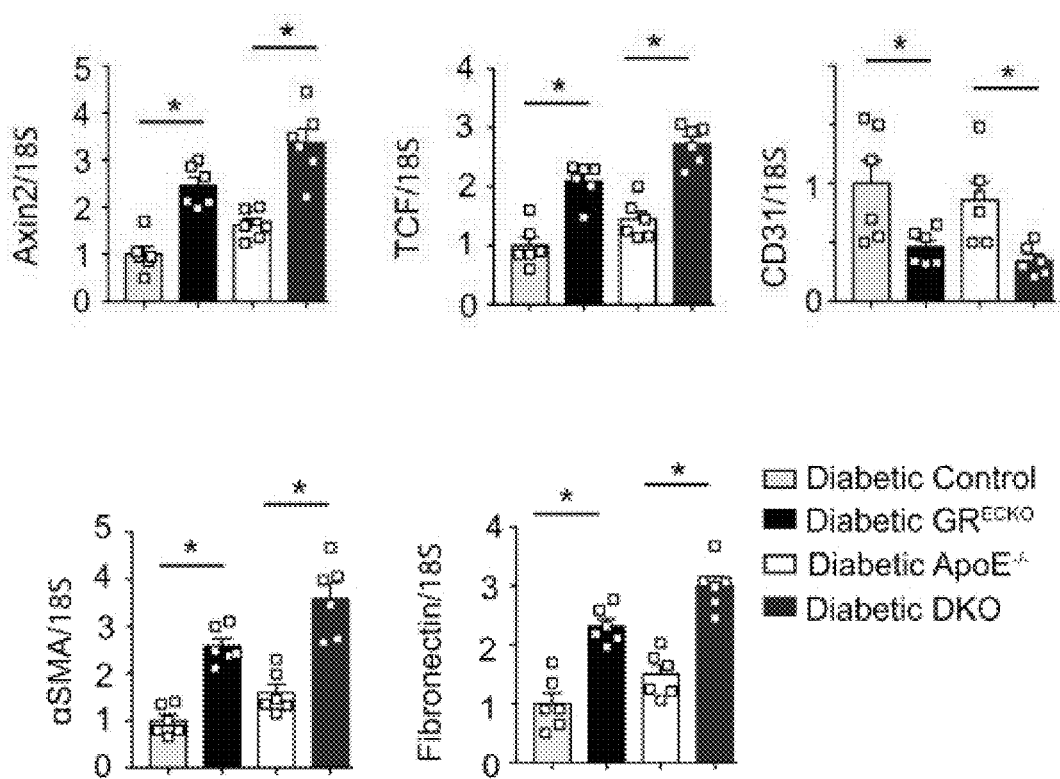
Figure 15C:
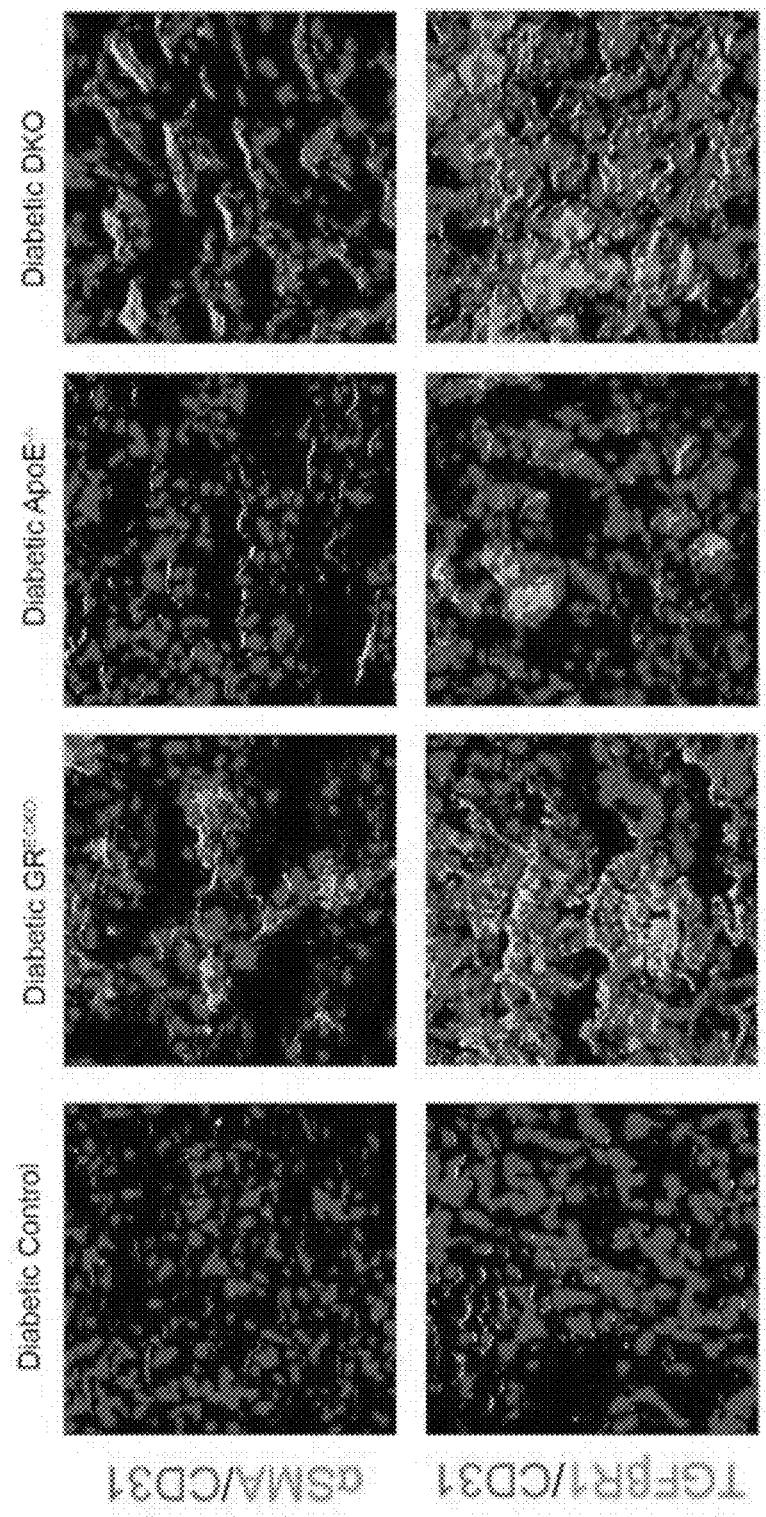
Figure 15C:
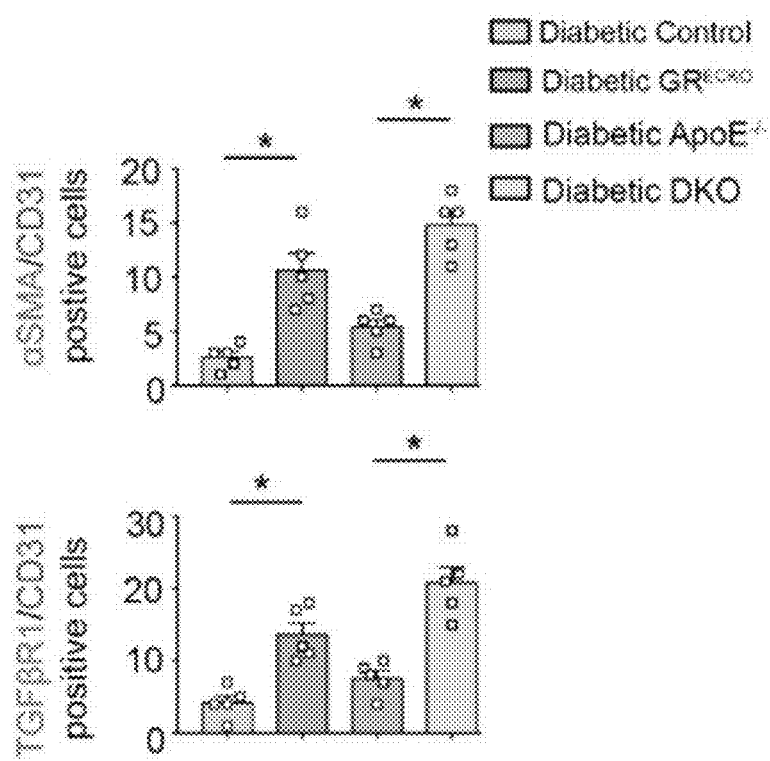

Example 13 Canonical Wnt Signaling is a New Drug Target for the Action of Endothelial GR The mRNA expression of Wnt-dependent genes and fibrogenic markers was assessed in EC isolated from the kidneys of diabetic $GR^{ECKO}$ and diabetic DKO mice and their diabetic littermate controls (FIG. 15B). The expression level of Wnt-dependent genes and fibrogenic markers was upregulated in kidneys of diabetic $GR^{ECKO}$ and diabetic DKO when compared to their respective controls. However, the kidneys of diabetic DKO mice showed the highest expression of both Wnt-dependent genes, such as axin2 and tcf, and fibrogenic markers, such as αSMA and fibronectin as well as the most severe suppression in CD31, suggestive of EndMT. These results were also confirmed at the protein level by Western blotting (FIG. 15B). Using immunofluorescent co-staining, the same pattern was also observed, with diabetic $GR^{ECKO}$ and diabetic DKO mice demonstrating higher levels of αSMA/CD31 and TGFβR1/CD31 co-staining in the kidneys when compared to their respective controls (FIG. 15C).

Example 14. Inhibition of Canonical Wnt Signaling Improves Renal Fibrosis

Figure 21A:
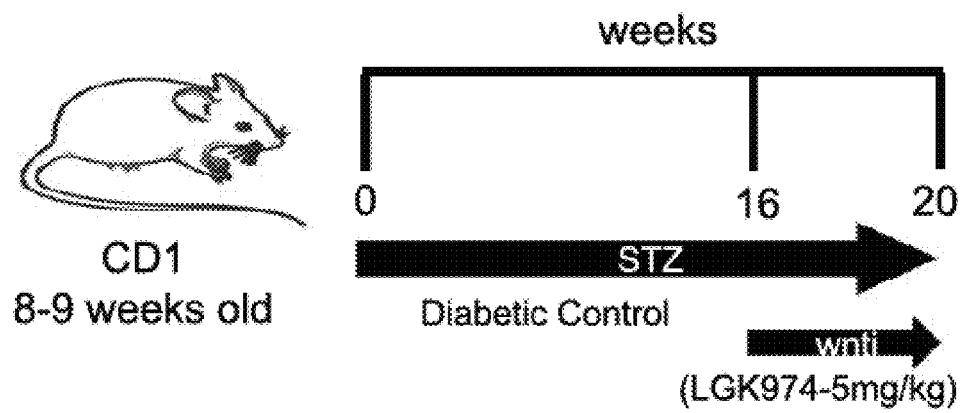
Figure 21B:
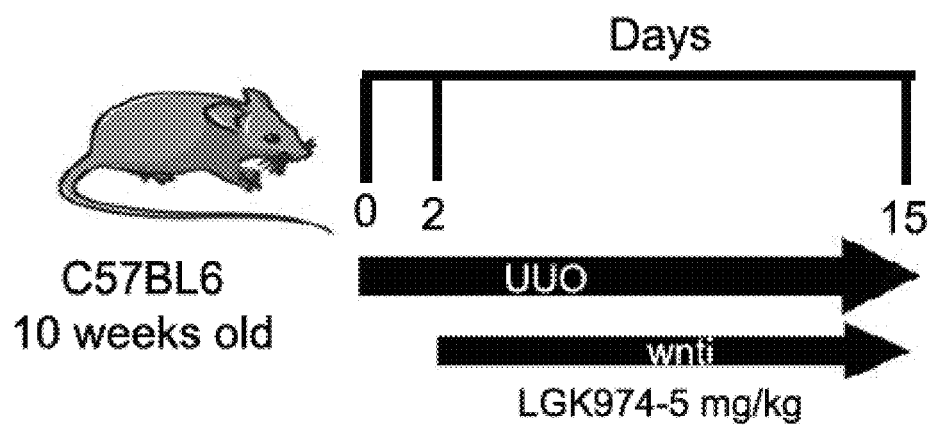
Figure 21C:
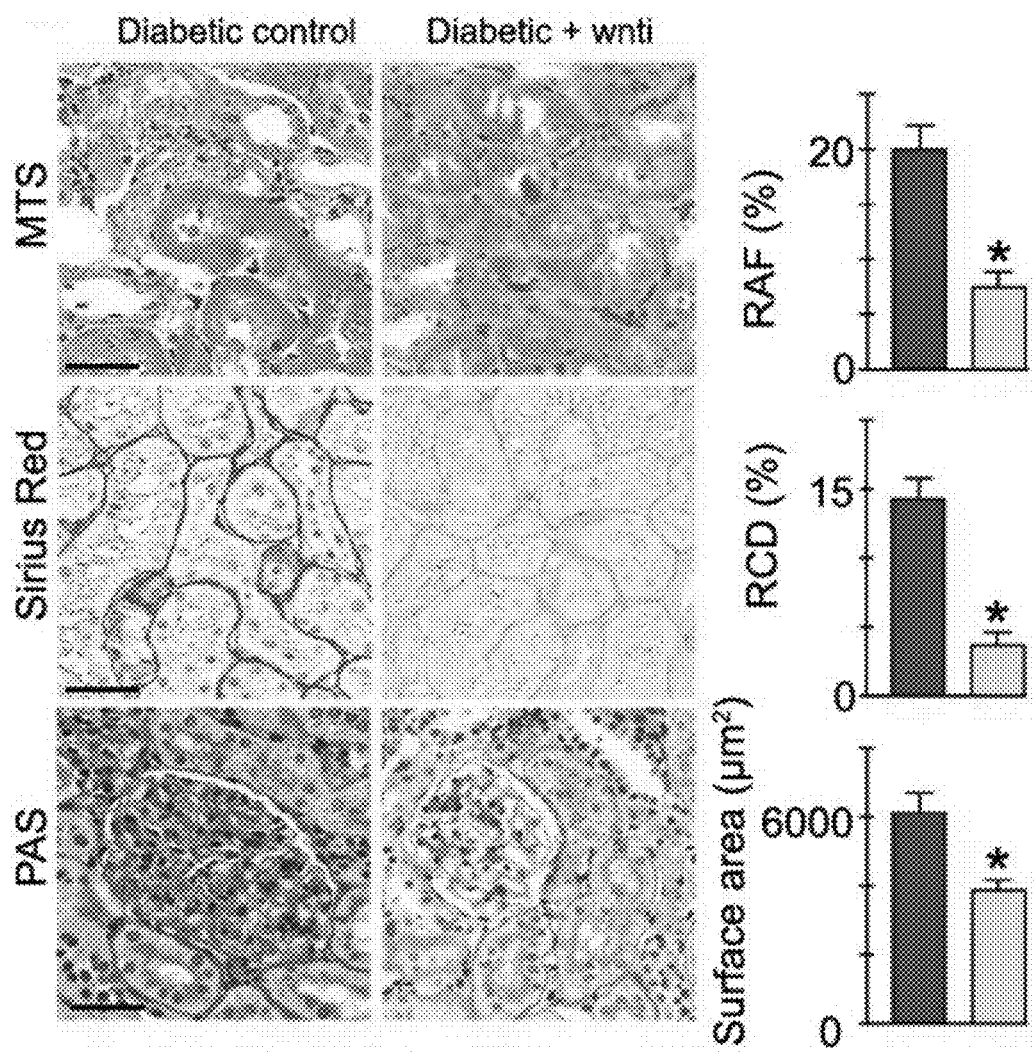
Figure 21D:
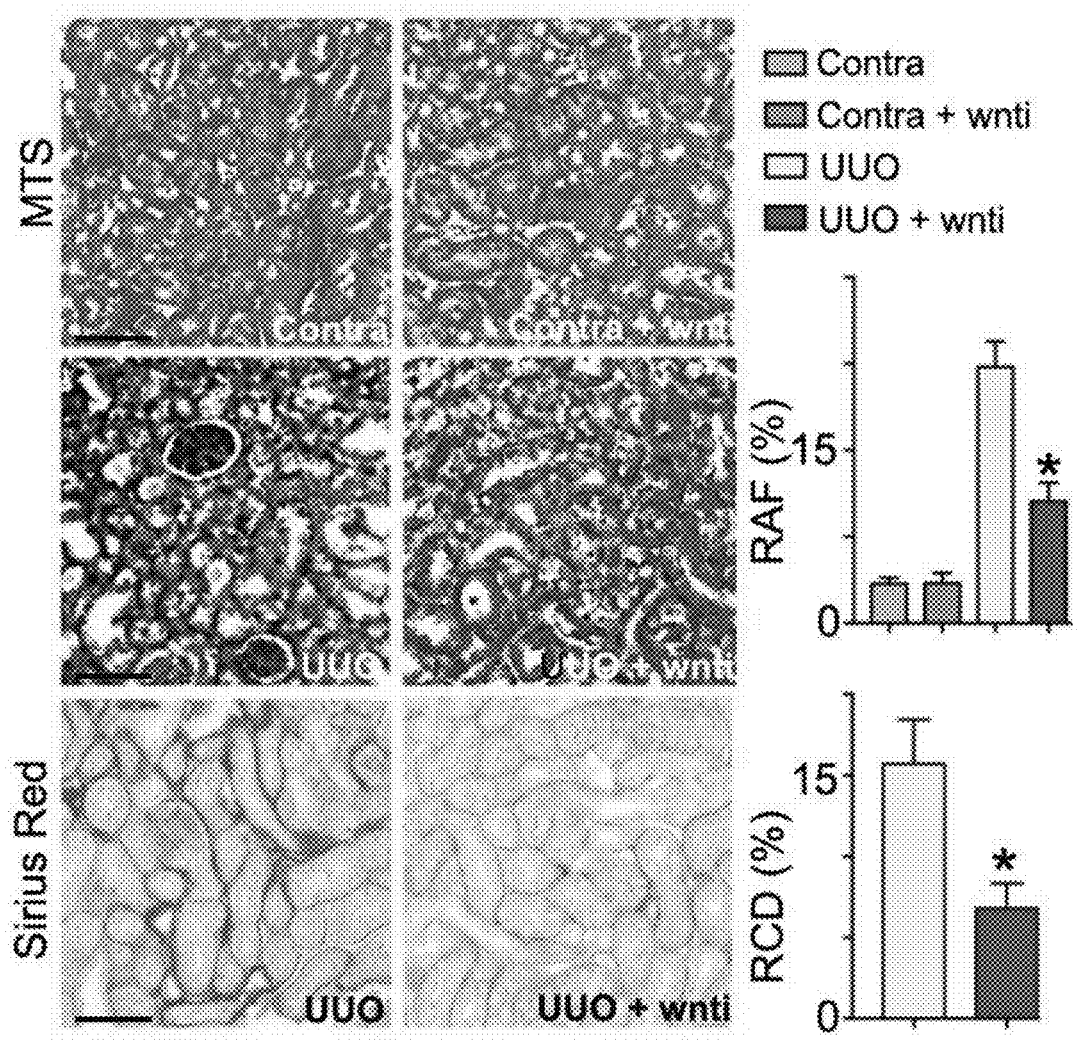
Figure 21G:
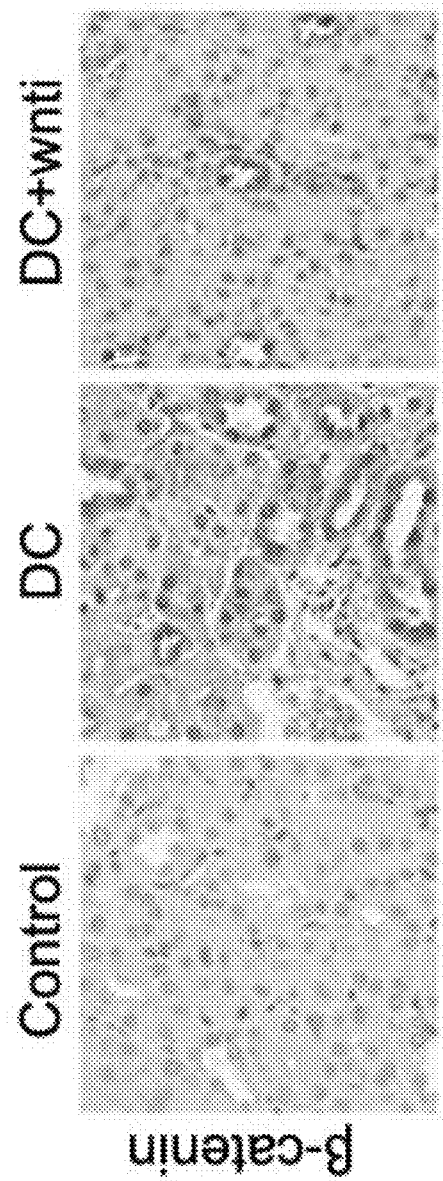
Figure 21H:
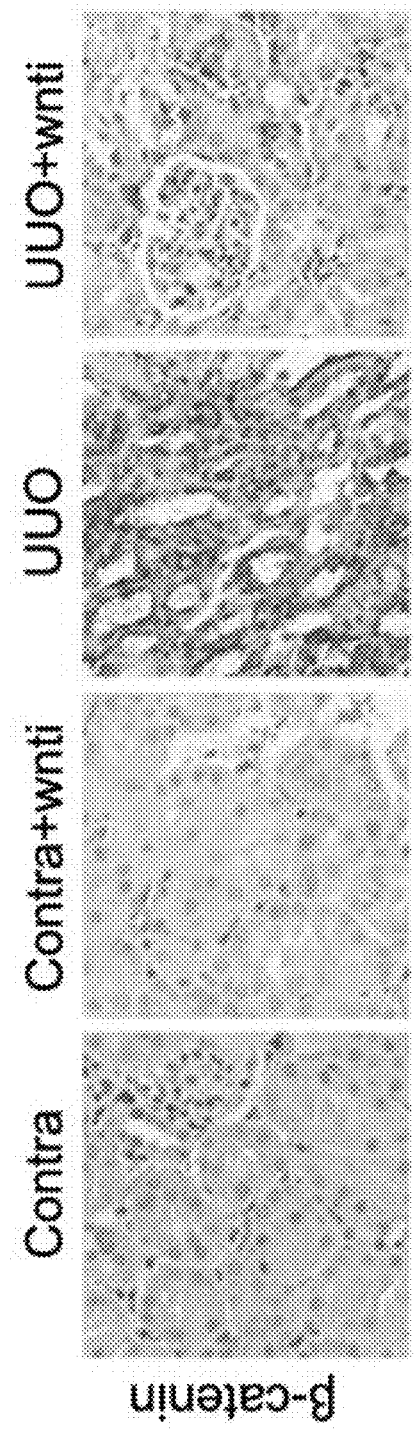
Figure 22:
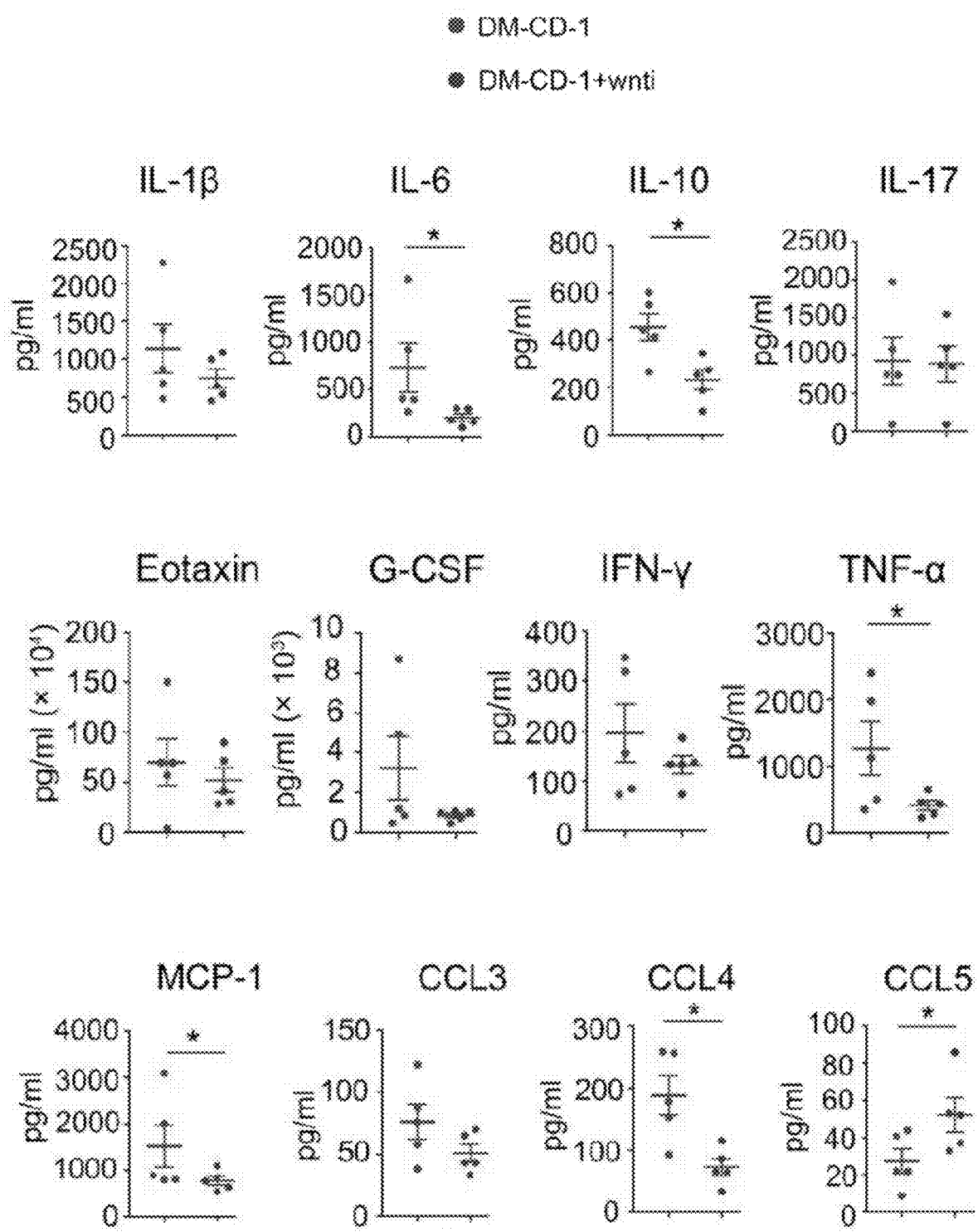
FIG. 22. Inhibition of canonical Wnt signaling disrupts the cytokine- and chemokine reprogramming in plasma of diabetic mice. Cytokines and chemokines were measured in plasma by using the cytokine array analysis (Luminex). The plasma of wnti-treated diabetic mice was analyzed for cytokine array analysis. N=5/group. Data are shown as mean±SEM. Tukey test was used for the analysis of statistical significance. *p<0.05.

To determine whether inhibition of the Wnt signaling pathway could ameliorate the observed fibrosis, LGK974, a small molecule inhibitor of all secreted Wnts (43), was utilized. FIGS. 21A-21B depict the schematic diagram showing the experimental protocol for LGK974 treatment in diabetic CD-1 and UUO mice. LGK974 greatly diminished the ECM deposition, relative area fibrosis, collagen accumulation and glomerulosclerosis in both models used (FIGS. 21C-21D). Wnt inhibition significantly restored the endothelial GR level and suppressed the level of β-catenin, a marker of canonical Wnt signaling, in the diabetic and UUO mice (FIGS. 21E-21H). LGK974 significantly suppressed the elevated level of IL-1β, IL-6, IL-10, G-CSF, TNFα, MCP-1, and CCL4, while elevating the level of CCL5 (FIG. 22).

Example 15. Wnt Inhibitor Partially Suppresses the Fibrogenic Phenotype in the Kidneys of Diabetic $GR^{ECKO}$ To further test the therapeutic potential of Wnt inhibition, the small molecule, Wnt inhibitor-LGK974, was used. Wnt inhibition clearly suppressed canonical Wnt signaling and substantially improved fibrogenic phenotype in the mouse model of diabetic kidney disease and restored the endothelial GR level. These data suggest that GR performs its anti-fibrotic action by tonic repression of canonical Wnt signaling in EC. Notably, this effect was less evident in $GR^{ECKO}$ possibly since Wnt inhibition was able to suppress EMT processes in other cell types (TECs) whereas, it was unable to mitigate EndMT processes. Cumulatively, these data suggest that endothelial GR is a key anti-EndMT molecule.

Figure 16A:
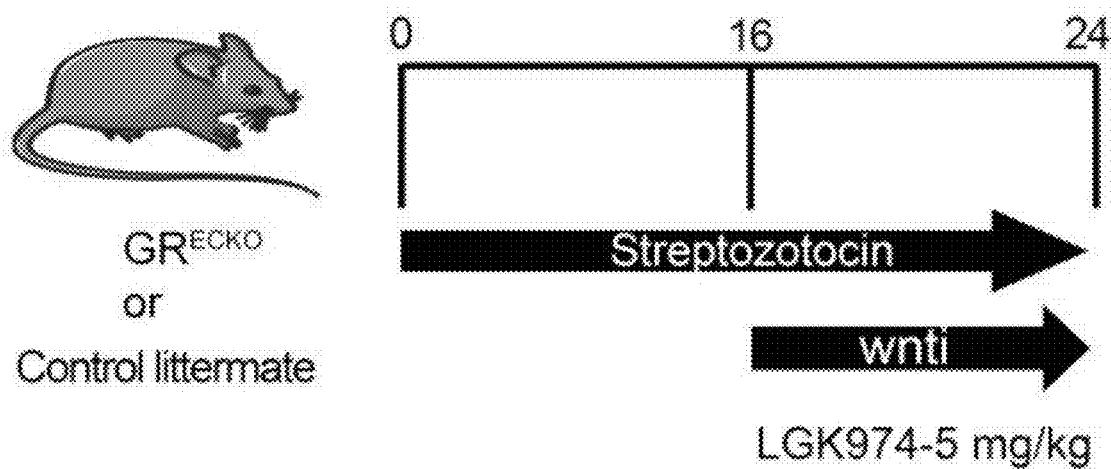
FIGS. 16A-16G. Wnt inhibitor partially abrogates the renal fibrosis in diabetic GR$^{ECKO}$ and DKO mice.
Figure 16B:
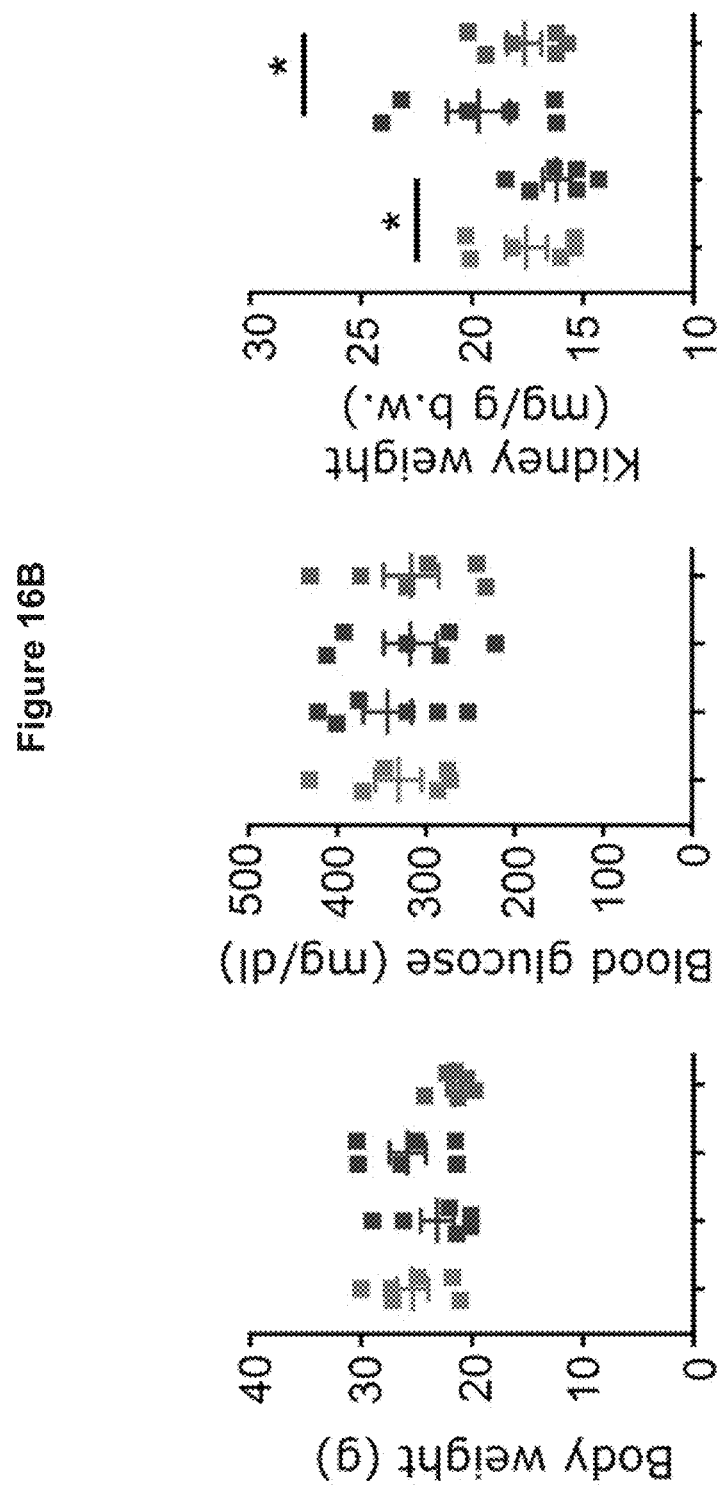
Figure 16C:
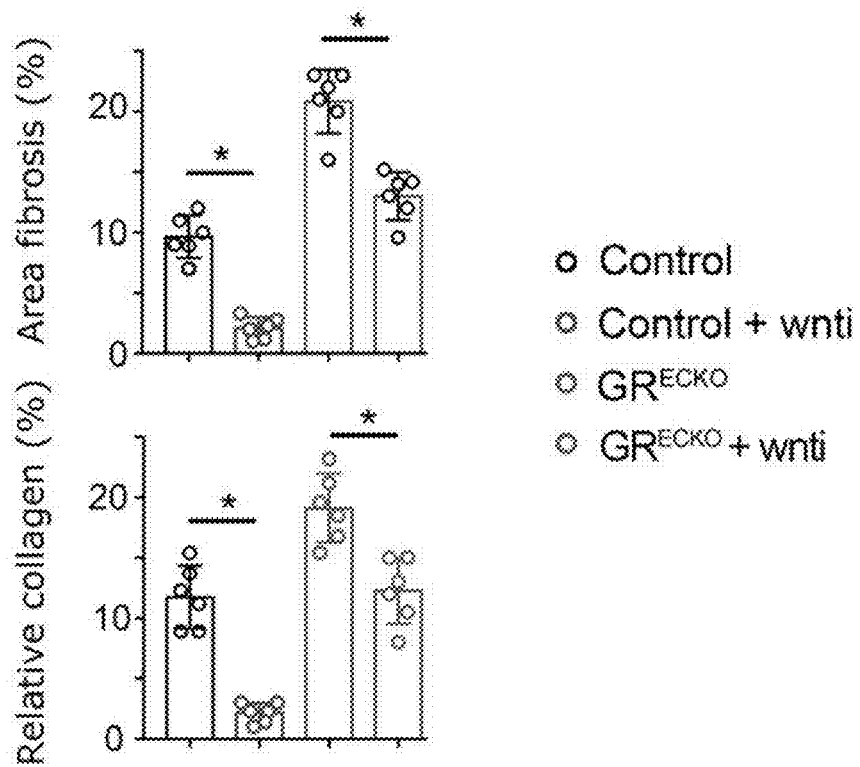
Figure 16D:
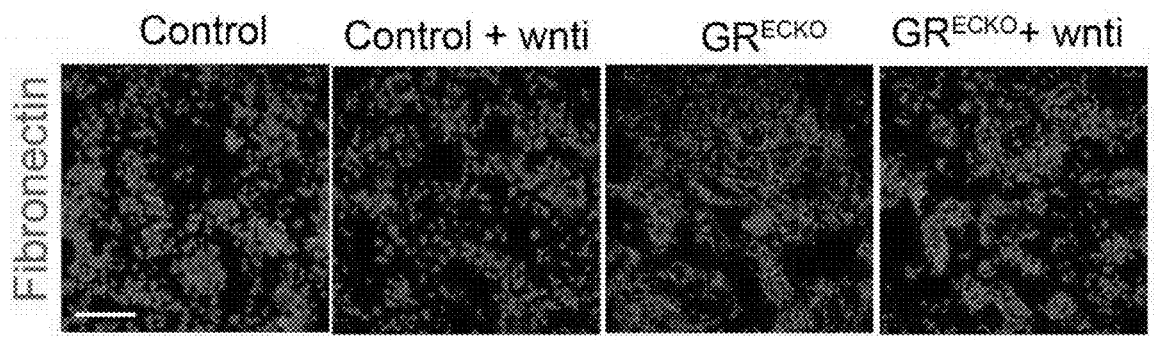
Figure 16E:
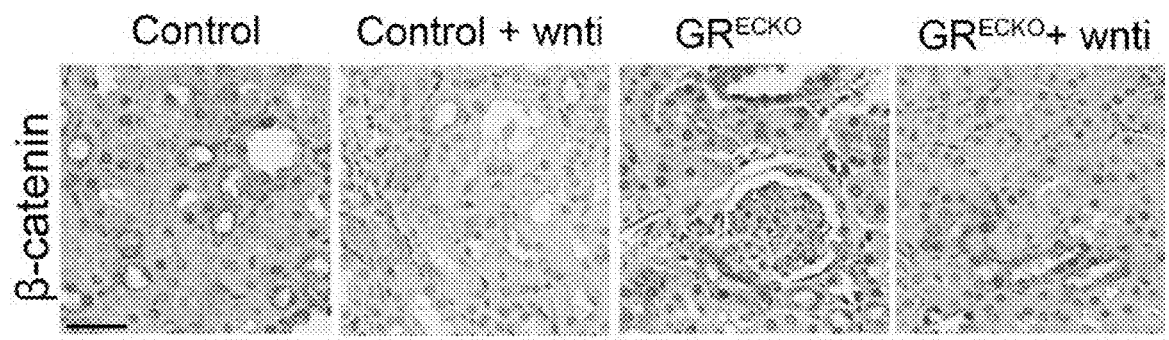
Figure 16F:
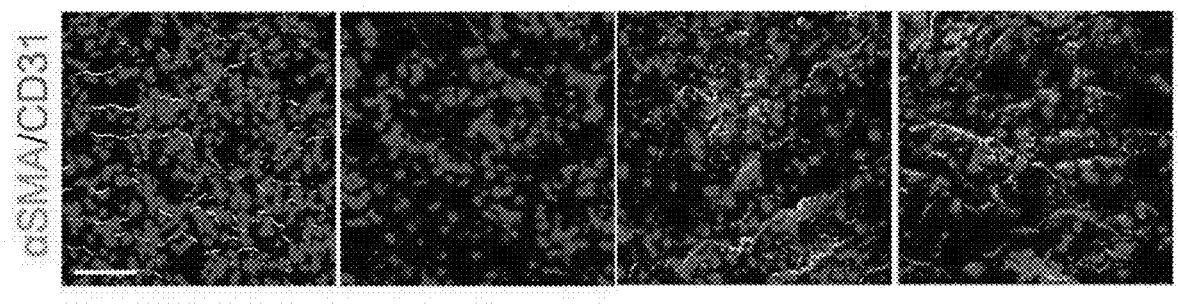
Figure 16G:
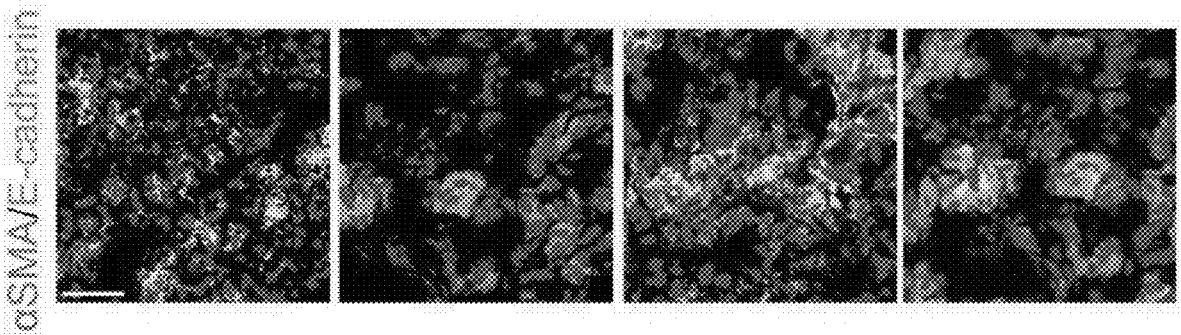

To determine whether Wnt inhibition could mitigate the renal fibrosis observed in diabetic mice lacking endothelial GR, a cohort of animals was treated with the Wnt inhibitor, LGK974. At the age of 8 weeks, control and $GR^{ECKO}$ mice were injected with STZ 50 mg/kg for five consecutive days. Sixteen weeks after injection, LGK974 was administered by oral gavage for eight additional weeks (FIG. 16A). At the time of sacrifice, there were no differences in body weight or glucose among the groups (FIG. 16B). However, a significant reduction in kidney weight was observed in the Wnt-inhibitor treated diabetic $GR^{ECKO}$ and diabetic control mice (FIG. 16A). Wnt inhibitor clearly improved the relative area of fibrosis, relative collagen deposition and tubular damage in the diabetic control mice; this effect was less pronounced, though still significant in the diabetic $GR^{ECKO}$ mice (FIG. 16C). A similar pattern was observed in the staining of fibronectin and β-catenin (FIG. 16D-16E). Wnt inhibitor significantly suppressed EndMT (CD31/αSMA co-positive cells) in the diabetic control mice; this effect was less pronounced in the diabetic $GR^{ECKO}$ mice (FIG. 16F). However, Wnt inhibition significantly reduced the level of EMT (E-cadherin/αSMA co-positive cells) in control and diabetic $GR^{ECKO}$ mice (FIG. 16G).

Figure 17A:
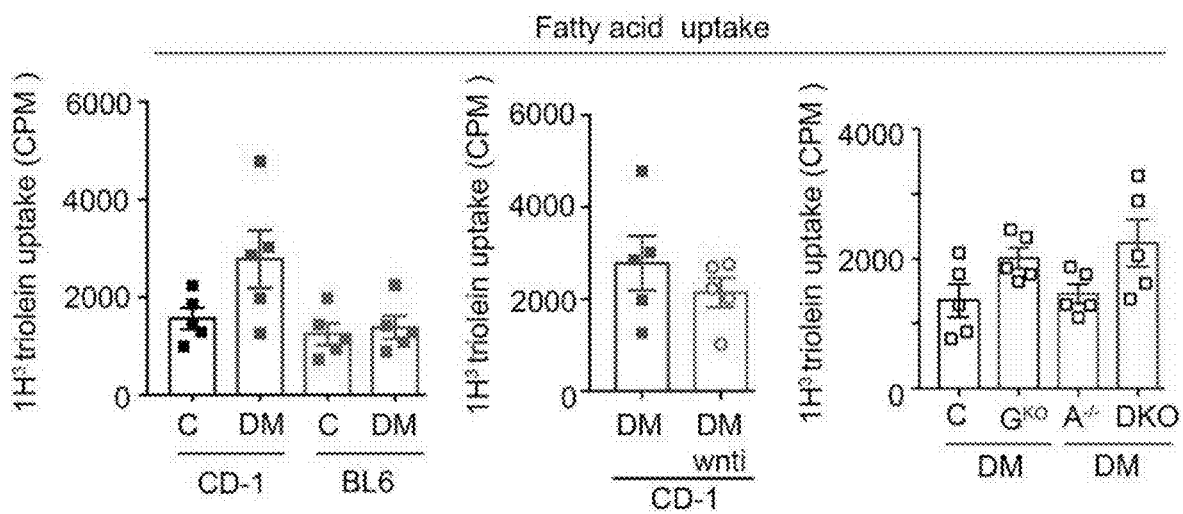
FIGS. 17A-17E. Metabolic reprogramming by loss of endothelial GR loss worsens the phenomenon of diabetic kidney disease.
Figure 17B:
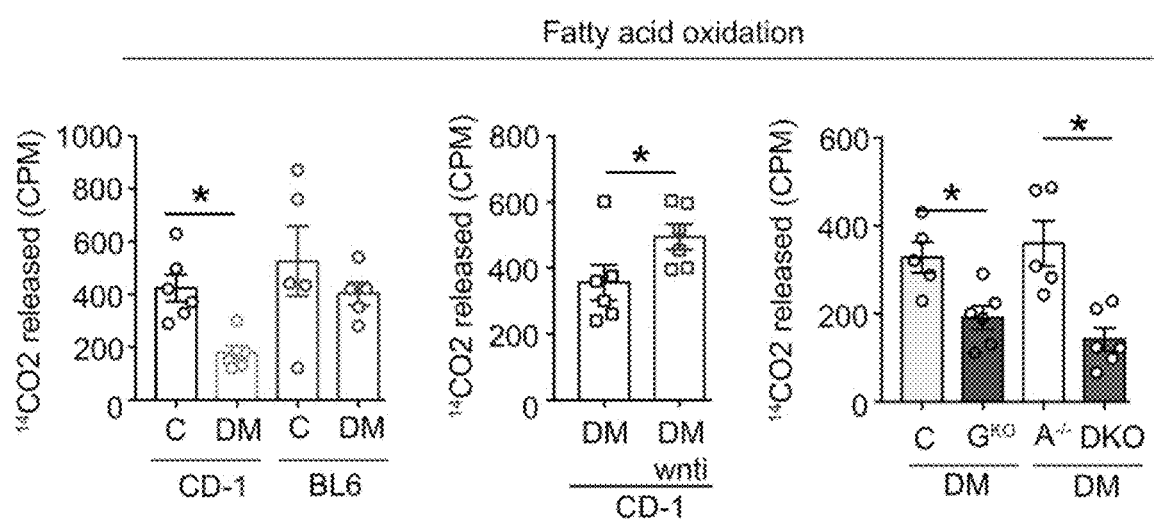
Figure 23A:
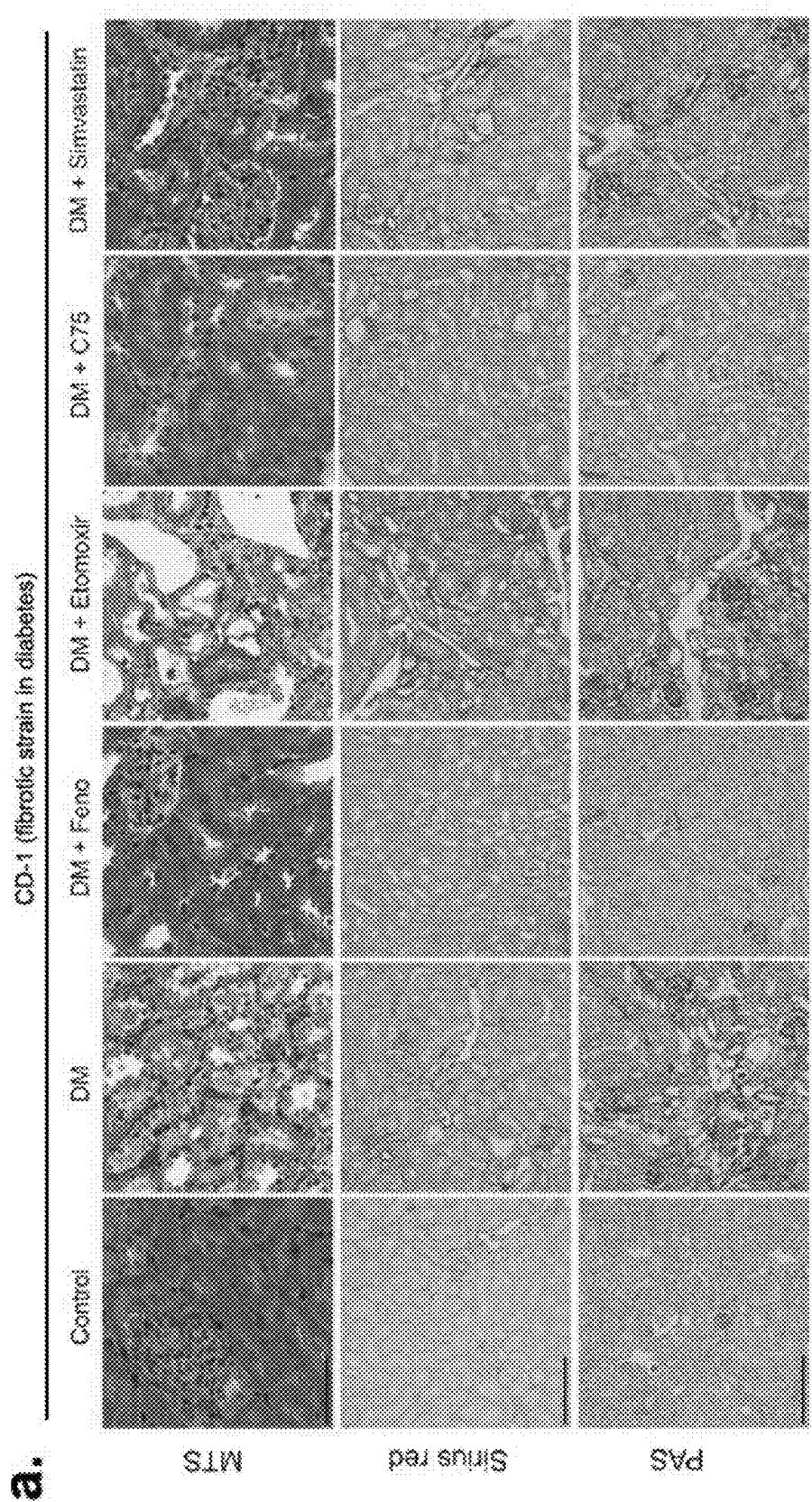
FIGS. 23A-23F. Endothelial GR is essential for the action of anti-dyslipidemic drugs in diabetic kidney disease.
Figure 23B:
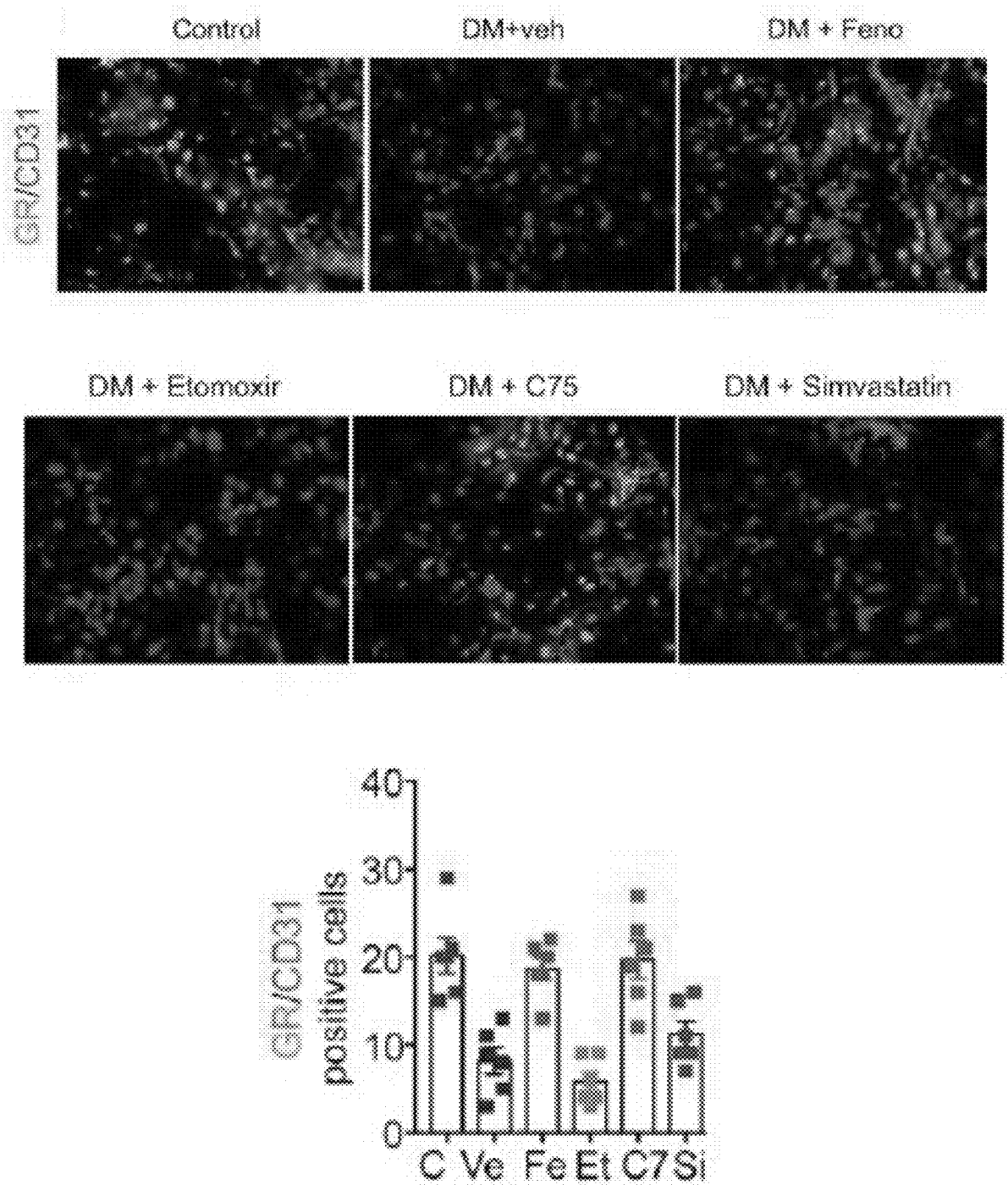
Figure 23C:
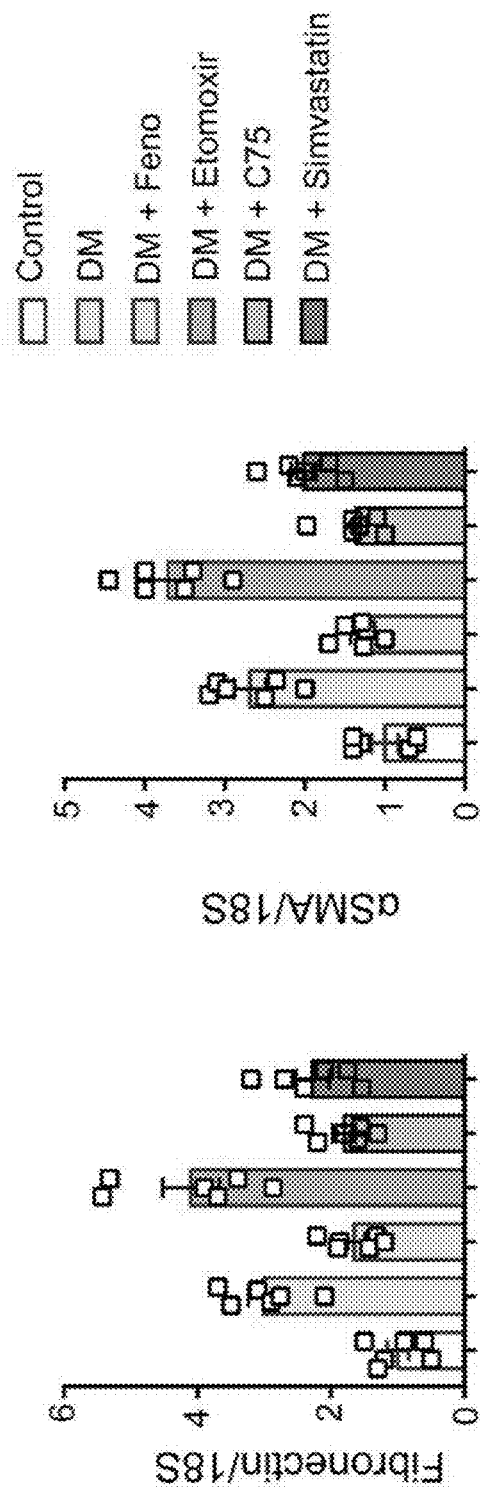
Figure 23D:
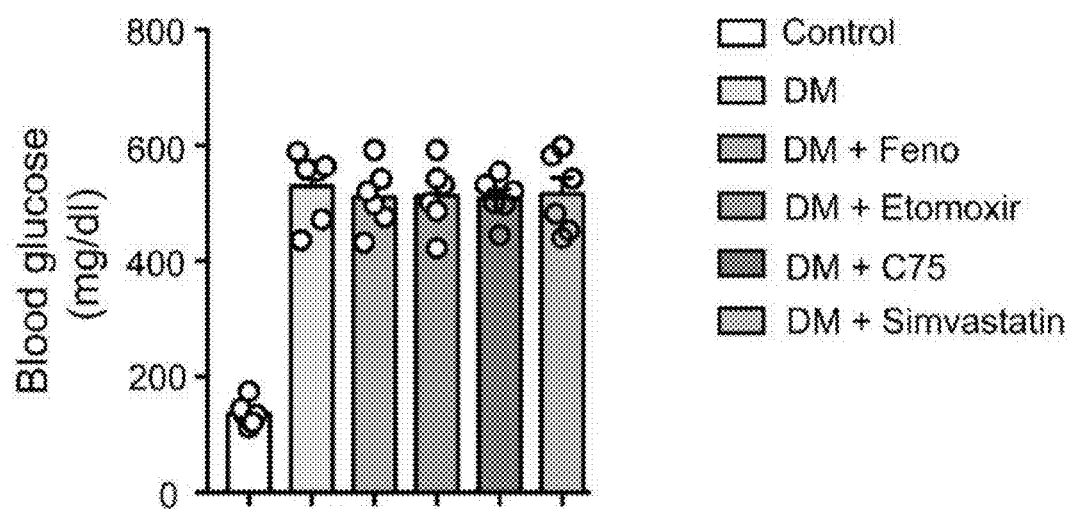
Figure 23E:
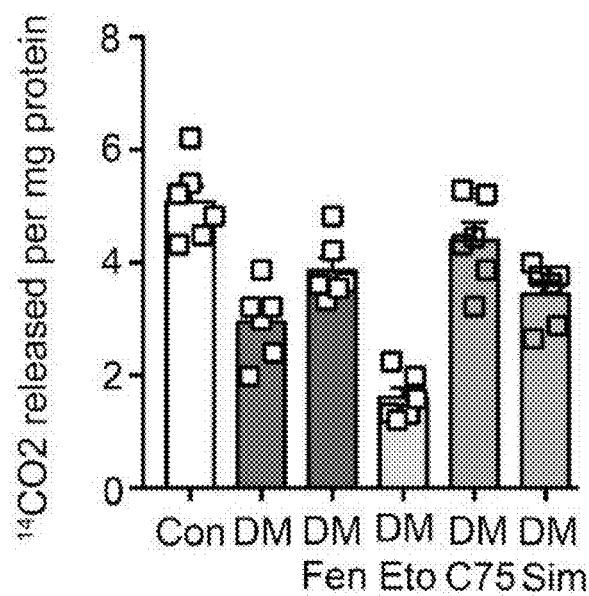
Figure 23F:
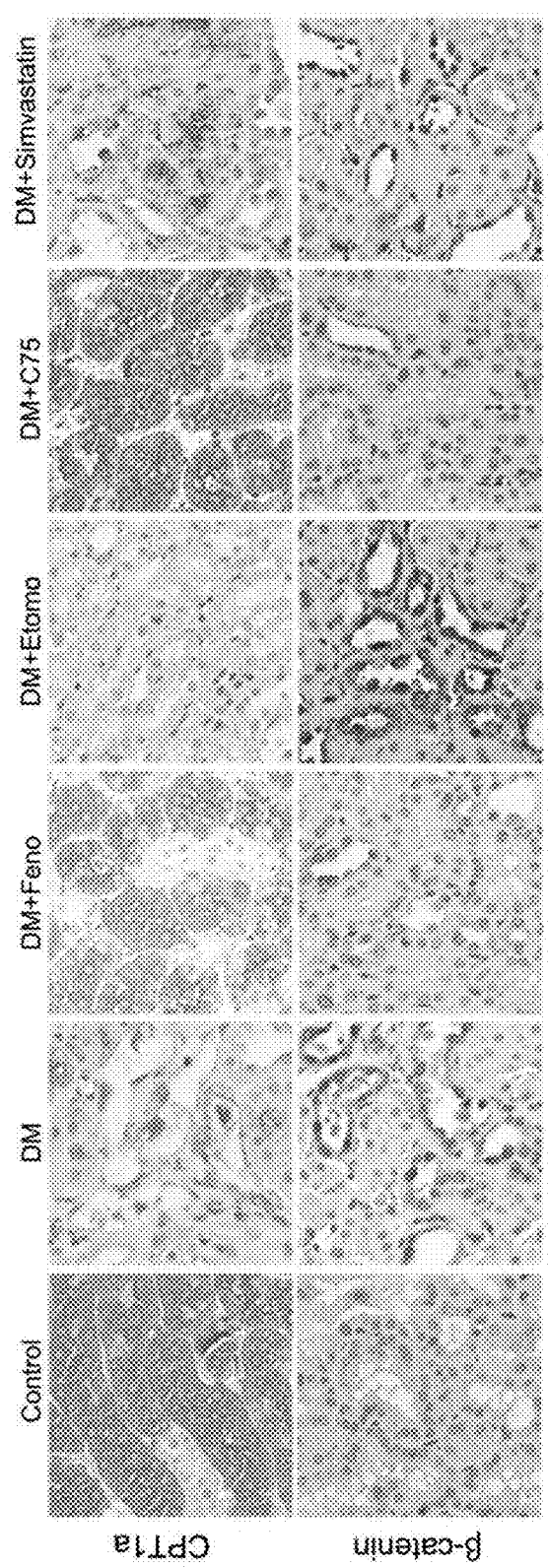

Example 16 Metabolic Reprogramming by Loss of Endothelial GR Accelerates Renal Fibrosis It is increasingly recognized that defects in central metabolism contribute to kidney fibrosis (69, 76). Defective FA metabolism in EC leads to EndMT events (77). To investigate whether FA metabolism was deranged in the model, radiolabeled [$^{14}$C]palmitate uptake experiments were performed in isolated EC from mouse kidneys. FA uptake was higher in isolated EC from the diabetic kidneys of the more fibrotic strain (diabetic CD-1) when compared to kidney EC from the less-fibrotic strain (diabetic C57BL/6). Administration of the Wnt inhibitor suppressed FA uptake. Kidney EC from both diabetic $GR^{ECKO}$ and DKO mice displayed higher FA uptake when compared to that of the diabetic control littermates (FIG. 17A). FA oxidation (FAO) was also assessed by measuring the $^{14}CO_2$ release from radiolabeled [$^{14}$C]palmitate in cultured EC isolated from kidneys. FAO was diminished in the isolated kidney EC of diabetic CD-1 mice and Wnt inhibitor was able to restore the level of FAO. The cultured kidney EC from diabetic $GR^{ECKO}$ and diabetic DKO mice showed a diminished level of FAO when compared to their diabetic control littermates (FIG. 17B). In the next set of experiments, diabetic CD-1 mice were treated with the FA synthase inhibitor C75, the FAO inhibitor etomoxir, the PPARα agonist fenofibrate, and the cholesterol-lowering drug simvastatin for 4 weeks. Fenofibrate and C75 ameliorated the fibrogenic phenotype, whereas etomoxir exacerbated the fibrosis. Simvastatin treatment did not cause any significant suppression in the level of fibrosis. (FIG. 23A). Fenofibrate and C75 restored the level of GR protein in CD31 positive cells, whereas etomoxir and simvastatin suppressed it (FIG. 23B). Fenofibrate and C75 downregulated the fibronectin and αSMA mRNA level, whereas etomoxir upregulated and simvastatin did not cause any significant change in the gene expression level of fibronectin and αSMA in the diabetic kidneys (FIG. 23C). These FA modulators did not cause any significant differences in the level of blood glucose (FIG. 23D). Etomoxir treatment caused significant suppression of FAO, as measured by $^{14}CO_2$ release, and CPT1a level, and induced the protein expression level and β-catenin whereas, C75 and fenofibrate increased the level of FAO, induced the level of CPT1a and suppressed the level of β-catenin in the diabetic CD-1 mice (FIGS. 23E-F).

Figure 17C:
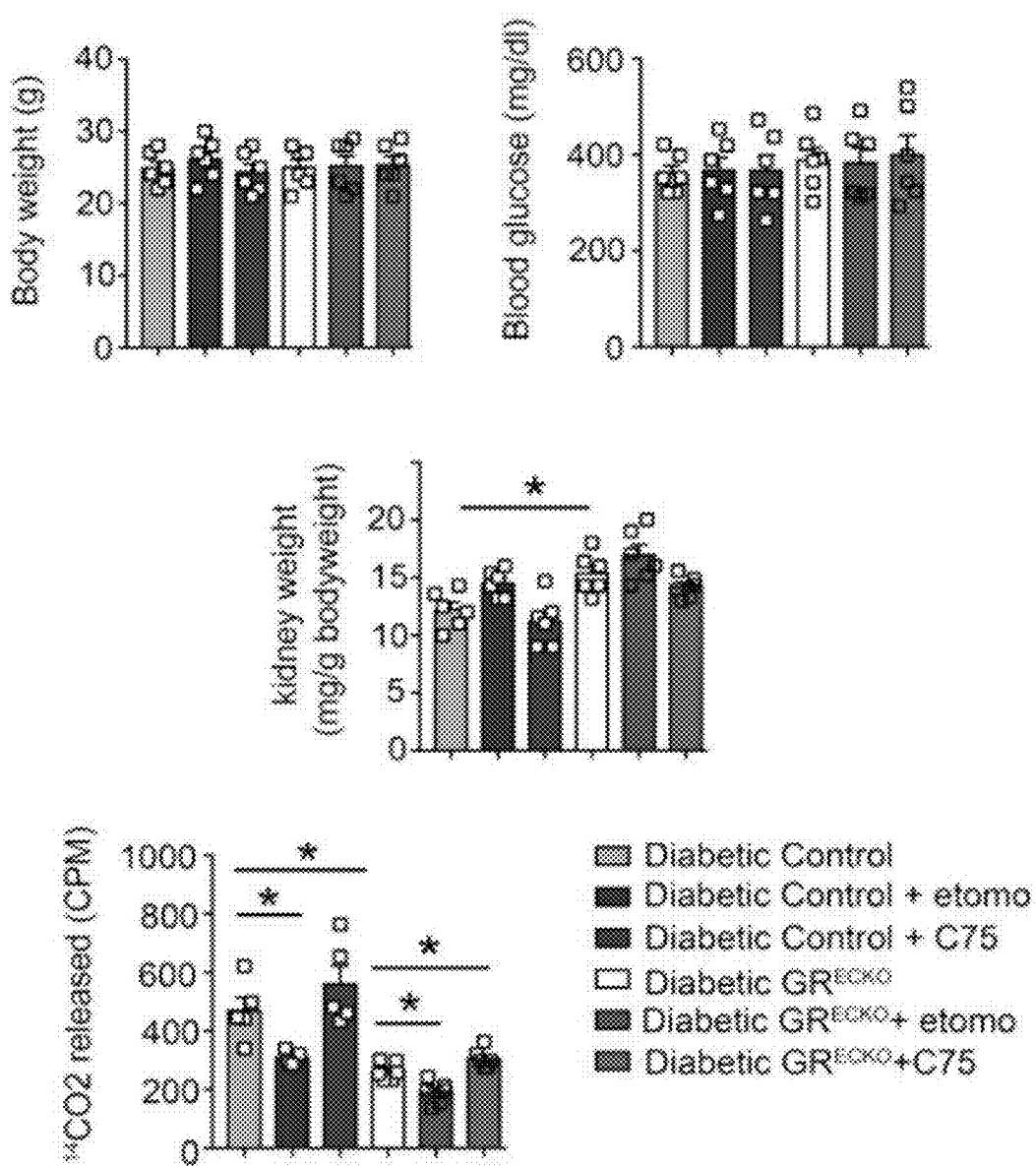
Figure 17D:
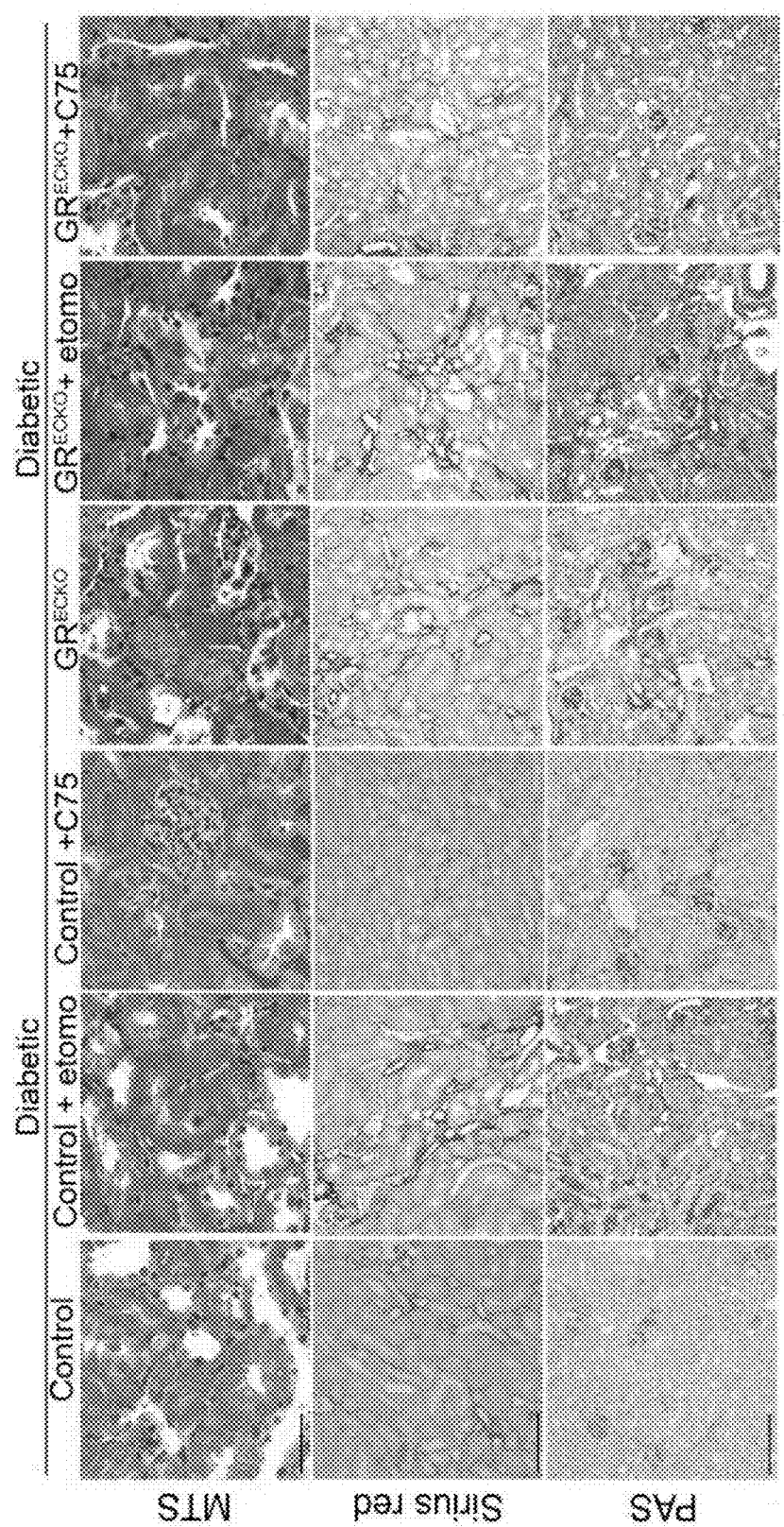
Figure 17E:
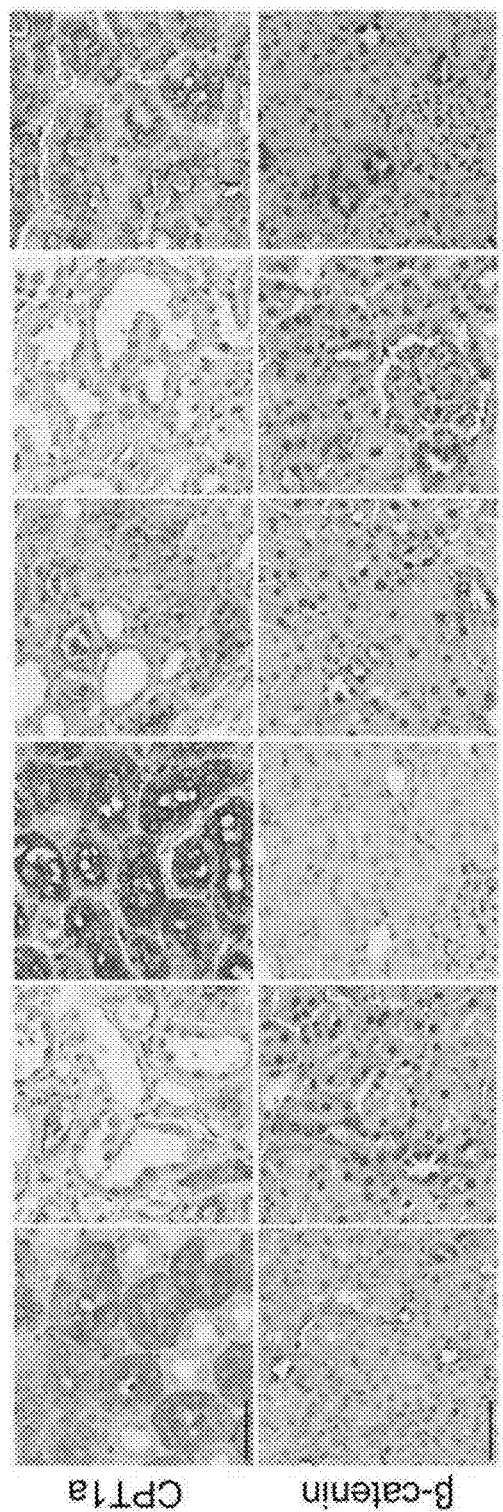

Etomoxir and C75 were also tested in the diabetic control littermates and diabetic $GR^{ECKO}$ mice. There were no significant differences in body weight, blood glucose or kidney weight in diabetic control littermates and $GR^{ECKO}$ mice after treatment with etomoxir or C75. Data from kidney EC revealed that etomoxir caused significant suppression in FAO, and C75 restored FAO in diabetic control littermates. However, etomoxir caused significant suppression in FAO and C75 was unable to rescue the level of FAO in kidney EC from diabetic $GR^{ECKO}$ mice (FIG. 17C). Etomoxir treatment accelerated the renal fibrogenic phenotype, suppressed the CPT1a level and increased the expression level of β-catenin in the kidneys of diabetic control and diabetic $GR^{ECKO}$ mice. C75 treatment clearly abolished the renal fibrogenic phenotype, restored CPT1a and completely diminished the level of β-catenin in the kidneys of diabetic control. These effects were also observed in the $GR^{ECKO}$ mice, though to a lesser extent. (FIG. 17D-E).

This in vivo data suggests that the $GR^{ECKO}$ mice exhibit enhanced EMT in their diabetic kidneys.

Figure 18A:
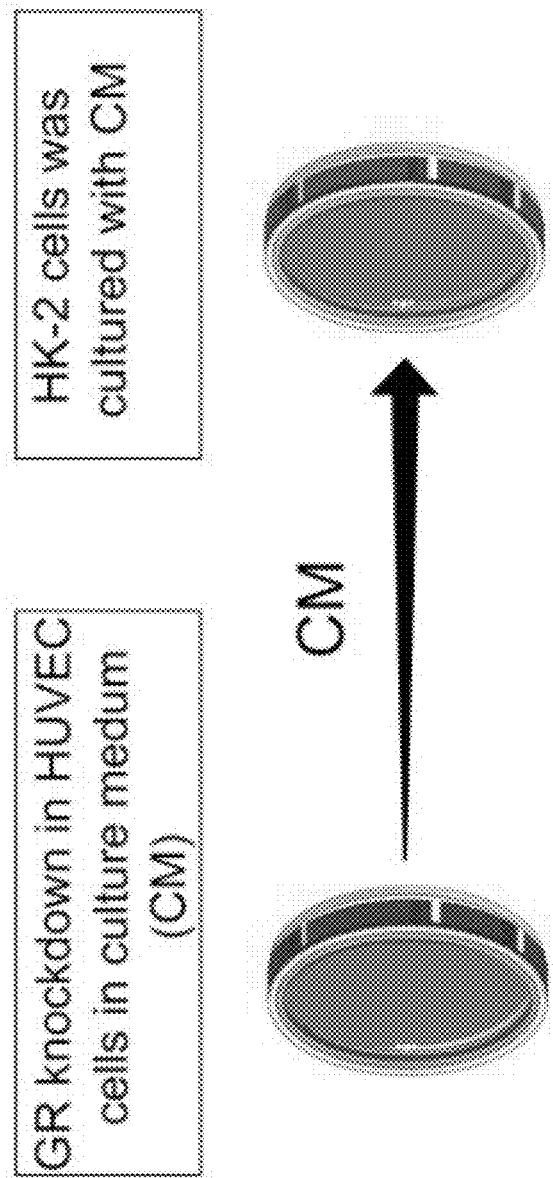
FIGS. 18A-18I. GR-loss in endothelial cells reprograms the central metabolism in the renal tubular cells, activates EMT processes.
Figure 18B:
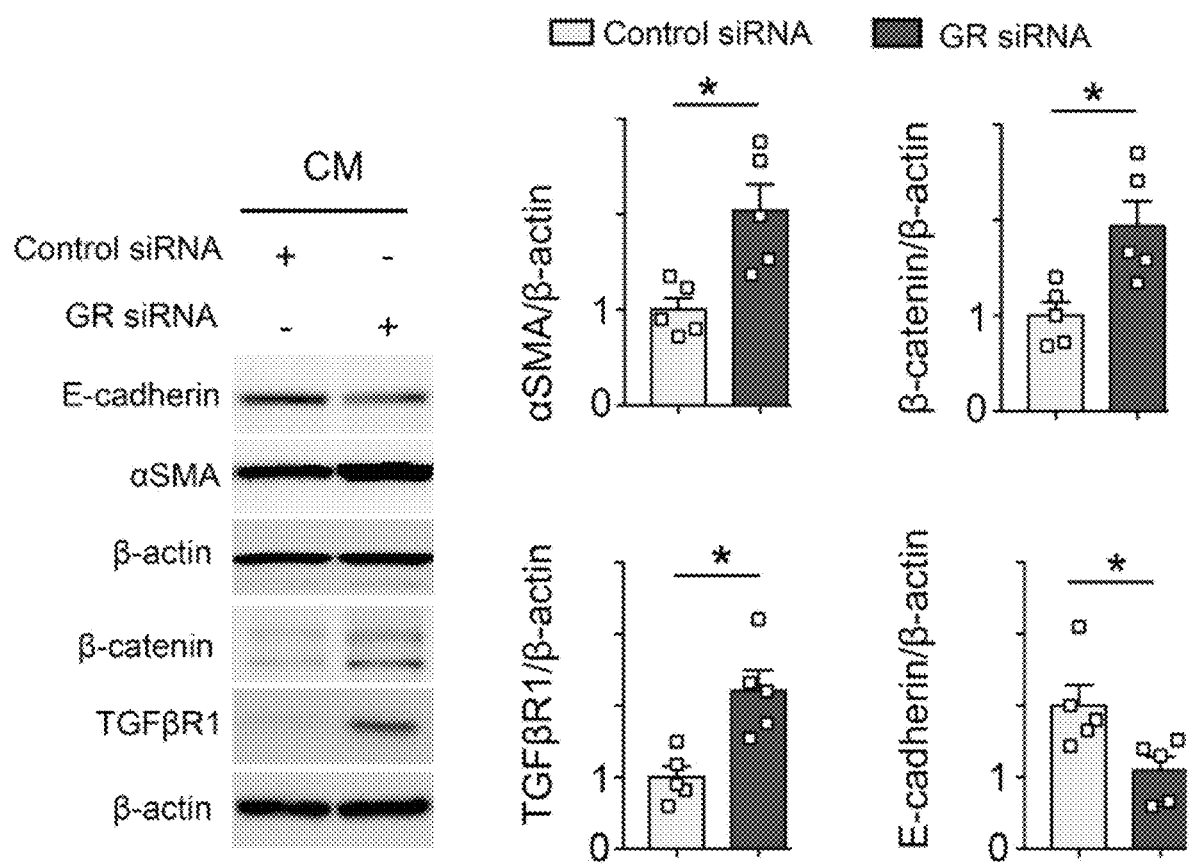
Figure 18C:
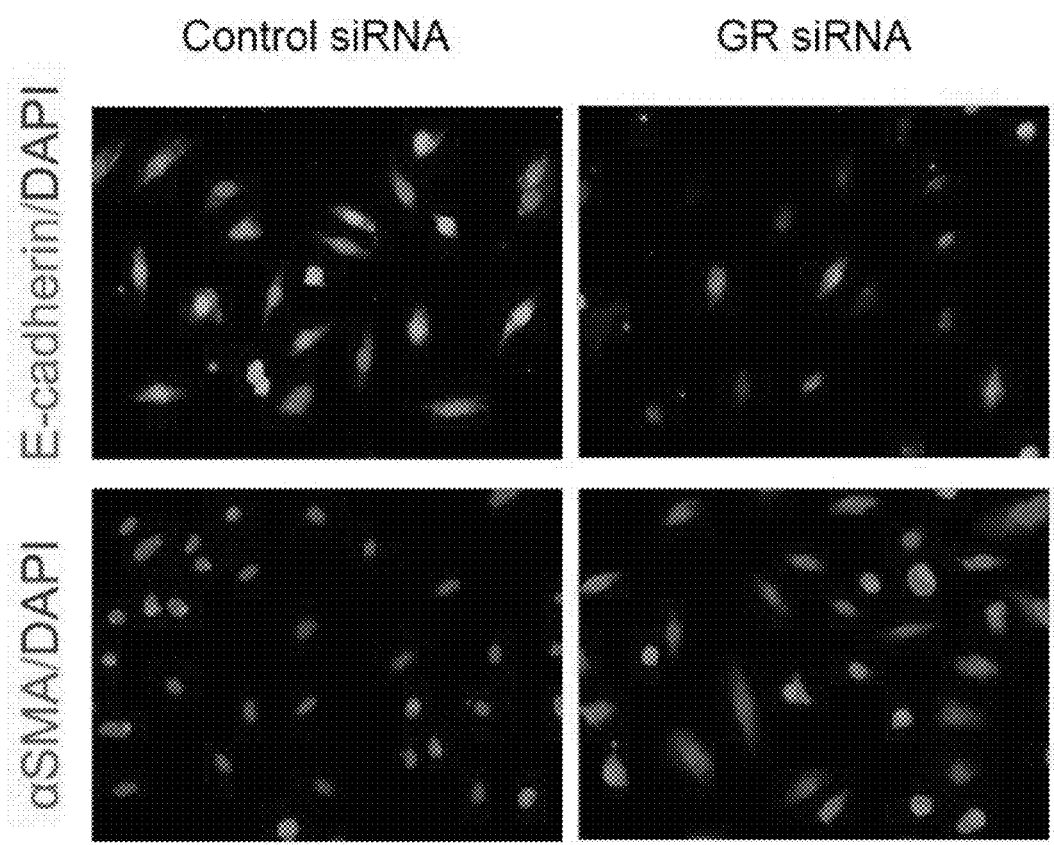
Figure 18D:
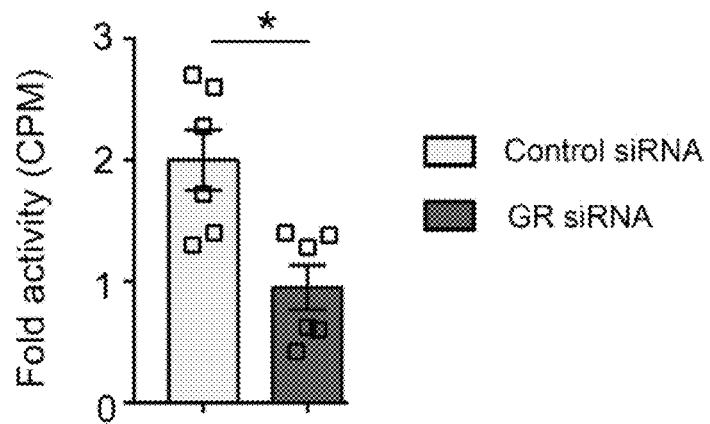
Figure 18E:
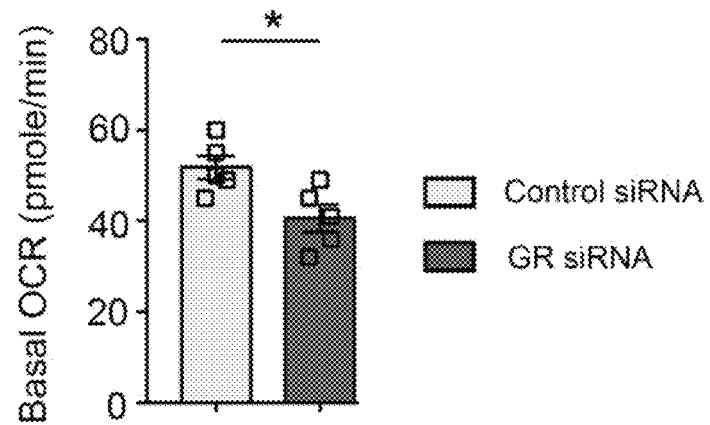
Figure 18F:
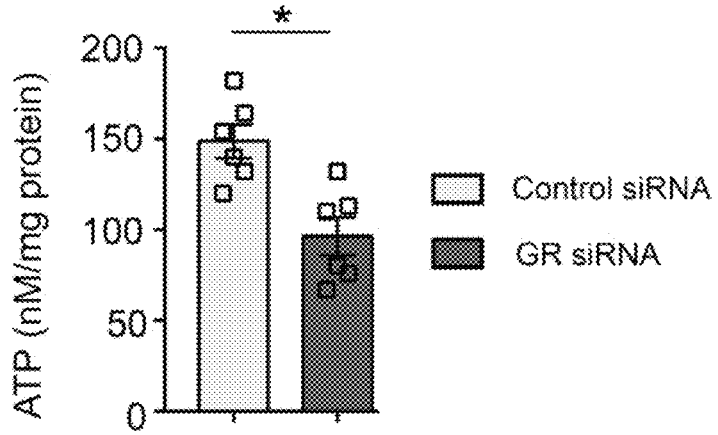
Figure 18G:
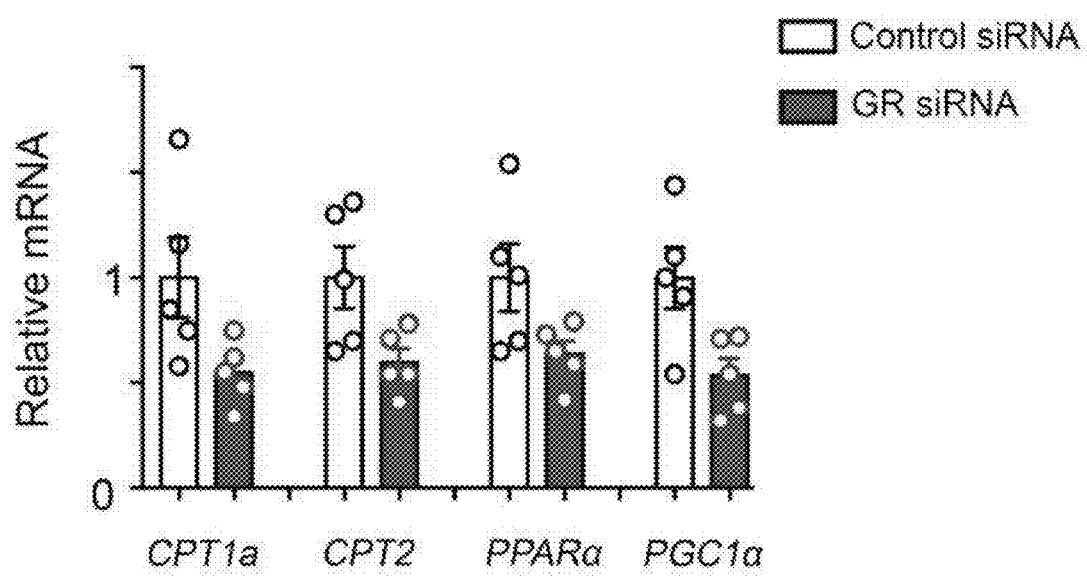

Example 17 GR Loss-Linked EndMT Disrupts Central Metabolism and Induces Mesenchymal Transformation in Tubular Epithelial Cells To test whether endothelial GR deficiency affects mesenchymal programs and causes defects in central metabolism in neighboring epithelial cells, the effects of culture media from GR knockdown HUVECs on the mesenchymal phenotype of HK-2 cells was analyzed (FIG. 18A). Conditioned media (CM) from GR siRNA-transfected HUVECs decreased E-cadherin protein levels and increased αSMA, TGFβR1 and β-catenin protein levels in HK-2 cells when compared to media from scrambled siRNA-transfected HUVECs (FIGS. 18B-C). CM treatment from GR siRNA-transfected HUVECs caused a significant reduction in the level of FAO, oxygen consumption rate and cellular ATP level in the HK-2 cells (FIGS. 18D-F). CM significantly down-regulated the level of the FAO-responsive genes Cpt1a, Cpt2, Pparα, and Pgc1α (FIG. 18G).

Figure 18H:
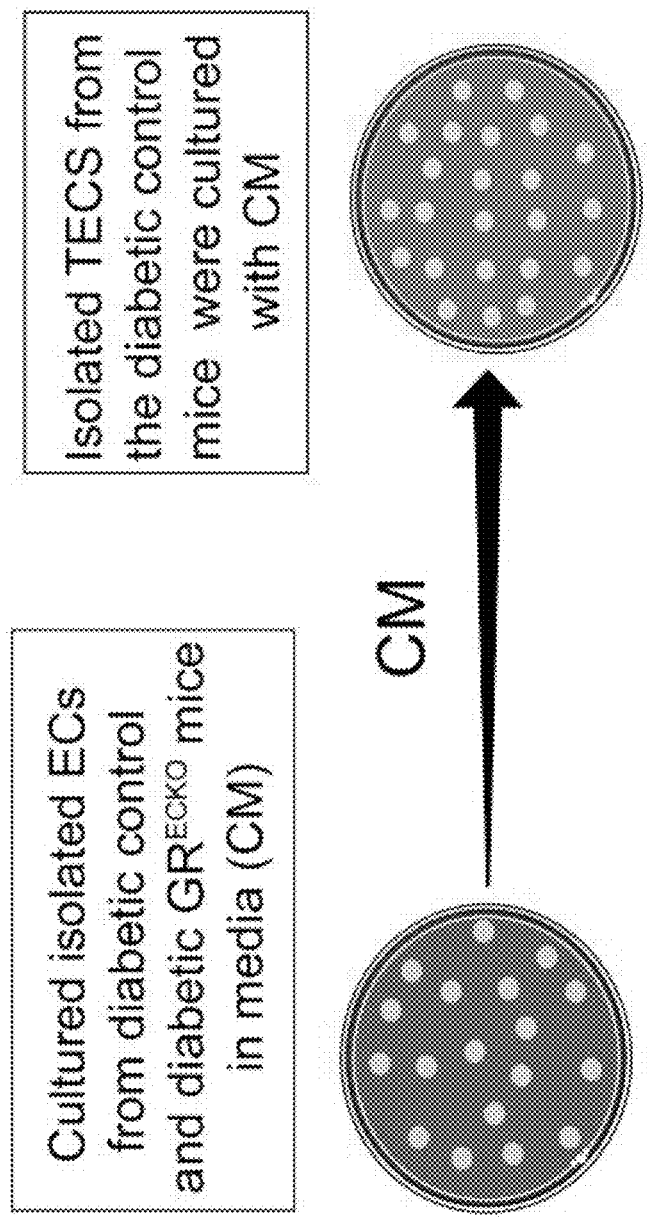
Figure 18I:
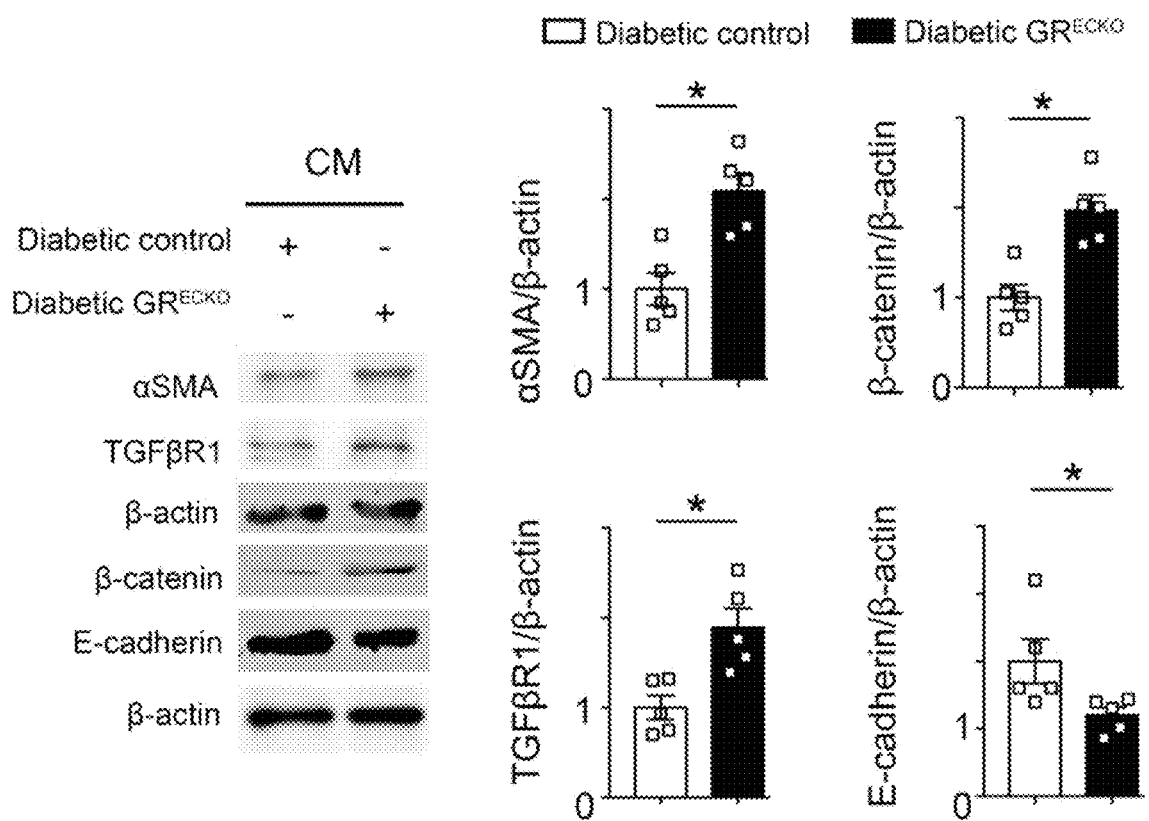

To confirm these in vitro results, primary EC were isolated from diabetic control and diabetic $GR^{ECKO}$ mice to analyze the contribution of GR-deficient EC on the mesenchymal activation in tubular epithelial cells (TECs). CM from isolated cultured EC from the kidneys of diabetic $GR^{ECKO}$ and diabetic control littermates was transferred to cultured TECs from diabetic control mice (FIG. 18H). The CM treatment from GR-deficient cells caused significant suppression of E-cadherin levels and induction of αSMA, TGFβR1 and β-catenin protein levels in TECs (FIG. 18I).

To further test the therapeutic potential of Wnt inhibition, the small molecule Wnt inhibitor-LGK974 was used. Wnt inhibition clearly suppressed canonical Wnt signaling and substantially improved fibrogenic phenotype in a mouse model of diabetic kidney disease and restored the endothelial GR level. Not wishing to be bound by any theory, these data suggest that GR performs its anti-fibrotic action by tonic repression of canonical Wnt signaling in EC. Notably, this effect was less evident in $GR^{ECKO}$ possibly since Wnt inhibition was able to suppress EMT processes in other cell types (TECs) whereas, Wnt inhibition was unable to mitigate EndMT processes. Cumulatively, these data suggest that endothelial GR is a key anti-EndMT molecule.

The data from the examples above demonstrate a role for EC GR in the regulation of fibrogenic processes in a mouse model of diabetic kidney disease. The data demonstrate that EC GR regulates the mesenchymal trans differentiation process by influencing FA metabolism and control over canonical Wnt signaling in the kidneys of diabetic mice. GR loss is one of the fibrotic phenotypes in diabetes that leads to disruption of cytokine and chemokine homeostasis by up regulating canonical Wnt signaling. These processes may alter the metabolic switch in favor of defective FA metabolism and associated mesenchymal activation in TECs.

Hypercholesterolemia may worsen the severity of renal fibrosis in endothelial cell GR knock-out mice, suggesting that hypercholesterolemia affects EC metabolism and contributes to renal fibrosis. However, similar to available clinical data, the cholesterol lowering drug simvastatin did not ameliorate the severity of renal fibrosis in this mouse model of diabetic kidney disease. Fibrates are a class of drugs that treat hypertriglyceridemia with residual elevation of non-HDL cholesterol. However, the role of fibrates in patients with diabetic kidney disease has yet to be determined (87, 98).

Figure 24:
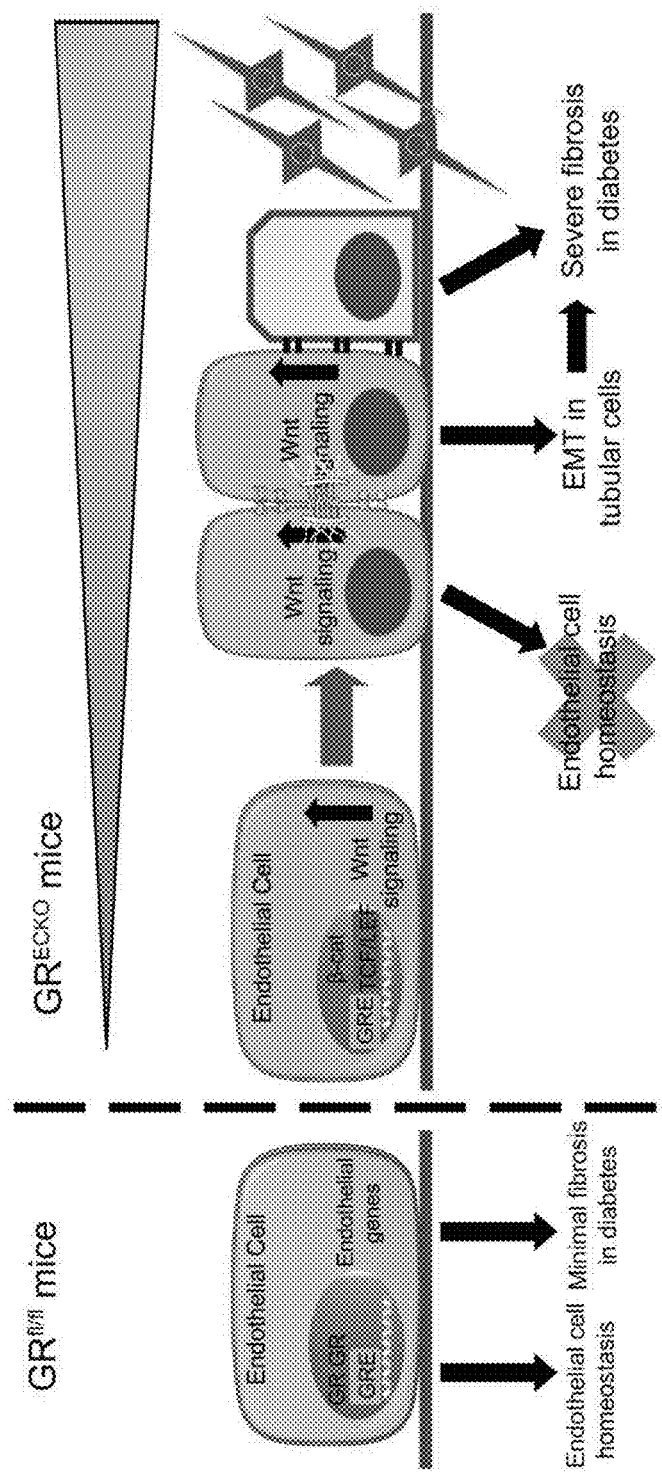
FIG. 24 shows a graphical representation of the role of GR in the endothelial cell homeostasis.

When conditioned media from GR-deplete EC from diabetic $GR^{ECKO}$ mice was transferred to cultured TECs from diabetic control kidneys, the following were observed: a gain of mesenchymal markers, activation of TGFβ and canonical Wnt signaling and concomitant suppression of epithelial cell markers. These findings suggest that EndMT leads to the activation of EMT processes in diabetes. GR-deplete cells have higher levels of TGFβ-smad3 and canonical Wnt signaling, associated with disrupted levels of plasma cytokines and suppressed FAO. The cumulative effects of these metabolic changes result in activation of mesenchymal transformation in EC which appears to exert paracrine effects on neighboring TECs. The graphical figure demonstrates the functional importance of GR protein in EC homeostasis (FIG. 24).

In conclusion, the results herein indicate a regulatory role of GR on EndMT in diabetic kidneys, mediated by control over canonical Wnt signaling and linked defective FA metabolism. This data provide new insight into the biology of GR and a critical role of GR in renal fibrosis and diabetes.

REFERENCES

1. Lusis A J (2000) Atherosclerosis. Nature 407(6801):233-241.
2. Ait-Oufella H, Maury E, Lehoux S, Guidet B, & Offenstadt G (The endothelium: physiological functions and role in microcirculatory failure during severe sepsis. Intensive Care Med 36(8):1286-1298.
3. Lorant D E, Zimmerman G A, McIntyre T M, & Prescott S M (1995) Platelet-activating factor mediates procoagulant activity on the surface of endothelial cells by promoting leukocyte adhesion. Semin Cell Biol 6(5):295-303.
4. Lee J I & Burckart G J (1998) Nuclear factor kappa B: important transcription factor and therapeutic target. J Clin Pharmacol 38(11):981-993.
5. Longui C A (2007) Glucocorticoid therapy: minimizing side effects. J Pediatr (Rio J) 83(5 Suppl):S163-177.

6. Goodwin J E, Feng Y, Velazquez H, & Sessa W C (2013) Endothelial glucocorticoid receptor is required for protection against sepsis. Proc Natl Acad Sci USA 110(1): 306-311.
7. Goodwin J E, et al. (2015) Endothelial glucocorticoid receptor suppresses atherogenesis-brief report. Arterioscler Thromb Vasc Biol 35(4):779-782.
8. King E M, Holden N S, Gong W, Rider C F, & Newton R (2009) Inhibition of N F-kappaB-dependent transcription by MKP-1: transcriptional repression by glucocorticoids occurring via p38 MAPK. J Biol Chem 284(39): 26803-26815.
9. Meduri G U, Muthiah M P, Carratu P, Eltorky M, & Chrousos G P (2005) Nuclear factor-kappaB- and glucocorticoid receptor alpha-mediated mechanisms in the regulation of systemic and pulmonary inflammation during sepsis and acute respiratory distress syndrome. Evidence for inflammation-induced target tissue resistance to glucocorticoids. Neuroimmunomodulation 12(6):321-338.
10. Reddy T E, et al. (2009) Genomic determination of the glucocorticoid response reveals unexpected mechanisms of gene regulation. Genome research 19(12):2163-2171.
11. Steinhauser S, Kurzawa N, Eils R, & Herrmann C (2016) A comprehensive comparison of tools for differential ChIP-seq analysis. Brief Bioinform 17(6):953-966.
12. Falkner K C, Ritter J K, & Prough R A (2008) Regulation of the rat UGT1A6 by glucocorticoids involves a cryptic glucocorticoid response element. Drug Metab Dispos 36(2):409-417.
13. Vockley C M, et al. (2016) Direct G R Binding Sites Potentiate Clusters of T F Binding across the Human Genome. Cell 166(5):1269-1281 e1219.
14. McEwan M V, Eccles M R, & Horsfield J A (2012) Cohesin is required for activation of MYC by estradiol. PloS one 7(11):e49160.
15. Latos P A, et al. (2015) Fgf and Esrrb integrate epigenetic and transcriptional networks that regulate self-renewal of trophoblast stem cells. Nat Commun 6:7776.
16. Carreras E, et al. (2010) Estrogen receptor signaling promotes dendritic cell differentiation by increasing expression of the transcription factor IRF4. Blood 115(2): 238-246.
17. Enuka Y, et al. (2017) Epigenetic mechanisms underlie the crosstalk between growth factors and a steroid hormone. Nucleic Acids Res 45(22):12681-12699.
18. Sarvari M, et al. (2016) Long-Term Estrogen Receptor Beta Agonist Treatment Modifies the Hippocampal Transcriptome in Middle-Aged Ovariectomized Rats. Front Cell Neurosci 10:149.
19. Duffy D J, et al. (2015) Integrative omics reveals MYCN as a global suppressor of cellular signalling and enables network-based therapeutic target discovery in neuroblastoma. Oncotarget 6(41):43182-43201.
20. Nakamoto M, et al. (2017) The Glucocorticoid Receptor Regulates the ANGPTL4 Gene in a CTCF-Mediated Chromatin Context in Human Hepatic Cells. PloS one 12(1):e0169225.
21. Starick S R, et al. (2015) ChIP-exo signal associated with DNA-binding motifs provides insight into the genomic binding of the glucocorticoid receptor and cooperating transcription factors. Genome Res 25(6):825-835.
22. Dendoncker K, et al. (2017) The nature of the GRE influences the screening for G R-activity enhancing modulators. PloS one 12(7):e0181101.
23. Goodwin A M, Kitajewski J, & D'Amore P A (2007) Wnt1 and Wnt5a affect endothelial proliferation and capillary length; Wnt2 does not. Growth Factors 25(1):25-32.
24. Masckauchan T N, Shawber C J, Funahashi Y, Li C M, & Kitajewski J (2005) Wnt/beta-catenin signaling induces proliferation, survival and interleukin-8 in human endothelial cells. Angiogenesis 8(1):43-51.
25. Lee J G & Heur M (2015) WNT10B enhances proliferation through beta-catenin and RAC1 GTPase in human corneal endothelial cells. J Biol Chem 290(44):26752-26764.
26. Kim J, et al. (2010) Wnt5a induces endothelial inflammation via beta-catenin-independent signaling. J Immunol 185(2):1274-1282.
27. Christman M A, 2nd, et al. (2008) Wnt5a is expressed in murine and human atherosclerotic lesions. Am J Physiol Heart Circ Physiol 294(6):H2864-2870.
28. Gelfand B D, et al. (2011) Hemodynamic activation of beta-catenin and T-cell-specific transcription factor signaling in vascular endothelium regulates fibronectin expression. Arterioscler Thromb Vasc Biol 31(7):1625-1633.
29. Krishna S M, et al. (2017) Wnt Signaling Pathway Inhibitor Sclerostin Inhibits Angiotensin II-Induced Aortic Aneurysm and Atherosclerosis. Arterioscler Thromb Vasc Biol 37(3):553-566.
30. Ackers I, et al. (2018) Blocking Wnt5a signaling decreases CD36 expression and foam cell formation in atherosclerosis. Cardiovasc Pathol 34:1-8.
31. Breton-Romero R, et al. (2016) Endothelial Dysfunction in Human Diabetes Is Mediated by Wnt5a-JNK Signaling. Arterioscler Thromb Vasc Biol 36(3):561-569.
32. Jubb A W, Boyle S, Hume D A, & Bickmore W A (2017) Glucocorticoid Receptor Binding Induces Rapid and Prolonged Large-Scale Chromatin Decompaction at Multiple Target Loci. Cell Rep 21(11):3022-3031.
33. Sacta M A, et al. (2018) Gene-specific mechanisms direct glucocorticoid-receptor-driven repression of inflammatory response genes in macrophages. Elife 7.
34. Zhang Y, et al. (2008) Model-based analysis of ChIP-Seq (MACS). Genome Biol 9(9):R137.
35. Trapnell C, Pachter L, & Salzberg S L (2009) TopHat: discovering splice junctions with RNA-Seq. Bioinformatics 25(9):1105-1111.
36. Trapnell C, et al. (2012) Differential gene and transcript expression analysis of RNA-seq experiments with TopHat and Cufflinks. Nat Protoc 7(3):562-578.
37. Bailey T L, Boden M, Whitington T, & Machanick P (2010) The value of position-specific priors in motif discovery using MEME. BMC Bioinformatics 11:179.
38. Kanasaki, K. et al. Linagliptin-mediated DPP-4 inhibition ameliorates kidney fibrosis in streptozotocin-induced diabetic mice by inhibiting endothelial-to-mesenchymal transition in a therapeutic regimen. Diabetes 63, 2120-2131, doi:10.2337/db13-1029 (2014).
39. Shi, S. et al. Interactions of DPP-4 and integrin beta1 influences endothelial-to-mesenchymal transition. Kidney Int 88, 479-489, doi:10.1038/ki.2015.103 (2015).
40. Li, J. et al. FGFR1 is critical for the anti-endothelial mesenchymal transition effect of N-acetyl-seryl-aspartyl-lysyl-proline via induction of the MAP4K4 pathway. *Cell Death Dis* 8, e2965, doi:10.1038/cddis.2017.353 (2017).
41. Nagai, T. et al. N-acetyl-seryl-aspartyl-lysyl-proline Inhibits Diabetes-Associated Kidney Fibrosis and Endothelial-Mesenchymal Transition. *Biomed Res Int* 2014, doi:10.1155/2014/696475 (2014).

42. Nitta, K. et al. Oral Administration of N-Acetyl-seryl-aspartyl-lysyl-proline Ameliorates Kidney Disease in Both Type 1 and Type 2 Diabetic Mice via a Therapeutic Regimen. *Biomed Res Int* 2016, 9172157, doi:10.1155/2016/9172157 (2016).
43. Zhang, L. S. & Lum, L. Delivery of the Porcupine Inhibitor WNT974 in Mice. *Methods Mol Biol* 1481, 111-117, doi:10.1007/978-1-4939-6393-5_12 (2016).
44. Zeisberg, E. M., Potenta, S. E., Sugimoto, H., Zeisberg, M. & Kalluri, R. Fibroblasts in kidney fibrosis emerge via endothelial-to-mesenchymal transition. *J Am Soc Nephrol* 19, 2282-2287 (2008).
45. Price, N. L. et al. Genetic deficiency or pharmacological inhibition of miR-33 protects from kidney fibrosis. *JCI Insight* 4, doi:10.1172/jci.insight.131102 (2019).
46. Reidy, K., Kang, H. M., Hostetter, T. & Susztak, K. Molecular mechanisms of diabetic kidney disease. *J Clin Invest* 124, 2333-2340, doi:10.1172/JCI72271 (2014).
47. Badal, S. S. & Danesh, F. R. New insights into molecular mechanisms of diabetic kidney disease. *Am J Kidney Dis* 63, S63-83, doi:10.1053/j.ajkd.2013.10.047 (2014).
48. Breyer, M. D. & Susztak, K. The next generation of therapeutics for chronic kidney disease. *Nat Rev Drug Discov* 15, 568-588, doi:10.1038/nrd.2016.67 (2016).
49. Humphreys, B. D. et al. Fate tracing reveals the pericyte and not epithelial origin of myofibroblasts in kidney fibrosis. *The American journal of pathology* 176, 85-97, doi:10.2353/ajpath.2010.090517 (2010).
50. LeBleu, V. S. et al. Origin and function of myofibroblasts in kidney fibrosis. *Nat Med* 19, 1047-1053, doi:10.1038/nm.3218 (2013).
51. Srivastava, S. P., Koya, D. & Kanasaki, K. MicroRNAs in Kidney Fibrosis and Diabetic Nephropathy: Roles on EMT and EndMT. *Biomed Res Int* 2013, 125469, doi:10.1155/2013/125469 (2013).
52. Srivastava, S. P., Hedayat, F. A., Kanasaki, K. & Goodwin, J. E. microRNA Crosstalk Influences Epithelial-to-Mesenchymal, Endothelial-to-Mesenchymal, and Macrophage-to-Mesenchymal Transitions in the Kidney. *Front Pharmacol* 10, 904, doi:10.3389/fphar.2019.00904 (2019).
53. Medici, D. Endothelial-Mesenchymal Transition in Regenerative Medicine. *Stem Cells Int* 2016, 6962801, doi:10.1155/2016/6962801 (2016).
54. Eelen, G. et al. Endothelial Cell Metabolism. *Physiol Rev* 98, 3-58, doi:10.1152/physrev.00001.2017 (2018).
55. Theodorou, K. & Boon, R. A. Endothelial Cell Metabolism in Atherosclerosis. *Front Cell Dev Biol* 6, 82, doi:10.3389/fcell.2018.00082 (2018).
56. Zhou, H. L. et al. Metabolic reprogramming by the S-nitroso-CoA reductase system protects against kidney injury. *Nature* 565, 96-100, doi:10.1038/s41586-018-0749-z (2019).
57. Cantelmo, A. R. et al. Inhibition of the Glycolytic Activator PFKFB3 in Endothelium Induces Tumor Vessel Normalization, Impairs Metastasis, and Improves Chemotherapy. *Cancer Cell* 30, 968-985, doi:10.1016/j.ccell.2016.10.006 (2016).
58. Cruys, B. et al. Glycolytic regulation of cell rearrangement in angiogenesis. *Nat Commun* 7, 12240, doi:10.1038/nc0mm512240 (2016).
59. Schoors, S. et al. Fatty acid carbon is essential for dNTP synthesis in endothelial cells. *Nature* 520, 192-197, doi:10.1038/nature14362 (2015).
60. Xiong, J. et al. A Metabolic Basis for Endothelial-to-Mesenchymal Transition. *Mol Cell* 69, 689-698 e687, doi:10.1016/j.molcel.2018.01.010 (2018).
61. Lovisa, S. & Kalluri, R. Fatty Acid Oxidation Regulates the Activation of Endothelial-to-Mesenchymal Transition. *Trends Mol Med* 24, 432-434, doi:10.1016/j.molmed.2018.03.003 (2018).
62. Zeisberg, M. & Neilson, E. G. Mechanisms of tubulointerstitial fibrosis. *Journal of the American Society of Nephrology: JASN* 21, 1819-1834, doi:10.1681/ASN.2010080793 (2010).
63. Zeisberg, E. M. et al. Endothelial-to-mesenchymal transition contributes to cardiac fibrosis. *Nat Med* 13, 952-961 (2007).
64. Medici, D. & Kalluri, R. Endothelial-mesenchymal transition and its contribution to the emergence of stem cell phenotype. *Semin Cancer Biol* 22, 379-384, doi:10.1016/j.semcancer.2012.04.004 (2012).
65. Goodwin, J. E., Feng, Y., Velazquez, H., Zhou, H. & Sessa, W. C. Loss of the endothelial glucocorticoid receptor prevents the therapeutic protection afforded by dexamethasone after LPS. *PLoS One* 9, e108126, doi:10.1371/journal.pone.0108126 (2014).
66. Zhou, H. et al. Loss of the podocyte glucocorticoid receptor exacerbates proteinuria after injury. *Sci Rep* 7, 9833, doi:10.1038/s41598-017-10490-z (2017).
67. He, W. et al. Wnt/beta-catenin signaling promotes renal interstitial fibrosis. *Journal of the American Society of Nephrology: JASN* 20, 765-776, doi:10.1681/ASN.2008060566 (2009).
68. Srivastava, S. P. et al. Effect of Antifibrotic MicroRNAs Crosstalk on the Action of N-acetyl-seryl-aspartyl-lysyl-proline in Diabetes-related Kidney Fibrosis. *Sci Rep* 6, 29884, doi:10.1038/srep29884 (2016).
69. Srivastava, S. P. et al. SIRT3 deficiency leads to induction of abnormal glycolysis in diabetic kidney with fibrosis. *Cell Death Dis* 9, 997, doi:10.1038/s41419-018-1057-0 (2018).
70. Sugimoto, H., Grahovac, G., Zeisberg, M. & Kalluri, R. Renal fibrosis and glomerulosclerosis in a new mouse model of diabetic nephropathy and its regression by bone morphogenic protein-7 and advanced glycation end product inhibitors. *Diabetes* 56, 1825-1833, doi:10.2337/db06-1226 (2007).
71. Fielding, C. A. et al. Interleukin-6 signaling drives fibrosis in unresolved inflammation. *Immunity* 40, 40-50, doi:10.1016/j.immuni.2013.10.022 (2014).
72. Apalset, E. M. et al. Interferon gamma (IFN-gamma)-mediated inflammation and the kynurenine pathway in relation to risk of hip fractures: the Hordaland Health Study. *Osteoporos Int* 25, 2067-2075, doi:10.1007/s00198-014-2720-7 (2014).
73. Fathy, S. A., Mohamed, M. R., Ali, M. A. M., El-Helaly, A. E. & Alattar, A. T. Influence of IL-6, IL-10, IFN-gamma and TNF-alpha genetic variants on susceptibility to diabetic kidney disease in type 2 diabetes mellitus patients. *Biomarkers* 24, 43-55, doi:10.1080/1354750X.2018.1501761 (2019).
74. Owens, E. P. et al. Biomarkers and the role of mast cells as facilitators of inflammation and fibrosis in chronic kidney disease. *Transl Androl Urol* 8, S175-S183, doi:10.21037/tau.2018.11.03 (2019).
75. Hickey, F. B. & Martin, F. Role of the Immune System in Diabetic Kidney Disease. *Curr Diab Rep* 18, 20, doi:10.1007/s11892-018-0984-6 (2018).
76. Kang, H. M. et al. Defective fatty acid oxidation in renal tubular epithelial cells has a key role in kidney fibrosis development. *Nat Med* 21, 37-46, doi:10.1038/nm.3762 (2015).

77. Lovisa, S. et al. Epithelial-to-mesenchymal transition induces cell cycle arrest and parenchymal damage in renal fibrosis. *Nat Med* 21, 998-1009, doi:10.1038/nm.3902 (2015).
78. Tran, M. T. et al. PGC1alpha drives NAD biosynthesis linking oxidative metabolism to renal protection. *Nature* 531, 528-532, doi:10.1038/nature17184 (2016).
79. Qi, W. et al. Pyruvate kinase M2 activation may protect against the progression of diabetic glomerular pathology and mitochondrial dysfunction. *Nat Med* 23, 753-762, doi:10.1038/nm.4328 (2017).
80. Herman-Edelstein, M., Scherzer, P., Tobar, A., Levi, M. & Gafter, U. Altered renal lipid metabolism and renal lipid accumulation in human diabetic nephropathy. *J Lipid Res* 55, 561-572, doi:10.1194/jlr.P040501 (2014).
81. Wahl, P., Ducasa, G. M. & Fornoni, A. Systemic and renal lipids in kidney disease development and progression. *Am J Physiol Renal Physiol* 310, F433-445, doi:10.1152/ajprenal.00375.2015 (2016).
82. Delgado, M. & Ganea, D. Inhibition of endotoxin-induced macrophage chemokine production by VIP and PACAP in vitro and in vivo. *Arch Physiol Biochem* 109, 377-382, doi:10.1076/apab.109.4.377.4237 (2001).
83. Kato, H. et al. Wnt/beta-catenin pathway in podocytes integrates cell adhesion, differentiation, and survival. *J Biol Chem* 286, 26003-26015, doi:10.1074/jbc.M111.223164 (2011).
84. Zhou, Z. et al. MicroRNA-27a promotes podocyte injury via PPARgamma-mediated beta-catenin activation in diabetic nephropathy. *Cell Death Dis* 8, e2658, doi:10.1038/cddis.2017.74 (2017).
85. Feng, Y., Liang, Y., Ren, J. & Dai, C. Canonical Wnt Signaling Promotes Macrophage Proliferation during Kidney Fibrosis. *Kidney Dis (Basel)* 4, 95-103, doi: 10.1159/000488984 (2018).
86. Wanner, C., Drechsler, C. & Krane, V. Lipid metabolism in chronic kidney disease: the role of statins in cardiovascular risk. *J Ren Nutr* 17, 75-78, doi:10.1053/j.jrn.2006.10.012 (2007).
87. Srivastava, S. P., Shi, S., Koya, D. & Kanasaki, K. Lipid mediators in diabetic nephropathy. *Fibrogenesis Tissue Repair* 7, 12, doi: 10.1186/1755-1536-7-12 (2014).
88. Kovesdy, C. P., Anderson, J. E. & Kalantar-Zadeh, K. Inverse association between lipid levels and mortality in men with chronic kidney disease who are not yet on dialysis: effects of case mix and the malnutrition-inflammation-cachexia syndrome. *J Am Soc Nephrol* 18, 304-311, doi:10.1681/ASN.2006060674 (2007).
89. Diamond, J. R. Analogous pathobiologic mechanisms in glomerulosclerosis and atherosclerosis. *Kidney Int Suppl* 31, S29-34 (1991).
90. Kwan, B. C., Kronenberg, F., Beddhu, S. & Cheung, A. K. Lipoprotein metabolism and lipid management in chronic kidney disease. *J Am Soc Nephrol* 18, 1246-1261, doi:10.1681/ASN.2006091006 (2007).
91. Baigent, C. et al. First United Kingdom Heart and Renal Protection (UK-HARP-I) study: biochemical efficacy and safety of simvastatin and safety of low-dose aspirin in chronic kidney disease. *Am J Kidney Dis* 45, 473-484, doi:10.1053/j.ajkd.2004.11.015 (2005).
92. Sharp Collaborative, G. Study of Heart and Renal Protection (SHARP): randomized trial to assess the effects of lowering low-density lipoprotein cholesterol among 9,438 patients with chronic kidney disease. *Am Heart J* 160, 785-794 e710, doi:10.1016/j.ahj.2010.08.012 (2010).
93. Kimura, S. et al. Randomized comparison of pitavastatin and pravastatin treatment on the reduction of urinary albumin in patients with type 2 diabetic nephropathy. *Diabetes Obes Metab* 14, 666-669, doi:10.1111/j.1463-1326.2012.01566.x (2012).
94. Abe, M. et al. Effects of lipid-lowering therapy with rosuvastatin on kidney function and oxidative stress in patients with diabetic nephropathy. *J Atheroscler Thromb* 18, 1018-1028, doi:10.5551/jat.9084 (2011).
95. Rutter, M. K. et al. Protection Against Nephropathy in Diabetes with Atorvastatin (PANDA): a randomized double-blind placebo-controlled trial of high- vs. low-dose atorvastatin(1). *Diabet Med* 28, 100-108, doi: 10.1111/j.1464-5491.2010.03139.x (2011).
96. Colhoun, H. M. et al. Effects of atorvastatin on kidney outcomes and cardiovascular disease in patients with diabetes: an analysis from the Collaborative Atorvastatin Diabetes Study (CARDS). *Am J Kidney Dis* 54, 810-819, doi:10.1053/j.ajkd.2009.03.022 (2009).
97. Coonrod, B. A. et al. Predictors of microalbuminuria in individuals with IDDM. Pittsburgh Epidemiology of Diabetes Complications Study. *Diabetes Care* 16, 1376-1383, doi:10.2337/diacare.16.10.1376 (1993).
98. Ting, R. D. et al. Benefits and safety of long-term fenofibrate therapy in people with type 2 diabetes and renal impairment: the FIELD Study. *Diabetes Care* 35, 218-225, doi:10.2337/dc11-1109 (2012).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for treating a condition or a disease in a subject in need thereof, wherein the condition or the disease is cardiovascular disease or peripheral artery disease, which method comprises administering to the subject a therapeutically effective amount of a compound having the structure according to formula (I):

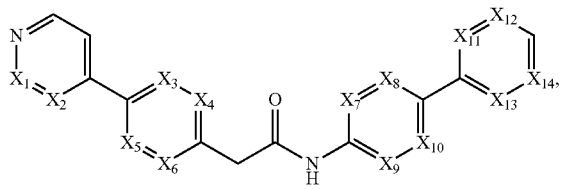

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

2. The method of claim 1, wherein the method is effective to reduce the size of an atherosclerotic deposition in the artery of the subject.

3. The method of claim 1, further comprising administering to the subject an additional agent effective to treat cardiovascular disease and/or peripheral artery disease.

4. The method of claim 1, wherein the subject is human.

5. A method for treating a condition or a disease in a subject in need thereof, wherein the condition or the disease is cardiovascular disease or peripheral artery disease, which method comprises administering to the subject a therapeutically effective amount of a pharmaceutical composition comprising a compound having the structure according to formula (I):

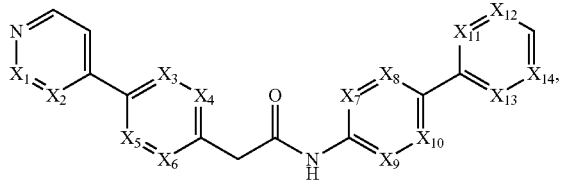

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

6. The method of claim 5, wherein the cardiovascular disease is selected from the group consisting of atherosclerosis, coronary artery disease, coronary heart disease, a condition associated with coronary artery disease or coronary heart disease, transient ischemic attack, and stroke.

7. The method of claim 5, wherein the method is effective to reduce the size of an atherosclerotic deposition in the artery of the subject.

8. The method of claim 5, further comprising administering to the subject an additional agent effective to treat cardiovascular disease and/or peripheral artery disease.

9. The method of claim 5, wherein the subject is human.

10. The method of claim 1, wherein one of $X_3$, $X_4$, $X_5$ and $X_6$ is N and the others are CR; and/or wherein one of $X_7$, $X_8$, $X_9$ and $X_{10}$ is N and the others are CR; and/or wherein two of $X_{11}$, $X_{12}$, $X_{13}$ and $X_{14}$ are N and the others are CR.

11. The method of claim 10, wherein $X_1$ is CR and R is methyl, and/or wherein $X_5$ is CR and R is methyl.

12. The method of claim 10, wherein one or more of $X_2$ is CH, $X_4$ is CH, $X_6$ is CH, $X_8$ is CH, $X_9$ is CH, $X_{10}$ is CH, $X_{12}$ is CH, and $X_{13}$ is CH.

13. The method of claim 10, wherein the compound has the structure

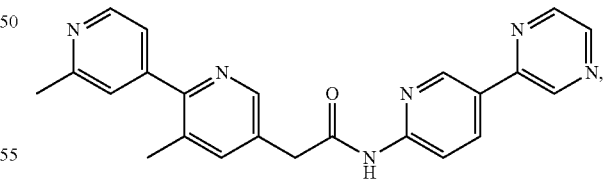

or a pharmaceutically acceptable salt thereof.

14. The method of claim 1, wherein the cardiovascular disease is selected from the group consisting of atherosclerosis, coronary artery disease, coronary heart disease, a condition associated with coronary artery disease or coronary heart disease, transient ischemic attack, and stroke.

15. The method of claim 1, wherein the cardiovascular disease is atherosclerosis.

16. A method for treating atherosclerosis in a subject in need thereof, which method comprises administering to the subject a therapeutically effective amount of a compound having the structure according to formula (I):

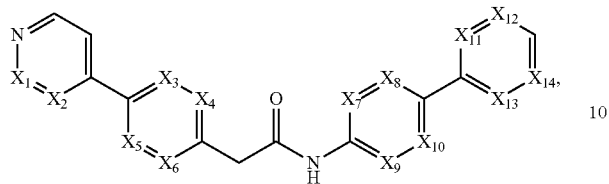

wherein $X_1$ and $X_2$ are selected from N and CR;
one of $X_3$, $X_4$, $X_5$ and $X_6$ is N and others are selected from N and CR;
one of $X_7$, $X_8$, $X_9$ and $X_{10}$ is N and others are selected from N and CR;
one of $X_{11}$, $X_{12}$, $X_{13}$ and $X_{14}$ is N and others are selected from N and CR, and
R is independently at each occurrence selected from hydrogen, halo, cyano, methyl, difluoromethyl, and trifluoromethyl,
or a pharmaceutically acceptable salt thereof.

* * * * *

SEQUENCE LISTING

```
<160> NUMBER OF SEQ ID NOS: 21

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)..(9)
<223> OTHER INFORMATION: a, c, g, t, unknown or other

<400> SEQUENCE: 1
agaacannnt gttct                                                          15

<210> SEQ ID NO 2
<211> LENGTH: 39656
<212> TYPE: DNA
<213> ORGANISM: Mus sp.

<400> SEQUENCE: 2
```

| | | | | | |
|---|---|---|---|---|---|
| aaaaggagca | gatagactgt | cttcttctga | aagttgtata | agccatttag | gaaagcagaa    60 |
| agaacaaaaa | atataaaaga | taattaacat | actggcagat | gccgaagaat | attgtgcaca   120 |
| catgacagat | gtttatgaga | aacaatagag | agaaggcaca | ggagcagaca | gacaggtgca   180 |
| cacatcctct | tctgggagga | atgcgaatcc | atctctggtt | ttagtaaaaa | ctaatttgga   240 |
| ttaaaggaaa | gttgcaagtc | ccagttgtga | tggtgcccac | attagatcct | agcactaggg   300 |
| aggcagaagc | aggcagatct | ctgtgagttt | caggctacct | gggtctatat | actgagttcc   360 |
| aggacagcca | gggctatata | gtgagatgct | atttcaaaaa | caaaagaaa | aacaaaacta   420 |
| agcaaaacaa | cagagagggg | gaagttggga | ggttggtgga | aggggagagc | ttgtgagagg   480 |
| atttggtggt | aagtgggtat | ctatctctga | agcaaagttc | attcatacct | gtggcaatgc   540 |
| gaccatcaaa | cactctactc | ctttcttcct | aaaaaatgtg | agatgaacac | aaaatatgtt   600 |
| taacaacctc | ttgagttcat | cgttcacctt | cgaattttt | acagatccct | atttctttta   660 |
| cctaataaag | cттстаaата | ттстттагт | gactgtттат | ааатстсссt | ttcagtattt   720 |
| gtgtttgtgt | gtttgtgtgc | atgtgtgtgt | gtgtgctttg | ccatttttca | ttgaattaat   780 |
| ttatataatg | ттттggcтттс | ttttctata | tgacaccaaa | taattgtaca | tcagccagag   840 |
| тттаттт | aattaaatgg | ctccctagcc | accatctgtt | gttgatttcc | tatgaagtag   900 |
| acacacttcc | ttccgaaaac | attgaagtca | caaaccgctg | gtaatgatca | ttttagagat   960 |
| aaaaattcca | таaактсаag | tcagccactg | acattcccta | agtgccattg | agccagcgca  1020 |
| ggggattaaa | gccgtatcct | actgtgtgct | ctgggaagta | gagacagact | ttatctgcct  1080 |
| agtattgaca | gcagggggt | gggcggtgcg | gaaggctggg | taaatcaggg | ctgctctagt  1140 |
| gacgtccggc | tttgttgtag | gttttgcctc | tgtgctcccg | ctgtcttctg | acactgcaat  1200 |
| ccctctgctc | aatggttttc | ctctgaaggg | gctcagtggt | tgggcctcgg | caggacttcc  1260 |
| cacgtacaat | gctcttaaag | ccaggggca | gccgggtgg | aaacaggaga | cttctgggag  1320 |
| gcgtagcctg | ggagggatct | gttttctatt | ttctcctctg | tattgaactc | atctggatgg  1380 |
| gaaccgttct | cctgtttact | attatcatta | cctgtgtggg | gtatttgct | tgcacgttta  1440 |
| ttcccctgt | tagaagaaac | cgcccgtggg | aagagttaga | taataaatgc | aatttcagt  1500 |
| aagaacactc | tggggtggg | gggcggaatc | caagtgcttt | aaagtgggct | ccacgcttcg  1560 |
| gttttaaaaa | agaaaaactc | aaaagttcga | atctacagg | gcaaagaaaa | acccggaagg  1620 |
| aagcagggag | ggagggagga | agggaaggaa | agaaaaaaaa | agaaggaggg | aagggaggaa  1680 |
| tcacaccatt | tccacgtttc | tgtggtcta | ттттgттстст | tgcgatttct | ttccctttgt  1740 |
| gaggtcaat | ttctccacgg | ttattccaat | cacagaccc | ccgaagtcat | tagtcctgcc  1800 |
| attgctctta | ggaggctgct | atctctgcga | catgacattt | aaagtgactt | tgctcgcgcc  1860 |
| ttcctgtctg | actttctgca | ggcggaggtg | cgctcgggtt | tgctgtgagg | aaagagctgc  1920 |

-continued

```
gggcaacgag ggacggtgtg ggctcgcggg gcgggataca ggggtgcgca tctctgtggt    1980
gcgttgagac cgtttctccc gtggggacca agggttcgtc tatggatcca gagccggggg    2040
tggagtgggg aaaggtgtgc ggctcctgtc gggagctgcc tggggctaca gcatcacaga    2100
tagacagggt ctcacactcc agtcccctga aaactcaaag ccttctcgga aggaggagcc    2160
ggagggcagg ggaccgcggg gcggagctct tgtcggccga ggtgggaagg cgcagctgcg    2220
agccaaggcg ctgacctcct ctgagctcct ctggccgctc gcaggatctt cccgaccctg    2280
caggacttgg caaactccca cctccgctcc cattagtcct cccaccccca ccaaatctcc    2340
tccctcggag gtcccctatc catctcactt tgcagaattt atcgcttctt ccaacacctt    2400
tttgcaacac cccagaactc cgagtccctt aactgaattt gacttttgtt tttatttctc    2460
tctggcttcc tcttctgccc cctcatctga ttgatgtgct aaggctgatg tctctgccag    2520
agcgagagga ataaatagat gctgcctcgc ctagaggctt gacgcttgg gaagagcagc    2580 cggcgcagcg aggcaccggg ctccgccaag ctagtggacc ggacctggga gcacttggat    2640
ccaagagaac tgtgattgtc ccaggggtgg gggcagctcc ccaggtcgtt gggatcaccc    2700
ctcggaaccg cagggggaga cttcggaacg aaagtgtctc ccgcgtccgt cgctcggctg    2760
cgccctgccc catcctgctg ggaccatggt ctgctgcggc ccgggacgga tgctgctagg    2820
atgggccggg ttgctagtcc tggctgctct ctgcctgctc caggtgcccg gagctcaggc    2880
tgcagcctgt gagcctgtcc gcatcccgct gtgcaagtcc cttccctgga acatgaccaa    2940
gatgcccaac cacctgcacc acagcaccca ggctaacgcc atcctggcca tggaacagtt    3000
cgaagggctg ctgggcaccc actgcagccc ggatcttctc ttcttcctct gtgcaatgta    3060
cgcacccatt tgcaccatcg acttccagca cgagcccatc aagccctgca agtctgtgtg    3120
tgagcgcgcc cgacagggct gcgagcccat tctcatcaag taccgccact cgtggccgga    3180
aagcttggcc tgcgacgagc tgccggtgta cgaccgcggc gtgtgcatct tcctgaggc    3240 catcgtcacc gcggacggag cgggtgagtc ctgaactttg cccgacctct gagaagttag    3300
ttatttgtct ttatcggcta gcttgctttc tgcgctgagc ccttaccttt cccttaagc    3360 acactcctct actgaatcct attcttttac ttaaaagcaa acaaaacaa acaaaattc    3420 acttttatca ttctcccaga caaacgcagt ctcttccaac aagtgatctg agcgatccat    3480
ccgttcccta cacttcacac ccaacctcca aagcgcccct tcccttccca ctctttgcgt    3540
gtggggctta gctgctttac tcttaacgac attggagttt cttctgtttc ttggtgcatt    3600
cttttgcaat ctcgatcgtt agtgttttca cggcttacaa ttgtatggag acatcagaaa    3660
aacaaaaaac cctatttct tctaatcatg aaaagtgcta atttagtcta aataaactgc    3720
taatacagaa atctcttagt gacatgtgcc tgctcagagc tcaatttcgt cggttgccat    3780
cgcctttcaa cagatttccc cttctcttga caaaatagat ggtgattcca atccagaatg    3840
aaacagctat gggacattat tgctatgccc tgctaattaa cttcggttgc tcacttcagt    3900
cagatagctg gggaaccgaa aatagcaggc ccttttcaca tgcccacgtg ccttcaagta    3960 atttttgtata tagcatatgg gtgagtggag ttatatttgg gccatgtcat cttcatagcc    4020
ttatataact ttgcttcaa tcttgccggt tattccaccc atactgtgtg tgtatacatg    4080
acccacacgt tcaccccctt ttccactacc gaactgtatt ttagctctac gtttaatggg    4140
tttaatcaca gctgttttct caccgatgtt tggtctaatt gtgacattca aacttcaag    4200 accacccta ccccctgacc cccaactcaa tccagttcaa agtggaatat tttcagtaaa    4260
ctcatcattt ccctactagg taacccaaga cttggatttt atccttcatg ttctttaaag    4320
```

```
agaacgcttg aacaaacaaa ccatccatca tctttcagtc tctcccagga tcaactgctg    4380
ttaagtgtgc ttcacttggt tggtccatct ctgttcattt cgttctgttt ctcagttggc    4440
tcaaactagg ctcatgtcct cagtccatag ttaattaatc aacagggccg attcagaaaa    4500
attatgctca ttaactaaga gagggtaaaa ggaaaggcag gaatagttga aaaccaagac    4560
tgaacagaaa gatctcacat ctttctcatg gtcaatttcc ttagcaaatc accacgaata    4620
taggtactgt cttcttaata tcaatgatga atcaaaagct agttttataa gacaatctga    4680
aataaataca ttcttttcac tattgggtca aagggaactc tgagatcttg tactaactaa    4740
catcccaggc cctgcagaca ttgctgttac agctcaatgc agttgctagc ctggcttgac    4800
agacgctgtt aaagtcagcc aaatgctagc acgcctctct ggccaagcac taggagtaat    4860
tcatttcaca ctgaaacgca tacttccctt agaagacaaa ctgctcctaa gcctaagcgt    4920
aagcctagag gaggaccggg aaagagtgag gtttgacaag gctcagggct ctcaaaggcc    4980
acagtcactg tggatgggaa gcagtttcat taagagtccc tgagttacct atccccatgg    5040
gccgaacatg gcacaactgt ctcaccgaag cactgaaaga gacatgcatg ccgacagaca    5100
gttaggcact ccctgattgc tgagtggctc aggagtccca gaggatttgt tttactgaag    5160
caaagcacct gccggcagga gatagtcagt atgctgacac tcctcggttt tggtttcttt    5220
cgtaggaaac agaaaccatg agctaaagat ggggttggct cacagccttt tgaaaaatta    5280
cacattgccc ctgttcagtg aaactgccag acacctggaa ttacttaatg tggtgacatg    5340
gggctggaga gatggttcac tcttaaccac tcttctagag gaccttggtt tgattcctgg    5400
tacagacatg ggagattaat aacctctgta acgctcattc tgggagcttt gcctccctct    5460
tctggcctcc atgagtactg cacacctctg gtgcacagac ttagagtgca aaaccagatg    5520
gtgaatctct acgcatactc catgggcact gcatacatgt ggtgtacaga catacaagca    5580
ggcaaaacac ccatatacat accacatatc accattttag ttaatttatt gtttgattta    5640
ttgggctgta atagtttaca aaacagagtt tatttgtctg tttgtttctc cttcagatat    5700
aagcagaatt ctggtgtttt ggtactgcat tctatttagc cagatatgaa aatgaaatct    5760
ctccttaaag agtggtacaa ctgttcacat tcctgtagca agaggatttt agttaattca    5820
tcccattcac ggttatctgt ttgcacctaa tatattgtga ctcggcccat aagcttagca    5880
catttaacag agccgtctca atgaaacaca ccgatgtgcc agacgatttt taactcctga    5940
aacactgaga atgaacatat ttttatgaag aacatgtgac gccttgacaa tcactagtaa    6000
tttcatatta agtttattgt gtattttgtg tttactgtaa agtgtggctt tgagcactac    6060
tatttgggaa cagctcaatt tggccatttt gccagttagt tgagactctt gggcaaattc    6120
gtagtactga accaggtgct aaatttctac atgagcccat gcctactcca gctataggg     6180 aatggtacaa cctcttcaac ccttacctgg gaataaaggc aaaagtgttt gtatcctaat    6240
ggcatggtga agactagatg gtatgtgaac tggctgagtc aaacctggcg cagagcaatc    6300
acagaacaaa tcactgatat tattttccta ttttttttctt ttgctaaagg tttttttaaa    6360
ttattatagt atgtaagtac agtgttgctg tcttcagaca caccagaaga gggtgtcaga    6420
tctcattatg gattgctgtt gagccaccat gtggttgctg ggatttgaac tcaggacctt    6480
ccgaagaaca gttggtgctc ttaaccactg agccatcttg ccgcagaccc tctgggtccc    6540
tgtgtctacg tggaatgagt ctctcgacgt gggtgggcaa agcgtggatg aaagacaaac    6600
agacacacac aggagaggtt gtgtggaatc tgagtgtaat tttcgaatcg agcatcagac    6660
```

```
tttttatgca gaggacaata agccctattt tcctattttt aatgttgctt tatcaactta    6720
actaactttt ccttttatt tgttttgtc tgtttgctcc ttttaactt gctaaataca       6780 gcagatatag cctcattctc ttattacttc atccctggag agcaagattt aacacttgga    6840
tttaactggt gaagcaaggg tcatttctct cagatacaga aaattagtat tttatttcat    6900
acaaatcaag ctagaactca ggtttaggag tttactccta cgggaataat agaaagaaaa    6960
gagtgagttt gatgtctgtt aactagaaat agtttattag gggaagagac tcacaagcct    7020
ccacctcttc ctgaggactt ccaagcagtt aatggggac aagggtaggg gtgaggggtg     7080
gaggtggatc tggggttcc acctgcccctt tattattgca ggttgtggtt gcaggcaagg    7140
gagatagata catgttcttc actagtgggg ccactgctaa gcggccctgt cttctctcac    7200
tggttcatca aaaggaaat taaaaaaaaa aagggaatca gtatttttt tttaatttaa      7260 aaaatattga ccgtggaaga cagatgatag ggtgtttcac agctgtttct gagactcctg    7320
cagcttgcag taagggctct ataatcaccc tgttattgct ggcttccagt tcgtactaat    7380 atccccgca cctaccaggc tcttgcacaa catattcttc aggctctggc ctggcagagt     7440
cctgctacct ttcacatgca gaaatggcta tttaatcatc tctccactct ccaaggaaca    7500
ggcagccttt tctttagtgt tagccctggt ctacaaatat ttgaaggggc caaataccaa    7560
ggaggaaagg tctgaacatg aacatgcgat ggaaagaagt gaaaatttga agttaagact    7620
cgagagaaaa ccaggattct aaggctctct cagcatgtcc ataccaaaaa gcagcctgcc    7680
tgtcttgggc agagaatctg tgttattaat tttatttaga agataaccta gtcgtcagtg    7740
cttgtgaaat cttagactgc ccctaagtta ttattttaat cagtcacctt ttgtcttctt    7800
tttactgaac attgaaataa ttatttgaag agcaaatttg accacactat ctctggtctt    7860 tgtcttctg ctaggtgttt aaaggaacac agccactggg tagtcacgca attttgagca     7920
gtggaacatt aacttcagca tataaactta aggccagtca cagcttcaga gctgcaagcc    7980
cttagttggt tttgtcattc actttgtatt tttagccact tgacattggc actggccagt    8040
attggtgtat gccaagggca gtgaatgatt ggtagttggt aaagcacatg cccgacagct    8100
caaccgcaac cacaccaggg agagaagacc tgcagcctta gggccagggt ccttagtgtt    8160
gatagaataa aagctgacaa catatactgt gctctaggta ttgccctgtg aggtgtacat    8220
gtgagttctc atcacagcta catggtacgt gttgttactc ccatttacag caaagaatgg    8280
aaacgcacac agagaagtga ctcgtcaaat taactcagtg tgtgagaaga caagggttta    8340
gactagagtc tggtctacac tacccacctt cctttgctaa gaaaagggat ttttgatcta    8400
tttggagaat ctgtgccttt ggttcatttg gttaaagtta aaggagcaat gcatttcat    8460 tatgttgacc ccttggctta aaagaataaa agagcaccca ggacaatggg ctccaagaga    8520
taaggaatgg ctgtttggtt gcactgctga gataggagag aatgcctctt ccagatccat    8580
ccaacgaagg gccctcaggc tcagcatgcc ctagagctgc ctgctcttct ctagcatgct    8640
tttagtggtt gcaaggcttt gataccgcag ttatccaggc ttaggagcct gccttgattc    8700
tttctctttt ctcatccctg gtgcacctga agctctaga acaaaagaa gcaaatacac      8760 ccaagaggag tagactgcag gaaataatca aactcagggc tgaaatcaac caaacagaga    8820 caaaagaac tatacaaaga atcaacaagg ggctagagag atggcacaga acttaagagc     8880
actgactgct ctttcagagg acctgagttc aattcccagc aaccacatgg tggctcacaa    8940
ccatcgtaat gaaatctgat gccctcttct ggggtatctg aagacagcta cagtgtactc    9000
atataaataa aaataaataa atcttaaaa aaaaaatcaa caaaaccagg agctggttct     9060
```

```
tggagaacat caacaagata gataaaccct tagccagact aaccagaggg cacagagaca    9120
gtatccaaat taataaaatc agaaatgaga agggagacat aacaacgaaa catatcttaa    9180
agtacttatt ctgtctgttg aatattaaca gttgaaaatg ttaaaatcat gttctcatcc    9240
ctggtggtta gtaggtatta agtgctagta ctcttttctg tgattctctt tgggctctct    9300
gcaccccaca aggattatga cagagcatga ttgtctggct ctttgtcctc agtattcctc    9360
ttccctcttc tggcgagatg gttgtttgga aacagtgtat ctattgctta catccttcag    9420
acccactctc ctcccccgct ctctgtaagt tcactctttg cttgtcccat ctctgttcta    9480
gccaagcagg aggacatgca gggccctttg cagagcagtt gtcacacagg ctcttcctga    9540
aatctccttg atgtcactac aaacacttga gatatagaat ctagccatca cacactacca    9600
ctatctacca cttccatcca gaacaatttt gatggtagaa tttcagattt taactatgta    9660
aaaaaatgat tggaaacctt tgggttcttc ttacacaatt ttaacaattg aatactcagt    9720
gtttaaaaag aaacatctct gctagtaagc atacggaata aggaaaactt cctcagtggc    9780
tacactgttt caaaggcgtt ctttttttc ccccaagaga ctttatttat ttattttta    9840 tttcatataa accttaactg cttggtgttt taaacgtgga ctaatataat ttattaatct    9900
tgagggagat tatttaatat aaaccatgta cattttaatc tcatcattct tcaggaatgg    9960
aaacattgta ttttgcttta aaatttggag acgtttatca tgaataaagt ctgaatagga   10020
taaaagtcat cgaagttaat ggtttatgtt taagttgagt caagtgcttg taaactcaac   10080
tagtatttgt tattttttcat ctatttagag acctctaata tatatatata tatatatata   10140
tatatatata tatatattta tagtgttagc tgacagccac atatgtagct cagtggtaga   10200
ggcaatgttt agcatgcacg aagccctggg ttcaatacac aacacctgga atccttcctc   10260
atttatgttt tatatgaagt ataacgacaa agaaagaatg ctggtttgtt aggttaagta   10320
gaggcattga gctcatttag cgttaagtgt taatacaagt gtactactct tggatgaaag   10380
tgtgagttga gtaccagcaa gaatccatgg ttagttactt tgtctctcag cagggtaca   10440 cagcgcaatt cattagaggc tgctctccta attagaacac agaaggccat tatcattacc   10500
attttctggg attacagcat cgtgagaagg acccatgctg aatcccaatt attgccacat   10560
ctctgaattg tactggctag agagatctac aggcgctagg cttcctttgt gctgaactat   10620
ttagtctgca ttcaacagag ggcctggagt tctttctgga tttcccatag atactgtgcc   10680
aggagagtat gacacagcca ttcattgaca aggtgtgttt ggttctatct gtcacaaagt   10740
cacacacatt gggccagtgc ctaatatttg tatggccttt gctgggatac aacattcatt   10800
tacagcattt atgaaactca agaacacgtt atttattaag tgctaaaatt ttactcacac   10860
atgatgctga ttcatgagca gcaactgtca atcatatctg agaaaggacc tcctccttat   10920
tcaatcccca atggtggggc agcctcacag ccctaataag ggaccatttc ctggagacaa   10980
ctgattcttc accaagtcta gctgtaatgg aattacactt tatagatgac gtcctgaggt   11040
agtcactctg tcatcattct ttcttcattc tgttgccttc cagattttcc tatggattca   11100
agtactggac actgcagagg ggcaagcagc ggtgagtgca cagctattcc tgcctttcgt   11160
ttgtggtgca gataattttt gatatggtct tcatacttaa gttttatttg cagatacttg   11220
tgtcctgttt taaaaacaaa cataaaaaaa tgaattctgc atttatgctg attttatttt   11280
ttgtgttatt atattaaagt caacctcttg ggttaaagtt tggtttacaa aaaatgctaa   11340
tgaatacata gattcatgta accacagcct ttcaggatac agaataattc tgtcatctct   11400
```

```
tcccatactc ctccatgtat aatctttat aatcagaagt ttcacctgct tttaagcact    11460
agctgttctc tggcactgta atgtcctgta ggaattgtca catagatgga atctagggat    11520
gtagcttcag tggtagagta tataatcttt ctatctgcca atctatttcc atacagcctg    11580
caacctggaa gtgggcacta tagatctggc tccaagagta cagaatctcc agctgctcct    11640
gtctcttgca acccatccct ctagctatcc caaagcaatg ctaatagtaa tagctatgcc    11700
aagtagccta aaaccccccac aaaggagacc cttctctctg attagggaac ctgtggtgct    11760
aagagaccag gcagatcctg ttggttggtt cataaccacc cacttcttgg ccccagatgc    11820
agtagccatc accataaatg aattgcagaa tggaagaaat aatgtcctag cttttctatca    11880
agtggggtgc tctaaggaat taaatagtac tggggatcga gagagagaga gacagacaga    11940
cagacagaca gacagacaga gacacacaga gagaagcttg ggaagtgatc ttgcatgcat    12000
gattgcaaac tgctagactc accccctggct gtgtgttgat ttgactaaac aatgtcccac    12060
agactgaata attaactatg gattatgcat caccttaagg gcctgggttg aatctgaaca    12120
ctgttgagag tacagaaaag cccacaatcg ttgtgtgttg gtaatacaaa cccaaaaagt    12180
cacatatgtg ttttgtttt gccttgagac aaggtttcct ttcctaatct tgctgttgtt    12240
tatgcttgag cattcccaag taactgcttc atgccttctg ctcaggctac gttcagtgag    12300
agagaaagaa tgggtctaat tattccatct accacacagt aaaccttta ataaagtgca    12360
aaaaagaaca aaaccaaatg agctggtgca attttcttt ttttaagtac agccttgtaa    12420
agaccacaca gcaggatatt tgatgttagc gtgttctaga ttctgtgagt cactgccact    12480
tttacatttc tttacaacgt ggcttctagt cagggctcta acaattgcag attagttttg    12540
cctgttcttg aattttgcat gaataaatcc gcagcttttc ctctttgtgc acaagagctt    12600
tctttgctct tctttataca cgatacagtt ttaggtttca ttgataacac tgtccatcac    12660
taaacatacc aggcacagtt cttcctgcta ttactagata ttaggattgc ttcctatttc    12720
tgttactgtg tctaaatgcg gctcagtttc tacctagttg ttttcactga ttttggtcag    12780
tatgctacag tttgtccagt acctcataag tgaaagggaa gcgtatttgt caatttatga    12840
ataagttagg aataaagatt ttcacagaac tggccacatc cattgagtat tatcattagg    12900
ttgacaagta tctgacctta ggtactgccc atcaaaagca gccctaaaaa ccacttacct    12960
tatttatgta aaaggaactg atttaaaaat tattaagaat ttttgaagat gaaaccttca    13020
ttttagtatc taaattcaaa ttatacagaa tgcagagcgt gggatgggag agtataagtg    13080
gcgtcggcag ccattgccct gattagcatt gtacactcat ttcaatggcc atagctgagc    13140
ccaaggtgcc accaccgcat cgtgattccc agtgcctcac accatcttgc aaccctcac    13200
cctgcttctg agacaggaaa aggtactcaa gagtaccca cccaccccca cagcagactc    13260
catgacaaag ccggtttcca tcctgctaag gcagctggcc tgcagatgcc ccataaggac    13320
ccatggccac ccacatcttg ctttctagag tatgctcatt cctgatgctt atttagagta    13380
tcttaagttc tggtgattca atgagaaaca tcttcggtca cacagagtag acattcttgg    13440
tgtctgtgct actctgagga ccactccttc tgttgtatct gtgtacaaca aactaaaaaa    13500
gctcacgaat tgttcactaa tacagttggt cagtcagaat ttcttgtcat gtgtgtgtgt    13560
gtgaattgtc aatttttttc tgaaagttat ggttacagtt tcagtgtgtc agtaagcaaa    13620
ggcatcaata acaaacaata tacagaaatg ggtccatttg gagcagggca cggtggtgca    13680
cacctttaat ttcaggtgtc tagagacaga gacagcgctc tagagccaga gccaaatgaa    13740
atctctgagt tcaagaccag cctggtctgc agagtgggtt ccaggaaact cggggctaaa    13800
```

```
cagagaaacc ttgtctcaaa aacaacaaca acaacaacaa aaaacccaaa catacaaaca    13860
cccacaaaca acaacaacac cccaaaacta gctccacttg gaaaacctcg gagtgtgtgg    13920
agtgttcctg gaatcagagt ttcctgttcc cttccctaaa aatgttttc tgttggctgg     13980 tataatgggg gcaaggagaa caagagagaa atgagagtcg attctgttta tggggggaaa    14040
cacgttgaca cagtcacatg tttcagaagt aggagtagtt tgctcacagt cgggatttta    14100
tcctttagag aaaggtcgca gctgaaaagg ctcacgataa aacaggaaat gaggaaggcc    14160
ccaaaccatc atacccgaca tcctgacccc tttccaaaat gtcaagctgt ttgtgtctgg    14220
aatttgggga agacattctt tctctccaat tagtttcttt gttgccttaa cacttaactt    14280
ttttttttct tcttctgttt cagagataat gactctgaac agcgtccaat ttgtgagtgt    14340
attttactgt cgtaaatcta ccatcataaa ataaatagat gtcctgtatt acaccacatg    14400
gggtgtaaat cacatcaaac caacatagaa aattaggagg gatgtttaac tccttcaggg    14460
aaagcgtatg gattttgttc atttgtgttt tagtttaatt ttgtttgttt ttttgaggta    14520
gggtctgtgc aacctaggct ggcctcgaac tcctgacgct tgtgaagatg agcacaggct    14580
tctgatcctg ctgcctccac ttcccaagct ctggcatgat agctgacgcc accacacttg    14640
gtttaagcac tgctggagag gaagtcaggc ctccatgcat gctaccaagc accctaacaa    14700
ccaagctaca gtcccaggcc aatgtgttgg tctttggaaa taaatcaaaa ataattctag    14760
ttttgcgtgt gtgatgacaa ccaatttatg agcatttaca tttaaaaaaa acacacatct    14820
cctcaccccc accccccagg aggcaacagc tgacaaaattc tgatatactg tgtgtacatg    14880
accaaatgac ttcacgggtc attcccaata tgaatatcag cttgtgttag cctctactct    14940
cctttctttt atctctcttt ctaaaaattg gatatcttat ttatttacat ttcaaatgtt    15000
atccccgttc ctaatttccc cccagaaacc ccctatcctc tcccctcccc ctgttcctct    15060
aagtctcctt tctacaaaca cttgctgact tcagagacta agttaaccag tcacaactag    15120
gggaaattag tactttttgt gactgtactg cagtttacaa tcataggtct ttccccaacc    15180
tacctgtcac acatgggagc tgccacttca aaccaatttt ctttctttcc cattcttttc    15240
cttgaactgt cagcaagatt gtcttagtgc ttctgtgtcc caggcactcc aaaggatctc    15300
atgcctggcc tcttctctct cttcacgagg gtttcttcct cttagaattc atctgcctac    15360
agaggttctt actcatatct ctgactggcc ttctgttcac tctctcagga agaatggcat    15420
atttctattt cctatccacc tatcctattt atatttcaaa cataattgat tcaacaacaa    15480
taatagtaac cttttgttt gtttggggt tttttttgt ttgtttgttt tttttgttt        15540 tttgttttca agacagggtt tctctgtata gctctggctg tcctggaact cactttgtag    15600
accaggctgg cctcgaactc agaaatccgc ctgcctctgc ctcccaagtg cttggattaa    15660
aggtgtgcac tactatgccc ggcgaacagt aacctttaa taaaaaaaca aaaacaaaa      15720 aaaccttcca ccttgaagga tgtggcgtca tctccttccc aggctccctg caggagagtg    15780
tcagcgttgg tttagtccat tcattctccc attcctcaaa aaaaagtaat ggaaacttgt    15840
ttctcccaga cccaccacat atcagggcat gagataatgt ggtcactgga cggccttttcc   15900 tcattcctgt ccttcttgta tggacttggt actgagcaga catgaccctg tcatggcggt    15960
gaggtctgtt tcatcctttc attctttaac tttaaggaca ttataaaaca gttgaaggga    16020
aaacaaagtt gaattgactc atattttga gaatttgaat gactcttaga gccaaaatcc    16080
ttgtgaagaa ccatttattt aaatatttcc gaaaatctaa tcttgaagaa ataaatggaa    16140
```

```
tttcctcttc ttagtgacgc aacgttagtc cttgcaatct taagcaattt cctcttacag    16200
agcacaaatc attatgaact gagtccttta ttaacaattc caggtttgtt ttcatagctg    16260
agtttgaccc tatgctactt ttgttttca aattttttg ttacctaggc tcagcagtca     16320
atttcataat gttttcctct aactcaaaat aaagatatat atatatatat atatcacttc    16380
attttgtgga aaaatgagat gttctgtgaa tttctaatta atggtatttt ctaaggtcta   16440
gtttacttag agtaaaatga accaatgtct agtgtgtgct gccctgagtt ttgacattgt    16500
ctgcacgcat gcagccatta ctgagtctgg gattaagaac attgttgtct tagagatttc    16560
ccattctaga ctagcagggt tctaattttc actactatag attagaacca ttacatcttc    16620
agctctctgc acacagatca acagttcaga tgtatcttat gcccttggca gttttgctt    16680 cctataatgc ttgagagatt tacctactca gttgtgtttc attgtttcca atgtatagcg    16740
caccttcaaa tggtatgata ccagtaaaat tagaaaatac tagccattta actattgcgc    16800
ccagcttgat ggagttactg gtttctgatt ctgtagaaac tgttatcata acaccctctc    16860
aaactctctc ctcccacttc ctgttttatt actgagatca gacaactagg attcggatgg    16920
attttgtttt taatgtccta gaaacaagaa gactctagag attttccat caagtattct     16980 tttgatgact agtaacatta gggtgagggg gtgtgcttgg ccaccagggt agactctctg    17040
atgtcttcca gtctccttgt ttctagaagg ctagtggaag tgcaaattat ttctaggcca    17100
ctctcggtca gaaagctgcc ctaacaagtc tgacatccgt cctgatccgt cctgttctgt    17160
ttggatggtt tgtgactgag ttgaagagcc tgcatcttct acccactccc ctagagccac    17220
gttccacggt ggccattctc tttcacaggc aggctttgct ctgccatggt tctgattttg    17280
taatcttaat ctcaagcatt ccactcttca gtaacttacc cccttcttcc tgatgattcg    17340
ttctgaagct gtagctgctg gttttttctta ctcctttgtc actgtctgtc catcagttgt   17400
acttactatc tgtccagcct ctgacttctt tatttaagtg agattttact gtttctgaga    17460
atggtttcct tgaaattttc ttcaattctt ttatttcccc catctctctt ttttggtctc    17520
aaattctttt tttcttcttc ttctttttc ttttcttttt cttttttttt tcttttcttt    17580 tcttttttt ttttttggc ttttagacag ggtttctctg tgtagccttg gctgtcctgg     17640
aactcacttt gtagaccaga ctggcctcca actcagaaat ctgcctgcct ctgcatcctg    17700
agtactggaa ttaaaggcgt gcaccaccac gcccggattg gtctcaaatt cttaacagat    17760
tcaacggagt gaatcactca aattggtgac acacgtcagg aaagaaactt tattgaagaa    17820
gcaatttgag tgcaggtttt atctactaca cagattgtcc ttaatttaaa acatcagttt    17880
catgttttct ccttgttccc cacaagctgt gtccctcatc ttcatgctgc acagctgaca    17940
acatcattcc atctttcaag gagagagtaa aagctgttga agggacggct ctcacacccc    18000
cacccccaac ccccattcat ctttcggtct ctgccaatac cccctgccct tacctcttgt    18060
gtggtgaaca agtgtctggc tttcaaagcc ctgttctcct tttttttttt tttttttttt    18120 cttttccaggg ccctgttatc tccttgccaa ttaaattcaa tggacccttt tatttgttaa   18180
ctaacttcag ctgtgagtgt caaagagatt gccctctttc ccccttttgac tcctgttttt   18240 ccagcttttg ggactccatc ccctcctgtg tttgctccca cgtctcttga tgatgcttct    18300
cctcagtttc tctttctttt ttctttctct ctctttttc ttttctcttt cttccttcct    18360
tccttccctt ctttctcctt cctccttcct ttccccacc ccactctct ttcttttcaa     18420 attagtgaga agtatttcat gacttgctta ttgtaactca cctttctaga tttaggtttt    18480
gcattgcaca cacataatgt gattcttttt catatcacac acagagttgc agattgtctt    18540
```

```
cgtgttgttg ttttgtacct tctgccctgg cagtgttgcc catcaggtgt cctgtagtca   18600
agggacagag cctagaatgt gacatgccaa gtaaatatta gcacagcaaa ttagtggaca   18660
taccagtggc tgaaagactt cagtagatgt tccatttcct tgttccactt catatctagg   18720
gaggtgtggc tgacccaggg gtatgaagta gagaacactg tcttttctac agcaggaagg   18780
cacagtcatg gtgtggtaga tattttttaga tgtctaaaac tacttaagga aagagtcaca   18840
aacactattt tgaggcagtt gaagatatag gaaggccaga attgagggta caggtcctca   18900
cattgtagga atttattttg tgagtcttta aaagtttgtt gtggtttcct cctaagtgtt   18960
ttagagtaga agggaggaga caagtagatt ttttttccca catcctttga ccacaagtcc   19020
aaagtataga ctggagatac cttcttagta aagttagata aatatctact caaaggtaga   19080
ctcttccaaa gccataattg gtttatgggg tgttgacatc cagtgaggtt aattatagtc   19140
ttacagctgt gcatgagatc aaaatgagtt caaacaaagg tcaggacgag ttagaaagtt   19200
gtatcacact taagcttggt cccagacaat gttgtactaa acagcaataa cccagccagt   19260
aacaaatttt ataattgtat cagtcctttg gaattgttta gatcttttaa acccatataa   19320
aaataatatt ctgtgtgttt ctaataagtg aggctgctgt catgatcaaa gtggcttttg   19380
ctcgccagaa gtctcactgt agccatagta ggcagtgcat tggttcaaac actgctgagt   19440 aacttgggc atctcagtgc tggggatgga atccagggcc ttgcttatgc tagctccgcc    19500
tctgcgctcg catctctgat tctgaggggt gttggacatg tttggctttc tcgtttgtat   19560
aagagtgata cactcctgct cataatagca taatcgacaa tattcctagc agctgggctg   19620
gaagagatgg atgaacaact gagagaatat aaagagtagc ctgaggcaga gacctagcca   19680
aggccactca cggatgagtg ctactctctg tctcacagtt cagggtattg tgtttaatgc   19740
tggacagtga agggaacaaa cttctaacat caaaactttt gaagattgtc ttaatttggg   19800
ttttattgct gtgaagggac accatgacca ggacaacttt tataaaagca cactttaatt   19860
gaggctggcc tacagggtca gaggtttagt ccattatcat catggcggga aacatggcaa   19920
catgcaggca gacatggtgc cggaggatac tgggggattc tgattccaca tttcatggag   19980
cttgagcata ggaaatctca aacccatgtc tccacactga cacacttcct ccaacaaggc   20040
cacacctacc ccaaaaaggc cacgtcttct aatagtgcca cttcttatga ccaagcattc   20100
aaacacatga atctatgagg gccagaccta ttcaaaccac tacaaagact ttcttatcac   20160
ttcagttaga aaaagtaaaa ttagcacctt taatgaaaag gttccttcca caaaataaac   20220
caccaaggca gcctaagttt tatatgtata tatatatata tatacatata tatatatata   20280
cacatacaca cacacatata tatattatat atatatatat ataatatata tatatgaatt   20340
tttattcata tatctatgaa tacactctaa ctgtcttcag acacaccaga agagggcatc   20400
agatcttatt acagatgttt gtgagctacc atgtagttgc tgggaattga actcaggact   20460
tctggaagag cagtcagtgc tcttaacctc tgagccatct ctccagcccc ctataattct   20520
tttataagat ttcactcttg atatgtaatg ttttattca aagtccagta ttatatttca    20580
ttttgtcatc aaagaaccca agactttaag ttctggtctc acccggaagc tggaagggga   20640
agaacactaa cagttacatc agtaggaatg gtaatcctac tggctcaata aaaagtccaa   20700
gaataaagaa atcaaactgc tgatagaaaa aaaataaatg gtcacagctt tatttatggt   20760
ggtggacaca aaaatttgc aaaagatgat gcatgcaggt tctcttttcca tggcttttttc   20820 cccccctaggc tttgtggacg taagtgtgag tatgcacatg tgtgtgcatg agtgtgtgtg   20880
```

```
tgagtatgcg tttgtgtgat ttaggacaga gataatactt tgggtctatt aatgtaaggt    20940
atgaatacat ttggattaaa tgattttaag taagtggaag gaaatgatac acttgtactt    21000
ggtggaggta aaattctact tacactgttg ataatatatt gaactattag tcaaattaga    21060
aaggtatttg cttataccag aagctaagaa ttagggcaga aagggtcata tttttatgca    21120
gtgtgataaa attccttttg tgaccagtaa gagtaatgag tatgttgcag aggaacaact    21180
tcagtcccca aggacatatt tgcctagctc attagatttt aggcaatctc tgcagaggca    21240
actgtacata tcactacgta aatgtcctcc tgagatattc ctaagtcatt ttacaatgca    21300
attaagaata atctctgcct tgtaagtttg atgtaatgca tttgtttacg cttcaggcaa    21360
aattacaaac actatcaaat tagattcaat tcagtgacac ttggtagata gttttttaact   21420 gaattttttaa taattagagc ataagcagtt tctgaagatt agaaatgtat aactaactta    21480
tgaacatgta ttattttaac gttattttttg caatgctggg gaccaaatcc aagacacttt   21540
cccagcttgt taaacagtca agtgctcagg taaaatctta gtccttgcag gcatcttggt    21600
gacactcatg tacttctaag tagagaaata acaaatgtat ttttatgagg ataatttgta    21660
aattcaaact acagcatttt taaaaatgat ttatttattt tatgtatgtg agtacactgt    21720
agctgtacag atggttgtga gccttgatgt ggttgttggg aattgaattt ttaggacctc    21780
tgcttcctcc agtcaacccc actcgctcca gttggcccca cttactctgg tcaaccctgc    21840
tcgctcaatc cctgtttgct ccagcccaaa gatttattta ttattataca taagtacact    21900
ttagctgtct tgtgacatac cagaagaggg tgtcagatct cattatgggt ggttgtgagc    21960
atttgaactc aggaccttca gaagagcagt cttacctact gagccatctc gccagcccat    22020
agcatttttt ttcttcagaa atattctcac atttaggaca ccttttataaa atgtacaata    22080 ttacaacata ttagaaaaaa tcaaacagct aacaaggcaa gacctagata acttaattttt   22140 ctttaaaagg taatacaaac atttttaataa tagggggtatt aattttgaag tagttgtctt   22200
tataaaatcc aattgttctg tgtgtgtttt ctttctcttt ctctctctct ctctctctct    22260
ctctctctct ctctctctgt ttctctcccc ctctctccct ccttctctct gtctctatct    22320
gtctgtctgt ctgtctctct ctctctctct ctctctctgt gtgtgtgtgt gtgtgtgtgt    22380
gtgatatgtg atgtgatatg tgtgagggag ggcaaccttg gggattgttt tttttttttt    22440 tttttttcttt tccttccacc ttttttgtcag ttccaggcat tgaactcagc cactttgctt   22500
gctgagtcat cttgtcaact gtggagtagt cctcttcaaa gtgtccacag acactgataa    22560
tatccattgt ttactggact gagctcctac agaaatctgc tgaaagttac ttgcagagca    22620
aagaaagggc aatgccatgt gcagtgttga gactttccca tcaccaccat gacaggaaca    22680 atgcaacag tgactgatag gagagatgct tacatctatg aaagctggca ggtagggtcc      22740
atctagcctg tgaactgctg atgctcatgt gcaagttcaa ttaaagtgaa attaattttg    22800
attagaaaat ataagggctg gcaagatggt gtatcaggca aagactccag ctgccaggtc    22860
ttatgacttg agtttgatcc caggccctac ctagtagaaa gagactcctg caagttttcc    22920
tttgacctac attcacaaac tgtggcatgt gtgcactcct acaatacaca tatgcacaca    22980
taaatgcact tagaacaaat acatatgtaa ttaagaatgt aaaatgtggg actggagaga    23040
tggctccaca ctaagagatg ttttttccgga ggacccagga ttgatttttt ttctgcatct   23100
acacagcagc tcccaaccat ttgtaatttc ggctccagag aatccagtgc ctccaaaagc    23160
attgtgcaga tgtggtgcac agacagacag atatgcaggc aaaatacccca tgcatataaa   23220 ttaatataat agcaaacggt caacacagaa gtttgcttta gttggtcccc atactaacgt    23280
```

```
aagacaattt ttaaacagaa caacaacaag aaattagctt gctttctcta attcctatgc    23340
tccatgtcac catatggaaa acactcatta cttttaggg gagccttctc aggggactca    23400
acgaagaaac ctttactaat caaatatcat ctaaggaaat tgtgttcttt ctttttatat    23460
agactttgct ggcagttcac aatgcttacc atgtgtgtgt gtgtgtgtgt gtgtgtgtgt    23520
gtgtgtgtgt gtgtatgtgt cttattttca gaagtttagt ccactattgt catccaggag    23580
gcatggcaga atacagggag gctatggtgc tggaaaaaga attgagagtt ctacatcatg    23640
atctgaaggc acccaggatg aaactgtgag ccactctggg catagcttga acatacaaga    23700
cttcaaagcc ctcctctaca gtggcacatt cctccaataa ggccacacct actccaataa    23760
ggtcacactt tctaatggtg ctgctcccta tggccaagca ttcaaacacc tgagtcttag    23820
ggggccactt atattcaaac tgccagatga gcagatatat tataactgag gtacatctcc    23880
aactccagtt tctcagctaa gtaattttgg aagtatagtg tttccataga agttttaaaa    23940
aatacactct tgaagatgtc aacttgtcta caaatgaaag attttgagat aatcagagat    24000
tttatgacat acacctctac taggtaaagt gtgttcaggg caccactcac aaataccttt    24060
taccatttat tttcactatt aaaaaatttt taaaattagc atcactttcc ccttctcttt    24120
tctccctcca acccctctca tatacttata taatatactt atatacttcc tttattcttt    24180
ctcaaattca tggcctcttt ttctttaatt gttgtcatat atatatatgt atatatatgt    24240
atatatgtgt atatatatgt atatatatat gtatatgtat atataaaaca tataacatca    24300
cacatacata tattcctaga tacagaacta cagtctatat aatgtctctt atatgcatat    24360
tatttcagtg ctaacaattt gcagatattt ttatatatgg gatttatgtt tacaaaagac    24420
aaagtttgtc tccaacaagc acagatatac cattttgtgt gatggcagct gttttaccag    24480
tggaaggggc tccttggctt aaagcacttc tagtttatct cctggagtgg ctttctgatc    24540
caggaactaa taagtggaga aatgccgtgt aatttataaa tgtatatata cagcaagtgg    24600
tcttccacag ggccgcacta gagcttaagt gcctctcagt gagctgacat ttttacttct    24660
gaaaacacta agtgccctc gttccagagt ctggggtcct gagcagctca agcaggacga    24720
tgagcagtgt tgccgaaggt tttgggtggg agagattggg aacgctcttc agagcctacg    24780
gatgcagagg aacaggctgt gaagatggaa gcaacagcaa gatagttcca ggagaaaaag    24840
atcagacaca gaaacccaga gatctctcac cactaagttc atatagagtc ttccttaaag    24900
cacatggggg aatgaaagac tgctaataga gaaaagtcac tcaccatttc atctctttca    24960
gaacgttgca aatgtaagcc tgtcagagct acacagaaga cctatttccg gaacaattac    25020
aactatggta aggataccat taccgtctgc ttatagattg ctgtgttttg ggaaaccttg    25080
catgagcatt ttaaaagtaa gccaggcagt gatggcacat gcctttaatc ccagcacttg    25140
ggaggcagag gcagatggat ttctgagttc gaggccagcc tggtctacag agtgagttcc    25200
aggacagcca gggctacaca gagaaactct gtcttggaaa aaaaaaaaaa gtaaggctta    25260
gaaacaaagg tcacttacaa gtgttgtttc cagtttcatg tatcatagtg acaaagttct    25320
tctcaaatgt gtgattgtga gagcatcggt tttattaatt cattaattaa aactatagca    25380
ttgagtacct taagatcagt ttccaagtag aagttcttgt ctctgggtta gtacctggat    25440
cccggctgtg ctccacaaga aacacccaaa ggacactggg aagcaacatt taatagttgt    25500
cgctattcat ctgagggaat cctttgctat ttaacttgac caaatataac attttaataa    25560
gttaagtgct aactgcagag cctcctgtac aagcagagct gactgacata atgggaggat    25620
```

```
gctatctctc ctggggacaa cttcaggcgc tttctgtgga ctatctcatt tcaattctca   25680
tgagcaccct tctcctcctg gctttatgag tgatgatgac tgagcaaaag ctacccnttc   25740
ttttatcgtg tataatgtac gtttgggtac ttttatgctt cagtgaatgt cagtcactgt   25800
tatgtgacac aggcaatcag tccctggtgt tcctctgtcg gaaggttggg ctgctcagtg   25860
ttactggttt ccacagattt tttttttggg ggggggggt  gggtttcgag acagggtttc   25920
tctgtgtagc cctggctgtc ctggagctca ctttgtagac caggctggcc tcgaactcag   25980
aaatctgcct gcctctgcct cccgagtgct gggattaaag gcgtgcgcca ccacacccgg   26040
cagatttttt ttttaaacta taatttcttt tcaagtagat gctgagtatt ccttatccaa   26100
aatgtttggg accagaagta tttaggatta taggctatca tttttgtatt ttggaatatt   26160
tgtgaatgtg tgggaatact cttaggagcg ggattcaggt tcaagcatga catttgtgtt   26220
tccctgacag ttcctgaagg tgcatcacta attggactgt gacctgtcac atgaagtcag   26280
gtgtggaatt ttccatgtgt aacattgtgt tggatttggt aggaggaatg cacagccagt   26340
cagtgaagct gacacgctca tgccgctctc tgatcccgag ttaatgacta aacatggatt   26400
agaaaattct aaagttaact atgctatgaa aatgagaagt ttgtctttat gtgctttaat   26460
tttagaagac gaagggtgta tagagatttg gctcaaattc tagagcagga gttctcaacc   26520
tgtgggtcac caaccccctcg ggggtcaaat gagccttca caggggttg cttaagacca   26580 cgggaaaaag gagctatagg gaactgcaac cctataggtg gaacaacaat atgaactaac   26640
cagtacccgg gagctcttgt ctttagctgc atatgtatca aagatggcc tagtcggcca   26700 tcactgcaaa gagaggccca ttggacttgc aaactttata tgccccagta caggggaacg   26760
ccagggccaa aaaggggag tgggtgggta ggggattggg ggggtgggta tgggggacct   26820
ttgggatagc attgaaaatg taaatgagga aaatacctaa tttaaaaaaa aagaaataa   26880 acttgaatcc aagtcaaaaa aaaaaaaaa aaaaaaga ccacgggaaa atacagatat   26940
ttacgttaca gttcatagca aaattagtta taaagcagca atgaaaataa tttatattag   27000
ggggtcacta caacataaag tactgtattc aaggatccca acactagaaa ggttgagaac   27060
cactgttcta gaattttggg attaggaga gaagtggaca tgaccaagac agtaatgttt   27120
ggaagtgcaa cttacgaaag agcataaaag aagctcttgg gggtagatga gtctgaatgc   27180 aatttcttc  ccaaattttt cttcagtaaa attatatctt tatttttat  tatgatttat   27240 ttgtttttag acagggagtc tgcacttcaa aggctagtct agaacttgct ctgtagccca   27300
ggttgcccct gaacttgtaa cctcagcctc tccagcacta cagttatagg catgagctac   27360
cagttggcag agtgcttatc ttaagaggat cttagccact cttggttaga gaggaacaga   27420
cagacatccc agggagggac agatgtccct gggtgaaggg cttagttcat ctaagaatca   27480
aaagctggtt acttatctac ttctccttat gcaaactgcc ctgactgcag ggatagggg   27540 gccttccgtt tcagaaggcc agctttttaa gacttataaa gtccatgtga acttttaaat   27600
atagctatca taaaaagcaa aaccataatt tcataccatg ggtcaggtag tggtggtaga   27660
ggccttgctt ggcattcacg gaactctgga ttagatcttc agcatcacat aaaatcggtt   27720
gtgttgttca atattattct ttgatacata gcaagtggga ggccagcctg ggatacatga   27780
gaacctgtct ccaagcaaac cagcagaaac acacacacac acacacacac acacacacac   27840
acacacacac acagatgcac gaatgaagac acagacactg aaaacagtaa caataaaaat   27900
tatttcaaag atatgagtta ttttatttta tctttactta caacttttaa ctttgcccag   27960
cttccttgtt aacacaatag ctggtggtac tcttaccatt aaaagttaaa atactaatct   28020
```

```
ttacaaatca ttttggagaa ggtagctgag tattataaca attgataaaa aggaggagct   28080
ttgtatggta ccctatctgt agtccctcca agcacttagg aataaggtca agattgctgc   28140
ggtaaatctc caacccaaac ccaaatatgc ctggcaatga aaacacaact cagttaatat   28200
gaatacatgc tgtgcgccta gactgggcag agctactgct acactaccat ctttcacatc   28260
ttatgagacc tcttcgaact ttctccaggc catgtgcttc tgctccactt ttcttcttcc   28320
tcctcctcct cctctgtgtc ctctccctct tccattttct ccttcttctc cctctccacc   28380
ttctgctcca ccttcccttt agtctgccca atcatcaact cttctttatt ttacaaatta   28440
aggtgggaag caggtttacc ggaaatcacc tgagtgctga ctctttcctt gcgaagctac   28500
tcacaggata acggaattaa catcaaatat aattagcccc agggctatcc ataacacaag   28560
aggatcaaga gttcaagtcc agttgagact gcattgcaag ttcaaggtca gcctaggttt   28620
ccccagtcgc tattgagaaa aagaaaaga aagagaaga gaagagaaga gaagagaaga   28680
gaagagaaga gaagagaaga gaaggaaaga aggaaggaag gaaggaagga aggaagacag   28740
acagacagac agaaagaaag aaagaaagag agagagagag aaaggaagaa agaaagagag   28800
agaaagaaag aaagaaagga aggaagaaag aaagaggggga gggagaaaaa tattctcttt   28860
gtcatagcta gacactatag ccaccaatga tttaaagatt gattttttggg tgggactaac   28920 agattcttag gagaaaatag cccctccaac gcttggctag aaggcaaact aatgggaaaga   28980 aaatattttt gttttaaaat atattgattt tcactattgt atgcatttgc atgtttctgt   29040
tgagacagga acaactgcta attcatatga aatctctgcc tcattcctga ccgagtcagt   29100
aaaaaattgt gagctttagc aaaattactt gaataatgaa gtaggtgttg tagagaggta   29160 ttatttttggg aggcagtaca tgtgctaaaa attcctaatg aaaatagtgg atgcaccgag   29220
aaaataaatc actggcctga caaccttcgc ccagctccct aatcgctcat ggctcatgga   29280
tactgggaag cacattcatt taagccagga ctcacacaaa catgtctgct agctggtctt   29340
gggaacttac cgtctggagg gaaaaccttta tctcttgtca aaatacaggg cagagagaac   29400
gggcaaagac agggcctcca gttgccattc aagccaggca gagccagctg ggcagttaga   29460
ctttgtctgc aacaaactct cacacttgtg ttgcaacaaa gtctctgaag attgaaatac   29520
tcatgaataa agcttacaga ttttggtaac tgagtctctg tccagtagat tgtcatacct   29580
gtagaccatt gagtcaccat ataaagttag gtcgatagtg gagaatgcat tatcaggtgg   29640
ttttatgttt tggtggaggg attttttttt ttttttttt ttactcaatc ctgtataatc   29700
ctgaacacct aaaatacctg ggagaatctg ccagtggcag tttgtacact cctacctaca   29760
gagctcctcc aaggtggatt ctcttgcata tattgtattt cctttgtgga cattgtatta   29820
atatgacaga gcttcctgag caattgctgt tggcttttta ttaaataaca agtttgactc   29880 tttctttta ataaatataa aactttcctg tacaaatgca tacttaccag aagcagatcc   29940
ctacacaatg tggctcttca aaaaaaaaa aaaaaaaga gacacggagg gaatagaaga   30000
aacatagctt ctaggttctg agtcacctca tttgactttg cagatggaag acagtttgtc   30060
tttgtgttga aaagtgaagc tgacacctgt agggagtgct ggggtcacta cttgcattgg   30120
gggaagagaa ctgatgcaat cagcatgcta gaacattgtc cccgacatag cagggtcacg   30180
gggtagcagc gtggctgagt ggaaggcaga tggaggagac aaggtctaat ggacaacttt   30240
tgctcacgaa gaaagttcat cgtccctaaa ggagatacaa accataacgc tgggggctgg   30300
agagatggct cagtgattaa gagcactgat tgctcttcca gaggtcctga gttcaattcc   30360
```

-continued

```
cagcaaccac atggtggctc acaaccatct ataatgagat accctcttct ggtgtgtctg    30420
actacagtga cattgtattc atataaataa aataaataaa ttagaaaaaa aaaaaaacct    30480 aaaccacat  aacattggtg tgaaggaagg aaagtgccaa tgtcagaatg gcgagatgtg    30540
gtgagggagg tgaatgtcca aggagttggt ttgggaacac caataaacaa gactgagttg    30600
tagctgggaa gagagcctgc cttgagaaaa ctgatcaact gaatagttct gatgaagaaa    30660
caaagcatcg agttgagtct aggccttaac atggggtaaa attagtttaa gttaatacct    30720
ttcagcagcc attggtacca cacacacaca tagccacaca tccaaagtga ggctgtgtag    30780
gggaattata atagattact caatcaacta tgattaccta agtgggttcg tgaaaatcaa    30840
acgtctatac acacatgcgt atataatcac caatgtctgc atacacagat acatacacaa    30900
attggcaggg aatcagggct gagcaagaag gccagtatgg catttagttt ctctaaagaa    30960
aaatgtctgc ctgacatttc ctttctaacc attgatcatg aaattgagag gaattggcta    31020
gaaagaggcc tactggcttt tttttttttt tgaagggtgt accttactgt gtgtcatcat    31080
ataaatcaaa tttactgtct tttattcagt catccgggct aaagttaaag aggtaaagat    31140
gaaatgtcat gatgtgaccg ccgttgtgga agtgaaggaa attctaaagg catcactggt    31200
aaacattcca agggacaccg tcaatcttta taccacctct ggctgcctct gtcctccact    31260
tactgtcaat gaggaatatg tcatcatggg ctatgaagac gaggaacgtt ccaggtaacc    31320 ttcccctaa  ggatgcaggg gaattggttt tccttccaca tcttgctggg cttttcttgt    31380
cttaggctct ttctactttc ttgagaacta tggttatata ttttaatttt acatattgga    31440
tagaaaaggg atgtgagcat agcttatggg tatagatttt tctggaaagc aagatcatag    31500
ttcatttatt tctaaagggg atccacgatt cctaaatggt taagactctt ctcagctctc    31560
tggcatcaga ttctaggatg aacatactta gttttttcttg ccaccaattc tttgaatttt    31620
tcaattatat actttggttt ttcaaaataa tttgattttt aaaatgcagg ttactcttgg    31680
tagaaggctc tatagctgag aagtggaagg atcggcttgg taagaaagtc aaggtaagct    31740
tggattttat gttcaaagta gtactggggc tgggacttag ctctgtggta gaatgcttac    31800
ctagcaagta tgctccaggt tcagtcccca gcaccagaag aaaaattctg tctgataata    31860
taatccatag aaaaccatct ttcacataag ctaaatagtt gtcctcaact acatgagaat    31920
attaagacct gatacacaca cacacacaca cacacacaca cacacacaca cacacacaca    31980
cacatacaca cacacacatg actattctga gaactgaaat tattgttaat gtctattcat    32040
ttatgaaatt aatttcctct acgtgtatca aagctctaag tacagttgcc ctaacttctt    32100
gggaaatcgc ctatagctag ccaatcatga cagactggct ttatgctagc attcagagcc    32160
ccagcctctg acagccatgg tcgggtaccg cttccatctt cttgttcagt aggaatcaca    32220
cagtgctgtt ctgccaccaa catcatacat cattccaggc agaaagatgc aaggaggtca    32280
acataggttt tcaagaactc tttccagaca ctttatcatg aaacttttga tccgaacatg    32340
ggccatgtct atctccactt gggaaagcag ggagtagggg ttttattgc  ttctaaacaa    32400 attgcttttc tctgagaaga gggggaaaaa ttagtgctga atagaaaaat accactgtgt    32460
ccaacggaca gatatggact cctatgagtg agatgctgcc acagtcataa gtgtagaaga    32520
gatgtcacca aactgggtac ttaaaacaat gatgtggctt taatatttta tattaagacc    32580
ctagaccata tatatgcatg tatgtatgta tgtatgtatg tatgtatgta tgtatatcaa    32640
gtagtacatt actcaataga aatggttttg tgtttcttat tactcacta  gcacatcttt    32700 ctcaaaaaga agaacgagtg ggagggggga atgcatagga ggcagaggac tcttctaggg    32760
```

```
tgtgtgctgg ggaagggtt gggagtggaa actgtaccaa acatacatcc tcttctgaga   32820
gctggagggc gtgggtagca tttccaggga aagttaaacc cctgaggcag tttatgacat   32880
atggcaccca gcgtgggtgg cagacacacc tgagtcgaag agacctacag aaatgtcgag   32940
ggcatggttt cattgataga aactaccgct actaagttcc ttttgtctct agagttttg    33000
tcagaagtga ggagcatttc agatgcggac tgtgagtgtt ttttgttccc atctctcacc   33060
aatgaacctg gtgtttaatt attagtggag aagtggctct tcttcagagt actgggatgt   33120
cctttcagct tttcaagtct gttttccgct tccaagtgca gaacaggaat tgtcctaaa    33180
ttcccgtacc agttgggaga acttcagcac ctctgctgct gtgtaaca agcctcgcca    33240
gttatgttcc cactgggagg cacggcttgt cctgttttgt agcatggtga atatattccc   33300
ttcagggaaa tcatagtttt tatgggatca ctgatgttct cagattgaat ttaaacacac   33360
taatgggaaa caatgaacca gtgacttgaa taactaatta atctttgttg ttttgagact   33420
gtcttgctat gcagctctgg ctggagtgat acttttgatt cagcacaggc tggactggta   33480
cctacaatgt agcacaggct ggactggtac ctacaatgta gcacaggctg gactggtacc   33540
tacaatatag cacaggctgg actggtacct acaatgtagc acaggctgga ctggtaccta   33600
caatgtagca caggctggac tggtacctac gatatagcac aggctgaact ggtacctatg   33660
atgtagcaca ggctggactg gtacctacaa tgtagcacag gctggcccag tacctatgat   33720
gtagcacggg ctggactggt acttgcaatg tagcataggc tggcctcaaa ctctgtcgtc   33780
ctcctatact gctgctgttt ttattatagt aatgtatcac tgctcccaat tctcttctga   33840
ggttcttctt ttgaaaaaag attcttaaat ttttatttta tatgtatgag tattgtctgt   33900
gtttatgtct atgcataagt tcctcgtgcc caagaaggcc aggagagggt gtgggatccc   33960
taggaactgg agttacaaat gtttgtgagc tatcccctgg gtgctgggaa cctctggttc   34020
tctgctagat cagcaagtgt ttttgttttt ggttgcttgg ttggttggtt ggttttaaac   34080
agttctgtgt agccttggct gtcctagaac ttgctctgta gaccaagctg ccctcaaact   34140
cagagatctg cctgtctttg cttcccaagt tctgggacta aaggtgcacc accactgcca   34200
ccgtttccag caagtgttca taaccgctaa gctatctctc caggcccagt gggccatttt   34260
taattcacgt ttatgctctg agtcagaagt ttggggagaa aatcagttct ggttggaatt   34320
attagcatac ctactgtagc ttttcagtta actcaggaat gtttaaaaga ctcttatgga   34380
ggatattatt tttaaattca atataagttg ctctttagag ctgatctttc tctctctctt   34440
tttgtttttg ttttgttttg tttttcaag acagggtttc tctgtatagc cacggctgtc   34500
ctggaactca ctttgtatac caggctggcc tcgaactcag aaatccgcct gcctctgcct   34560
cccaagtgct gggattaaag gcgtgaatca ccacatctgg cgctgaactt tctcttaata   34620
gtaggccagt taaaagatc atttaccatt ttcctatgta aatgattatt tgtctctgtt    34680
tcgagacagc caattgttca agatatttga attatcttgg agagagttaa gaatcagatt   34740
attttttaaa tatgaaagca atattactat gcaataaagt cagccaagat gaagatgtat   34800
tttaatagaa aaacaagtaa taactaatgt attatatgct gtgcactttg caattttca    34860
atcttcagaa taatgctatt attagttatt aatcccaata tagaaacaat aaaaatgtcg   34920
attagttcag aagctttgta cggttaagta gtgagttaga atcaggattt gggccatctg   34980
ccattagctt cttgctactt aaaatgaggt cattgaacca gcagcccaca gatcatctgg   35040
gagctcctgg cctgtggaaa tcatggactg cattcagagc tgataaagag gagtctgttc   35100
```

| | | | | | |
|---|---|---|---|---|---|
| tcagtacggg | cctctggttt | ctatgtttgc | tgaagtttgt | ggagtacaga | tgttcttatc | 35160 |
| atttcataca | ctttcaccat | gtaacttcca | ttcaatttct | tatatcacaa | ataagcagta | 35220 |
| ttgacatcat | tcatatgaaa | tacaagtcaa | tgtgactttt | cttatttaaa | aagatgtatg | 35280 |
| caacaacaat | taacacctcc | cctccccca | tgcattgtaa | agcctgtggc | agggaaggat | 35340 |
| cttgtgggtt | tgctgtaatt | ggtggaaaat | actagaaaaa | tattttagag | gcaccatttt | 35400 |
| cccttatat | cttcactatt | tagatcagct | tattttgtgt | atatgtgtat | gtacatgttc | 35460 |
| atacatatgc | acttttgtgc | ttactggtga | atgtgcatat | gatggctgga | agtcactgct | 35520 |
| aggggtcttc | ctcaattgct | ctctgcccta | cttttccaga | caaggtcttt | ccctgaaact | 35580 |
| gattctcact | cataagctag | actcactgac | tatggaactc | taggacctgc | ctgtctttgc | 35640 |
| ccctggcctt | gctgctctct | cagcactgag | gctgtagata | cacccaga | tgctcagtac | 35700 |
| caaacatcag | gttcttgcac | gtgtgccatc | tccctaacca | ctcaaccagt | ttttaaaaag | 35760 |
| tttcgttact | ttagtcttaa | gaaaatgatg | agaaaaaaa | agcccttctt | tcaaactgcc | 35820 |
| aacataaatc | ttccacttaa | atataaattc | tgaaagtata | gatactgttg | actttgtat | 35880 |
| catttacaga | catggaattt | tagttctatg | ttttggtacg | atggcatcct | tgaatatctt | 35940 |
| acagatgaga | tggcttctgc | tgtggttttt | ggaatcagag | cattgtgttt | atacagtgtc | 36000 |
| attgttatcc | ttggatagag | attttgtact | ttggaaaag | tagcaaaaca | ctttagagat | 36060 |
| ctgaccctgg | actctccctc | ggttgatagc | atcatagaaa | taacacccca | cgtgatgtgt | 36120 |
| cctcgtgact | gttctctctt | ttacatttca | cagcgctggg | atatgaaact | ccgacacctt | 36180 |
| ggactgggta | aaactgatgc | tagcgattcc | actcagaatc | agaagtctgg | caggaactct | 36240 |
| aatccccggc | cagcacgcag | ctaaatcctg | aaatgtaaaa | ggccacaccc | acggactccc | 36300 |
| ttctaagact | ggcgctgctg | gactaacaaa | ggaaaaccgc | acagttgtgc | tcgtgaccga | 36360 |
| ttgtttaccg | cagacaccgc | gtggctaccg | aagttacttc | cggtcccctt | tctcctgctt | 36420 |
| cttaatggcc | tggggttaga | tcctttaata | tgttatatat | tctgtttcat | caatcacgtg | 36480 |
| gggactgttc | ttttgcaacc | agaatagtaa | attaaatatg | ttgatgctaa | ggtttctgta | 36540 |
| ctggactccc | tgggtttaat | ttggtgttct | gtaccctgat | tgagaatgca | atgtttcatg | 36600 |
| taaagagaga | atcctggtca | tatctcaaga | actagatatt | gctgtaagac | agcctctgct | 36660 |
| gctgcgctta | tagtcttgtg | tttgtatgcc | tttggccatt | tccctcatgc | tgtgaaagtt | 36720 |
| atacatgttt | ataaaggtag | aacggcattt | tgaaatcaga | cactgcacaa | gcagagtagc | 36780 |
| ccaacaccag | gaagcattta | tgaggaaacg | ccacacagca | tgacttattt | tcaagattgg | 36840 |
| caggcagcaa | aataaatagt | gttgggagcc | aagaaaagaa | tattttgcct | ggttaagggg | 36900 |
| cacactggaa | tcagtagccc | ttgagccatt | aacagcagtg | ttcttctggc | aacgtttttg | 36960 |
| atttgttcat | aaatgtattc | acgagcatta | gagatgaact | tataactaga | catctgttgt | 37020 |
| tatcactata | gctctgcttc | cttctaaatc | aaacccattg | ttggatgctc | cctctccatt | 37080 |
| cataaataaa | tttggcttgc | tgtattggcc | aggaaaagaa | agtattaaag | tatgcatgca | 37140 |
| tgtgcaccag | ggtgttattt | aacagaggta | tgtaactcta | taaagacta | taatttacag | 37200 |
| gacacggaaa | tgtgcacatt | tgtttacttt | ttttcttcct | tttgctttgg | gcttgtgatt | 37260 |
| ttggttttg | gtgtgtttat | gtctgtattt | tgggggggtgg | gtaggtttaa | gccattgcac | 37320 |
| attcaagttg | aactagatta | gagtagacta | ggctcattgg | cctagacatt | atgatttgaa | 37380 |
| tttgtgttgt | ttaatgctcc | atcaagatgt | ctaataaaag | gaatatggtt | gtcaacagag | 37440 |
| acgacaacaa | caacaaaaat | gttttttctta | tgtgtgctgc | actgagaccc | caacaaccca | 37500 |

```
tgggtggggg ggaacccacg atgccttttc ttccttccct gcagcaggga tgtgcccatc    37560
acctgaaagt ctcattccct gaaatttaca catgtggtag tagtaggtcc agattcctaa    37620
gttacagtgt gctgaaaaat aaaacaggta tgaagcaaat ggtgctgtgt ttccttctgt    37680
gagaacaacc acgcaaggat gaagatcatt cccaagcgga cgttttctat cttggcaact    37740
tttctaaatt ctttcttttta gaagaaaaaa accatcctca ctttccaatg agccctaaac    37800
accaaaaatt cccccaattc tagaaccata ctcccatctt tgcccctagg aggacagcac    37860
aggcttcaat ctactatgta gttactttct ggtaccttgt actgtgtgtt ctgatgctgg    37920
gagagggtta tcttttccta ggtgttgcta ttatcctttc aaggtgaatt ttgtgtccct    37980
gggtattgag gagtactgct ctggggatgc tgaggtaggg ggttggggga gggaagtgca    38040
gtactaagga tgctggtctc caatctctcc cagggtatct gtctcggctt tgggctccca    38100
ggatgaacac atacatccta ttcatagcaa ccctgcagaa agggcaggac ttggtgacag    38160
gagccttaag ggatctggca tctggagtcc ctaacatgcc atcagtgttt ctagggtgta    38220
cttgaagcta ttttaagtga tgaaaatttt acggtatatt tatttccttt tttatggtcc    38280
tgaagataga atctggccct atgaatgcta gatagctgtt ctatctacat tgccatctgt    38340
atctgcctac atcaagctac tcagccagtg atgaaatatc tttacataaa caagaaccta    38400
tatgtaggtg ctttgtttag gtggatagat gggaaaacat atttgttttc agtgtaggaa    38460
tttctcacat agtagatgta actcctacac agttacactc atagataacg ggggcagtct    38520
ctgagataaa gcagaatttc tactctcttc catttctggg ccaacacctg tgaactaaat    38580
gcatggctgt ttctcagttt ggtagctgcg acatcttcac taataaactg tgcagatatc    38640
ttggagggag gcatgatttc atcatgacat gcaggttttt gtgcacactg caaaaccatt    38700
tccactccac tattgtcata taagtctcac cagtgcctct ctgcaggtcc tttatgctcc    38760
ccttgaaagc cactaaaagc tgagttggtg gtacattcat ttcatctcat cactggggag    38820
gcagaggcag gcagatctct gagcgtgagg ctagccctac agattgagtt ccaagatagt    38880
cagggcaaca cagagaaacc tcttgttgaa aaacaaacaa acaaataaat aaataaacaa    38940
aaccaaaaca aaaggccact acaaatttaa catgcatgcc tgcttgttag taaaccttga    39000
ggcctttgaa atcaattgaa attttcttaa gacaattttg ctcaccttca ggatttaat    39060 tttctcaccc agcacagcag caaaacagtc gtgtgcacgg tgaatgaacc atcgaaaaca    39120
cgagcagcaa gcatgtatcc tcttttcat ggatccatga gtatgtgact gtgttgtatg     39180
tagtaatctg acccggtgcc acatggtcca ctgagcattg ggggtgggggt gggacaatcc    39240 cgtgtctttc tccatctgga acctattacc aagtcaaata caagagttac aatcactgtg    39300
agtaaatagc tctgcttact gccttctgca agaaattatt tgctattaca tttcaacagt    39360
aaaatgactc cttaaaaagc atttcaaggc tggtaattgt tcagccctat ggattttaac    39420
gttttaatac agaataaaga agcagtaag gaagaagtta aaatccaagc ccagacttt     39480 agtagtgtgt cactgaaatg caagcatatg gctcccagct gcatccaagt taccgaataa    39540
cgaaaataac gtacgcatag ctttgatggg gatctcctct gcatcctgtc tagcagtggc    39600
taaaagttat acaaaccact tacacatgtc ctgttggtgc cttaaaactt tatggt        39656
```

<210> SEQ ID NO 3
<211> LENGTH: 19
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 3
aaggctgtgt gcatgtcct                                                    19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agagggaggt gacgtcaaag                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcagatgtct ggaggtgctg                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggaacctcc agtaagccag                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aacctatgcc cgtttcctct a                                                 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagtgtaaag acttggtcca cc                                                22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ttcttacttg agggcggaga                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgtcgggtc aagagaggag                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgacacctcc caagtccttt                                               20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgcatactg cccgtcaat                                                19

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtggccgaa tgcacattga aaga                                          24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgcctgtt cttccctgga ca                                            22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctcaatgta tcactctgtg                                                                                    20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttccaagag ttgtttgtg                                                                                     19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tctgtcccca aagagacata t                                                                                  21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggcctacta ttaagagaaa                                                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcattcaa cgtttagttt                                                                                    20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccagggcta tacagagaaa c                                                                                  21

<210> SEQ ID NO 21
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 21
gaacatttct ctatcgataa ggtaccctct gcctcccaag tgctgggatt aaaggcgtga      60
ctctgcctcc caagtgctgg gattaaaggc gtgactctgc ctcccaagtg ctgggattaa     120
aggcgtgact ctgcctccca agtgctggga ttaaaggcgt gactcgagat ctgcgatctg     180
catctcaa                                                              188
```